(12) United States Patent
Tang et al.

(10) Patent No.: US 11,230,543 B2
(45) Date of Patent: Jan. 25, 2022

(54) BIARYL MONOBACTAM COMPOUNDS AND METHODS OF USE THEREOF FOR THE TREATMENT OF BACTERIAL INFECTIONS

(71) Applicant: Merck Sharp & Dohme Corp., Rahway, NJ (US)

(72) Inventors: Haifeng Tang, Metuchen, NJ (US); Weiguo Liu, Princeton Junction, NJ (US); Fa-Xiang Ding, Staten Island, NY (US); Wanying Sun, Edison, NJ (US); Yi Zang, Princeton, NJ (US); Weidong Pan, Hillsborough, NJ (US); Anthony Ogawa, Mateo, CA (US); Linda Brockunier, Orange, NJ (US); Xianhai Huang, Warren, NJ (US); Hongwu Wang, Westfield, NJ (US); Rudrajit Mal, Edison, NJ (US); Tesfaye Biftu, Freehold, NJ (US); Min Park, Morristown, NJ (US); Yan Guo, Westfield, NJ (US); Jinlong Jiang, Scotch Plains, NJ (US); Helen Y. Chen, Marlboro, NJ (US); Christopher W. Plummer, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/912,146

(22) Filed: Jun. 25, 2020

(65) Prior Publication Data
US 2020/0361928 A1 Nov. 19, 2020

Related U.S. Application Data

(63) Continuation of application No. 15/775,487, filed as application No. PCT/US2016/066064 on Dec. 12, 2016, now abandoned.
(Continued)

(51) Int. Cl.
| | |
|---|---|
| *C07D 417/14* | (2006.01) |
| *C07D 471/04* | (2006.01) |
| *C07C 53/18* | (2006.01) |
| *C07F 9/6558* | (2006.01) |
| *A61K 31/433* | (2006.01) |
| *A61K 31/444* | (2006.01) |
| *A61K 31/4439* | (2006.01) |
| *A61K 45/06* | (2006.01) |

(Continued)

(52) U.S. Cl.
CPC .......... *C07D 417/14* (2013.01); *A61K 31/427* (2013.01); *A61K 31/433* (2013.01); *A61K 31/444* (2013.01); *A61K 31/4439* (2013.01); *A61K 45/06* (2013.01); *A61P 31/04* (2018.01); *C07C 53/18* (2013.01); *C07D 471/04* (2013.01); *C07F 9/65583* (2013.01); *A61K 31/424* (2013.01); *A61K 31/431* (2013.01); *A61K 31/551* (2013.01); *A61K 2300/00* (2013.01)

(58) Field of Classification Search
None
See application file for complete search history.

(56) References Cited

U.S. PATENT DOCUMENTS

| 4,537,886 A | 8/1985 | Taylor et al. |
|---|---|---|
| 9,174,978 B2 | 11/2015 | Aulakh et al. |

(Continued)

FOREIGN PATENT DOCUMENTS

| CN | 101410111 B | 12/2012 |
|---|---|---|
| CN | 104203237 A | 12/2014 |

(Continued)

OTHER PUBLICATIONS

Brown, Matthew, F. et al., Pyridone-Conjugated Monobactam Antibiotics with Gram-Negative Activity, Journal of Medicinal Chemistry, 2013, p. 5541-5552, vol. 56.
(Continued)

*Primary Examiner* — Amanda L. Aguirre
(74) *Attorney, Agent, or Firm* — Baerbel R. Brown; Catherine D. Fitch

(57) ABSTRACT

The present invention relates to biaryl monobactam compounds of Formula I:

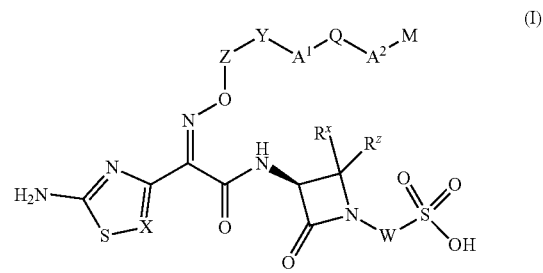

and pharmaceutically acceptable salts thereof, wherein X, Y, Z, $A^1$, Q, $A^2$, M, W, $R^x$ and $R^z$ are as defined herein. The present invention also relates to compositions which comprise a biaryl monobactam compound of the invention or a pharmaceutically acceptable salt thereof, and a pharmaceutically acceptable carrier. The invention further relates to methods for treating a bacterial infection comprising administering to the patient a therapeutically effective amount of a compound of the invention, either alone or in combination with a therapeutically effective amount of a second beta-lactam antibiotic.

20 Claims, No Drawings

Related U.S. Application Data

(60) Provisional application No. 62/267,855, filed on Dec. 15, 2015.

(51) Int. Cl.
*A61P 31/04* (2006.01)
*A61K 31/427* (2006.01)
*A61K 31/424* (2006.01)
*A61K 31/431* (2006.01)
*A61K 31/551* (2006.01)

(56) References Cited

U.S. PATENT DOCUMENTS

| | | |
|---|---|---|
| 2013/0296555 A1 | 11/2013 | Gu et al. |
| 2014/0275007 A1 | 9/2014 | Glinka et al. |
| 2015/0045340 A1* | 2/2015 | Klenke ............ C07D 417/14 514/210.09 |
| 2015/0266867 A1 | 9/2015 | Aulakh et al. |

FOREIGN PATENT DOCUMENTS

| | | |
|---|---|---|
| CN | 103228652 B | 2/2015 |
| EP | 0229012 B1 | 6/1991 |
| JP | 2015504907 A | 2/2015 |
| WO | 2007065288 A2 | 6/2007 |
| WO | 2012073138 A1 | 6/2012 |
| WO | 2013110643 A1 | 8/2013 |
| WO | 2015103583 A1 | 7/2015 |
| WO | 2017106064 A1 | 6/2017 |

OTHER PUBLICATIONS

Drawz, Sarah, M. et al., Three Decades of B-Lactamase Inhibitors, Clinical Microbiology Reviews, 2010, p. 160-201, vol. 23, No. 1.
International Search Report for PCT/US2016/066064 dated Feb. 28, 2017, 9 pages.
Kline, T., Antimicrobial Effects of Novel Siderophores Linked to beta-Lactam Antibiotics, Bioorganic & Medicinal Chemistry, 2000, 73-93, vol. 8, No. 1.
Mitton-Fry, Mark, J. et al., Novel monobactams utilizing a siderophore uptake mechanism for the treatment of gram-negative infections, Bioorganic & Medicinal Chemistry Letters, 2012, p. 5989-5994, vol. 22.
Ready, Joseph, M. et al., Asymmetic Catalytic Synthesis of a-Aryloxy Alcohols: Kinetic Resolution of Terminal Epoxides via Highly Enantioselective Ring-Opening with Phenols, J. Am. Chem. Soc., 1999, p. 6086-6087, vol. 121.

* cited by examiner

BIARYL MONOBACTAM COMPOUNDS AND METHODS OF USE THEREOF FOR THE TREATMENT OF BACTERIAL INFECTIONS

This application is a continuation of Application No. U.S. Ser. No. 15/775,487, filed May 11, 2018, co-pending herewith, which is a U.S. National Phase application under 35 U.S.C. § 371 of PCT Application PCT/US16/066064, filed Dec. 12, 2016, which claims priority from and the benefit of U.S. Provisional Application U.S. Provisional Application No. U.S. Ser. No. 62/267,855 filed Dec. 15, 2015.

FIELD OF THE INVENTION

This invention relates to novel biaryl monobactam compounds, processes for their preparation and their use as therapeutic agents. More particularly, the invention relates to biaryl monobactam compounds and their use as antibiotic agents for the treatment of bacterial infections.

BACKGROUND OF THE INVENTION

The introduction of antibiotics for treatment of bacterial infections is one of the great medical achievements of the 20$^{th}$ century. Over the past few decades, however, bacteria resistant to multiple antibiotics have begun to emerge throughout the world, threatening the effectiveness of antibiotic therapy. In the United States alone, at least 23,000 people each year die as a direct result of infections caused by antibiotic-resistant bacteria, and numerous others die from pre-existing conditions exacerbated by similar infections. *Antibiotic Resistance Threats in the United States,* 2013, Centers for Disease Control, Atlanta, Ga. New antibiotics are needed to combat the current and future threat of multidrug resistant bacteria.

β-lactams are the most widely used antibiotics for treatment of serious bacterial infections. These include carbapenems, cephalosporins, penicillins, and monobactams. As has been observed for other antibiotic classes, resistance to β-lactams has emerged. For most Gram-negative bacteria, this resistance is primarily driven by the expression of β-lactamases, enzymes that hydrolyze β-lactam compounds. There are 4 different classes of β-lactamases (A, B, C, and D) capable of hydrolyzing overlapping but distinct subsets of β-lactams (Drawz and Bonomo, *Clin. Micro. Rev.,* 2010, 23:160-201). While the class B β-lactamases, also known as metallo β-lactamases (MBLs), are not the most prevalent β-lactamases found in the clinic, the frequency and distribution of their expression is on the rise and represent a significant medical threat because (i) MBLs have to ability to hydrolze all β-lactams except monobactams, and (ii) unlike the class A and C β-lactamases, there are no inhibitors available for the MBLs.

Aztreonam, a monobactam, was first approved in the U.S. in 1986 for the treatment of aerobic Gram-negative bacterial infections and remains the only monobactam in use in the U.S. today. However, aztreonam has poor activity against *Pseudomonas* and *Acinetobacter* strains. Because monobactams are inherently resistant to hydrolysis by MBLs, several companies have begun developing novel monobactam compounds for the treatment of infections caused by Gram-negative bacteria. Monobactam compounds comprising a siderophore moiety are disclosed in WO 2007/065288, WO2012/073138, *J. Medicinal Chemistry* 56: 5541-5552 (2013), and *Bioorganic and Medicinal Chemistry Letters* 22:5989 (2012).

U.S. Patent Application Publication No. US 2014/0275007 discloses oxamazin monobactams and their use as antibacterial agents, and U.S. Patent Application Publication No. US 2015/0266867 also discloses novel monobactam compounds for the use as antibacterial agents. International Patent Application Publication No. WO 2013/110643 discloses novel amidine substituted monobactam derivatives and their use as antimicrobial reagents.

The need for new antibiotics to overcome multidrug resistance continues. Compounds disclosed in this invention are designed to fill this medical need, through administration either on their own or in combination with a suitable β-lactamase inhibitor.

SUMMARY OF THE INVENTION

The invention relates to the design and synthesis of a series of bi-aryl monobactam analogs, a novel class of highly potent antibiotics effective against a broad range of Gram-negative bacteria. These compounds and their pharmaceutically acceptable salts may be useful as therapeutic agents for clinical treatment of various infections caused by Gram-negative bacteria, including strains that are multidrug resistant. The compounds can be used alone or in combination with a suitable β-lactamase inhibitor. More particularly, the present invention includes compounds of Formula I:

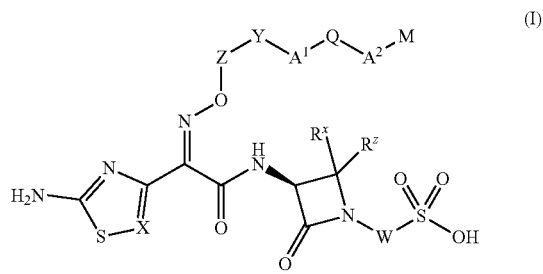

or a pharmaceutically acceptable salt thereof, wherein:

W is a bond or O;

$R^X$ and $R^Z$ are independently hydrogen, —S$C_1$-$C_3$alkyl, $C_1$-$C_3$ alkyl, —($C_1$-$C_3$alkylene)$_n$O$C_1$-$C_3$alkyl, or —($C_1$-$C_3$alkylene)$_n$N$C_1$-$C_3$alkyl, wherein the —S$C_1$-$C_3$alkyl, the $C_1$-$C_3$ alkyl, the —($C_1$-$C_3$alkylene)$_n$O$C_1$-$C_3$alkyl and the —($C_1$-$C_3$alkylene)$_n$N$C_1$-$C_3$alkyl are optionally substituted with one to seven fluorines;

or, alternatively, $R^X$ and $R^Z$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and said $C_4$-$C_7$ heterocycloalkyl are optionally substituted with one to three substituents independently selected from —F, —OH and —O$C_1$-$C_3$alkyl;

X is N or $CR^1$;

$R^1$ is hydrogen, $C_1$-$C_3$ alkyl, or halogen; wherein said $C_1$-$C_3$ alkyl is optionally substituted with one to three $R^a$;

each occurrence of $R^a$ is independently hydrogen, halogen, $C_1$-$C_3$alkyl, —N$R^cR^d$ or —O$R^e$;

Z is $C_1$-$C_3$ alkylene, optionally substituted with one to three $R^b$;

each occurrence of $R^b$ is independently —$C_1$-$C_8$ alkyl, —$C_3$-$C_7$ cycloalkyl, —C(O)O$R^e$, —C(O)N$R^cR^d$, tetrazolyl, oxadiazolonyl, HetA, AryA, —S(O)$_m$R, —S(O)$_m$N$R^cR^d$, or —P(O)(R$^e$)$_p$ wherein said —C$_1$-C$_8$ alkyl and said —C$_3$-C$_7$ cycloalkyl are optionally substituted with one to three R$^a$;

HetA is a 4- to 6-membered saturated or monounsaturated monocyclic ring with 1, 2, or 3 heteroatom ring atoms independently selected from N, N as a quaternary salt, O and S, optionally substituted with one to four R$^4$;

AryA is a 5- to 6-membered monocyclic aromatic ring with 0, 1, 2, or 3 ring atoms independently selected from N, N as a quaternary salt, O and S, optionally substituted with one to four R$^4$;

Y is a bond, O, NR$^2$, S, or CH$_2$;

R$^2$ is hydrogen, —C$_1$-C$_3$ alkyl, —C(O)R$^e$, —C(O)NR$^c$R$^d$, —S(O)$_m$R$^e$, or —S(O)$_m$NR$^c$R$^d$, wherein said —C$_1$-C$_3$ alkyl is optionally substituted with one to three R$^a$;

A$^1$ is AryA;

A$^2$ is —(CH$_2$)$_n$N(R$^3$)$_2$—, C$_3$-C$_7$ cycloalkyl, AryC or HetC, wherein said C$_3$-C$_7$ cycloalkyl is optionally substituted with one to four R$^4$;

AryC is a 5- to 6-membered monocyclic aromatic ring with 0, 1, 2, or 3 ring atoms independently selected from N, N as a quaternary salt, O and S, optionally substituted with one to four R$^4$;

HetC is a 4- to 7-membered saturated or monounsaturated monocyclic ring with 1, 2, or 3 heteroatom ring atoms independently selected from N, N as a quaternary salt, O and S, optionally substituted with one to four R$^4$;

each occurrence of R$^4$ is independently: —C$_1$-C$_8$ alkyl, —C$_2$-C$_8$ alkenyl, —C$_2$-C$_5$ alkynyl, halogen, —OR$^e$, —S(O)$_m$ R$^e$, —S(O)$_m$NR$^c$R$^d$, —C(O)R$^e$, —OC(O)R$^e$, —C(O)OR$^e$, —CN, —C(O)NR$^c$R$^d$, —NR$^c$R$^d$, —(CH$_2$)$_n$NR$^c$R$^d$; —NR$^c$C(O)R$^e$, —NR$^c$C(O)OR$^e$, —NR$^c$C(O)NR$^c$R$^d$, —NR$^c$S(O)$_m$R$^e$, =NH, —CF$_3$, —OCF$_3$, —OCHF$_2$, —C$_3$-C$_6$ cycloalkyl, —O—C$_3$-C$_6$cycloalkyl, —C$_1$-C$_{10}$alkylene-C$_3$-C$_6$cycloalkyl, —O—C$_1$-C$_{10}$ alkylene-C$_3$-C$_6$cycloalkyl, HetB, —O-HetB, —C$_1$-C$_{10}$alkylene-HetB, —O—C$_1$-C$_{10}$ alkylene-HetB, AryA, —O-AryA, —C$_1$-C$_{10}$ alkylene-AryA, or —O—C$_1$-C$_{10}$alkylene-AryA, wherein each R$^4$ is unsubstituted or substituted with one to four substituents selected from halogen, —C$_1$-C$_6$ alkyl and —(CH$_2$)$_n$NR$^c$R$^d$, or wherein R$^4$ and M, together with the atoms to which they are attached, form a 4- to 7-membered cycloheteroalkyl optionally containing one to two additional heteroatoms independently selected from O, S and —NR$^g$;

HetB is a 3- to 6-membered saturated or monounsaturated monocyclic ring with 1, 2, or 3 heteroatom ring atoms independently selected from N, N as a quaternary salt, O and S, optionally substituted with one to three R$^a$;

Q is a bond, CH$_2$, O, S, —(CH$_2$)$_n$NR$^3$—, or —NR$^3$(CH$_2$)$_n$—, wherein each CH$_2$ is unsubstituted or substituted with one to two substituents selected from halogen, —C$_1$-C$_6$ alkyl, OR$^e$ and —(CH$_2$)$_n$NR$^c$R$^d$;

R$^3$ is hydrogen or —C$_1$-C$_3$ alkyl, wherein said —C$_1$-C$_3$ alkyl is optionally substituted with one to three R$^a$;

M is R$^5$, —NHR$^5$, —N(R$^5$)$_2$, —OR$^5$, —(CH$_2$)$_n$R$^5$, —C(O)R$^5$, —C(NH)R$^5$, or —S(O)$_m$R$^5$;

R$^5$ is H, C$_2$-C$_{10}$ alkyl, C$_3$-C$_7$ cycloalkyl, C$_1$-C$_6$ alkyl-C$_3$-C$_7$ cycloalkyl, HetB, AryB, or —NH(C$_1$-C$_6$ alkyl), wherein said C$_1$-C$_6$ alkyl, said C$_2$-C$_{10}$ alkyl and said C$_3$-C$_7$ cycloalkyl are optionally substituted with one to four R$^6$;

AryB is a 5- to 6-membered monocyclic aromatic ring with 0, 1, 2, or 3 ring atoms independently selected from N, O and S, optionally substituted with one to four R$^4$;

each occurrence of R$^6$ is independently selected from the group consisting of: halogen, —OR$^e$, —S(O)$_m$R$^e$, —S(O)$_m$NR$^c$R$^d$, —C(O)R$^e$, —OC(O)R$^e$, —C(O)OR$^e$, —CN, —C(O)NR$^c$R$^d$, —C(NH)NR$^c$R$^d$, —NR$^c$R$^d$, —(CH$_2$)$_n$NR$^c$R$^d$, —N(R)(C(O)R$^e$), —N(R$^c$)(C(O)OR$^e$), —N(R$^c$)(C(O)NR$^c$R$^d$), —N(R$^c$)(S(O)$_m$R$^e$), and HetB;

each occurrence of R$^c$ and R$^d$ is independently: hydrogen, —C$_1$-C$_{10}$ alkyl, —C$_2$-C$_{10}$ alkenyl, —C$_3$-C$_6$ cycloalkyl, —C$_1$-C$_{10}$ alkylene-C$_3$-C$_6$ cycloalkyl, HetA, —C$_1$-C$_{10}$alkylene-HetB, AryB, —C$_1$-C$_{10}$ alkylene-AryB, and —C$_1$-C$_{10}$ alkylene-HetB, or, alternatively, R$^c$ and R$^d$ together with the nitrogen atom to which they are attached, form a 4- to 7-membered cycloheteroalkyl optionally containing one to two additional heteroatoms independently selected from O, S and —NR$^g$, and wherein each R$^c$ and R$^d$ is optionally substituted with one to three R$^f$;

each occurrence of R$^e$ is independently: hydrogen, —C$_1$-C$_{10}$alkyl, —C$_2$-C$_{10}$ alkenyl, —OH, —OC$_1$-C$_4$ alkyl, —C$_3$-C$_6$ cycloalkyl, —C$_1$-C$_{10}$ alkylene-C$_3$-C$_6$ cycloalkyl, HetB, —C$_1$-C$_{10}$ alkylene-HetB, AryB, —C$_1$-C$_{10}$ alkylene-AryB, or —C$_1$-C$_{10}$ alkylene-HetB; wherein each R$^e$ is optionally substituted with one to three R$^h$;

each occurrence of R$^f$ is independently: halogen, —C$_1$-C$_{10}$ alkyl, —OH, —OC$_1$-C$_4$ alkyl, —S(O)$_m$C$_1$-C$_4$ alkyl, —CN, —CF$_3$, —OCHF$_2$, —OCF$_3$, or NH$_2$, wherein said —C$_1$-C$_{10}$ alkyl is optionally substituted with one to three substituents independently selected from: —OH, halogen, cyano, and —S(O)$_2$CH$_3$;

each occurrence of R$^g$ is independently: hydrogen, —C(O)R$^e$, and —C$_1$-C$_{10}$ alkyl, wherein said —C$_1$-C$_{10}$alkyl is optionally substituted with one to five fluorines;

each occurrence of R$^h$ is independently: halogen, —C$_1$-C$_{10}$alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_{10}$ alkyl is optionally substituted with one to three substituents independently selected from: —OH, halogen, cyano, or —S(O)$_2$CH$_3$;

each n is independently 0, 1, 2, 3 or 4;

each m is independently 0, 1 or 2, and each p is independently 1 or 2.

The present invention also includes compounds of Formula I:

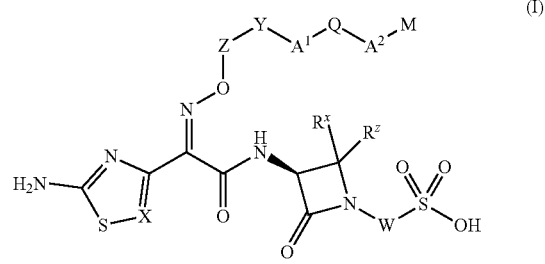

or a pharmaceutically acceptable salt thereof, wherein:

W is a bond or O;

R$^X$ and R$^Z$ are independently hydrogen, —SC$_1$-C$_3$alkyl, C$_1$-C$_3$ alkyl, —(C$_1$-C$_3$alkylene)$_n$OC$_1$-C$_3$alkyl, or —(C$_1$-C$_3$alkylene)$_n$NC$_1$-C$_3$alkyl, wherein the —SC$_1$-C$_3$alkyl, the C$_1$-C$_3$ alkyl, the —(C$_1$-C$_3$alkylene)$_n$OC$_1$-C$_3$alkyl and the —(C$_1$-C$_3$alkylene)$_n$NC$_1$-C$_3$alkyl are optionally substituted with one to seven fluorines;

or, alternatively, R$^X$ and R$^Z$, together with the carbon to which they are attached, form a monocyclic C$_4$-C$_7$ cycloalkyl or a monocyclic C$_4$-C$_7$ heterocycloalkyl with 1, 2, or 3 heteroatom ring atoms independently selected from N, O and S, wherein said C$_4$-C$_7$ cycloalkyl and said C$_4$-C$_7$ heterocycloalkyl are optionally substituted with one to three substituents independently selected from —F, —OH and —OC$_1$-C$_3$alkyl;

X is N or CR$^1$;

R$^1$ is hydrogen, C$_1$-C$_3$ alkyl, or halogen; wherein said C$_1$-C$_3$ alkyl is optionally substituted with one to three R$^a$;

each occurrence of R$^a$ is independently hydrogen, halogen, C$_1$-C$_3$alkyl, —NR$^c$R$^d$ or —OR$^e$;

Z is C$_1$-C$_3$ alkylene, optionally substituted with one to three R$^b$;

each occurrence of R$^b$ is independently —C$_1$-C$_8$ alkyl, —C$_3$-C$_7$ cycloalkyl, —C(O)OR$^e$, —C(O)NR$^c$R$^d$, tetrazolyl, oxadiazolonyl, HetA, AryA, —S(O)$_m$R, —S(O)$_m$NR$^c$R$^d$, or —P(O)(R$^e$)$_p$ wherein said —C$_1$-C$_8$ alkyl and said —C$_3$-C$_7$ cycloalkyl are optionally substituted with one to three R$^a$;

HetA is a 4- to 6-membered saturated or monounsaturated monocyclic ring with 1, 2, or 3 heteroatom ring atoms independently selected from N, N as a quaternary salt, O and S, optionally substituted with one to four R$^4$;

AryA is a 5- to 6-membered monocyclic aromatic ring with 0, 1, 2, or 3 ring atoms independently selected from N, N as a quaternary salt, O and S, optionally substituted with one to four R$^4$;

Y is a bond, O, NR$^2$, S, or CH$_2$;

R$^2$ is hydrogen, —C$_1$-C$_3$ alkyl, —C(O)R$^e$, —C(O)NR$^c$R$^d$, —S(O)$_m$R$^e$, or —S(O)$_m$NR$^c$R$^d$, wherein said —C$_1$-C$_3$ alkyl is optionally substituted with one to three R$^a$;

A$^1$ is AryA;

A$^2$ is C$_3$-C$_7$ cycloalkyl, AryC or HetC, wherein said C$_3$-C$_7$ cycloalkyl is optionally substituted with one to four R$^4$;

AryC is a 5- to 6-membered monocyclic aromatic ring with 0, 1, 2, or 3 ring atoms independently selected from N, N as a quaternary salt, O and S, optionally substituted with one to four R$^4$;

HetC is a 4- to 7-membered saturated or monounsaturated monocyclic ring with 1, 2, or 3 heteroatom ring atoms independently selected from N, N as a quaternary salt, O and S, optionally substituted with one to four R$^4$;

each occurrence of R$^4$ is independently: —C$_1$-C$_8$ alkyl, —C$_2$-C$_8$ alkenyl, —C$_2$-C$_5$ alkynyl, halogen, —OR$^e$, —S(O)$_m$ R$^e$, —S(O)$_m$NR$^c$R$^d$, —C(O)R$^e$, —OC(O)R$^e$, —C(O)OR$^e$, —CN, —C(O)NR$^c$R$^d$, —NR$^c$R$^d$, —NR$^c$C(O) R$^e$, —NR$^c$C(O)OR$^e$, —NR$^c$C(O)NR$^c$R$^d$, —NR$^c$S(O)$_m$R$^e$, —NH, —CF$_3$, —OCF$_3$, —OCHF$_2$, —C$_3$-C$_6$ cycloalkyl, —O—C$_3$-C$_6$cycloalkyl, —C$_1$-C$_{10}$alkylene-C$_3$-C$_6$cycloalkyl, —O—C$_1$-C$_{10}$ alkylene-C$_3$-C$_6$cycloalkyl, HetB, —O-HetB, —C$_1$-C$_{10}$alkylene-HetB, —O—C$_1$-C$_{10}$ alkylene-HetB, AryA, —O-AryA, —C$_1$-C$_{10}$ alkylene-AryA, or —O—C$_1$-C$_{10}$alkylene-AryA;

HetB is a 3- to 6-membered saturated or monounsaturated monocyclic ring with 1, 2, or 3 heteroatom ring atoms independently selected from N, N as a quaternary salt, O and S, optionally substituted with one to three R$^a$;

Q is a bond, CH$_2$, O, S, —(CH$_2$)$_n$NR$^3$—, or —NR$^3$(CH$_2$)$_n$—;

R$^3$ is hydrogen or —C$_1$-C$_3$ alkyl, wherein said —C$_1$-C$_3$ alkyl is optionally substituted with one to three R$^a$;

M is R$^5$, —NR$^5$, —OR$^5$, —(CH$_2$)$_n$R$^5$, —C(O)R$^5$, —CH(NH)R$^5$, or —S(O)$_m$R$^5$;

R$^5$ is C$_2$-C$_{10}$ alkyl, C$_3$-C$_7$ cycloalkyl, HetB, or AryB, wherein said C$_2$-C$_{10}$ alkyl and said C$_3$-C$_7$ cycloalkyl are optionally substituted with one to four R$^6$;

AryB is a 5- to 6-membered monocyclic aromatic ring with 0, 1, 2, or 3 ring atoms independently selected from N, O and S, optionally substituted with one to four R$^4$;

each occurrence of R$^6$ is independently selected from the group consisting of: halogen, —OR$^e$, —S(O)$_m$R$^e$, —S(O)$_m$NR$^c$R$^d$, —C(O)R$^e$, —OC(O)R$^e$, —C(O)OR$^e$, —CN, —C(O)NR$^c$R$^d$, —C(NH)NR$^c$R$^d$, —NR$^c$R$^d$, —N(R$^c$)(C(O) R$^e$), —N(R$^c$)(C(O)OR$^e$), —N(R$^c$)(C(O)NR$^c$R$^d$), and —N(R$^c$)(S(O)$_m$R$^e$);

each occurrence of R$^c$ and R$^d$ is independently: hydrogen, —C$_1$-C$_{10}$ alkyl, —C$_2$-C$_{10}$ alkenyl, —C$_3$-C$_6$ cycloalkyl, —C$_1$-C$_{10}$ alkylene-C$_3$-C$_6$ cycloalkyl, HetA, —C$_1$-C$_{10}$alkylene-HetB, AryB, —C$_1$-C$_{10}$ alkylene-AryB, and —C$_1$-C$_{10}$ alkylene-HetB, or, alternatively, R$^c$ and R$^d$ together with the nitrogen atom to which they are attached, form a 4- to 7-membered cycloheteroalkyl optionally containing one to two additional heteroatoms independently selected from O, S and —NR$^g$, and wherein each R$^c$ and R$^d$ is optionally substituted with one to three R$^f$;

each occurrence of R$^e$ is independently: hydrogen, —C$_1$-C$_{10}$alkyl, —C$_2$-C$_{10}$ alkenyl, —OH, —OC$_1$-C$_4$ alkyl, —C$_3$-C$_6$ cycloalkyl, —C$_1$-C$_{10}$ alkylene-C$_3$-C$_6$ cycloalkyl, HetB, —C$_1$-C$_{10}$ alkylene-HetB, AryB, —C$_1$-C$_{10}$ alkylene-AryB, or —C$_1$-C$_{10}$ alkylene-HetB; wherein each R$^e$ is optionally substituted with one to three R$^h$.

each occurrence of R$^g$ is independently: halogen, —C$_1$-C$_{10}$ alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_{10}$ alkyl is optionally substituted with one to three substituents independently selected from: —OH, halogen, cyano, and —S(O)$_2$CH$_3$;

each occurrence of R$^g$ is independently: hydrogen, —C(O)R$^e$, and —C$_1$-C$_{10}$ alkyl, wherein said —C$_1$-C$_{10}$alkyl is optionally substituted with one to five fluorines;

each occurrence of R$^h$ is independently: halogen, —C$_1$-C$_{10}$alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_{10}$ alkyl is optionally substituted with one to three substituents independently selected from: —OH, halogen, cyano, or —S(O)$_2$CH$_3$;

each n is independently 0, 1, 2, 3 or 4;

each m is independently 0, 1 or 2, and each p is independently 1 or 2.

The present invention also relates to a pharmaceutical composition for treating a bacterial infection in a subject, including infection with multidrug resistant Gram-negative bacterial strains, comprising a biaryl monobactam compound of the invention and a pharmaceutically acceptable carrier, diluent or excipient.

The Compounds of Formula (I) (also referred to herein as the "biaryl monobactam compounds") and pharmaceutically acceptable salts thereof can be useful, for example, for inhibiting the growth of Gram-negative bacterial strains, including but not limited to, *Pseudomonas* and *Acinetobacter* strains, and/or for treating or preventing the clinical maifestations thereof in a patient.

The present invention is also directed to methods of treating Gram-negative bacterial infections in a subject in need of treatment thereof, comprising administering to the subject an effective amount of a biaryl monobactam compound of the invention. In specific embodiments of the invention, the method includes administration of a beta lactamase inhibitor compound.

Embodiments, sub-embodiments and features of the present invention are either further described in or will be apparent from the ensuing description, examples and appended claims.

DETAILED DESCRIPTION OF THE INVENTION

The invention relates to novel biaryl monobactam analogs, a class of highly potent antibiotics effective against a broad range of Gram-negative bacteria. These compounds have utility as therapeutic agents for clinical treatment of various infections caused by Gram-negative bacteria, including strains that are multidrug resistant, and for the treatment or prevention of the clinical pathologies associated therewith.

In each of the various embodiments of the compounds of the invention described herein, each variable including those of Formulas I, II-1, II-2, II-3, III-1, III-2, and III-3, and the various embodiments thereof, each variable is selected independently of the others unless otherwise indicated.

The present invention encompasses all compounds of Formulas I, II-1, II-2, II-3, III-1, III-2, and III-3, and the various embodiments thereof, for example, any solvates, hydrates, stereoisomers, and tautomers of said compounds and of any pharmaceutically acceptable salts thereof.

The Compounds of Formula (I)

In one aspect, the present invention includes compounds of Formula I:

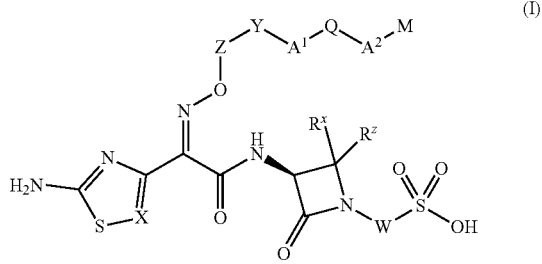

(I)

or a pharmaceutically acceptable salt thereof, wherein X, Y, Z, $A^1$, Q, $A^2$, M, W, $R^x$ and $R^z$ are as defined herein for the Compounds of Formula (I); wherein the compounds may be suitable for use for the treatment of bacterial infections.

A first embodiment of the invention (Embodiment E1) is a compound of Formula I, or a pharmaceutically acceptable salt thereof, wherein X, Y, Z, $A^1$, Q, $A^2$, M, W, $R^x$ and $R^z$ are as defined in Formula I in the Summary of the Invention.

A second embodiment (Embodiment E2) is a compound of Formula I, or a pharmaceutically acceptable salt thereof, wherein W is a bond, and all other variables are as defined in Embodiment E1.

A third embodiment (Embodiment E3) is a compound of Formula I, or a pharmaceutically acceptable salt thereof, wherein W is O, and all other variables are as defined in Embodiment E1.

A fourth embodiment (Embodiment E4) is a compound of Formula I, or a pharmaceutically acceptable salt thereof, wherein W is defined in Embodiment E2 or E3, X is N, and all other variables are as defined in Embodiment E1.

A fifth embodiment (Embodiment E5) is a compound of Formula I, or a pharmaceutically acceptable salt thereof, wherein W is defined in Embodiment E2 or E3, X is $CR^1$, and $R^1$ is hydrogen, halogen or $C_1$-$C_3$ alkyl optionally substituted with one to three $R^a$, and all other variables are as defined in Embodiment E1.

In a sub-embodiment of Embodiment E5 (Embodiment E5-A), $R^1$ is hydrogen.

In another sub-embodiment of Embodiment E5 (Embodiment E5-B), $R^1$ is halogen.

In a further sub-embodiment of Embodiment E5 (Embodiment E5-C), $R^1$ is chlorine.

In yet another sub-embodiment of Embodiment E5 (Embodiment E5-D), $R^1$ is fluorine.

In a further sub-embodiment of Embodiment E5 (Embodiment E5-E), $R^1$ is $C_1$-$C_3$ alkyl optionally substituted with one to three $R^a$, wherein each occurrence of $R^a$ is independently hydrogen, halogen, $C_1$-$C_3$alkyl, —$NR^cR^d$ or —$OR^e$.

A sixth embodiment (Embodiment E6) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_8$ alkylene optionally substituted with one to three $R^b$, wherein each occurrence of $R^b$ is independently hydrogen, $C_1$-$C_8$ alkyl, $C_3$-$C_7$ cycloalkyl, —$C(O)OR^e$, —$C(O)NR^cR^d$, tetrazolyl, oxadiazolonyl, HetA, AryA, —$S(O)_mR^e$, —$S(O)_mNR^cR^d$, or —$P(O)(R^e)_p$, wherein said $C_1$-$C_8$ alkyl and said $C_3$-$C_7$ cycloalkyl are optionally substituted with one to three $R^a$; and all other variables are as defined in Embodiment E1.

In a sub-embodiment of Embodiment E6, Z is $C_1$-$C_3$ alkylene substituted with one occurrence of $R^b$. In another sub-embodiment of Embodiment E6, Z is $C_1$-$C_3$ alkylene substituted with two occurrences of $R^b$. In a further sub-embodiment of Embodiment E6, Z is $C_1$-$C_3$ alkylene substituted with three occurrences of $R^b$.

A seventh embodiment (Embodiment E7) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with —$C(O)OR^e$; and all other variables are as defined in Embodiment E1.

An eighth embodiment (Embodiment E8) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with —$C(O)OH$; and all other variables are as defined in Embodiment E1.

A ninth embodiment (Embodiment E9) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with tetrazolyl; and all other variables are as defined in Embodiment E1.

A tenth embodiment (Embodiment E10) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with $C_1$-$C_8$ alkyl, optionally substituted with one to three $R^a$, and all other variables are as defined in Embodiment E1.

An eleventh embodiment (Embodiment E1) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with methyl; and all other variables are as defined in Embodiment E1.

A twelfth embodiment (Embodiment E12) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with methyl and —$C(O)OH$; and all other variables are as defined in Embodiment E1.

A thirteenth embodiment (Embodiment E13) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is —$CH(C(O)OH)CH_2$— and all other variables are as defined in Embodiment E1.

A fourteenth embodiment (Embodiment E14) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is $C_1$-$C_3$ alkylene substituted with oxadiazolonyl, and all other variables are as defined in Embodiment E1.

A fifteenth embodiment (Embodiment E15) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is a bond, and all other variables are as defined in Embodiment E1.

A sixteenth embodiment (Embodiment E16) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is O, and all other variables are as defined in Embodiment E1.

A seventeenth embodiment (Embodiment E17) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is $NR^2$, and all other variables are as defined in Embodiment E1.

In a sub-embodiment of Embodiment E17, $R^2$ is hydrogen. In another sub-embodiment of Embodiment E17, $R^2$ is $C_1$-$C_3$ alkyl optionally substituted with one to three $R^a$. In a further sub-embodiment of Embodiment E17, $R^2$ is $C(O)R^e$. In yet another sub-embodiment of Embodiment E17, $R^2$ is —$C(O)NR^cR^d$. In still another sub-embodiment of Embodiment E17, $R^2$ is —$S(O)_mR^e$. In a further sub-embodiment of Embodiment E17, $R^2$ is —$S(O)_mNR^cR^d$.

An eighteenth embodiment (Embodiment E18) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is S, and all other variables are as defined in Embodiment E1.

An nineteenth embodiment (Embodiment E19) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is $CH_2$, and all other variables are as defined in Embodiment E1.

A twentieth embodiment (Embodiment E20) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, Ai a 5- to 6-membered monocyclic aromatic ring with 0, 1, 2, or 3 ring atoms independently selected from N, N as a quaternary salt, O and S, optionally substituted with one to four $R^4$, and all other variables are as defined in Embodiment E1.

A twenty-first embodiment (Embodiment E21) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, Ai is a 5-membered monocyclic aromatic ring with 0, 1, 2, or 3 ring atoms independently selected from N, N as a quaternary salt, O and S, optionally substituted with one to four $R^4$, and all other variables are as defined in Embodiment E1.

A twenty-second embodiment (Embodiment E22) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, Ai is a 6-membered monocyclic aromatic ring with 0, 1, 2, or 3 ring atoms independently selected from N, N as a quaternary salt, O and S, optionally substituted with one to four $R^4$, and all other variables are as defined in Embodiment E1.

In a sub-embodiment of Embodiment E21 or E22, Ai has 1 ring atoms independently selected from N, N as a quaternary salt, O and S. In a further sub-embodiment of Embodiment E21 or E22, Ai has 2 ring atoms independently selected from N, N as a quaternary salt, O and S. In another sub-embodiment of Embodiment E21 or E22, A has 2 ring atoms independently selected from N, N as a quaternary salt, O and S. In yet another sub-embodiment of Embodiment E21 or E22, $A^1$ has 3 ring atoms independently selected from N, N as a quaternary salt, O and S.

A twenty-third embodiment (Embodiment E23) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is an 6-membered monocyclic aromatic ring, optionally substituted with one to four $R^4$, and all other variables are as defined in Embodiment E1.

A twenty-fourth embodiment (Embodiment E24) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is an unsubstituted 6-membered monocyclic aromatic ring, and all other variables are as defined in Embodiment E1.

A twenty-fifth embodiment (Embodiment E25) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is.

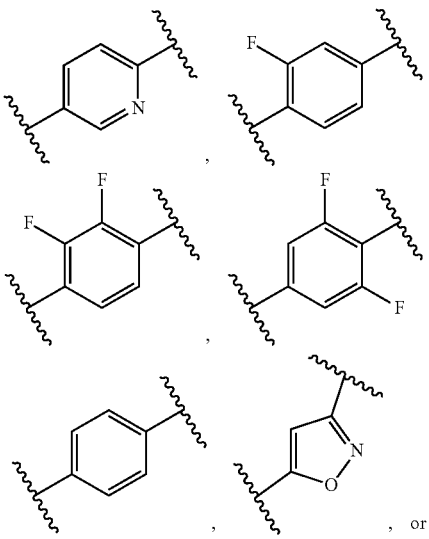

, or

[pyrazole structure fragment], and all other variables are as defined in Embodiment E1.

A twenty-sixth embodiment (Embodiment E26) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is a bond, and all other variables are as defined in Embodiment E1.

A twenty-seventh embodiment (Embodiment E27) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is $CH_2$, and all other variables are as defined in Embodiment E1.

A twenty-eighth embodiment (Embodiment E28) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is O, and all other variables are as defined in Embodiment E1.

A twenty-ninth embodiment (Embodiment E29) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is S, and all other variables are as defined in Embodiment E1.

A thirtieth embodiment (Embodiment E30) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is —$(CH_2)_n NR^3$—, and all other variables are as defined in Embodiment E1.

A thirty-first embodiment (Embodiment E31) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is —$NR^3(CH_2)_n$—, and all other variables are as defined in Embodiment E1.

A thirty-second embodiment (Embodiment E32) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is NH, and all other variables are as defined in Embodiment E1.

A thirty-third embodiment (Embodiment E33) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is $N(C_1-C_3$ alkyl) optionally substituted with one to three $R^a$, and all other variables are as defined in Embodiment E1.

A thirty-fourth embodiment (Embodiment E34) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is $C_3-C_7$ cycloalkyl optionally substituted with one to four $R^4$; and all other variables are as defined in Embodiment E1.

A thirty-fifth embodiment (Embodiment E35) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is AryC; and all other variables are as defined in Embodiment E1.

A thirty-sixth embodiment (Embodiment E36) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is a 5-membered monocyclic aromatic ring with 0, 1, 2, or 3 ring atoms independently selected from N, N as a quaternary salt, O and S, optionally substituted with one to four $R^4$; and all other variables are as defined in Embodiment E1.

A thirty-seventh embodiment (Embodiment E37) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is a 6-membered monocyclic aromatic ring with 0, 1, 2, or 3 ring atoms independently selected from N, N as a quaternary salt, O and S, optionally substituted with one to four $R^4$, and all other variables are as defined in Embodiment E1.

A thirty-eighth embodiment (Embodiment E38) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is HetC; and all other variables are as defined in Embodiment E1.

A thirty-ninth embodiment (Embodiment E39) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is a 4- to 7-membered saturated or monounsaturated monocyclic ring with 1 heteroatom ring atom selected from N, N as a quaternary salt, O and S, optionally substituted with one to four $R^4$; and all other variables are as defined in Embodiment E1.

A fortieth embodiment (Embodiment E40) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is a 4- to 7-membered saturated or monounsaturated monocyclic ring with 2 heteroatom ring atoms independently selected from N, N as a quaternary salt, O and S, optionally substituted with one to four $R^4$; and all other variables are as defined in Embodiment E1.

A forty-first embodiment (Embodiment E41) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is a 4- to 7-membered saturated or monounsaturated monocyclic ring with 3 heteroatom ring atoms independently selected from N, N as a quaternary salt, O and S, optionally substituted with one to four $R^4$; and all other variables are as defined in Embodiment E1.

In sub-embodiments of Embodiments E34-E41, $A^2$ is unsubstituted. In other sub-embodiments, $A^2$ is substituted with one $R^4$. In further sub-embodiments $A^2$ is substituted with two $R^4$. In additional sub-embodiments, $A^2$ is substituted with three $R^4$. In still further sub-embodiments, $A^2$ is substituted with four $R^4$.

In sub-embodiments of Embodiments E34-E41, $A^2$ is substituted with methyl. In additional sub-embodiments, $A^2$ is substituted with —$NH_2$. In further sub-embodiments, $A^2$ is substituted with =NH. In other sub-embodiments, $A^2$ is substituted with one to four substitutents selected from: =NH, —$NH_2$, and —$CH_3$.

A forty-second embodiment (Embodiment E42) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

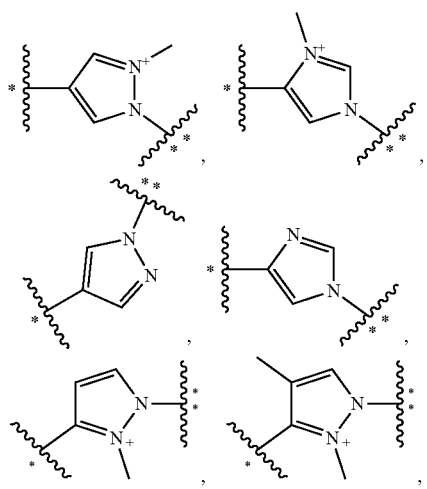

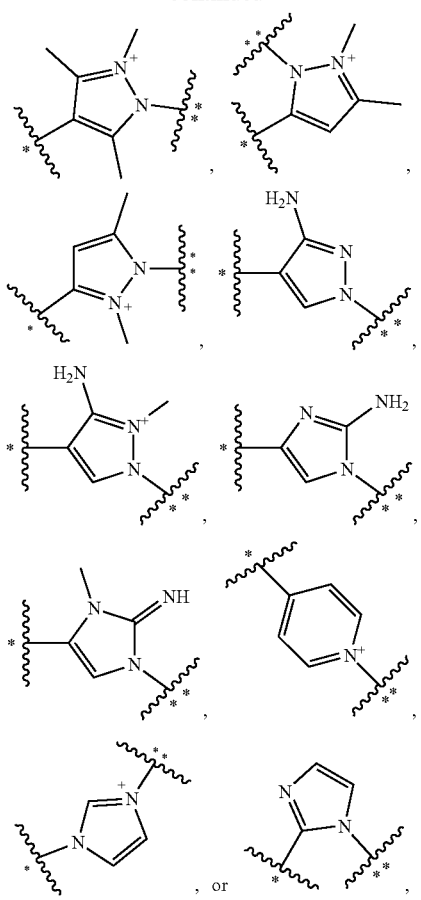

wherein * indicates attachment to Q and ** indicates attachment to M, and all other variables are as defined in Embodiment E1.

A forty-third embodiment (Embodiment E43) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

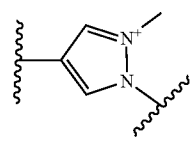

and all other variables are as defined in Embodiment E1.

A forty-fourth embodiment (Embodiment E44) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

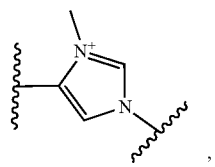 [SMILES: *c1cn(*)c[n+]1C]

and all other variables are as defined in Embodiment E1.

A forty-fifth embodiment (Embodiment E45) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

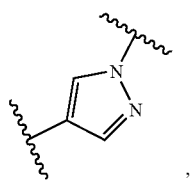 [SMILES: *c1cnn(*)c1]

and all other variables are as defined in Embodiment E1.

A forty-sixth embodiment (Embodiment E46) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

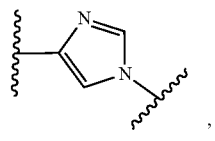 [SMILES: *c1cn(*)cn1]

and all other variables are as defined in Embodiment E1.

A forty-seventh embodiment (Embodiment E47) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

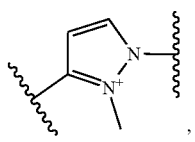

and all other variables are as defined in Embodiment E1.

A forty-eighth embodiment (Embodiment E48) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

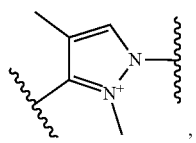

and all other variables are as defined in Embodiment E1.

A forty-ninth embodiment (Embodiment E49) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

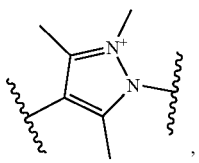 [SMILES: *c1c(C)n(*)[n+](C)c1C]

and all other variables are as defined in Embodiment E1.

A fiftieth embodiment (Embodiment E50) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

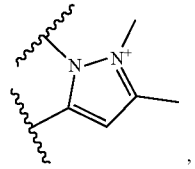 [SMILES: *c1cc(C)[n+](C)n1*]

and all other variables are as defined in Embodiment E1.

A fifty-first embodiment (Embodiment E51) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

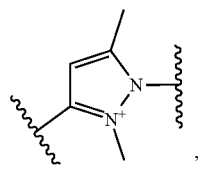 [SMILES: *c1cc(C)n(*)[n+]1C]

and all other variables are as defined in Embodiment E1.

A fifty-second embodiment (Embodiment E52) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

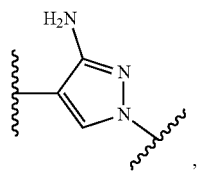 [SMILES: *c1cn(*)nc1N]

and all other variables are as defined in Embodiment E1.

A fifty-third embodiment (Embodiment E53) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

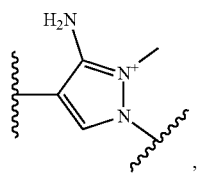 [SMILES: *c1cn(*)[n+](C)c1N]

and all other variables are as defined in Embodiment E1.

A fifty-fourth embodiment (Embodiment E54) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

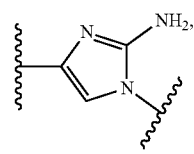 [SMILES: *c1cn(*)c(N)n1]

and all other variables are as defined in Embodiment E1.

A fifty-fifth embodiment (Embodiment E55) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

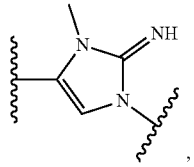 [SMILES: *c1cn(*)c(=N)n1C]

and all other variables are as defined in Embodiment E1.

A fifty-sixth embodiment (Embodiment E56) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

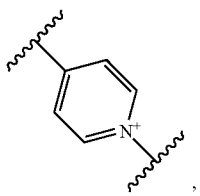 [SMILES: *c1cc[n+](*)cc1]

and all other variables are as defined in Embodiment E1.

A fifty-seventh embodiment (Embodiment E57) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

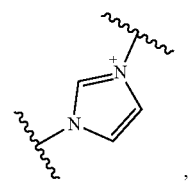

and all other variables are as defined in Embodiment E1.

A fifty-eighth embodiment (Embodiment E58) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is:

and all other variables are as defined in Embodiment E1.

A fifty-ninth embodiment (Embodiment E59) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is $R^5$, and all other variables are as defined in Embodiment E1.

A sixtieth embodiment (Embodiment E60) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is $C_2$-$C_{10}$ alkyl optionally substituted with one to four $R^6$, and all other variables are as defined in Embodiment E1.

A sixty-first embodiment (Embodiment E61) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is $C_3$-$C_7$ cycloalkyl optionally substituted with one to four $R^6$, and all other variables are as defined in Embodiment E1.

A sixty-second embodiment (Embodiment E62) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is HetB, and all other variables are as defined in Embodiment E1.

A sixty-third embodiment (Embodiment E63) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is AryB, and all other variables are as defined in Embodiment E1.

A sixty-fourth embodiment (Embodiment E64) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$NR^5$, and all other variables are as defined in Embodiment E1.

A sixty-fifth embodiment (Embodiment E65) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$OR^5$, and all other variables are as defined in Embodiment E1.

A sixty-sixth embodiment (Embodiment E66) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$(CH_2)_n R^5$, and all other variables are as defined in Embodiment E1.

A sixty-seventh embodiment (Embodiment E67) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$C(O)R^5$, and all other variables are as defined in Embodiment E1.

A sixty-eighth embodiment (Embodiment E68) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$CH(NH)R^5$, and all other variables are as defined in Embodiment E1.

A sixty-ninth embodiment (Embodiment E69) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$S(O)_m R^5$ and all other variables are as defined in Embodiment E1.

A seventieth embodiment (Embodiment E70) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$(CH_2)_3 NH_2$, and all other variables are as defined in Embodiment E1.

A seventy-first embodiment (Embodiment E71) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$(CH_2)_{1-2}$HetB, and all other variables are as defined in Embodiment E1.

A seventy-second embodiment (Embodiment E72) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is —$CH_2$AryB, and all other variables are as defined in Embodiment E1.

A seventy-third embodiment (Embodiment E73) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, $R^X$ and $R^Z$ are methyl, and all other variables are as defined in Embodiment E1.

A seventy-fourth embodiment (Embodiment E74) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, $R^X$ is hydrogen and $R^Z$ is methyl, and all other variables are as defined in Embodiment E1.

A seventy-fifth embodiment (Embodiment E75) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, one of $R^X$ and $R^Z$ is $SCH_3$, and all other variables are as defined in Embodiment E1.

A seventy-sixth embodiment (Embodiment E76) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, one of $R^X$ and $R^Z$ is $SC_1$-$C_3$ alkyl, optionally substituted with one to seven fluorines, and all other variables are as defined in Embodiment E1.

A seventy-seventh embodiment (Embodiment E77) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, one of $R^X$ and $R^Z$ is $SCH_3$, optionally substituted with one to three fluorines, and all other variables are as defined in Embodiment E1.

A seventy-eighth embodiment (Embodiment E78) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, one of $R^X$ and $R^Z$ is $C_1$-$C_3$ alkyl, optionally substituted with one to seven fluorines, and all other variables are as defined in Embodiment E1.

A seventy-ninth embodiment (Embodiment E79) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, one of $R^X$ and $R^Z$ is $(C_1$-$C_3$alkylene$)_n$O$C_1$-$C_3$alkyl, optionally substituted with one to seven fluorines, and all other variables are as defined in Embodiment E1.

An eightieth embodiment (Embodiment E80) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, one of $R^X$ and $R^Z$ is $(C_1$-$C_3$alkylene$)_n$N$C_1$-$C_3$alkyl, optionally substituted with one to seven fluorines, and all other variables are as defined in Embodiment E1.

An eighty-first embodiment (Embodiment E81) is a compound of Formula I, or a pharmaceutically acceptable salt thereof, wherein W is defined in Embodiment E2 or E3, X is defined in any of Embodiment E4, E5, E5-A, E5-B, E5-C, E5-D, or E5-E, Z is defined in any of Embodiments E6-E13, Y is defined in any of Embodiments E15-E19, $A^1$ is defined in any of Embodiments E20-E25, Q is defined in any of Embodiments E26-E33, $A^2$ is defined in any of Embodiments E34-E58, M is defined in any of Embodiments E59-E72, $R^X$ and $R^Z$, together with the carbon to which they are attached, come together to form a monocyclic $C_4$-$C_7$cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and said $C_4$-$C_7$ heterocycloalkyl are optionally substituted with one to three substituents independently selected from —F, —OH and —O$C_1$-$C_3$alkyl; and all other variables are as defined in Embodiment E1.

An eighty-second embodiment (Embodiment E82) is a compound of Formula II-1, II-2, II-3, III-1, III-2 or III-3, or a pharmaceutically acceptable salt thereof, (II-1)
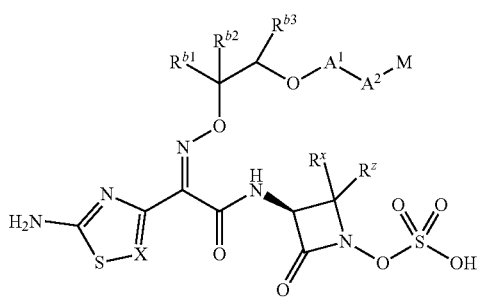

(III-1)
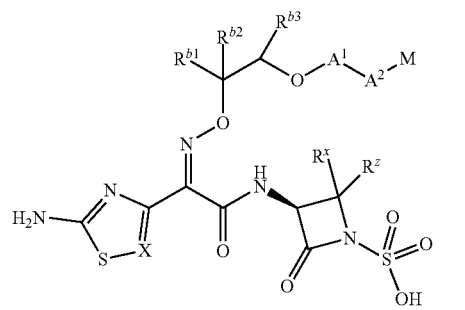

(II-2)
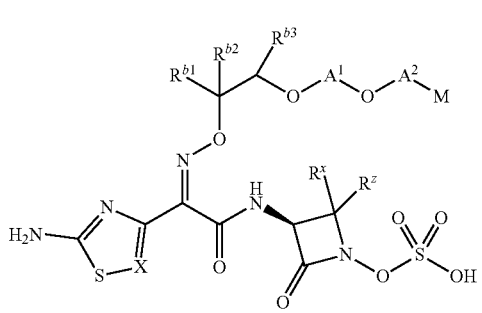

(III-2)
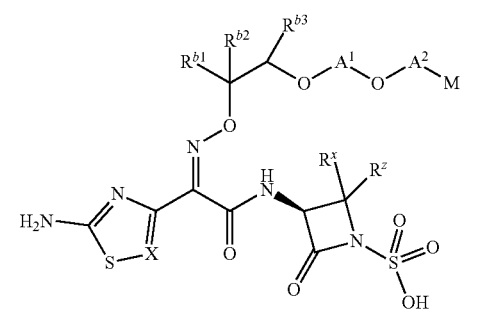

(II-3)
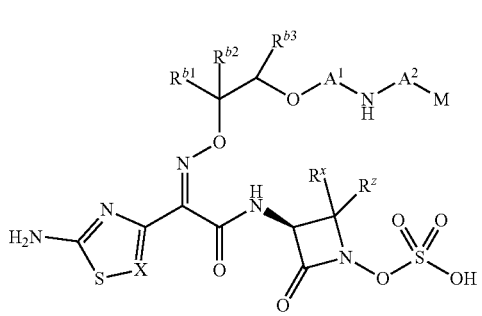

(III-3)
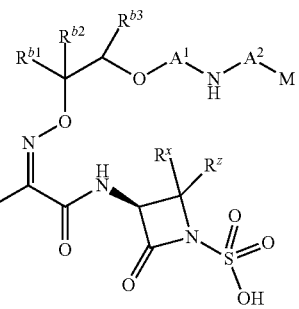

wherein X is defined in any of Embodiments E1, E4, E5, E5-A, E5-B, E5-C, E5-D, or E5-E;

$A^1$ is defined in any of Embodiments E1, E20-E25;

$A^2$ is defined in any of Embodiments E1, E34-E58;

M is defined in any of Embodiments E1, E59-E72;

$R^X$ and $R^Z$ are defined in any of Embodiments E1, E73-E81;

$R^{b1}$, $R^{b2}$, and $R^{b3}$ are independently hydrogen, $C_1$-$C_8$ alkyl, $C_3$-$C_7$ cycloalkyl, —C(O)$OR^e$, —C(O)$NR^cR^d$, tetrazolyl, oxadiazolonyl, HetA, AryA, —S(O)$_m$R, —S(O)$_m$$NR^cR^d$, or —P(O) $(R^e)_p$, wherein said $C_1$-$C_8$ alkyl and said $C_3$-$C_7$ cycloalkyl are optionally substituted with one to three $R^a$; and all other variables are as defined in Embodiment E1.

An eighty-third embodiment (Embodiment E83) is a compound of Formula II-1, II-2, II-3, III-1, III-2, or III-3, or a pharmaceutically acceptable salt thereof, wherein $R^{b1}$ and $R^{b2}$ are independently hydrogen, $C_1$-$C_3$ alkyl, tetrazolyl, oxadiazolonyl or —C(O)$OR^e$; and $R^{b3}$ is hydrogen, and all other variables are as defined in Embodiment E82.

An eighty-fourth embodiment (Embodiment E84) is a compound having the structure:

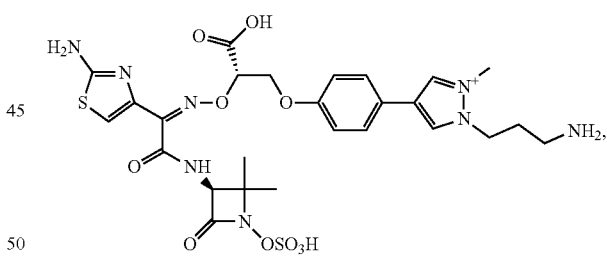

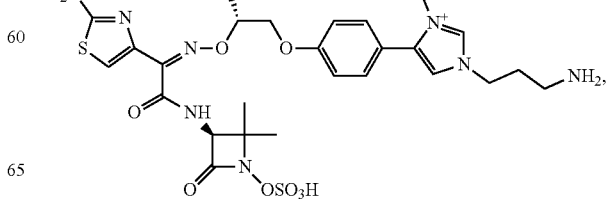

25
-continued
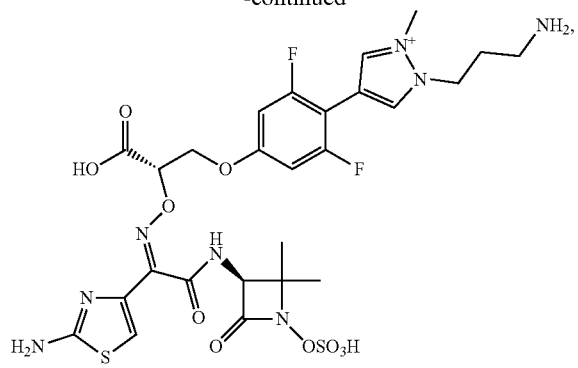
26
-continued
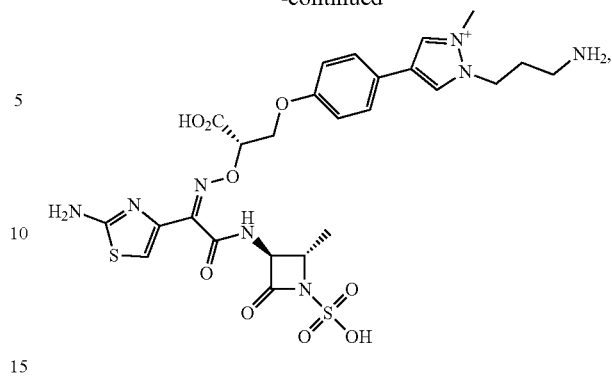
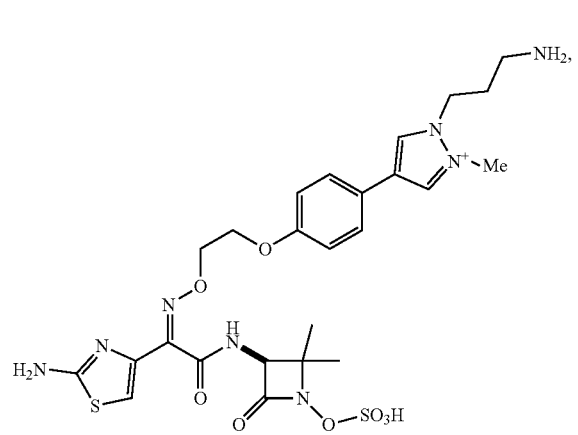
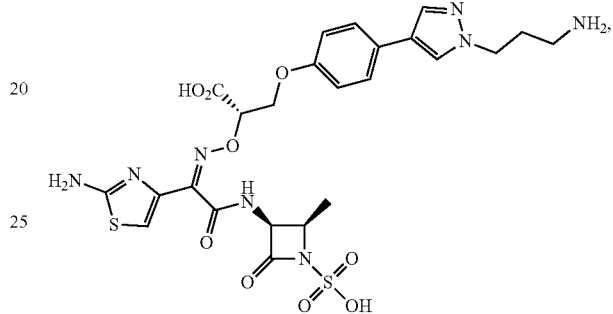
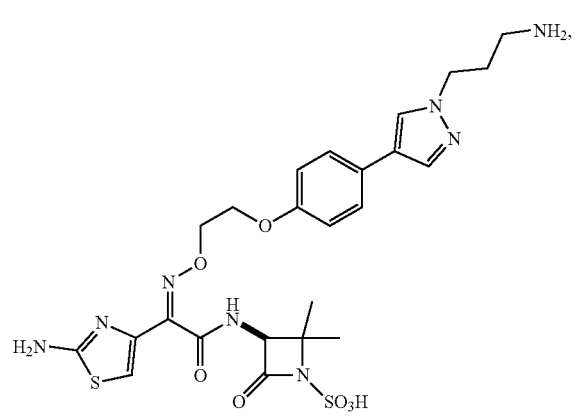
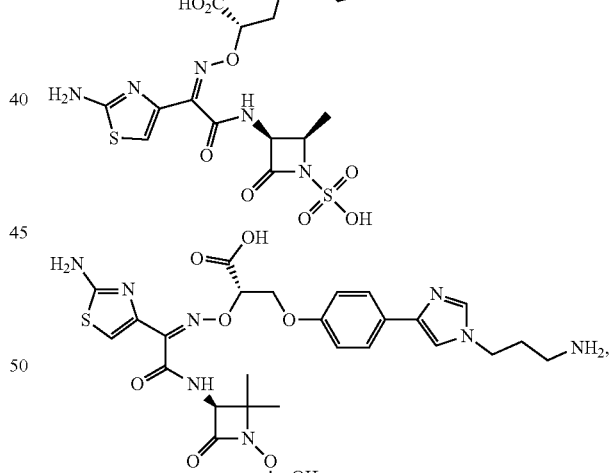
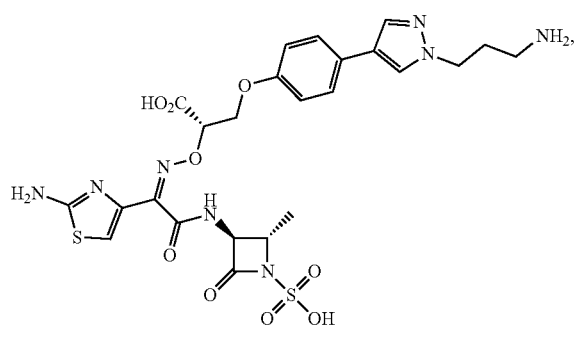
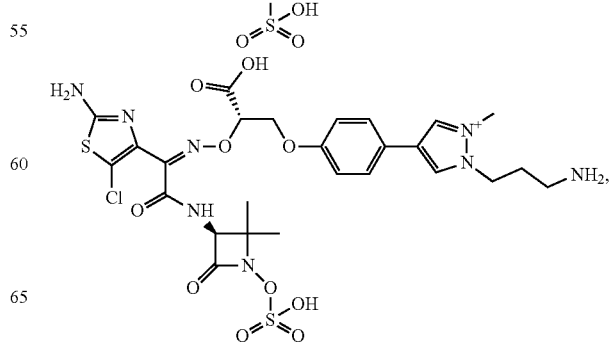

-continued
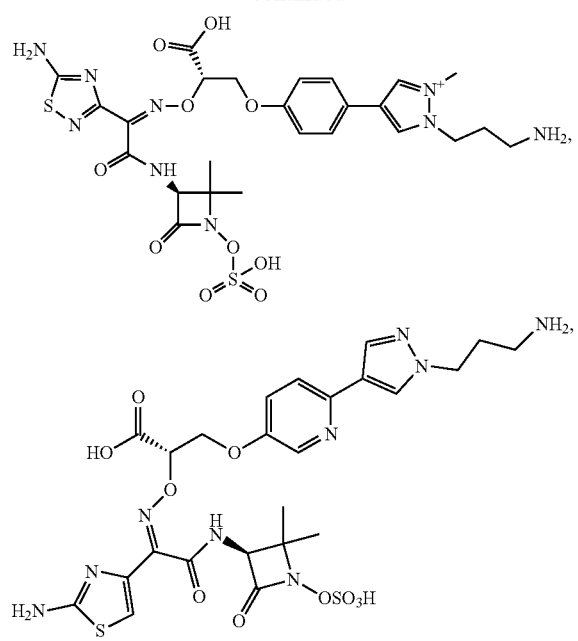
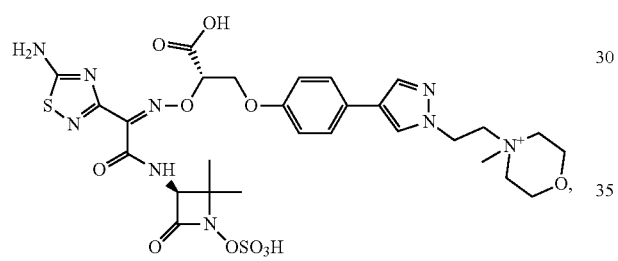
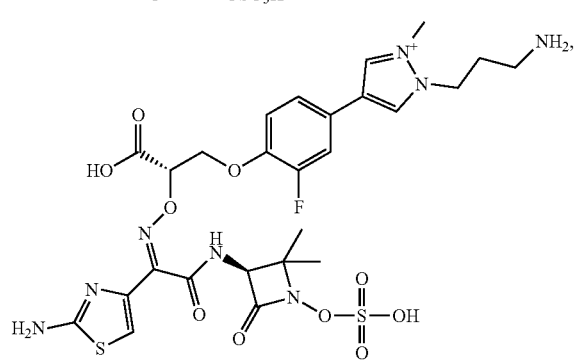
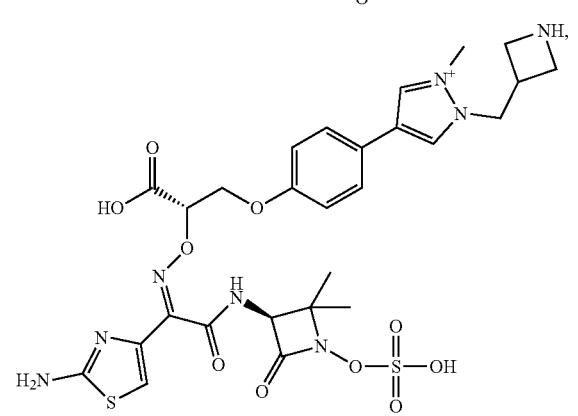
-continued
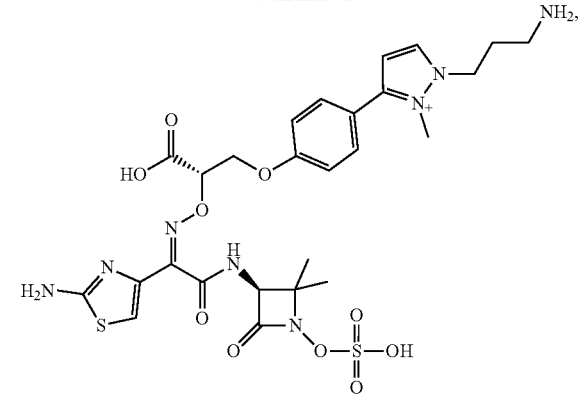
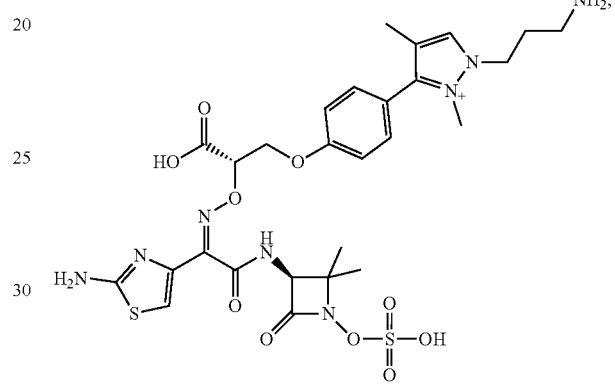
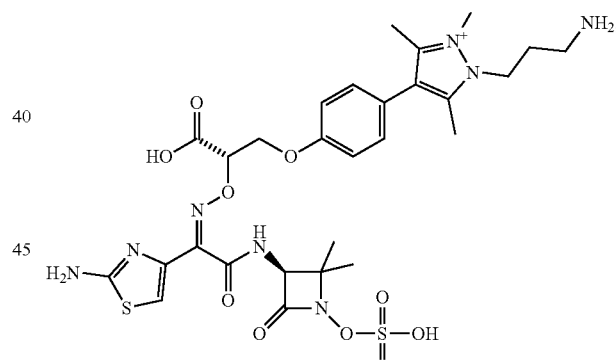
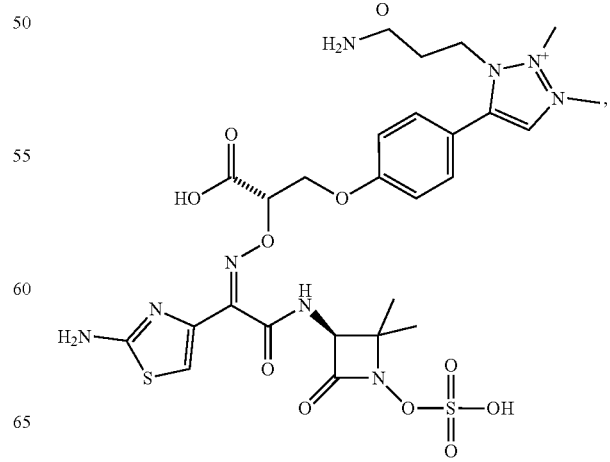

29
-continued
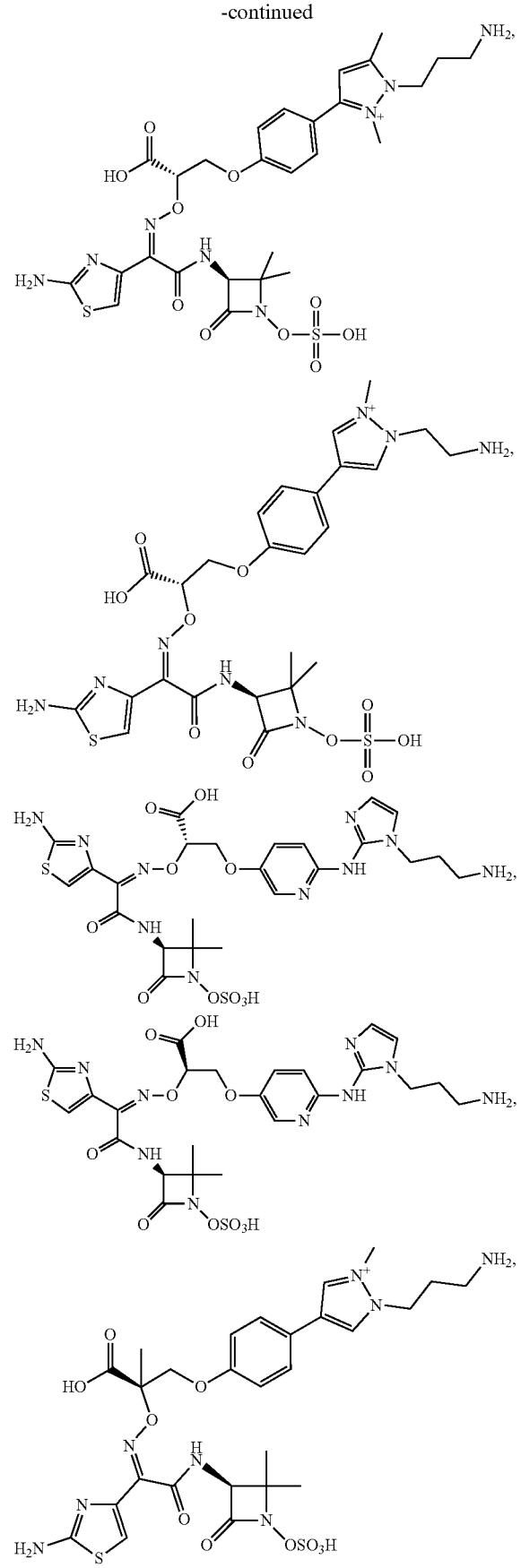
30
-continued
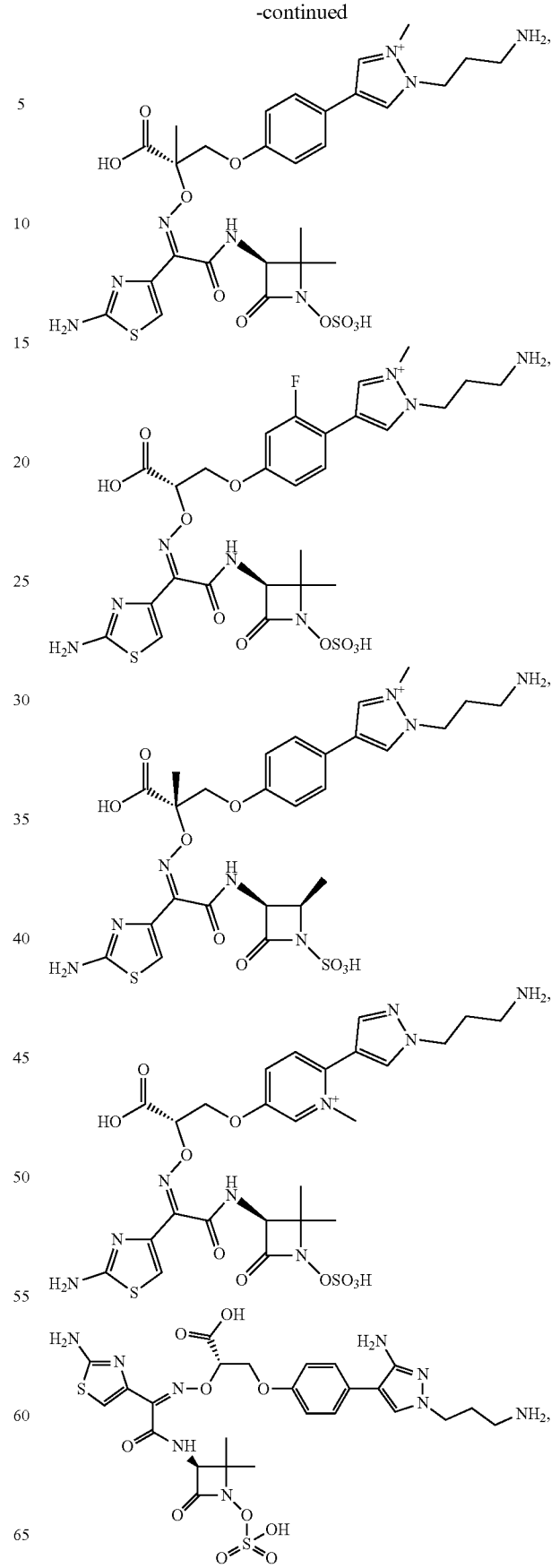

-continued

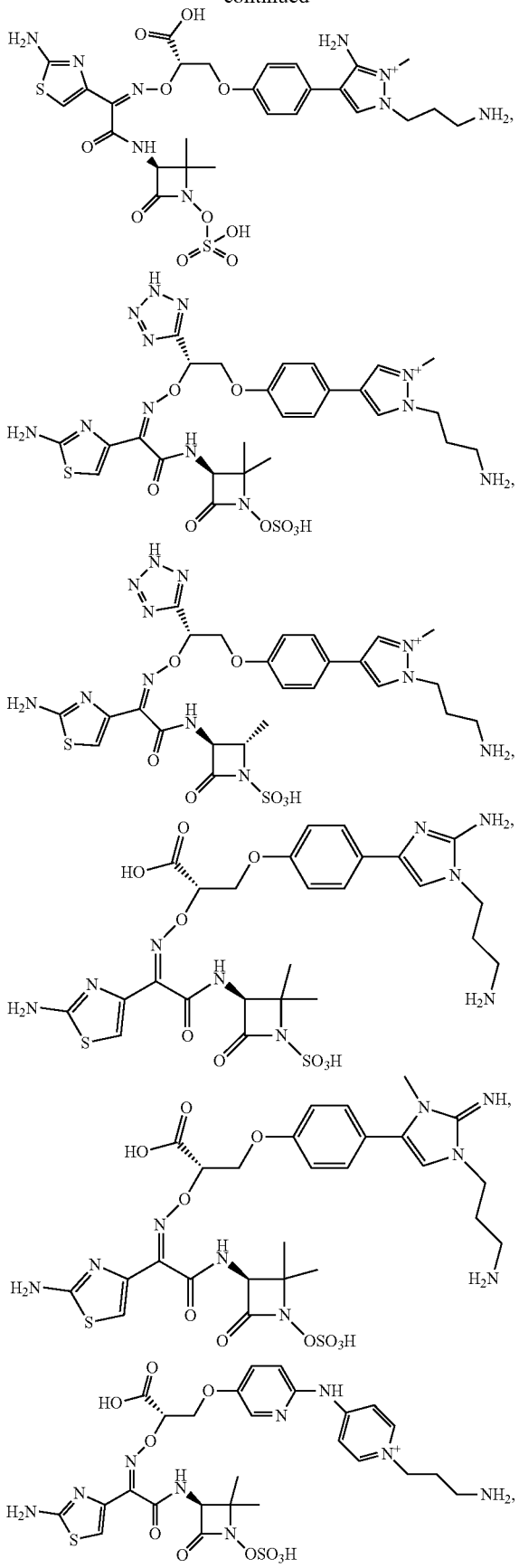

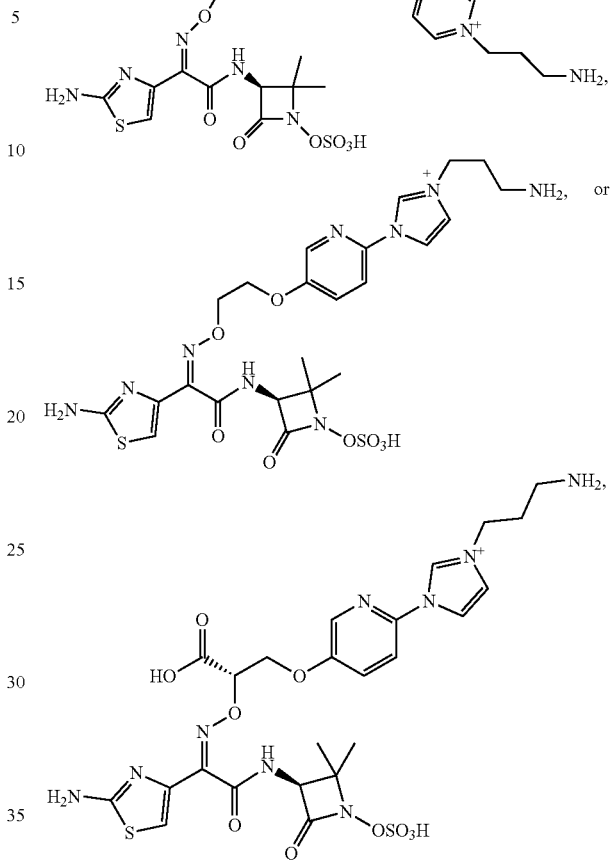

or a pharmaceutically acceptable salt thereof.

In an eighty fifth embodiment, each occurrence of $R^4$ is independently: $-C_1-C_8$ alkyl, $-C_2-C_8$ alkenyl, $-C_2-C_8$ alkynyl, halogen, $-OR^e$, $-S(O)_mR^e$, $-S(O)_mNR^cR^d$, $-C(O)R^e$, $-OC(O)R^e$, $-C(O)OR^e$, $-CN$, $-C(O)NR^cR^d$, $-NR^cR^d$, $-(CH_2)_nNR^cR^d$; $-NR^cC(O)R^e$, $-NR^cC(O)$ OR, $-NR^cC(O)NR^cR^d$, $-NR^cS(O)_mR^e$, $=NH$, $-CF_3$, $-OCF_3$, $-OCHF_2$, $-C_3-C_6$ cycloalkyl, $-O-C_3-C_6$cycloalkyl, $-C_1-C_{10}$alkylene-$C_3-C_6$cycloalkyl, $-O-C_1-C_{10}$ alkylene-$C_3-C_6$cycloalkyl, HetB, $-O$-HetB, $-C_1-C_{10}$alkylene-HetB, $-O-C_1-C_{10}$ alkylene-HetB, AryA, $-O$-AryA, $-C_1-C_{10}$ alkylene-AryA, or $-O-C_1-C_{10}$alkylene-AryA, wherein each $R^4$ is unsubstituted or substituted with one to four substituents selected from halogen, $-C_1-C_6$ alkyl and $-(CH_2)_nNR^cR^d$.

In an eighty sixth embodiment, $R^5$ is $C_2-C_{10}$ alkyl, $C_3-C_7$ cycloalkyl, $C_1-C_6$ alkyl-$C_3-C_7$ cycloalkyl, HetB, AryB, or $-NH(C_1-C_6$ alkyl), wherein said $C_1-C_6$ alkyl, said $C_2-C_{10}$ alkyl and said $C_3-C_7$ cycloalkyl are optionally substituted with one to four $R^6$.

Reference to different embodiments with respect to Formula I compounds, specifically includes different embodiments of Formula II and Formula III such as Formula II-1, II-2, II-3, III-1, III-2, and III-3, sub-embodiments of Formula I, II-1, II-2, II-3, III-1, III-2, and III-3, other embodiments provided herein, and individual compounds described herein.

Other embodiments of the present invention include the following:

(a) A pharmaceutical composition comprising an effective amount of a compound of Formula I, II-1, II-2, II-3, III-1, III-2, or III-3, as defined herein, or a pharmaceutically acceptable salt thereof, and a pharmaceutically acceptable carrier.

(b) The pharmaceutical composition of (a), further comprising a second compound, wherein the second compound is a beta-lactamase inhibitor.

(c) The pharmaceutical composition of (b), wherein the second compound is selected from the group consisting of: relebactam, tazobactam, clavulanic acid, sulbactam, and avibactam.

(d) A pharmaceutical composition comprising (i) a compound of Formula I, II-1, II-2, II-3, III-1, III-2, and III-3, or a pharmaceutically acceptable salt thereof, and (ii) a second compound, wherein the second compound is an beta-lactamase inhibitor compound, wherein the compound of Formula I, II-1, II-2, II-3, III-1, III-2, and III-3, and the second compound are each employed in an amount that renders the combination effective for treating or preventing bacterial infection.

(e) The combination of (d), wherein the second compound is selected from the group consisting of: relebactam, tazobactam, clavulanic acid, sulbactam, and avibactam.

(f) A method for treating a bacterial infection in a subject which comprises administering to a subject in need of such treatment an effective amount of a compound of Formula I, II-1, II-2, II-3, III-1, III-2, or III-3, or a pharmaceutically acceptable salt thereof.

(g) A method for preventing and/or treating a bacterial infection which comprises administering to a subject in need of such treatment a pharmaceutical composition comprising an effective amount of a compound of Formula I, II-1, II-2, II-3, III-1, III-2, and III-3, or a pharmaceutically acceptable salt thereof, and a pharmaceutically acceptable carrier.

(h) A method for treating a bacterial infection which comprises administering to a subject in need of such treatment a therapeutically effective amount of the composition of (a), (b), (c), (d), or (e).

(i) The method of treating a bacterial infection as set forth in (f), (g), or (h), wherein the bacterial infection is due to Gram negative bacteria.

(j) The method of treating a bacterial infection as set forth in (f), (g), (h), or (i), wherein the bacterial infection is due to *Pseudomonas aeruginosa* or *Acinetobacter baumannii*.

The present invention also includes a compound of Formula I, II-1, II-2, II-3, III-1, III-2, or III-3, or a pharmaceutically acceptable salt thereof, (i) for use in, (ii) for use as a medicament for, or (iii) for use in the preparation (or manufacture) of a medicament for, medicine or treating bacterial infection, including infection with a multidrug resistant bacterial strain. In these uses, the compounds of the present invention can optionally be employed in combination with one or more second therapeutic agents including relebactam, tazobactam, clavulanic acid, sulbactam, and avibactam.

Additional embodiments of the invention include the pharmaceutical compositions, combinations and methods set forth in (a)-(j) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (j) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I, II-1, II-2, II-3, III-1, III-2, or III-3 or its salt and a pharmaceutically acceptable carrier and optionally one or more excipients, it is understood that the term "substantially pure" is in reference to a compound of Formula I, II-1, II-2, II-3, III-1, III-2, or III-3 or its salt per se; i.e., the purity of this active ingredient in the composition.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

The term "β-lactamase inhibitor" refers to a compound which is capable of inhibiting enzyme activity from β-lactamases. As used herein, inhibiting β-lactamase activity means inhibiting the activity of a class A, C, and/or D-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of β-Lactams, M. I Page, Ed.; Chapman and Hall, London, $(1992)_{198}$-228.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include metallo-β-lactamases of *Escherichia coli* (such as New Delhi Metallo-f-lactamase, NDM), *Serratia*

*marcescens* (such as IMP), and *Klebsiella* spp. (such as Verona integron-encoded metallo-β-lactamase, VIM).). Additional metallo-ρ-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics include penicillins, cephalosporins and carbapenems.

The term "β-lactam antibiotic" refers to a compound with antibiotic properties that contains a β-lactam functionality. Non-limiting examples of β-lactam antibiotics include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of 0.1, 0.2, 0.3, 0.4, 0.5, 1.0, 2.0, 3.0, 4.0, or 5.0 of the appropriate unit. In certain embodiments, "about" can mean a variation of 1%, 2%, 3%, 4%, 5%, 10%, or 20%.

Another embodiment of the present invention is a compound of Formula I, II-1, II-2, II-3, III-1, III-2, or III-3, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I, II-1, II-2, II-3, III-1, III-2, or III-3 or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula I, II-1, II-2, II-3, III-1, III-2, and III-3. Unless a specific stereochemistry is indicated, the present invention is meant to comprehend all such isomeric forms of these compounds. Centers of asymmetry that are present in the compounds of Formula I, II-1, II-2, II-3, III-1, III-2, and III-3 can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, II-1, II-2, II-3, III-1, III-2, and III-3 or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In one embodiment, an alkylene group has from 1 to about 3 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Aromatic ring system" or "aromatic" in reference to a ring means monocyclic, bicyclic or tricyclic aromatic ring or ring system containing 5-14 ring atoms, wherein at least one of the rings is aromatic. The term may be used to describe a saturated or monounsaturated carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quaternary amine. In certain embodiments, an N ring atom can be in the form of an N-oxide.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, and the like. In one embodiment of the present invention, cycloalkyl is selected from: cyclopropane, cyclobutane, cyclopentane, and cyclohexane.

"Cycloalkenyl" means a nonaromatic monocyclic or bicyclic carbocylic ring containing at least one double bond. Examples of cycloalkenyl include cyclopropenyl, cyclobutenyl, cyclopentenyl, cyclohexenyl, cycloheptenyl, cyclooxtenyl and the like.

The term "heterocycloalkyl," as used herein, refers to a non-aromatic saturated monocyclic or multicyclic ring system comprising 3 to 11 ring atoms, wherein from 1 to 4 of the ring atoms are independently N, NH, S (including SO and $SO_2$) and O, and the remainder of the ring atoms are carbon atoms. A heterocycloalkyl group can be joined via a ring carbon or ring nitrogen atom (if present). Where the ring or ring system contains one or more N atoms, the N can be in the form of quaternary amine. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. When a heterocycloalkyl contains two rings, the rings may be fused or spirocyclic. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocycloalkyl (if present) can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, delta-lactam, delta-lactone, silacyclopentane, silapyrrolidine and the like, and all isomers thereof.

"Drug resistant" means, in connection with a Gram-negative bacterial strain, a strain which is no longer susceptible to at least one previously effective drug; which has developed the ability to withstand antibiotic attack by at least one previously effective drug. "Multi-drug resistant" means a strain that is no longer susceptible to two or more previously effective drugs; which has developed the ability to withstand antibiotic attack by two or more previously effective drugs. A drug resistant strain may relay that ability to withstand to its progeny. Said resistance may be due to random genetic mutations in the bacterial cell that alters its sensitivity to a single drug or to different drugs.

"Heterocycloalkenyl" means a nonaromatic monocyclic, bicyclic or bridged carbocyclic ring or ring system containing at least one double bond and containing at least one heteroatom selected from N, NH, S and O.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. In the case of a heteroaryl ring system where one or more of the rings are saturated and contain one or more N atoms, the N can be in the form of quaternary amine. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more ring system substituents which may be the same or different. Any nitrogen atom of a heteroaryl can be optionally oxidized to the corresponding N-oxide. The term "heteroaryl" also encompasses a heteroaryl group, as defined above, which is fused to a benzene ring. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. In one embodiment of the present invention, heteroaryl is selected from: pyridine, pyrimidine, thiazole, benzimidazole, benzthiazole, benzoxazole, and benzisoxazole. In another embodiment of the present invention, heteroaryl is pyridine. Examples of bicyclic rings include:

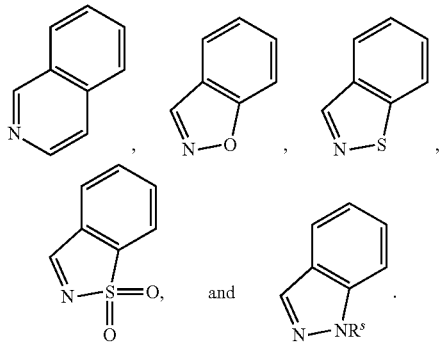

"Heterocycle" means a monocyclic or bicyclic saturated, partially unsaturated, or unsaturated ring system containing 5-10 atoms and containing at least one ring heteroatom selected from N, S and O. In select embodiments, the ring system contains 1-4 heteroatoms selected from N, S and O. When a heterocycle contains two rings, the rings may be fused, bridged or spirocyclic. Examples of monocyclic heterocycle rings include piperazine, piperidine, and morpholine. Examples of bicyclic heterocycle rings include 1,4-diazabicyclo[2,2,2]octane and 2,6-diazaspiroheptane.

"Halogen" includes fluorine, chlorine, bromine and iodine.

"Oxo" means an oxygen atom connected to another atom by a double bond and is can be represented "=O".

When any variable (e.g., $R^1$, $R^a$, etc.) occurs more than one time in any constituent or in Formula I, II-1 II-2, II-3, III-1, III-2, or III-3, its definition on each occurrence is independent of its definition at every other occurrence. Also, combinations of substituents and/or variables are permissible only if such combinations result in stable compounds. A squiggly line across a bond in a substituent variable represents the point of attachment.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I, II-1 II-2, II-3, III-1, III-2, and III-3.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. When a group, e.g., $C_1$-$C_8$ alkyl, is indicated as being substituted, such substitutions can also occur where such group is part of a larger substituent, e.g., —$C_1$-$C_6$alkyl-$C_3$-$C_7$cycloalkyl and —$C_1$-$C_8$alkyl-aryl.

In the compounds of Formula I, II-1, II-2, II-3, III-1, III-2, and III-3, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I, II-1 II-2, II-3, III-1, III-2, and III-3. For example, different isotopic forms of hydrogen (H) include protium (H) and deuterium (2H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I, II-1, II-2, II-3, III-1, III-2, and III-3 can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

It should also be noted that any carbon as well as heteroatom with unsatisfied valences in the text, schemes, examples and tables herein is assumed to have the sufficient number of hydrogen atom(s) to satisfy the valences.

The compounds of the present invention have at least one asymmetric center and can have one or more additional centers as a result of the presence of certain substituents and/or substituent patterns. Accordingly, compounds of the invention can occur as mixtures of stereoisomers, or as individual diastereomers, or enantiomers. All isomeric forms of these compounds, whether individually or in mixtures, are within the scope of the present invention.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The term "pharmaceutically acceptable salt" refers to a salt which possesses the effectiveness of the parent compound and which is not biologically or otherwise undesirable (e.g., is neither toxic nor otherwise deleterious to the recipient thereof). The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The compound of the invention can also be employed in the form of a prodrug. Any prodrug precursor known in the art can be used to form a prodrug of the invention. In certain aspects of this embodiment, the hydrogen in —COOH in formula I can be replaced with any the following groups: $C_{1-6}$alkyl, $C_{3-6}$cycloalkyl, —$C_{1-6}$alkylene-$C_{3-6}$cycloalkyl, $C_{3-7}$cycloheteroalkyl, —$C_{1-6}$alkylene-$C_{3-7}$cycloheteroalkyl, aryl, —$C_{1-10}$alkylene-aryl, heteroaryl, and —$C_{1-10}$alkylene-heteroaryl. In certain aspects of this embodiment, the $C_{1-6}$alkyl, $C_{3-6}$cycloalkyl, or $C_{3-7}$cycloheteroalkyl can be substituted. In other aspects of this embodiment, each aryl and heteroaryl can be substituted.

As set forth above, the present invention includes pharmaceutical compositions comprising a compound of Formula I of the present invention, optionally one other active components (e.g., a β-lactamase inhibitor), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula I, II-1, II-2, II-3, III-1, III-2, and III-3, or a pharmaceutically acceptable salt thereof, optionally in combination with a β-lactamase inhibitor. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula I, II-1, II-2, II-3, III-1, III-2, and III-3 mean providing the compound, or a pharmaceutically acceptable salt thereof, to the individual in need of treatment. When a compound or a salt thereof is provided in combination with one or more other active agents (e.g., a β-lactamase inhibitor), "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein means the amount of active compound sufficient to inhibit bacterial growth and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance). In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, 21$^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 microgram/mL, and in additional embodiment at least about 10 micrograms/mL, and at least about 25 micrograms/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula I, II-1, II-2, II-3, III-1, III-2, and III-3. Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula I, II-1, II-2, II-3, III-1, III-2, and III-3 to an experimental cell culture in vitro to prevent the growth of β-lactam resistant bacteria. The method can alternatively involve administration of a compound of Formula I to an animal, including a human, to prevent the growth of β-lactam resistant bacteria in vivo. In these cases the compound of Formula I, II-1, II-2, II-3, III-1, III-2, and III-3 is typically co-administered with a β-lactamase inhibitor.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Compounds of the invention can be employed for the treatment, prophylaxis or inhibition of bacterial growth or infections due to bacteria that are resistant to β-lactam antibiotics. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 μg/mL, and bacterial strains which are slightly resistant to imipenem are those against which the MIC of imipenem is >4 μg/mL.

Compounds of the invention can be used in combination with a β-lactamase inhibitor for the treatment of infections caused by β-lactamase producing strains, in addition to those infections which are subsumed within the antibacterial spectrum of the antibiotic agent. Examples of β-lactamase producing bacteria are *Pseudomonas aeruginosa, Pseudomonas putida, Enterobacter cloacae, Klebsiella pneumoniae, Klebsiella oxytoca, Escherichia coli, Serratia marcescens, Enterobacter aerogenes, Enterobacter asburiae, Citrobacter freundii, Proteus mirabilis, Morganella morganii, Providencia rettgeri, Stenotrophomonas maltophilia* and *Acinetobacter baumannii*.

It is generally advantageous to use a compound of Formula I, II-1, II-2, II-3, III-1, III-2, and III-3 in admixture or conjunction with a β-lactamase inhibitor, or a prodrug thereof. It is advantageous to use a compound of Formula I in combination with a class A and C β-lactamase inhibitor because of the class B β-lactamase resistant properties of the compounds. It is also advantageous to use a compound of Formula I in combination with one or more Class A, C, or D β-lactamase inhibitors to further limit β-lactam susceptability. As already noted, the compound of Formula I and the β-lactamase inhibitor can be administered separately (at the same time or as different times) or in the form of a single composition containing both active ingredients.

Relebactam, tazobactam, clavulanic acid, sulbactam, avibactam and other β-lactamase and metallo-β-lactamase inhibitors suitable for use in the present invention include those known to show inhibitory activity to β-lactamases.

Abbreviations employed herein include the following: aq.=aqueous; ACN=acetonitrile; BLI=β-lactamase inhibitor; Bn=benzyl; BOC (or Boc)=t-butyloxycarbonyl; BOC$_2$O=di-tert-butyl dicarbonate; CAN=ceric ammonium nitrate; CBZ (or Cbz)=carbobenzoxy (alternatively, benzyloxycarbonyl); CDCl$_3$=deuterated chloroform; CH$_3$CN=acetonitrile; Co-Catalyst=(R,R')—N,N'-bis(3,5-di-tert-butylsalicylidene)-1,2-cyclohexanediamino-cobalt(III) 1,1,1,3,3,3-hexafluoro-2-(trifluoromethyl)propan-2-olate; cv=column volume; DBU=1,8-diazabicyclo[5.4.0]undec-7-ene; DCC=dicyclohexyl carbodiimide; DCE=dichloroethane; DCM=dichloromethane; DEAD=diethyl azodicarboxylate; DIAD=diisopropyl azodicarboxylate; DIPEA=di-isopropylethylamine; DMA=dimethylacetamide; DMAP=4-dimethylaminopyridine or N,N-dimethylamino-pyridine; DMF=N,N-dimethylformamide; DMSO=dimethyl sulfoxide; EDC=1-ethyl-3-(3-dimethylaminopropyl) carbodiimide; eq. or equiv.=equivalent(s); Et=ethyl; Et$_3$N=triethyl amine; Et$_2$O=ethylene oxide; EA or EtOAc=ethyl acetate; EtOH=ethanol; g=gram(s); h or hr=hour; hex=hexane; HiVac=high vacuum; HMDS=hexamethyl-disilazide; HOBT=1-hydroxy benzotriazole; HPLC=high-performance liquid chromatography; IPA=isopropyl alcohol; iPrMgCl=isopropyl magnesium chloride; IPAc=isopropyl acetate; L or l=liter(s); LC/MS or LC-MS=liquid chromatography/mass spectrometry; LDA=lithium diisopropylamide; min=minute(s); mg=milligram(s); ml or ML= milliliter(s); m-CPBA=m-chloroperoxybenzoic acid; MBL=metallo β-lactamase; Me=methyl; MeCN=acetonitrile; MeOH=methanol; MeI=methyl iodide; MITC=minimum inhibitory threshold concentration; MOPS=3-(N-morpholino)propanesulfonic acid; MPLC=medium pressure liquid chromatography; MTBE=methyl tert-butyl ether; NBS=N-bromosuccinimide; NCS=N-chlorosuccinimide; NMR=nuclear magnetic resonance; MS=mass spectrometry; MW=molecular weight; Pd/c=palladium on carbon; PdCl$_2$(dppf)=[1,2' bis(diphenylphosphino)-ferrocene] dichloropalladium(II); di-t-BuDPPF-PdCl$_2$=1,1'-bis(di-tert-butylphosphino)ferrocene palladium dichloride; PE=petroleum ether; PG=protective group; Ph=phenyl; PPTS=pyridinium p-toluenesulfonate; RP-HPLC=reverse-phase high-performance liquid chromatography; rt or RT=room temperature; sat'd=saturated; tBu=tert butyl; TBAI=tetrabutylammonium iodide; TBAF=tetrabutylammonium fluoride; TBS=tert-butyldimethylsilyl; TBS-Cl=tert-butyldimethylsilyl chloride; TBDMS-Cl=tert-butyldimethylsilyl chloride; t-BuOH=tert-butanol; TBSO=tert-butyldimethylsilyl; TEA=triethylamine; TEMPO is (2,2,6,6-tetramethylpiperidin-1-yl)oyl; TFA=trifluoroacetic acid; THF=tetrahydrofuran; TLC=thin layer chromatography; TMS=trimethylsilyl; TMS-Cl=trimethylsilyl chloride; TMS-I=trimethylsilyl iodide; and TMS-N$_3$=trimethylsilyl azide.

Methods for Making the Compounds of Formula (I).

The compounds disclosed herein can be prepared and tested according to the following reaction schemes and Examples, or modifications thereof, using readily available starting materials, reagents and conventional synthesis procedures. In these reactions, it is also possible to make use of variations which are themselves known to those of ordinary skill in this art, but are not mentioned here in greater detail. Furthermore, other methods for preparing compounds disclosed herein will be readily apparent to the person of ordinary skill in the art in light of the following reaction scheme and Examples. Unless otherwise indicated, all variables are as defined above.

Scheme 1

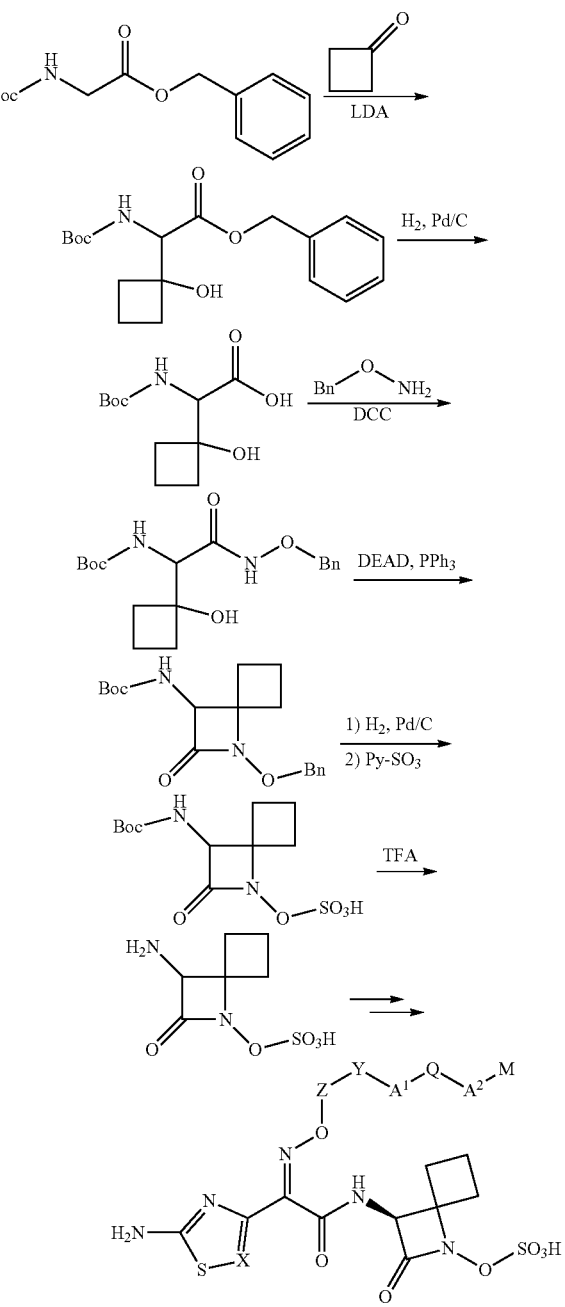

The β-lactam intermediate can be either purchased from commercial sources or synthesized following the scheme below, which shows the synthesis of β-lactam analogs wherein Rx and Rz come together to form a 4-membered spirocyclic ring. The synthetic scheme has been discussed in detail in the literature. (See EP 0229012). This amine can be converted to the final monobactam compounds with a similar procedure demonstrated in the following Examples.

Intermediate 1 tert-Butyl oxirane-2-carboxylate

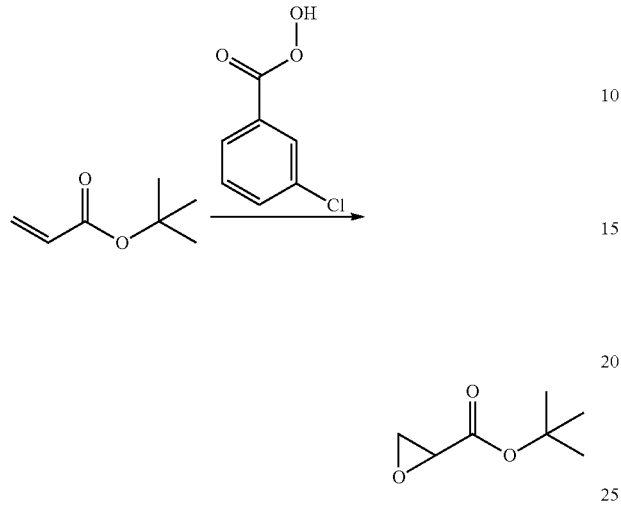

To a 1 L 2-neck round bottom flask fitted with a condenser, a solution of tert-butyl acrylate (20 g, 156 mmol) in DCM (200 ml) was added portion wise m-CPBA (48.5 g, 281 mmol). The resulting solution was heated to 58-60° C. with oil bath and refluxed for 2½ days. The mixture was then cooled to room temperature, to which was added in small portions of saturated sodium thiosulfate solution (about 40 mL, exotherm, added in small portions until no more heat was generated). After stirring about 1 hour, a large amount of precipitate occurred. About 60-100 mL of water and 100-200 mL of DCM was added to dissipate the emulsion and generate a two-phase system. The aqueous phase was separated and the organic phase was washed with saturated NaHCO$_3$(2×200 mL) and brine (100 mL), dried over MgSO$_4$ and concentrated to dryness (water bath temperature at 35° C.). The solid was suspended in 150 mL of hexane and allowed to stand at room temperature for 1 hour. The mixture was then filtered, and the filtrate was concentrated to remove hexane in a rotavapor (<35° C.) to obtain the title compound. $^1$HNMR (500 MHz, CDCl$_3$) δ 3.35 (m, 1H), 2.86 (m, 2H), 1.52 (s, 9H).

Intermediate 2

(R, R)-Co Catalyst

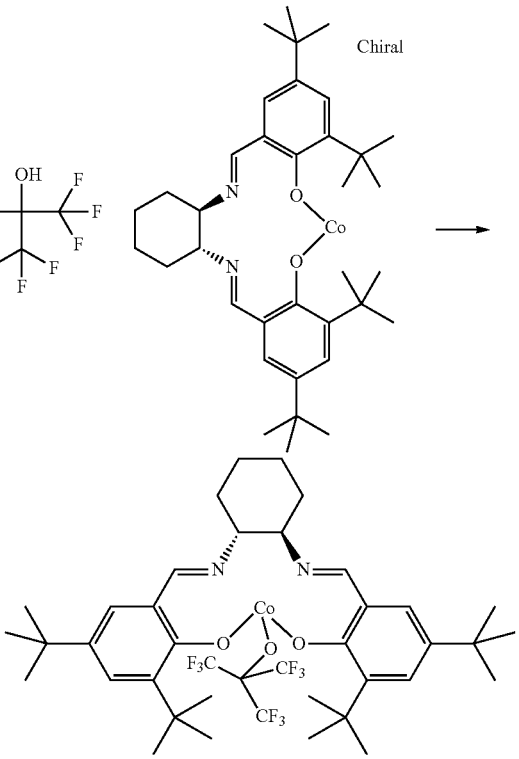

Reference: *J. Am. Chem. Soc.* 1999, 121, 6086-6087. To a solution of perfluoro-tert-butanol (1.96 g, 8.28 mmol) in DCM (97 ml) was added (R,R)-(−)—N,N'-bis(3,5-di-tert-butylsalicylidene)-1,2-cyclohexanediaminocobalt(II) (5 g, 8.28 mmol). The solution was then stirred at 30° C. for 45 minutes open to air. The reaction was then concentrated, HiVac dried to give the title compound.

Intermediate 3 tert-Butyl(R)-3-(4-bromophenoxy)-2-hydroxypropanoate

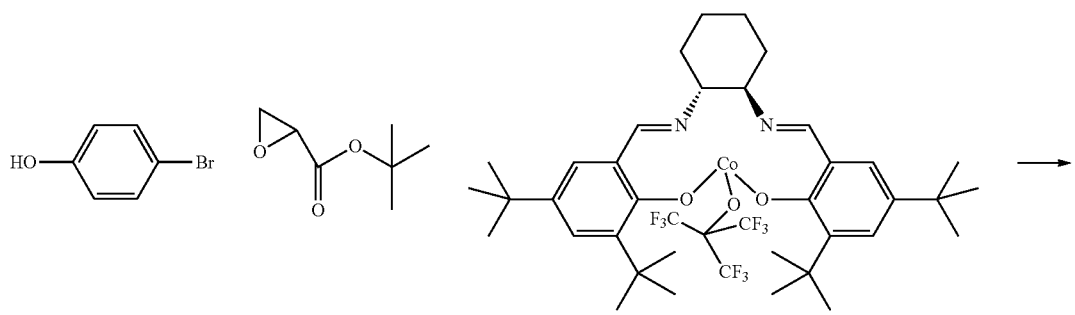

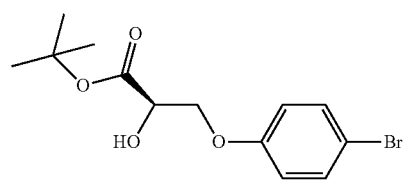

To the mixture of 4-bromophenol (2 g, 11.56 mmol), molecular sieves 4 Å (4 g) and tert-butyl oxirane-2-carboxylate (3.67 g, 25.4 mmol) was added tert-butyl methyl ether (50 ml) and (R,R)—Co catalyst (0.97 g, 1.15 mmol) under N$_2$. The resulting suspension was stirred at room temperature under N$_2$ over weekend. LC-MS indicated about 60% conversion. Extra epoxide intermediate 1 (0.5 g) and the Co catalyst (100 mg) were added, and stirred overnight. LC-MS indicated about 80% conversion. More epoxide (0.5 g) and the catalyst (100 mg) were added, and stirred overnight. The mixture was worked up by filtration, and the residue was washed by EtOAc. The filtrate was concentrated and the residue was purified on silica gel column (240 g) using 0-100% EtOAc/Hex to give the title compound. $^1$HNMR (500 MHz, CDCl$_3$) δ 7.31 (d, J=7.2 Hz, 2H), 6.83 (d, J=7.2 Hz, 2H).4.45 (m, 1H), 4.28 (m, 2H), 1.52 (s, 9H).

Intermediate 4 tert-Butyl(R)-2-hydroxy-3-(4-(4,4,5,5-tetramethyl-1,3,2-dioxaborolan-2-yl)phenoxy)propanoate

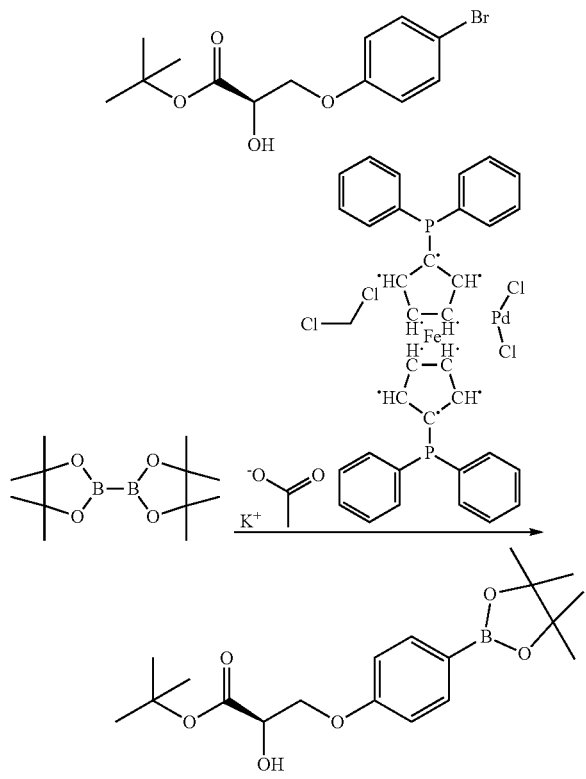

To a solution of (R)-tert-butyl 3-(4-bromophenoxy)-2-hydroxypropanoate (1.95 g, 6.15 mmol), 4,4,4',4',5,5,5',5'-octamethyl-2,2'-bi(1,3,2-dioxaborolane) (2.342 g, 9.22 mmol), and 1,1'-bis(diphenylphosphino)ferrocene-palladium(II)dichloride dichloromethane complex (0.309 g, 0.378 mmol) in 1,4-dioxane (22 ml) was added potassium acetate (1.81 g, 18.4 mmol). The mixture was degassed and refilled with nitrogen and heated at 85° C. overnight. The mixture was filtered and concentrated to dryness under vacuum. The residue was purified by colunm chromatography on silica gel (120 g), and eluted with hexane/AcOEt (0-50%) to obtain the title compound. LC-MS [M+H+Na]: m/z 387.00. $^1$HNMR (500 MHz, CDCl$_3$) δ 7.67 (d, J=7.2 Hz, 2H), 6.82 (d, J=7.2 Hz, 2H).4.33 (m, 1H), 4.16 (m, 2H), 1.41 (s, 9H), 1.29 (s, 12H).

Intermediate 5

2-(2-((tert-Butoxycarbonyl)amino)thiazol-4-yl)-2-oxoacetic acid

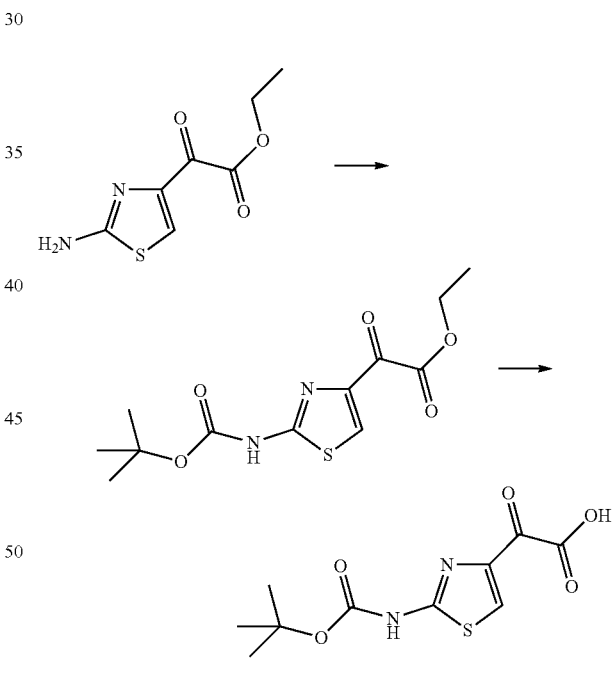

Step A: ethyl 2-(2-((tert-butoxycarbonyl)amino)thiazol-4-yl)-2-oxoacetate

To a solution of ethyl 2-(2-aminothiazol-4-yl)-2-oxoacetate (10 g, 49.9 mmol) in acetonitrile (250 ml) was added BOC-anhydride (23.2 ml, 100 mmol) followed by N,N,N',N'-tetramethyl-ethylenediamine (9.80 ml, 64.9 mmol). The mixture was stirred at room temperature for 3 hours. Solvent was removed, and the residue was partitioned between EtOAc and 1N HCl. The organic layer was washed with NaHCO$_3$(Saturated aq. solution), brine, dried over Na$_2$SO$_4$.

Solvent was removed under vacuum. The residue was purified by column chromatography on silica gel (redi flash 220 g), eluted with EtOAc/hexane (0-30%, 5 cv; 30%, 10 cv) to give the title compound. LC-MS [M+H]⁺: m/z 301.

Step B: 2-(2-((tert-butoxycarbonyl)amino)thiazol-4-yl)-2-oxoacetic acid

Ethyl 2-(2-((tert-butoxycarbonyl)amino)thiazol-4-yl)-2-oxoacetate (10.2 g, 34.1 mmol) was dissolved in THF (140 ml)/MeOH (50 ml) and sodium hydroxide was added (68.3 ml, 68.3 mmol, 1M). The solution was stirred at room temperature for 4 hours. The reaction mixture was poured into water (1 L) and extracted with EtOAc (3×200 ml). The aqueous layer was acidified with HCl (1N) solution and re-extracted with EtOAc (3×200 ml). The organic layer was washed with brine and dried over $Na_2SO_4$, and concentrated to give the title compound. LC-MS [M+H]⁺: m/z 273. ¹HNMR (500 MHz, CDCl₃) δ 8.35 (s, 1H), 1.55 (s, 9H).

Intermediate 6

2-(2-((tert-Butoxycarbonyl)amino)-5-chlorothiazol-4-yl)-2-oxoacetic acid

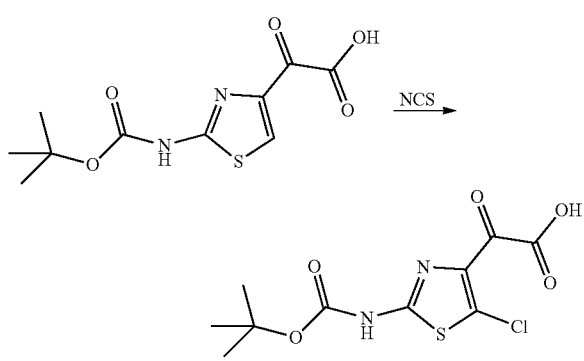

To a suspension of 2-(2-((tert-butoxycarbonyl)amino)thiazol-4-yl)-2-oxoacetic acid (intermediate 5) (1 g, 3.67 mmol) in DMF (10.0 ml) was added NCS (0.589 g, 4.41 mmol). The mixture was heated to 50° C. overnight. It was then diluted with EtOAc (100 ml), washed with water (3×30 ml), and brine. The organic layer was dried over $Na_2SO_4$. Solvent was removed under vacuum to give the title compound. LC-MS [M+H]⁺: m/z 307.

Intermediate 7

2-(5-((tert-Butoxycarbonyl)amino)-1,2,4-thiadiazol-3-yl)-2-oxoacetic acid

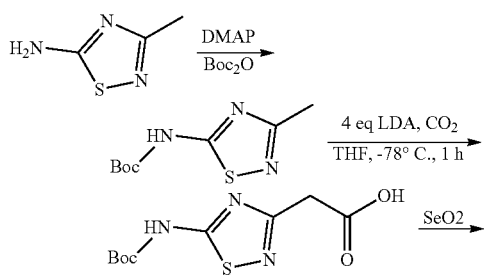

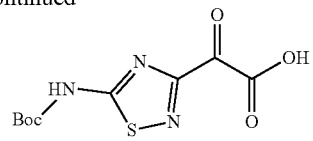

Step A: tert-butyl (3-methyl-1,2,4-thiadiazol-5-yl)carbamate

Into a 5-L 4-necked round-bottom flask purged and maintained with an inert atmosphere of nitrogen, was placed 3-methyl-1,2,4-thiadiazol-5-amine (167 g, 1.45 mol, 1.00 equiv), 4-dimethylamino-pyridine (17.7 g, 144.88 mmol, 0.10 equiv), di-tert-butyl dicarbonate (348 g, 1.59 mol, 1.10 equiv), and butan-1-ol (1670 mL). The resulting solution was stirred for 1 hour at 40° C. The resulting mixture was concentrated under vacuum. The residue was washed with Hexane.

This resulted in the title compound.

Step B: 2-(5-((tert-butoxycarbonyl)amino)-1,2,4-thiadiazol-3-yl)acetic acid

Into a 5000-mL 4-necked round-bottom flask purged and maintained with an inert atmosphere of nitrogen, was placed a solution of tert-butyl N-(3-methyl-1,2,4-thiadiazol-5-yl)carbamate (128 g, 595 mmol, 1.00 equiv) in tetrahydrofuran (640 mL). The resulting solution was stirred at −78° C., LDA (1190.69 mL, 4.00 equiv) was added. 30 minutes later, $CO_2$ (g) was introduced in over 30 minutes at −30° C. The reaction was then quenched by the addition of 1280 mL of water. The resulting solution was extracted with 640 mL of ethyl acetate and the aqueous layers were combined. The pH value of the solution was adjusted to 2 with HCl (2M mol/L). The resulting solution was extracted with 2.5 L of ethyl acetate and the organic layers were combined. The resulting mixture was washed with 2000 mL of brine. The mixture was dried over anhydrous sodium sulfate and concentrated under vacuum, which resulted in the title compound.

Step C: 2-(5-((tert-Butoxycarbonyl)amino)-1,2,4-thiadiazol-3-yl)-2-oxoacetic acid Into a 2000-mL 4-necked round-bottom flask purged and maintained with an inert atmosphere of nitrogen, was placed a solution of 2-(5-[[(tert-butoxy)carbonyl]amino]-1,2,4-thiadiazol-3-yl)acetic acid (76 g, 293.12 mmol, 1.00 equiv) in dioxane (1520 mL), $SeO_2$ (65.14 g, 587 mmol, 2.00 equiv). The resulting solution was stirred for 3 hours at 80° C. in an oil bath and then concentrated. The crude product was purified by Flash-Prep-HPLC with the following conditions (IntelFlash-1): Column, silica gel; mobile phase, ACN/$H_2O$ (0.5% HCl)=10/90-30/70 increasing to ACN/$H_2O$ (0.5% HCl)=90/10 to 70/30 within 20 min; Detector, UV 254 nm. This resulted in the title compound. LC-M: (ES, m/z): [M+H]⁺=274. H-NMR (300 MHz, DMSO, ppm): δ 1.523-1.502 (s, 9H), 12.806 (s, 1H).

Intermediate 8 tert-Butyl 2-((tert-butyldimethylsilyl)oxy)-3-(4-(4,4,5,5-tetramethyl-1,3,2-dioxaborolan-2-yl)phenoxy)propanoate

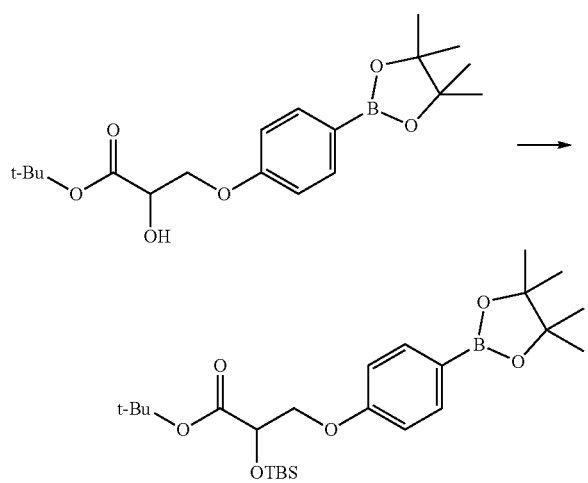

To the solution of tert-butyl 2-hydroxy-3-(4-(4,4,5,5-tetramethyl-1,3,2-dioxaborolan-2-yl)phenoxy)propanoate (0.5 g, 1.37 mmol) (Intermediate 4), imidazole (0.467 g, 6.86 mmol), and TBS-Cl in DCM (3.43 ml, 3.43 mmol) in acetonitrile (5 ml) was added DMAP (0.017 g, 0.137 mmol). The resulting solution was stirred at room temperature for 3 hours. After concentration, the residue was purified on a silica gel column (40 g) using 0-10% EtOAc/hexane as gradient to give the title compound.

Intermediate 9

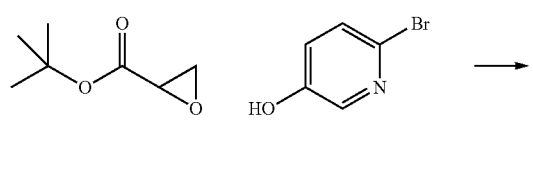

Step A: tert-butyl 3-((6-bromopyridin-3-yl)oxy)-2-hydroxypropanoate

Potassium carbonate (7.94 g, 57.5 mmol) was added to a stirred mixture of 6-bromopyridin-3-ol (5 g, 28.7 mmol) and tert-butyl oxirane-2-carboxylate (20.7 g, 144 mmol) in $CH_3CN$ (60 ml) and the mixture was stirred at 90° C. for 3 hours. The mixture was cooled and filtered through a short pad of celite and washed with EtOAc. Solvent was removed under reduced pressure and the residue was purified with ISCO column (gold, 120 g) eluting with 0-60% EtOAc/hexane gradient to give the title compound. LC-MS $[M+H]^+$: m/z 318.2.

Step B: tert-butyl 3-((6-bromopyridin-3-yl)oxy)-2-((tert-butyldimethyl-silyl)oxy)propanoate To a solution of tert-butyl 3-((6-bromopyridin-3-yl)oxy)-2-hydroxypropanoate (6700 mg, 21.1 mmol), imidazole (3440 mg, 50.5 mmol), and TBDMS-Cl (3800 mg, 25.3 mmol) in acetonitrile (100 ml) was added DMAP (257 mg, 2.11 mmol). The resulting solution was stirred at room temperature overnight. The reaction was concentrated and the residue was purified by ISCO column (gold, 120 g), eluting with 0-25% EtOAc/hexane gradient to give the title compound. LC-MS $[M+H]^+$: m/z 432.4.

Intermediate 10

2-(difluoromethyl)-6-(1-(trifluoromethyl)cyclopropyl)benzoic acid

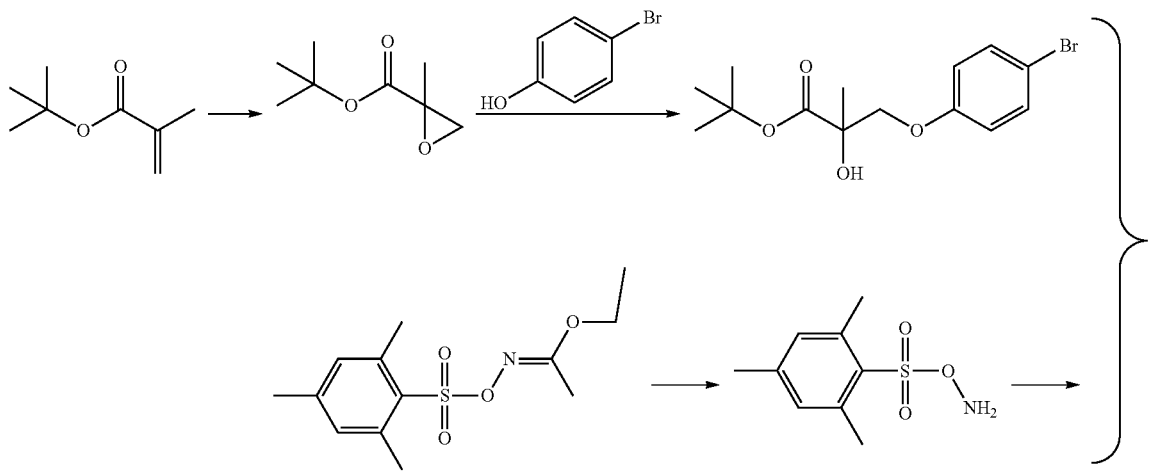

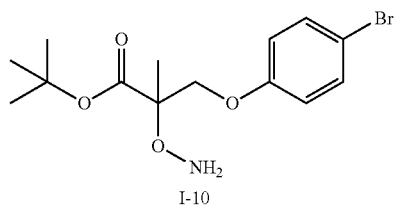

I-10

Step A: tert-butyl 2-methyloxirane-2-carboxylate

To a 2000 mL 3-neck round bottom flask fitted with a condenser, a solution of tert-butyl methacrylate (44 g, 309 mmol) in $CH_2Cl_2$ (1000 mL) was added portion wise m-CPBA (120 g, 557 mmol). The resulting solution was stirred at 30° C. for 20 hours, resulting large amount of precipitate. The slurry was filtered, to the filtrate was added in small portions of saturated sodium thiosulfate solution (about 100 mL, added in small portions until no more heat is generated). The aqueous was separated and the organic phase was washed with saturated $NaHCO_3$ (2×400 mL) and brine (400 mL), dried over $Na_2SO_4$, filtered and concentrated to obtain the title compound. $^1$H-NMR (400 MHz, Chloroform-d) δ 3.02 (d, J=5.95 Hz, 1H), 2.68 (d, J=6.17 Hz, 1H), 1.51 (s, 3H), 1.46 (s, 9H).

Step B: tert-butyl 3-(4-bromophenoxy)-2-hydroxy-2-methylpropanoate

A mixture of 4-bromophenol (15 g, 87 mmol), $K_2CO_3$ (17.97 g, 130 mmol) and tert-butyl 2-methyloxirane-2-carboxylate (20.6 g, 130 mmol) in DMF (200 mL) was heated and stirred at 80° C. for 16 hours. TLC indicated complete conversion. The mixture was diluted with water (100 mL) and extracted with $CH_2Cl_2$ (3×100 mL), washed with brine (2×40 mL). The organic layer was dried over $Na_2SO_4$, filtered and concentrated in vacuum. The residue was purified by column chromatography (SiO$_2$, PE:EtOAc=1: 0-9:1) to give the title compound. $^1$H-NMR (400 MHz, Chloroform-d) δ 7.37 (d, J=8.61 Hz, 2H), 6.77 (d, J=9.00 Hz, 2H), 4.09 (d, J=9.00 Hz, 1H), 3.95 (d, J=9.00 Hz, 1H), 3.60 (s, 1H), 1.44-1.47 (m, 12H).

Step C: O-(mesitylsulfonyl)hydroxylamine

A solution of (E)-ethyl N-(mesitylsulfonyl)oxyacetimidate (20 g, 70.1 mmol) in 1,4-dioxane (20 mL) was cooled to 0° C. Perchloric acid (8.45 g, 84 mmol) was added dropwise (slowly). After stirring for 15 minutes, the mixture solidified. The contents of the reaction were transferred to 200 mL of ice water, and the flask rinsed with water (100 mL) and tert-butyl methyl ether (100 mL). The contents were transferred to a separatory funnel and extracted with tert-butyl methyl ether (2×100 mL). The organic layer was neutralized and partially dried with anhydrous potassium carbonate and then filtered. The filtrate was concentrated to less than 80 mL total volume and then poured into 400 mL of ice cold hexane and left to crystallize for 30 minutes. The white crystals were isolated by filtration to give the title compound, which was transferred to a plastic Falcon tube and stored at −20° C. $^1$H-NMR (400 MHz, Chloroform-d) δ 7.01 (s, 2H), 2.65 (s, 6H), 2.33 (s, 3H).

Step D: tert-butyl 2-(aminooxy)-3-(4-bromophenoxy)-2-methylpropanoate

Tert-Butyl 3-(4-bromophenoxy)-2-hydroxy-2-methylpropanoate (9 g, 27.2 mmol) was dissolved in anhydrous THF (120 mL) under $N_2$, cooled to 0° C. NaH (1.96 g, 48.9 mmol, (60% in paraffin) was added in 3 portions. The mixture was stirred at 0° C. for 30 min. Then 0-(mesitylsulfonyl)hydroxylamine (6.43 g, 29.9 mmol) was added to this mixture. The mixture was stirred at 0° C. for 2 hours. LCMS showed the starting material was consumed, the desired compound was formed. The mixture was quenched with saturated $NH_4Cl$ (20 mL), extracted with EtOAc (3×45 mL). The combined organic layer was dried over $Na_2SO_4$, filtered and concentrated in vacuum. The residue was purified by column chromatography (SiO$_2$, PE:EtOAc=1: 0-10:1) to give the title compound. $^1$H-NMR (400 MHz, Chloroform-d) δ 7.38 (d, J=8.61 Hz, 2H), 6.84 (d, J=8.61 Hz, 2H), 4.34 (d, J=9.78 Hz, 1H), 4.07 (d, J=9.78 Hz, 1H), 1.47-1.52 (m, 12H).

Intermediate 11

Ethyl (R)-3-(4-bromophenoxy)-2-hydroxypropanoate

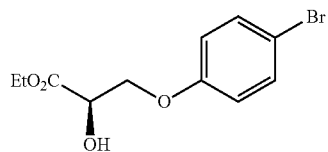 [SMILES: CCOC(=O)[C@H](O)COc1ccc(Br)cc1]

The title compound was prepared following procedures similar to Intermediate 3, substituting ethyl oxirane-2-carboxylate for tert-butyl oxirane-2-carboxylate. LC-MS [M+H]: m/z 289.1.

Intermediate 12 tert-butyl (R)-3-((6-bromopyridazin-3-yl)oxy)-2-hydroxypropanoate

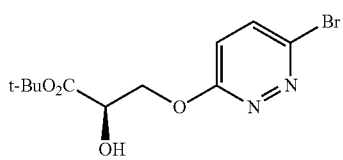

The title compound was prepared following procedures similar to Intermediate 3, substituting 3-bromo-6-hydroxypyridazine for 4-bromophenol. LC-MS [M+Na]: m/z 341.0.

Intermediate 13

Ethyl (R)-2-hydroxy-3-(4-(4,4,5,5-tetramethyl-1,3,2-dioxaborolan-2-yl)phenoxy)propanoate

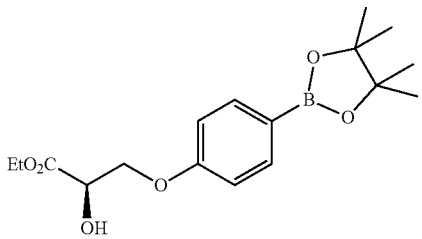 [SMILES: CCOC(=O)[C@H](O)COc1ccc(B2OC(C)(C)C(C)(C)O2)cc1]

The title compound was prepared following procedures similar to the procedures of Intermediate 8, substituting ethyl oxirane-2-carboxylate for tert-butyl oxirane-2-carboxylate. LC-MS [M+H]: m/z 337.3.

Intermediate 14 tert-butyl (S)-2-(aminooxy)-3-(4-bromo-3-fluorophenoxy)-2-methylpropanoate

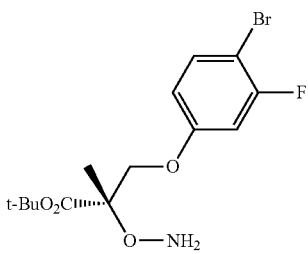

Step A: 1-bromo-2-fluoro-4-((2-methylallyl)oxy)benzene

3-Bromo-2-methylprop-1-ene (5.3 mL, 52 mmol) was added to a stirred suspension of 4-bromo-3-fluorophenol (10 g, 52 mmol) and K$_2$CO$_3$ (8.7 g, 63 mmol) in DMF (105 mL). The reaction mixture was stirred at rt for 1.5 h, then partitioned between ether and water. The layers were separated, and the organic layer was washed with water and brine, dried (MgSO$_4$), filtered and concentrated in vacuo to afford the title compound, which was used without further purification.

Step B: (R)-3-(4-bromo-3-fluorophenoxy)-2-methylpropane-1,2-diol

AD-mix α (12 g, 0.035 mmol of osmium) was added to a suspension of 1-bromo-2-fluoro-4-((2-methyl-allyl)oxy) benzene (2.1 g, 8.5 mmol) in tert-butanol (41 mL) and water (41 mL). The reaction was stirred at rt for 4 h, then partitioned between EtOAc and water. The layers were separated, and the aqueous layer was extracted with EtOAc. The combined organic layers were washed with brine, dried (MgSO$_4$), filtered and concentrated in vacuo. The resulting residue was purified by column chromatography on silica gel (0-100% EtOAc in hexanes as eluent) to give the title compound. LC-MS [M+H]: m/z 279.0.

Step C: (S)-3-(4-bromo-3-fluorophenoxy)-2-hydroxy-2-methylpropanoic acid

A mixture of NaH$_2$PO$_4$ (2.43 g, 20.2 mmol) in water (41 mL) was added to a stirred solution of (R)-3-(4-bromo-3-fluorophenoxy)-2-methylpropane-1,2-diol (2.26 g, 8.10 mmol) in THF (41 mL). Then TEMPO (0.127 g, 0.81 mmol) was added, followed by solutions of sodium chlorite (1.83 g, 16.2 mmol) and sodium hypochlorite (0.83 mL, 0.81 mmol) in water (1.5 mL each). The reaction mixture was stirred at rt for 24 h, then additional portions of TEMPO (0.127 g, 0.81 mmol) and sodium hypochlorite (0.83 mL, 0.81 mmol) were added. After 2 h, the reaction was partitioned between EtOAc and saturated aqueous sodium thiosulfate. The layers were separated, and the organic layer was washed with brine, dried (MgSO$_4$), filtered and concentrated in vacuo to give the title compound. LC-MS [M+2Na]: m/z 336.9.

Step D: tert-butyl (S)-3-(4-bromo-3-fluorophenoxy)-2-hydroxy-2-methylpropanoate tert-Butyl-N,N'-diisopropylcarbammidate (1.87 mL, 8.0 mmol) was added to a stirred solution of (S)-3-(4-bromo-3-fluorophenoxy)-2-hydroxy-2-methylpropanoic acid (1.17 g, 4.0 mmol) in THF (20 mL). The resulting mixture was heated to 60° C. After 3 h, the reaction was cooled to rt, filtered through a pad of Celite™ and concentrated in vacuo. The resulting residue was purified by column chromatography on silica gel (0-80% EtOAc in hexanes as eluent) to give the title compound. LC-MS [M+(Na−tBu)]: m/z 314.6.

Step E: tert-butyl (S)-2-(aminooxy)-3-(4-bromo-3-fluorophenoxy)-2-methylpropanoate The title compound was prepared following a procedure similar to the procedure of Intermediate 10, Step D. LC-MS [M+H]: m/z 364.2.

Intermediate 15

Methyl (R)-3-(4-bromophenoxy)-2-hydroxypropanoate

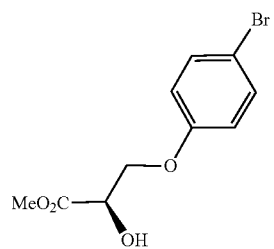 [SMILES: COC(=O)[C@H](O)COc1ccc(Br)cc1]

Step A: (R)-3-(4-bromophenoxy)-2-hydroxypropanoic acid

TFA (850 μL, 11.0 mmol) was added to a stirred solution of Intermediate 3 (350 mg, 1.10 mmol) in DCM (5.5 mL). The reaction mixture was stirred at rt. After 1.5 h, the reaction was concentrated in vacuo, and the resulting solid was carried on without further purification. LC-MS [M+Na]: m/z 283.2.

Step B: Methyl (R)-3-(4-bromophenoxy)-2-hydroxypropanoate

Trimethylsilyldiazomethane (2.2 mL of a 2.0 M solution in hexanes, 4.41 mmol) was added to a (1:1) mixture of DCM:CH₃OH (2 mL). The resulting mixture was added to a stirred solution of (R)-3-(4-bromophenoxy)-2-hydroxy-propanoic acid (288 mg, 1.10 mmol) in (1:1) DCM:CH₃OH (10 mL). The reaction mixture was stirred at rt for 30 min. Then the reaction was concentrated in vacuo to give the title compound, which was used without further purification. LC-MS [M+H]: m/z 275.2.

Intermediate 16 tert-butyl 3-((4-bromo-1H-pyrazol-1-yl)methyl)-3-fluoroazetidine-1-carboxylate

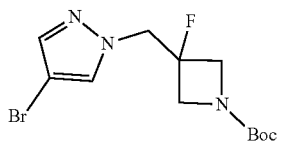

Step A: tert-butyl 3-fluoro-3-((tosyloxy)methyl) azetidine-1-carboxylate p-Toluenesulfonyl chloride (1.02 g, 5.32 mmol) was added to a stirred solution of tert-butyl 3-fluoro-3-(hydroxymethyl)azetidine-1-carboxylate (993 mg, 4.84 mmol) and triethylamine (742 μL, 5.32 mmol) in DCM (20 mL) at 0° C. The reaction mixture was allowed to warm to rt, then additional triethylamine (337 μL, 2.66 mmol) was added. After stirring overnight, the reaction mixture was concentrated in vacuo, and the resulting residue was purified by column chromatography on silica gel (0-60% EtOAc in hexanes as eluent) to give the title compound. LC-MS [M-(ᵗBu+H)]: m/z 304.2.

Step B: tert-butyl 3-((4-bromo-1H-pyrazol-1-yl) methyl)-3-fluoroazetidine-1-carboxylate Sodium hydride (116 mg of a 60% dispersion in mineral oil, 2.89 mmol) was added in several portions to a stirred solution of tert-butyl 3-fluoro-3-((tosyloxy)methyl)azetidine-1-carboxylate (1.04 g, 2.89 mmol) and 4-bromo-1H-pyrazole (425 mg, 2.89 mmol) in DMF (13 mL) at 0° C. The reaction mixture was allowed to warm to rt and stirred overnight. Then the reaction mixture was diluted with EtOAc and poured over ice. The layers were separated, and the organic layer was washed with brine, dried (MgSO₄), filtered and concentrated in vacuo. The resulting residue was purified by column chromatography on silica gel (0-100% EtOAc in hexanes as eluent) to give the title compound. LC-MS [M+H]: m/z 334.0.

Intermediate 17

3-azidopropyl trifluoromethanesulfonate

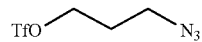

The title compound was prepared using a procedure similar to the procedure of intermediate 16 Step A, substituting 3-azidopropan-1-ol for tert-butyl 3-fluoro-3-(hydroxymethyl)-azetidine-1-carboxylate, and triflic anhydride for p-tosyl chloride.

Intermediate 18 tert-butyl (2-((5-bromopyridin-2-yl)amino)ethyl) carbamate

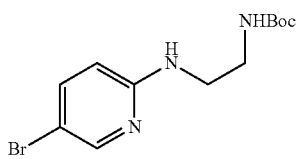 [SMILES: CC(C)(C)OC(=O)NCCNc1ccc(Br)cn1]

Step A: N¹-(5-bromopyridin-2-yl)ethane-1,2-diamine

Ethylenediamine (25.4 mL, 380 mmol) was added to a stirred solution of 2,5-dibromopyridine (5.00 g, 21.1 mmol). The reaction was heated to 100° C. for 16 h, then cooled to rt, and concentrated in vacuo. The resulting residue was diluted in DCM. The organic layers were washed with water, dried (MgSO₄), filtered and concentrated in vacuo to give the title compound, which was used in the next step without purification. LC-MS [M+H]: m/z 215.8.

Step B: tert-butyl (2-((5-bromopyridin-2-yl)amino) ethyl)carbamate

Di-tert-butyl dicarbonate (5.53 g, 25.3 mmol) was added to a stirred suspension of N¹-(5-bromopyridin-2-yl)ethane-1,2-diamine (4.56 g, 21.1 mmol) and sodium carbonate (2.35 g, 22.2 mmol) in a (1:1) dioxane:water solution (64 mL total volume). The reaction mixture was stirred at rt overnight, then the reaction mixture was extracted with EtOAc. The organic layer was washed with brine, dried (MgSO₄), filtered and concentrated in vacuo. The resulting residue was purified by column chromatography on silica gel (0-30% EtOAc in hexanes as eluent) to give the title compound. LC-MS [M+H]: m/z 316.3.

Intermediate 19 tert-butyl (3-((6-chloropyridazin-3-yl)amino)propyl)carbamate

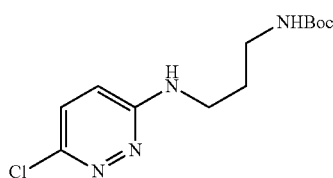 [SMILES: CC(C)(C)OC(=O)NCCCNc1ccc(Cl)nn1]

Step A: tert-butyl (3-((6-chloropyridazin-3-yl)amino)propyl)carbamate

To a stirred solution of 3,6-dichloropyridazine (1.00 g, 6.71 mmol) in DMSO (10.0 mL) in a microwave vial was added tert-butyl (3-aminopropyl)carbamate (1.23 g, 7.05 mmol), followed by triethylamine (1.50 mL, 10.8 mmol). The microwave vial was sealed, and the reaction mixture was heated in a microwave reactor to 130° C. for 15 min. After cooling to rt, the reaction mixture was partitioned between EtOAc and saturated aqueous NH$_4$Cl. The layers were separated, and the organic layer was washed with water and brine. The organic layer was dried (Na$_2$SO$_4$), filtered and concentrated. The resulting residue was purified by column chromatography on silica gel (0-50% (3:1 EtOAc:EtOH) in hexanes as eluent) to give the title compound. LC-MS [M+H]: m/z 287.2.

Intermediate 20 tert-butyl (3-(4-bromo-1H-pyrazol-1-yl)-2-fluoropropyl)carbamate

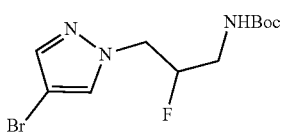

Step A: 3-((tert-butoxycarbonyl)amino)-2-fluoropropyl 4-methyl benzenesulfonate The title compound was prepared using a procedure similar to the procedure of Intermediate 16, Step A substituting tert-butyl (2-fluoro-3-hydroxypropyl)carbamate for tert-butyl 3-fluoro-3-(hydroxymethyl)azetidine-1-carboxylate. LC-MS [M+Na]: m/z 370.2.

Step B: tert-butyl (3-(4-bromo-1H-pyrazol-1-yl)-2-fluoropropyl)carbamate

The title compound was prepared according to the procedure of intermediate 16 Step B. LC-MS [M+H]: m/z 322.2.

Intermediate 21 tert-butyl (3-(1H-imidazol-4-yl)propyl)carbamate

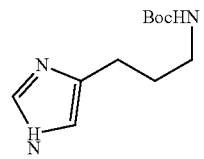 [SMILES: CC(C)(C)OC(=O)NCCCc1c[nH]cn1]

Step A: 3-(1-trityl-1H-imidazol-4-yl)propan-1-ol

Lithium aluminum hydride (2.5 mL of a 1 M THF solution, 2.5 mmol) was added to a stirred solution of methyl 3-(1-trityl-1H-imidazol-4-yl)propanoate (500 mg, 1.26 mmol) in THF (4.0 mL) at 0° C. The resulting mixture was warmed to 70° C. and allowed to stir at 70° C. for 2 h. Then the reaction was cooled to rt and quenched by the addition of water, followed by 2 N NaOH. The resulting slurry was filtered through a column of Celite™, which was washed with EtOAc. The filtrate was concentrated in vacuo to give the title compound, which was used without further purification. LC-MS [M+H]: m/z 369.4.

Step B: 2-(3-(1-trityl-1H-imidazol-4-yl)propyl)isoindoline-1,3-dione

Phthalimide (278 mg, 1.89 mmol) was added to a stirred solution of 3-(1-trityl-1H-imidazol-4-yl)propan-1-ol (465 mg, 1.26 mmol) and triphenylphosphine (496 mg, 1.89 mmol) in THF (12 mL). The reaction was cooled to 0° C., then DIAD (0.37 mL, 1.89 mmol) was slowly added dropwise, and the resulting mixture was allowed to warm to rt. After stirring overnight, the reaction mixture was filtered, and the solids were washed with THF to give the title compound. LC-MS [M+H]: m/z 498.5.

Step C: 3-(1-trityl-1H-imidazol-4-yl)propan-1-amine

Methylamine (11 mL of a 33% w/v EtOH solution, 88 mmol) was added to a stirred solution of 2-(3-(1-trityl-H-imidazol-4-yl)propyl)isoindoline-1,3-dione (1.92 g, 3.86 mmol) in EtOH (40 mL) and water (3.5 mL). The resulting mixture was stirred at rt overnight, then the reaction mixture was concentrated in vacuo and azeotroped several times with toluene to give the title compound, which was used without further workup or purification. LC-MS [M+H]: m/z 368.4.

Step D: tert-butyl (3-(1-trityl-1H-imidazol-4-yl)propyl)carbamate

Di-tertbutyl dicarbonate (1.69 g, 7.72 mmol) was added to a stirred solution of 3-(1-trityl-1H-imidazol-4-yl)propan-1-amine (1.42 g, 3.86 mmol) and triethylamine (1.08 mL, 7.72 mmol) in DCM (30 mL). The reaction mixture was stirred at rt. When complete, the reaction was concentrated in vacuo onto a pad of Celite™, and the resulting slurry was purified by column chromatography on silica gel (0-100% EtOAc in hexanes as eluent) to give the title compound. LC-MS [M+H]: m/z 468.4.

Step E: tert-butyl (3-(1H-imidazol-4-yl)propyl)carbamate

Anisole (377 mg, 3.49 mmol) was added to a stirred solution of tert-butyl (3-(1-trityl-H-imidazol-4-yl)propyl)carbamate (1.63 g, 3.49 mmol) in acetic acid (5.0 mL), and the reaction mixture was heated to 60° C. After 24 h, the reaction mixture was concentrated in vacuo and azeotroped successively with toluene and acetonitrile. The resulting residue was suspended in EtOAc and DCM, and the mixture was adsorbed onto Celite™. The resulting slurry was purified by column chromatography on silica gel (0-100% (3:1 EtOAc:EtOH) in hexanes as eluent) to give the title compound. LC-MS [M+H]: m/z 226.2.

Intermediate 22

(S)-3-(2-(2-((tert-butoxycarbonyl)amino)thiazol-4-yl)-2-oxoacetamido)-2,2-dimethyl-4-oxoazetidin-1-yl hydrogen sulfate

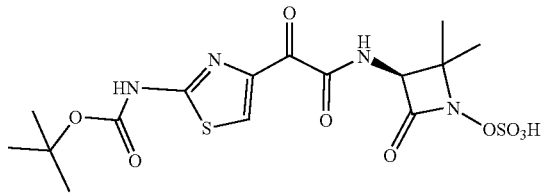

To a solution of 2-(2-((tert-butoxycarbonyl)amino)thiazol-4-yl)-2-oxoacetic acid (Intermediate 5, 2 g, 7.4 mmol), (S)-3-amino-2,2-dimethyl-4-oxoazetidin-1-yl hydrogen sulfate (3.1 g, 14.7 mmol, from commercial sources CAS: 102507-49-3) and pyridine (1.8 ml, 22 mmol) in MeCN (37 mL) was added EDC (3.5 g, 18 mmol) at 0° C. The reaction was allowed to warm to ambient temperature overnight. After 16 h, the reaction was poured into brine (100 mL) and extracted with MeCN (50 mL). The organic layers were dried over MgSO4, filtered, and concentrated in vacuo. The resulting residue was purified by SiO$_2$ flash chromatography and eluted with hexanes/(3:1 EtOAc/EtOH) 0-100% to give the title compound. LC-MS [M+H]: m/z 465.2

Intermediate 23 tert-butyl (S)-(3-(4-bromo-1H-pyrazol-1-yl)-2-((tert-butyldimethylsilyl)oxy)propyl)carbamate

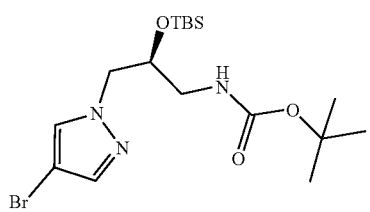

Step A: tert-butyl N-[(2S)-2,3-dihydroxypropyl]carbamate

Into a 500-mL 4-necked round-bottom flask was placed a solution of (2S)-3-aminopropane-1,2-diol (20 g, 220 mmol, 1 eq) in methanol (200 mL), and di-tert-butyl dicarbonate (57 g, 261 mmol, 1.2 eq). The reaction was stirred overnight at room temperature, and then concentrated in vacuo. The resulting residue was purified on a silica gel column with dichloromethane/methanol (10:1) to give the title compound.

Step B: tert-butyl (S)-(2,3-bis((tert-butyldimethylsilyl)oxy)propyl)carbamate Into a 500 mL 3-necked round-bottom flask was placed a solution of tert-butyl N-[(2S)-2,3-dihydroxypropyl]carbamate (20 g, 105 mmol, 1 eq) in N,N-dimethylformamide (200 mL), and imidazole (32 g, 470 mmol, 4.50 equiv). Then tert-butyl(chloro)dimethylsilane (40.8 g, 271 mmol, 2.6 eq) was added in several batches at 0° C. The reaction was stirred overnight at room temperature, and then diluted with ethyl acetate (500 mL). The resulting mixture was washed with water (2×400 mL) and brine (400 mL), and then concentrated under vacuum. The resulting residue was applied onto a silica gel column with ethyl acetate/petroleum ether (1:20) to give the title compound.

Step C: tert-butyl (S)-(2-((tert-butyldimethylsilyl)oxy)-3-hydroxpropyl)carbamate Into a 5 L 4-necked round-bottom flask was placed a solution of tert-butyl N-[(2S)-2,3-bis[(tert-butyldimethylsilyl)oxy]propyl]carbamate (200 g, 476 mmol, 1 eq) in ethanol (2 L), and PPTS (110 g, 1 eq). The reaction was stirred overnight at room temperature, and then quenched by the addition of TEA (100 mL). The resulting mixture was concentrated under vacuum. The resulting solution was diluted with 2 L of ethyl acetate, then washed with H$_2$O (2 L). The mixture was dried over anhydrous magnesium sulfate and concentrated under vacuum. The resulting residue was purified on a silica gel column with ethyl acetate/petroleum ether (1:3) to give the title compound.

Step D: (S)-3-((tert-butoxycarbonyl)amino)-2-((tert-butyldimethylsilyl)oxy)propyl methanesulfonate A solution of tert-butyl N-[(2S)-2-[(tert-butyldimethylsilyl)oxy]-3-hydroxypropyl]carbamate (40 g, 131 mmol, 1 equiv) in dichloromethane (400 mL), TEA (36.5 mL, 2 eq), and methanesulfonyl chloride (14.5 mL, 1.50 eq) was stirred for 2 h at room temperature. Then the reaction was quenched by the addition of sodium bicarbonate (aqueous, 200 mL). The resulting solution was extracted with ethyl acetate (300 mL). The organic layers combined, dried over anhydrous magnesium sulfate and concentrated under vacuum to give the title compound.

Step E: tert-butyl (S)-(3-bromo-2-((tert-butyldimethylsilyl)oxy)propyl)carbamate A solution of tert-butyl N-[(2S)-2-[(tert-butyldimethylsilyl)oxy]-3-(methanesulfonyloxy)propyl]-carbamate (47 g, 123 mmol, 1 eq) in tetrahydrofuran (1600 mL) and bromolithium (53 g, 610 mmol, 5 eq) was stirred for 2 days at 70° C. Then the reaction mixture was diluted with H$_2$O (500 mL), and the resulting solution was extracted with 500 mL of ethyl acetate. The combined organic layers were dried over anhydrous sodium sulfate and concentrated under vacuum. The resulting residue was purified on a silica gel column with ethyl acetate/petroleum ether (1:30) to give the title compound.

Step F: tert-butyl (S)-(3-(4-bromo-1H-pyrazol-1-yl)-2-((tertbutyldimethylsilyl)oxy)-propyl)carbamate A solution of tert-butyl N-[(2S)-3-bromo-2-[(tert-butyldimethyl-silyl)oxy]propyl]carbamate (210 g, 570 mmol, 1.20 equiv), N,N-dimethylformamide (2 L), 4-bromo-1H-pyrazole (70 g, 476 mmol, 1 eq), and $Cs_2CO_3$ (313 g, 957 mmol, 2 eq) was stirred overnight at 70° C. Then the reaction mixture was diluted with 2 L of EA. The resulting mixture was washed with $H_2O$ (2×4 L). The mixture was dried over anhydrous magnesium sulfate and concentrated under vacuum. The resulting residue was applied onto a silica gel column with ethyl acetate/petroleum ether (1:10) to give the title compound. LC-MS: (ES, m/z): 434 [M−H]⁻ ¹H-NMR: (400 MHz, d-DMSO, ppm): δ−0.32 (3H, s), 0.05 (3H, s), 0.76 (9H, s), 1.38 (9H, s), 2.93-3.00 (2H, m), 3.91-3.96 (2H, m), 4.10-4.15 (2H, m), 6.93-6.96 (1H, t), 7.54 (1H, s), 7.87 (1H, s)

Example 1

(S)-3-((Z)-2-(2-aminothiazol-4-yl)-2-(((S)-2-(4-(1-(3-ammoniopropyl)-2-methyl-1H-pyrazol-2-ium-4-yl)phenoxy)-1-carboxyethoxy)imino)acetamido)-2,2-dimethyl-4-oxoazetidin-1-yl sulfate 2,2,2-trifluoroacetate (C1)

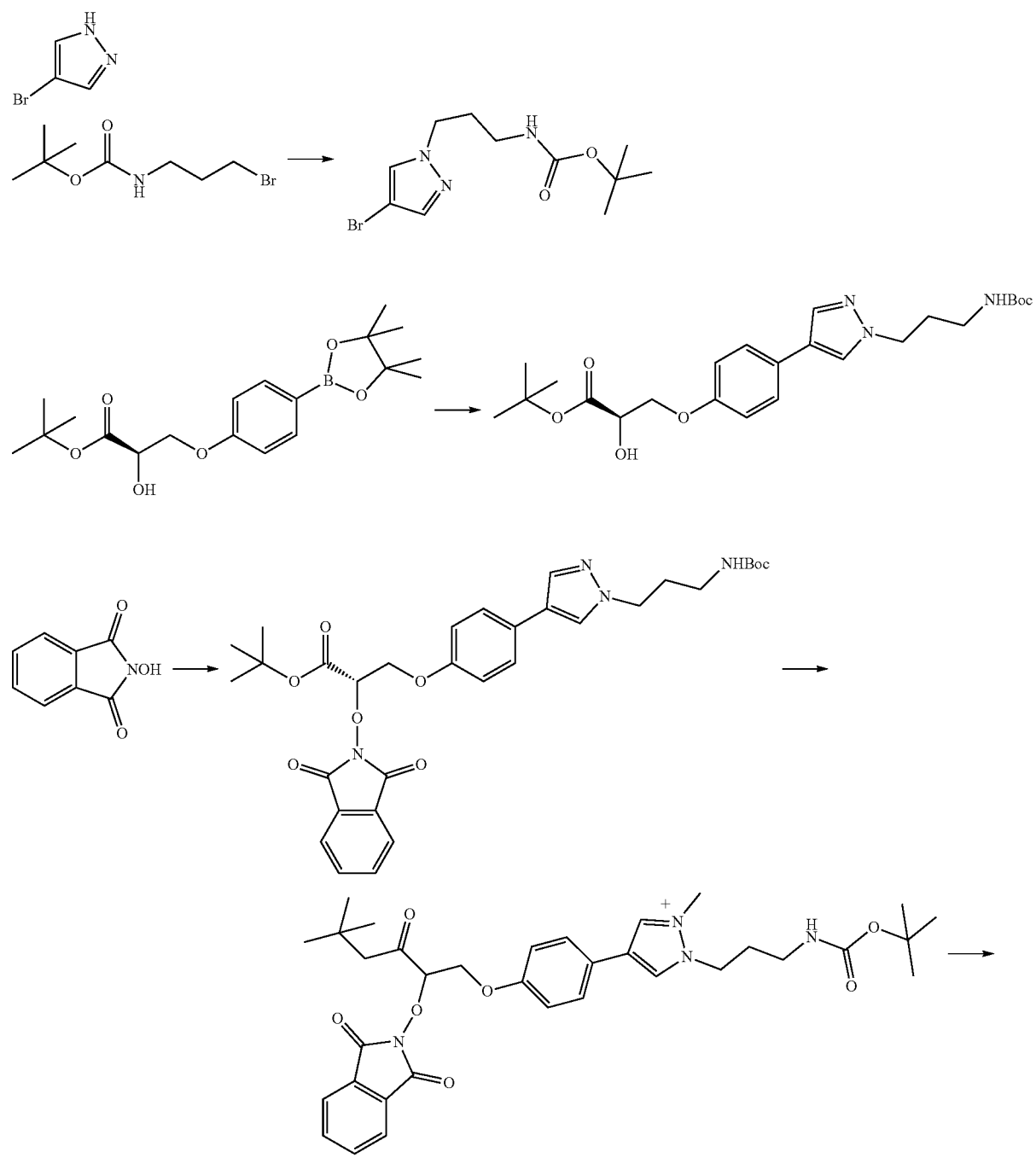

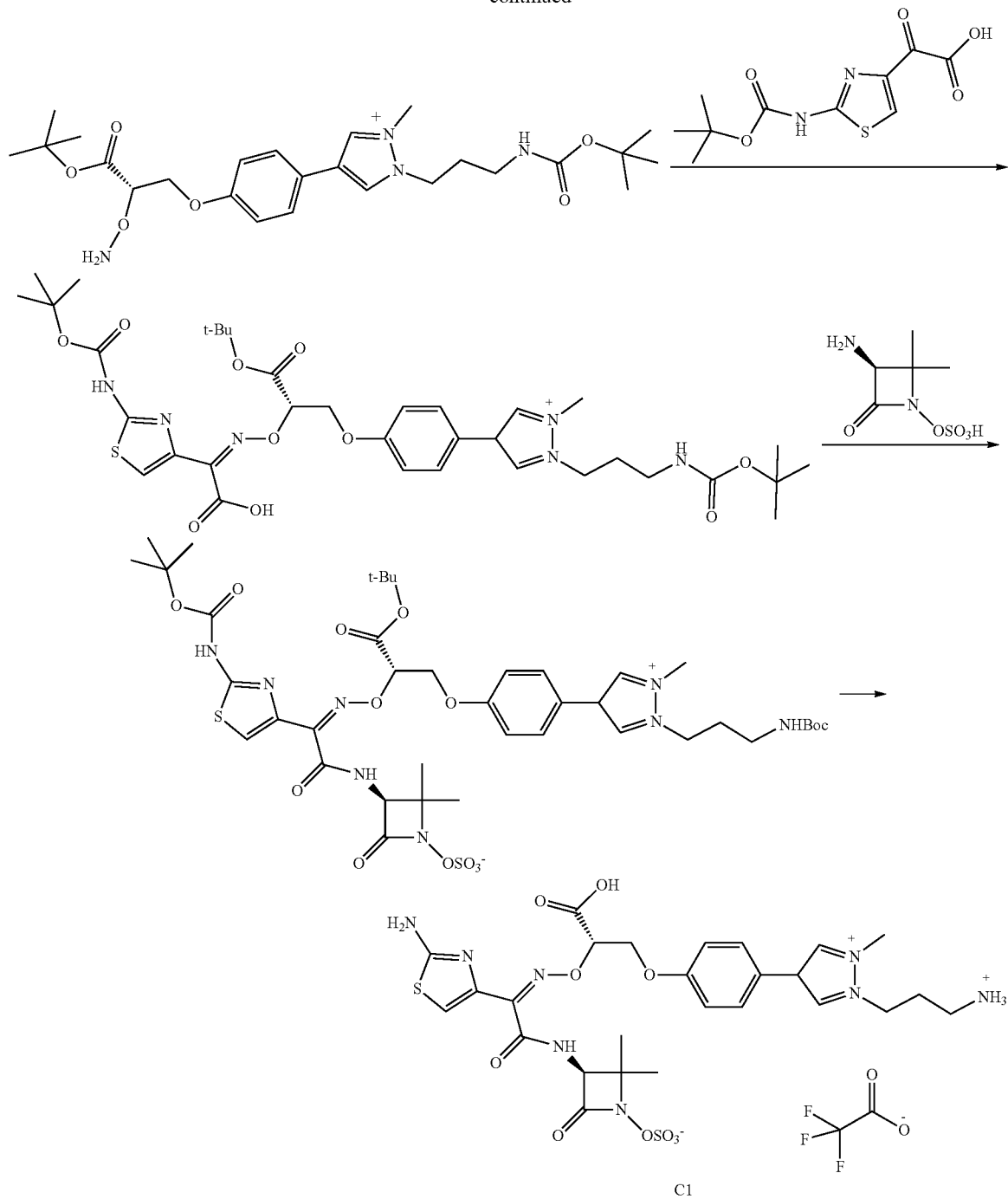

C1

Step A: tert-Butyl (3-(4-bromo-1H-pyrazol-1-yl)propyl)carbamate

A solution 4-bromo-1H-pyrazole (3 g, 20.4 mmol), tert-butyl (3-bromopropyl)carbamate (4.86 g, 20.4 mmol) and cesium carbonate (9.98 g, 30.6 mmol) in DMF (20 ml) was stirred at room temperature overnight. The mixture was diluted with water (30 ml) and extracted with EtOAc (3×10 ml). The extracts were combined, dried over MgSO$_4$ and concentrated to dryness. The residue was purified by flash column (biotage 80 g gold silica column) chromatography, eluted with a gradient of DCM/MeOH (0-10%) to obtain the title compound. LC-MS [M+H]$^+$: m/z 304.19. $^1$HNMR (500 MHz, CDCl$_3$) δ 7.45 (s, 2H), 4.15 (m, 2H), 3.10 (m, 2H), 1.99 (m, 2H), 1.27 (s, 9H)

Step B: tert-Butyl (R)-3-(4-(1-(3-((tert-butoxycarbonyl)amino)propyl)-1H-pyrazol-4-yl)phenoxy)-2-hydroxypropanoate To a solution of (S)-tert-butyl 2-hydroxy-3-(4-(4,4,5,5-tetramethyl-1,3,2-dioxaborolan-2-yl)phenoxy)propanoate (5 g, 13.7 mmol), tert-butyl (3-(4-bromo-1H-pyrazol-1-yl)propyl)carbamate (4.18 g, 13.7 mmol), and 1,1'-bis(di-tertbutylphosphino)ferrocene palladium dichloride (0.895 g, 1.37 mmol) in THF (150 ml) was added the 1M aqueous solution of potassium phosphate tribasic (41.2 ml, 41.2 mmol) in a 25 mL vial. The vial was sealed, degased (3×), and refilled with $N_2$, and stirred at 60° C. overnight. LC-MS indicated complete conversion. The reaction mixture was diluted with saturated $NH_4Cl$ solution (100 mL). The organic phase was separated and the aqueous phase was extracted with EtOAc (2×60 mL). The organic extracts were combined, dried over $MgSO_4$ and concentrated to dryness. The residue was purified on Flash $SiO_2$ column (120 g gold) with Hexane/EtOAc (0-100%) to obtain the title compound. LC-MS $[M+H]^+$: m/z 462.56. $^1$HNMR (500 MHz, $CDCl_3$) δ 7.78 (s, 1H), 7.61 (s, 1H), 7.40 (d, J=7.5 Hz, 2H), 6.96 (d, J=7.5 Hz, 2H).4.92 (s, 1H), 4.40 (m, 2H), 4.23 (m, 2H), 3.16 (m, 2H), 2.01 (m, 2H), 1.48 (s, 9H).

Step C: tert-Butyl (S)-3-(4-(1-(3-((tert-butoxycarbonyl)amino)propyl)-1H-pyrazol-4-yl)phenoxy)-2-((1,3-dioxoisoindolin-2-yl)oxy)propanoate To a solution of (S)-tert-butyl 3-(4-(1-(3-((tert-butoxycarbonyl)amino)propyl)-H-pyrazol-4-yl)phenoxy)-2-hydroxypropanoate (2.2 g, 4.77 mmol), 2-hydroxyisoindoline-1,3-dione (0.933 g, 5.72 mmol), and triphenylphosphine (1.50 g, 5.72 mmol) in DCM (100 ml) was added DIAD (1.11 ml, 5.72 mmol). The mixture was stirred at room temperature for 2 hours. LC-MS indicated complete conversion. The mixture was concentrated to dryness, and purified by $SiO_2$ flash chromotography (120 g gold), eluted with Hexane/EtOAc 0-100% to obtain the title compound. LC-MS $[M+H]^+$: m/z 607.59. $^1$HNMR (500 MHz, $CDCl_3$) δ 7.82-7.92 (m, 4H), 7.78 (s, 1H), 7.61 (s, 1H), 7.41 (d, J=7.5 Hz, 2H), 6.92 (d, J=7.5 Hz, 2H).5.12 (s, 1H), 4.54 (m, 2H), 4.25 (s, 2H), 3.18 (m, 2H), 2.12 (m, 2H), 1.48 (s, 9H).

Step D: (S)-4-(4-(3-(tert-Butoxy)-2-((1,3-dioxoisoindolin-2-yl)oxy)-3-oxopropoxy)phenyl)-1-(3-((tert-butoxycarbonyl)amino)propyl)-2-methyl-1H-pyrazol-2-ium To a solution of (S)-tert-butyl 3-(4-(1-(3-((tert-butoxycarbonyl)amino)propyl)-H-pyrazol-4-yl)phenoxy)-2-((1,3-dioxoisoindolin-2-yl)oxy)propanoate (1.8 g, 2.97 mmol) in acetonitrile (100 ml) was added iodomethane (4.21 g, 29.7 mmol). The mixture was sealed in a 250 ml pressure bottle and stirred at 70° C. for 16 hours. LC-MS indicated completion of conversion. The mixture was then cooled to room temperature and concentrated under vacuum to dryness to give the title compound, which was used directly for the next step without further purification. LC-MS $[M]^+$: m/z 621.61

Step E: (S)-4-(4-(2-(Aminooxy)-3-(tert-butoxy)-3-oxopropoxy)phenyl)-1-(3-((tert-butoxycarbonyl)amino)propyl)-2-methyl-1H-pyrazol-2-ium To a solution of (S)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-2-methyl-1H-pyrazol-2-ium iodide (2 g, 2.67 mmol) in acetonitrile (20 ml) was added hydrazine (0.092 ml, 2.94 mmol). The mixture was stirred at room temperature for 2 hours. LC-MS indicated completion of conversion. The mixture was then concentrated under vacuum to dryness to give the title compound, which was used directly for the next step without further purification. LC-MS $[M]^+$: m/z 491.35

Step F: (S,Z)-4-(4-(3-(tert-Butoxy)-2-((((2-((tert-butoxycarbonyl)amino)-thiazol-4-yl)(carboxy)methylene)amino)oxy)-3-oxopropoxy)phenyl)-1-(3-((tert-butoxycarbonyl)amino)propyl)-2-methyl-1H-pyrazol-2-ium To a solution of (S)-4-(4-(2-(aminooxy)-3-(tert-butoxy)-3-oxopropoxy)phenyl)-1-(3-((tert-butoxycarbonyl)amino)-propyl)-2-methyl-1H-pyrazol-2-ium iodide (1.6 g, 2.59 mmol) in ethanol (100 ml) and $ClCH_2CH_2Cl$ (20 ml) was added 2-(2-((tert-butoxycarbonyl)amino)thiazol-4-yl)-2-oxoacetic acid (0.775 g, 2.85 mmol, intermediate 5). The mixture was stirred at room temperature for 4 hours. LC-MS indicated complete conversion. The mixture was concentrated to give the title compound, which was used directly for the next step without further purification. LC-MS $[M]^+$: m/z 745.43

Step G: (S)-3-((Z)-2-(((((S)-1-(tert-Butoxy)-3-(4-(1-(3-((tert-butoxy-carbonyl)amino)propyl)-2-methyl-1H-pyrazol-2-ium-4-yl)phenoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate To a solution of (S,Z)-4-(4-(3-(tert-butoxy)-2-((((2-((tert-butoxycarbonyl)amino)thiazol-4-yl)(carboxy)methylene)amino)oxy)-3-oxopropoxy)phenyl)-1-(3-((tert-butoxycarbonyl)-amino)propyl)-2-methyl-1H-pyrazol-2-ium (1.9 g, 2.17 mmol) in DMF (20 ml) was added DCC (0.898 g, 4.35 mmol) and HOBt (0.667 g, 4.35 mmol). The mixture was then stirred at room temperature for 30 minutes, followed by addition of (S)-3-amino-2,2-dimethyl-4-oxoazetidin-1-yl hydrogen sulfate (0.915 g, 4.35 mmol, from commercial sources CAS: 102507-49-3) and sodium bicarbonate (1.10 g, 13.1 mmol). The final mixture was stirred at room temperature overnight (16 hours). LC-MS indicated complete conversion. The DMF solution was dried under a stream of $N_2$ overnight. The residue was re-dissolved in MeCN/water (2:1, 2.5 mL) and purified by reverse phase ISCO column (130 g), eluted with MeCN/$H_2O$/0.05% TFA (0-100%). The fractions were collected and lyophilized to obtain the title compound. LC-MS $[M]^+$: m/z 938.00. $^1$HNMR (500 MHz, $CDCl_3$) δ 9.53 (s, 1H), 8.94 (m, 2H), 7.68 (m, 2H), 7.14 (m, 2H), 4.95 (s, 1H), 4.60 (m, 2H), 4.42 (s, 2H), 3.08 (m, 2H), 2.14 (m, 2H), 1.47 (s, 9H), 1.40 (s, 9H), 1.37 (s, 9H).

Step H: Mono(4-(4-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)phenyl)-1-(3-ammoniopropyl)-2-methyl-1H-pyrazol-2-ium) mono(2,2,2-trifluoroacetate)

To a solution of 4-(4-((S)-3-(tert-butoxy)-2-(((E)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxo-propoxy)phenyl)-1-(3-((tert-butoxycarbonyl)amino)propyl)-2-methyl-1H-pyrazol-2-ium (40 mg, 0.043 mmol) in DCM (1 mL) was added 1 mL of TFA. The mixture was stirred at room temperature for 30 minutes. LC-MS indicated complete conversion. The mixture was concentrated to dryness under vacuum (no heat), DCM (10 ml) was added and concentrated for three times to remove TFA. The residue was washed with dry MeCN (2×2 ml) to remove impurities. The residue was dissolved in $H_2O$ and purified on prep-HPLC with a MeCN/$H_2O$ (0.05% TFA in both) gradient 0-40% in 10 minutes. Product fractions were collected and lyophilized to obtain the title compound. LC-MS [M]+: m/z 681.48. ¹HNMR (500 MHz, CDCl₃) δ) δ 8.72 (s, 1H), 8.68 (s, 1H), 7.78 (d, J=6.8 Hz, 2H), 7.16 (d, J=6.8, 2H), 7.08 (s, 1H), 5.18 (s, 1H), 4.63 (m, 2H), 4.58 (m, 2H), 4.19 (s, 3H), 3.16 (m, 2H), 2.39 (m, 2H).
Example 2
(S)-3-((Z)-2-(2-aminothiazol-4-yl)-2-(((S)-2-(4-(1-(3-ammoniopropyl)-3-methyl-1H-imidazol-3-ium-4-yl)phenoxy)-1-carboxyethoxy)imino)acetamido)-2,2-dimethyl-4-oxoazetidin-1-yl-sulfate C2)
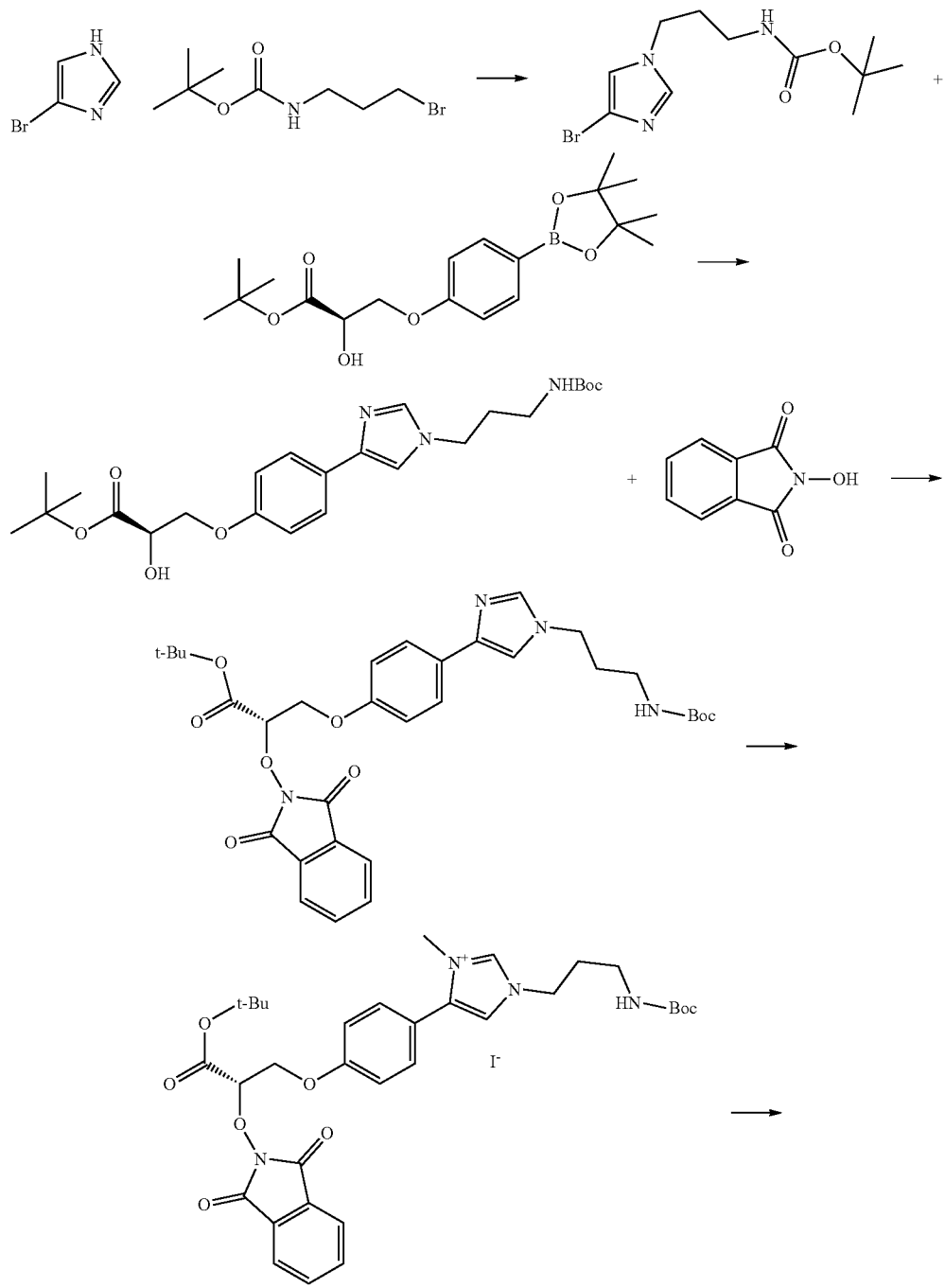

-continued
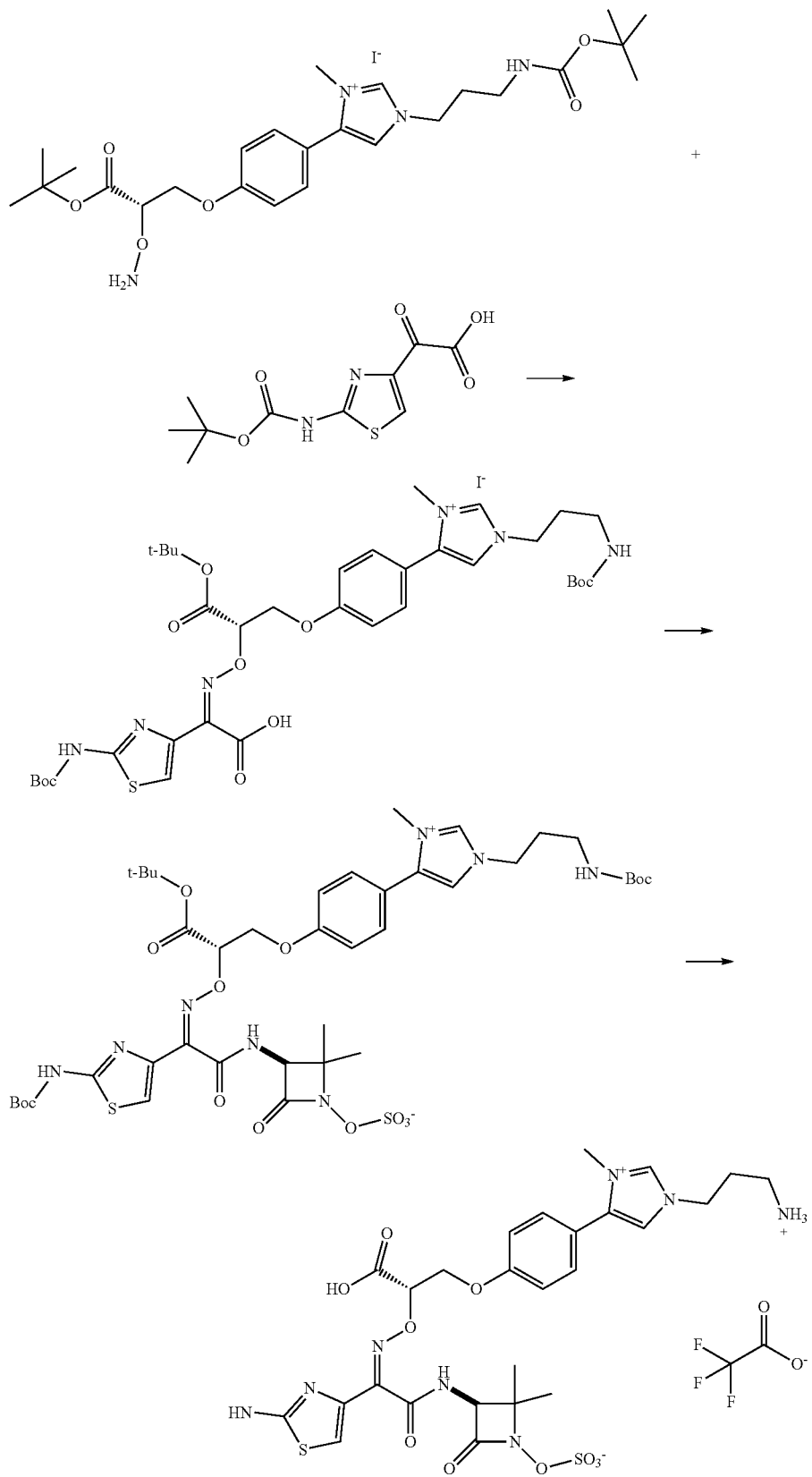

Step A: tert-Butyl (3-(4-bromo-1H-imidazol-1-yl) propyl)carbamate

To a solution of 4-bromo-1H-imidazole (1 g, 6.80 mmol) in DMF (20 ml) was added NaH (0.272 g, 6.80 mmol) at 0° C. The mixture was stirred for 10 minutes. tert-butyl (3-bromopropyl)carbamate (1.62 g, 6.80 mmol) was added. The solution was stirred at room temperature for 2 hours and then heated at 50° C. for 1 hour. The mixture was quenched with water (50 ml) and extracted with EtOAc (3×20 ml). The organic layer was washed with water (30 mL), brine (30 mL) and dried over $Na_2SO_4$. The solvent was removed under vacuum. The residue was purified by column chromatography on silica gel (Redi 40 g gold column), and eluted with EtOAc/Hexane (0-100%, 6 cv; 100%, 10 cv) to give the title compound. LC-MS $[M+H]^+$: m/z 304.19. $^1$HNMR (500 MHz, $CDCl_3$) δ 7.40 (s, 1H); 6.94 (s, 1H); 4.67 (s, 1H); 3.98 (t, J=7.0 Hz, 2H); 3.17 (d, J=7.5 Hz, 2H); 1.98 (p, J=6.8 Hz, 2H); 1.47 (s, 9H).

Step B: tert-Butyl (R)-3-(4-(1-(3-((tert-butoxycarbonyl)amino)propyl)-H-imidazol-4-yl)phenoxy)-2-hydroxypropanoate The procedure was the same as step B in Example 1 with the reagent of tert-butyl (3-(4-bromo-H-imidazol-1-yl)propyl)carbamate, (R)-tert-butyl 2-hydroxy-3-(4-(4,4,5,5-tetramethyl-1,3,2-dioxaborolan-2-yl)phenoxy)propanoate (300 mg, 0.824 mmol), tert-butyl (3-(4-bromo-1H-imidazol-1-yl)propyl)carbamate (276 mg, 0.906 mmol)(intermediate 4), 1,1'-bis(di-tert-butylphosphino)ferrocene palladium dichloride (53.7 mg, 0.082 mmol), THF (4 ml) and potassium phosphate (2.471 ml, 2.471 mmol, 1M aq.). LC-MS $[M+H]^+$: m/z 462.

Step C: tert-Butyl (S)-3-(4-(1-(3-((tert-butoxycarbonyl)amino)propyl)-1H-imidazol-4-yl)phenoxy)-2-((1,3-dioxoisoindolin-2-yl)oxy)propanoate The procedure was the same as Step C in Example 1 with the reagent of tert-butyl (R)-3-(4-(1-(3-((tert-butoxycarbonyl)-amino)propyl)-1H-imidazol-4-yl)phenoxy)-2-hydroxypropanoate (0.25 g, 0.542 mmol), 2-hydroxyisoindoline-1,3-dione (0.097 g, 0.596 mmol), triphenylphosphine (0.170 g, 0.650 mmol), DIAD (0.126 ml, 0.650 mmol) and THF (2 ml). LC-MS [M+H]: m/z 607.

Step D: (S)-4-(4-(3-(tert-Butoxy)-2-((1,3-dioxoisoindolin-2-yl)oxy)-3-oxopropoxy)phenyl)-1-(3-((tert-butoxycarbonyl)amino)propyl)-3-methyl-1H-imidazol-3-ium iodide The procedure was the same as Step D in Example 1 with the reagents tert-butyl (S)-3-(4-(1-(3-((tert-butoxycarbonyl)amino)propyl)-H-imidazol-4-yl)phenoxy)-2-((1,3-dioxoisoindolin-2-yl)oxy)propanoate (0.17 g, 0.280 mmol), MeI (0.105 ml, 1.681 mmol) in MeCN (2 ml). LC-MS $[M]^+$: m/z 621.

Step E: (S)-4-(4-(2-(Aminooxy)-3-(tert-butoxy)-3-oxopropoxy)phenyl)-1-(3-((tert-butoxycarbonyl)amino)propyl)-3-methyl-1H-imidazol-3-ium iodide The procedure was the same as step E in Example 1 with the reagents (S)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-3-methyl-1H-imidazol-3-ium iodide (0.210 g, 0.28 mmol), hydrazine (8.79 µl, 0.280 mmol) in EtOH (4 ml). LC-MS $[M]^+$: m/z 491.

Step F: (S,Z)-4-(4-(3-(tert-butoxy)-2-((((2-((tert-butoxycarbonyl)amino)-thiazol-4-yl)(carboxy)methylene)amino)oxy)-3-oxopropoxy)phenyl)-1-(3-((tert-butoxy-carbonyl)amino)propyl)-3-methyl-1H-imidazol-3-ium iodide The procedure was the same as step F in Example 1 with the reagents (S)-4-(4-(2-(aminooxy)-3-(tert-butoxy)-3-oxopropoxy)phenyl)-1-(3-((tert-butoxycarbonyl)amino)propyl)-3-methyl-1H-imidazol-3-ium(0.173 g, 0.28 mmol), 2-(2-((tert-butoxycarbonyl)amino)thiazol-4-yl)-2-oxoacetic acid (0.080 g, 0.294 mmol)(intermediate 5) in EtOH (4 ml) and $ClCH_2CH_2Cl$ (2 ml). LC-MS $[M]^+$: m/z 745.

Step G: (S)-3-((Z)-2-((((S)-1-(tert-Butoxy)-3-(4-(1-(3-((tert-butoxycarbonyl)amino)propyl)-3-methyl-1H-imidazol-3-ium-4-yl)phenoxy)-1-oxopropan-2-yl)oxy)imino)-2-(2-((tert-butoxycarbonyl)amino) thiazol-4-yl)acetamido)-2,2-dimethyl-4-oxoazetidin-1-yl sulfate The procedure was same as step G in Example 1 with the reagent (S,Z)-4-(4-(3-(tert-butoxy)-2-((((2-((tert-butoxycarbonyl)amino)thiazol-4-yl)(carboxy)methylene)amino)oxy)-3-oxopropoxy)phenyl)-1-(3-((tert-butoxycarbonyl)amino)propyl)-3-methyl-1H-imidazol-3-ium, I-(0.244 g, 0.280 mmol) in DMF (4 ml), DCC (0.144 g, 0.699 mmol), HOBT (0.107 g, 0.699 mmol, (S)-3-amino-2,2-dimethyl-4-oxoazetidin-1-yl hydrogen sulfate (0.118 g, 0.559 mmol) and sodium bicarbonate (0.117 g, 1.398 mmol). After reaction completion, the crude mixture was filtered and purified directly by RP-HPLC(Gilson) (C-18 column), eluting with $ACN/H_2O/0.05\%$ TFA (20-100%, 10 min). The product fraction was lyophilized to give the title compound. LC-MS: $[M]^+$ m/z 937.85.

Step H: Mono(4-(4-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)phenyl)-1-(3-ammoniopropyl)-3-methyl-1H-imidazol-3-ium) mono(2,2,2-trifluoroacetate)

To a solution of 4-(4-((S)-3-(tert-butoxy)-2-(((Z)-1-(2-((tert-butoxycarbonyl)amino)thiazol-4-yl)-2-(((S)-2,2-dimethyl-4-oxo-1-(sulfoxy)azetidin-3-yl)amino)-2-oxoethylidene)amino)oxy)-3-oxopropoxy)phenyl)-1-(3-((tert-butoxycarbonyl)amino)propyl)-3-methyl-1H-imidazol-3-ium (0.17 g, 0.162 mmol) in $CH_2Cl_2$ (0.5 ml) was added TFA (0.5 ml). The solution was stirred at room temperature for hour. The solvent was removed under vacuum. The residue was washed with $Et_2O$ twice and dried under vacuum to give the crude solid. The crude product was dissolved in water (2 ml) and DMSO (0.5 ml), and then purified on RP-HPLC (Gilson) (C-18 colunm), eluted with MeCN/Water (0.05% formic acid in both), gradient 0-60% in 15 minutes. Product fractions were collected and lyophilized to obtain the title compound. LC-MS $[M]^+$: m/z 681.38. $^1$H NMR (500 MHz, MeOD): $δ_H$ 8.97 (d, J=1.8 Hz, 1H); 7.73 (s, 1H); 7.49 (d, J=8.4 Hz, 2H); 7.15-7.17 (m, 2H); 6.93 (s, 1H); 5.15-5.16 (m, 1H); 4.64-4.67 (m, 1H); 4.53-4.57 (m, 2H); 4.38 (t, J=7.0 Hz, 2H); 3.86 (s, 3H); 3.07-3.10 (m, 2H); 2.30-2.33 (m, 2H); 1.53 (s, 3H); 1.18 (s, 3H).

TABLE 1

By using generally the same procedures as in Example 2, substituting the appropriate reagents, Example 3 was synthesized and characterized by LC/MS.

| EXAMPLE | Name | Structure | LCMS [M]+ |
|---|---|---|---|
| 33 | (S)-3-((Z)-2-(((S)-2-(4-(1-(3-aminopropyl)-2-methyl-1H-pyrazol-2-ium-4-yl)-3,5-difluorophenoxy)-1-carboxyethoxy)imino)-2-(2-aminothiazol-4-yl)acetamido)-2,2-dimethyl-4-oxoazetidin-1-yl sulfate compound with 2,2,2-trifluoroacetic acid (1:1) | 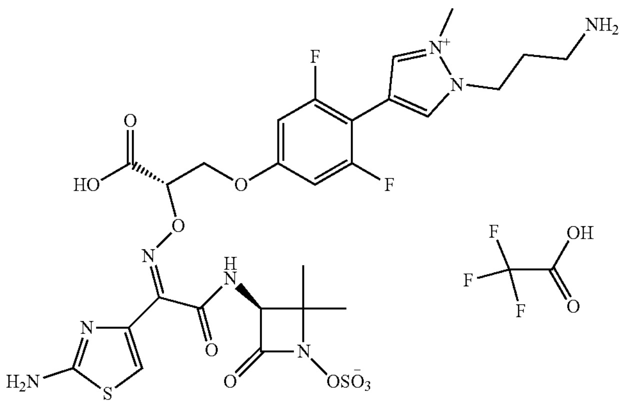 | 717.46 |

Example 4

(S,Z)-3-(2-((2-(4-(1-(3-aminopropyl)-2-methyl-1H-pyrazol-2-ium-4-yl)phenoxy)ethoxy)imino)-2-(2-aminothiazol-4-yl)acetamido)-2,2-dimethyl-4-oxoazetidin-1-yl sulfate (C4)

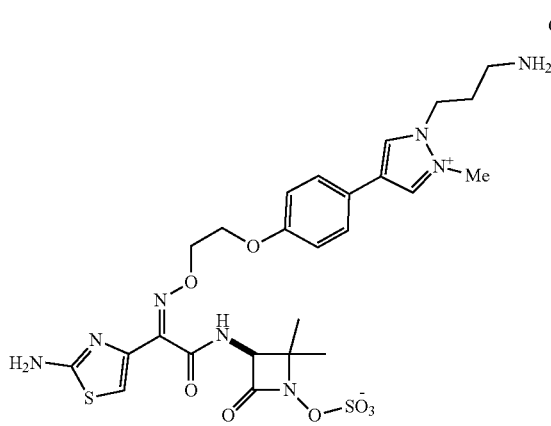

C4

Step A: tert-Butyl (3-(4-(4,4,5,5-tetramethyl-1,3,2-dioxaborolan-2-yl)-1H-pyrazol-1-yl)propyl)carbamate A solution 4-(4,4,5,5-tetramethyl-1,3,2-dioxaborolan-2-yl)-1H-pyrazole (2 g, 10.3 mmol) tert-butyl (3-bromopropyl)carbamate tert-butyl (3-bromopropyl)carbamate (2.45 g, 10.3 mmol) and cesium carbonate (3.36 g, 10.3 mmol) in DMF (20 ml) was stirred at 60° C. overnight. The mixture was partitioned between EtOAc and water. The layers were separated, and the organic layer was washed with water. The organics were washed with brine, dried ($Na_2SO_4$) and concentrated to dryness. The resulting title compound was carried to the next step without purification. LC-MS [M+H]+: m/z 352.6.

Step B: 1-Bromo-4-(2-bromoethoxy)benzene 1,2-Dibromoethane (4.26 mL, 49.4 mmol) and cesium carbonate (6.83 g, 49.4 mmol) were added to a stirred solution of 4-bromophenol (1.40 g, 8.09 mmol) in acetone (10 mL). The reaction mixture was heated to 80° C. for 8 hours, at which time, the reaction was cooled to room temperature and filtered. The organic filtrate was concentrated, and the resulting crude residue was purified by column chromatography on silica gel (10-100% gradient of EtOAc:hexane as eluent) to afford the title compound. $^1$H-NMR (500 MHz, $CDCl_3$) δ 7.42 (br, 2H), 6.90 (br, 2H), 4.31 (m, 2H), 3.71 (m, 2H).

Step C: tert-Butyl (3-(4-(4-(2-bromoethoxy)phenyl)-1H-pyrazol-1-yl)propyl)carbamate 2.0 M aqueous sodium carbonate (1.60 mL, 3.20 mmol) was added to a microwave vial containing a stirred solution of 1-bromo-4-(2-bromoethoxy)benzene (300 mg, 1.07 mmol), tert-butyl (3-(4-(4,4,5,5-tetramethyl-1,3,2-dioxaborolan-2-yl)-1H-pyrazol-1-yl)propyl)-carbamate (565 mg, 1.61 mmol) and 1,1'-bis(di-tert-butylphosphino)ferrocene palladium dichloride (78 mg, 0.11 mmol) in 1,4-dioxane (4.3 mL). The mixture was degassed via a stream of nitrogen gas for approximately 5 minutes, at which point, the vial was sealed and heated in a microwave reactor to 120° C. for 20 minutes. After cooling to room temperature, the mixture was filtered through a pad of Celite™ (diatomaceous earth), and the solid layer was rinsed with EtOAc. The combined organics were concentrated, and the resulting crude residue was purified by column chromatography on silica gel (0-60% EtOAc:hexanes as eluent) to afford the title compound. LC-MS [M+Na]+: m/z 446.3.

Step D: tert-Butyl (3-(4-(4-(2-((1,3-dioxoisoindolin-2-yl)oxy)ethoxy)phenyl)-1H-pyrazol-1-yl)propyl)carbamate N-Hydroxyphthalimide (185 mg, 1.13 mmol) was added to a stirred solution of tert-butyl (3-(4-(4-(2-bromoethoxy)phenyl)-1H-pyrazol-1-yl)propyl)carbamate (320 mg, 0.754 mmol) and DBU (138 mg, 0.905 mmol) in DMF (3.8 mL), and the resulting mixture was heated to 50° C. After 16 hours, the reaction mixture was cooled to room temperature and EDC (117 mg, 0.754 mmol) was added. After stirring at room temperature for 30 minutes, the reaction mixture was partitioned between EtOAc and water. The layers were separated, and the organic layer was washed with water, followed by brine. The organics were dried (Na$_2$SO$_4$), filtered and concentrated to yield a crude residue that was purified by column chromatography on silica gel (0-50% gradient EtOAc:hexanes as eluent) to afford the title compound. LC-MS [M+H]$^+$: m/z 507.3.

The above intermediate (the product of Step D) was converted to (S,Z)-3-(2-((2-(4-(1-(3-aminopropyl)-2-methyl-1H-pyrazol-2-ium-4-yl)phenoxy)ethoxy)imino)-2-(2-aminothiazol-4-yl)acetamido)-2,2-dimethyl-4-oxoazetidin-1-yl sulfate following procedures similar to those described in steps D-H for Example 1. LC-MS [M+H]$^+$: m/z 637.2.

Example 5

(S,Z)-3-(2-((2-(4-(1-(3-aminopropyl)-1H-pyrazol-4-yl)phenoxy)ethoxy)imino)-2-(2-aminothiazol-4-yl)acetamido)-2,2-dimethyl-4-oxoazetidin-1-yl sulfate (C5)

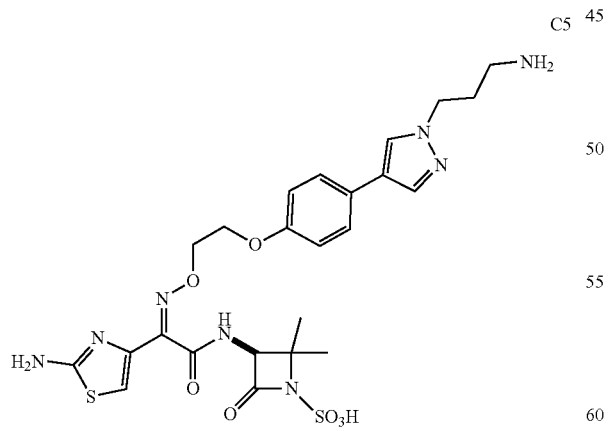

Compound 5 was prepared from tert-Butyl (3-(4-(4-(2-((1,3-dioxoisoindolin-2-yl)oxy)ethoxy)phenyl)-1H-pyrazol-1-yl)propyl)carbamate following procedures similar to those described in steps E-H for Example 1. LC-MS [M+H]$^+$: m/z 623.3.

Example 6

(S)-3-(4-(1-(3-aminopropyl)-1H-pyrazol-4-yl)phenoxy)-2-((((Z)-1-(2-aminothiazol-4-yl)-2-(((2S,3S)-2-methyl-4-oxo-1-sulfoazetidin-3-yl)amino)-2-oxoethylidene)amino)oxy)propanoic acid (C6)

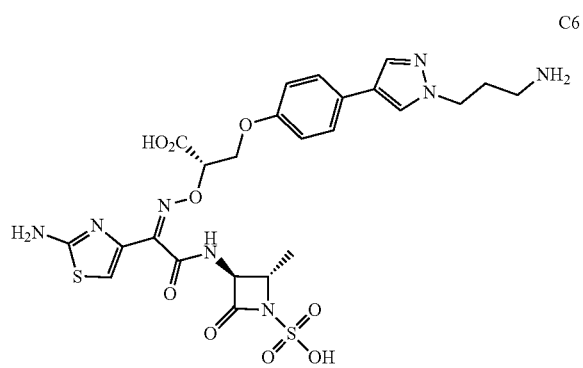 [SMILES: C[C@H]1[C@H](NC(=O)/C(=N\O[C@@H](COc2ccc(-c3cnn(CCCN)c3)cc2)C(=O)O)c2csc(N)n2)C(=O)N1S(=O)(=O)O]

Compound 6 was prepared following procedures similar to those described above for Example 1, by omitting step D and substituting (2S,3S)-3-amino-2-methyl-4-oxoazetidine-1-sulfonic acid (from commercial sources CAS: 80080-65-1) for (S)-3-amino-2,2-dimethyl-4-oxoazetidin-1-yl hydrogen sulfate where appropriate. LC-MS [M+H]$^+$: m/z 637.4.

Example 7

(2S,3S)-3-(((Z)-2-(((S)-2-(4-(1-(3-aminopropyl)-2-methyl-1H-pyrazol-2-ium-4-yl)phenoxy)-1-carboxyethoxy)imino)-2-(2-aminothiazol-4-yl)acetamido)-2-methyl-4-oxoazetidine-1-sulfonate (C7)

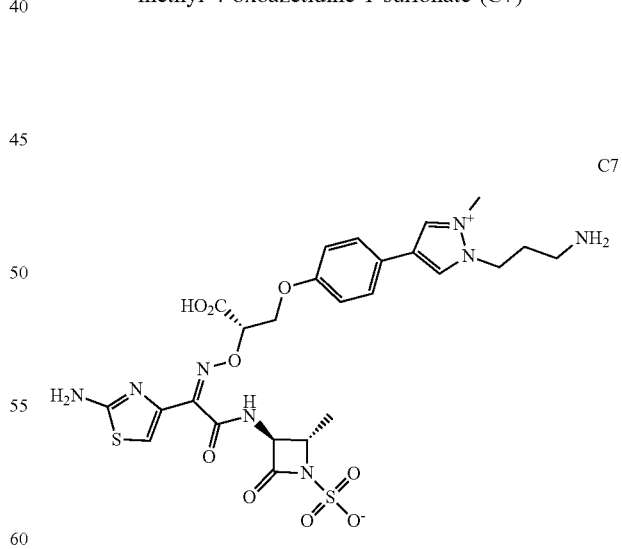

Compound 7 was prepared following procedures similar to those described above for Example 1, substituting (2S,3S)-3-amino-2-methyl-4-oxoazetidine-1-sulfonic acid (CAS: 80582-09-8) for (S)-3-amino-2,2-dimethyl-4-oxoazetidin-1-yl hydrogen sulfate. LC-MS [M+H]$^+$: m/z 651.4.

81

Example 8

(S)-3-(4-(1-(3-aminopropyl)-1H-pyrazol-4-yl)phenoxy)-2-((((Z)-1-(2-aminothiazol-4-yl)-2-(((2R,3S)-2-methyl-4-oxo-1-sulfoazetidin-3-yl)amino)-2-oxoethylidene)amino)oxy)propanoic acid (C8)

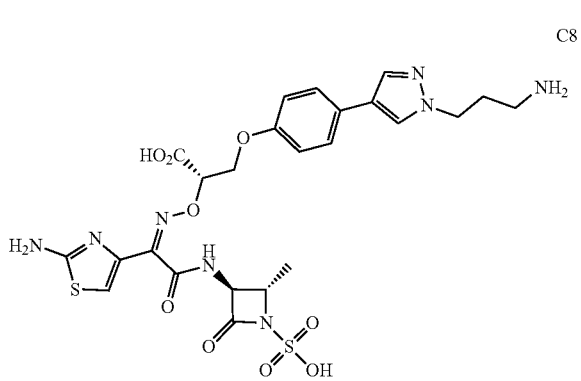 [SMILES: C[C@H]1[C@H](NC(=O)/C(=N\O[C@@H](COc2ccc(-c3cnn(CCCN)c3)cc2)C(=O)O)c2csc(N)n2)C(=O)N1S(=O)(=O)O]

Compound 8 was prepared following procedures similar to those described above for Example 1, by omitting step D and substituting (2R,3S)-3-amino-2-methyl-4-oxoazetidine-1-sulfonic acid for (S)-3-amino-2,2-dimethyl-4-oxoazetidin-1-yl hydrogen sulfate where appropriate. LC-MS [M+H]⁺: m/z 637.4.

Example 9

(2R,3S)-3-((Z)-2-(((S)-2-(4-(1-(3-aminopropyl)-2-methyl-1H-pyrazol-2-ium-4-yl)phenoxy)-1-carboxyethoxy)imino)-2-(2-aminothiazol-4-yl)acetamido)-2-methyl-4-oxoazetidine-1-sulfonate (C9)

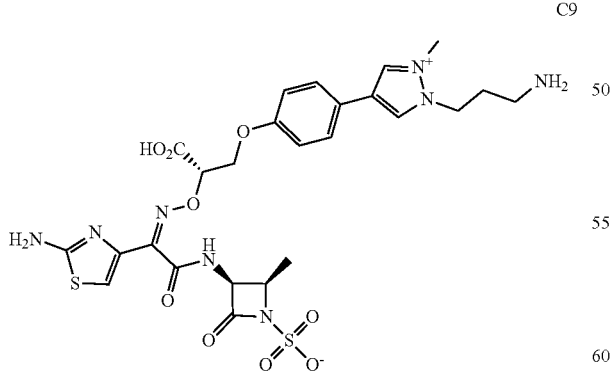

Compound 9 was prepared following procedures similar to those described above for Example 1, substituting (2R,3S)-3-amino-2-methyl-4-oxoazetidine-1-sulfonic acid for (S)-3-amino-2,2-dimethyl-4-oxoazetidin-1-yl hydrogen sulfate. LC-MS [M+H]⁺: m/z 651.3.

82

Example 10

(S)-3-(4-(1-(3-Aminopropyl)-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (C10)

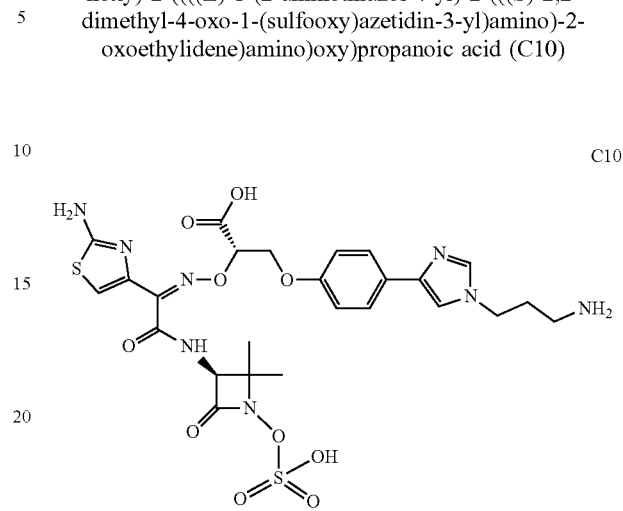

Step A: tert-Butyl (S)-2-(aminooxy)-3-(4-(1-(3-((tert-butoxycarbonyl)amino)propyl)-1H-imidazol-4-yl)phenoxy)propanoate The procedure was the same as step E in Example 1 with the reagents (S)-tert-butyl 3-(4-(1-(3-((tert-butoxycarbonyl)amino)propyl)-H-imidazol-4-yl)phenoxy)-2-((1,3-dioxoisoindolin-2-yl)oxy)propanoate (80 mg, 0.109 mmol) (from step C in Example 2), hydrazine (3.42 μl, 0.109 mmol) in EtOH (4 ml). LC-MS [M+H]⁺: m/z 477.26.

Step B: (S,Z)-2-(((1-(tert-Butoxy)-3-(4-(1-(3-((tert-butoxycarbonyl)amino)propyl)-1H-imidazol-4-yl)phenoxy)-1-oxopropan-2-yl)oxy)imino)-2-(2-((tert-butoxycarbonyl)-amino)thiazol-4-yl)acetic acid The procedure was the same as step F in Example 1 with the reagents 2-(2-((tert-butoxycarbonyl)amino)thiazol-4-yl)-2-oxoacetic acid (42.0 mg, 0.154 mmol) (intermediate 6) and (S)-tert-butyl 2-(aminooxy)-3-(4-(1-(3-((tert-butoxycarbonyl)amino)propyl)-1H-imidazol-4-yl)phenoxy)propanoate (70 mg, 0.147 mmol) in EtOH (4 ml) and ClCH₂CH₂Cl (2 ml). LC-MS [M+H]⁺: m/z 731.34.

Step C: tert-Butyl (S)-3-(4-(1-(3-((tert-butoxycarbonyl)amino)propyl)-1H-imidazol-4-yl)phenoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate The procedure was the same as step G in Example 1 with the reagents (S,Z)-2-(((1-(tert-butoxy)-3-(4-(1-(3-((tert-butoxycarbonyl)amino)propyl)-1H-imidazol-4-yl)phenoxy)-1-oxopropan-2-yl)oxy)imino)-2-(2-((tert-butoxycarbonyl)amino)thiazol-4-yl)acetic acid (107 mg, 0.146 mmol), DCC (76 mg, 0.366 mmol), HOBT (56.1 mg, 0.366 mmol), (S)-3-amino-2,2-dimethyl-4-oxoazetidin-1-yl hydrogen sulfate (61.6 mg, 0.293 mmol) and sodium bicarbonate (61.5 mg, 0.732 mmol) in DMF (4 ml). The purification method was the same as in step G in Example 2. LC-MS [M+HM+H]⁺: m/z 923.48.

Step D: (S)-3-(4-(1-(3-Aminopropyl)-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid The procedure was the same as step H in Example 2 with the reagents (S)-tert-butyl 3-(4-(1-(3-((tert-butoxycarbonyl)amino)propyl)-H-imidazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate (36 mg, 0.035 mmol) in CH$_2$Cl$_2$ (0.5 ml) and TFA (0.5 m, 6.49 mmol). LC-MS [M]$^+$: m/z 667.24. $^1$H NMR (500 MHz, DMSO): δ$_H$ 9.42 (d, J=8.0 Hz, 1H); 7.76 (s, 1H); 7.27 (s, 2H); 7.00 (d, J=8.4 Hz, 2H); 6.79 (s, 1H); 4.93 (s, 1H); 4.61 (d, J=7.9 Hz, 1H); 4.34 (d, J=32.5 Hz, 2H); 4.14 (s, 2H); 2.78 (s, 2H); 2.06 (br s, 2H); 1.36 (s, 3H); 1.12 (s, 3H).

Example 11

(S)-3-((Z)-2-(2-Amino-5-chlorothiazol-4-yl)-2-(((S)-2-(4-(1-(3-aminopropyl)-2-methyl-1H-pyrazol-2-ium-4-yl)phenoxy)-1-carboxyethoxy)imino)acetamido)-2,2-dimethyl-4-oxoazetidin-1-yl sulfate
(C11)

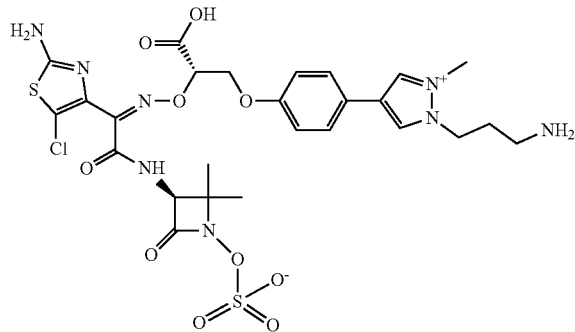

C11

Step A: (S,Z)-4-(4-(3-(tert-Butoxy)-2-((((2-((tert-butoxycarbonyl)amino)-5-chlorothiazol-4-yl)(carboxy)methylene)amino)oxy)-3-oxopropoxy)phenyl)-1-(3-((tert-butoxycarbonyl)-amino)propyl)-2-methyl-1H-pyrazol-2-ium iodide The procedure was the same as step F in Example 1 with the reagents 2-(2-((tert-butoxycarbonyl)amino)-5-chlorothiazol-4-yl)-2-oxoacetic acid (0.052 g, 0.170 mmol, Intermediate 6) and (S)-4-(4-(2-(aminooxy)-3-(tert-butoxy)-3-oxopropoxy)phenyl)-1-(3-((tert-butoxycarbonyl)amino)propyl)-2-methyl-1H-pyrazol-2-ium, Iodide (0.1 g, 0.162 mmol) (from step E in Example 1), EtOH (4 ml) and ClCH$_2$CH$_2$Cl (2 ml). LC-MS [M]$^+$: m/z 779.30.

Step B: (S)-3-((Z)-2-((((S)-1-(tert-Butoxy)-3-(4-(1-(3-((tert-butoxycarbonyl)amino)propyl)-2-methyl-1H-pyrazol-2-ium-4-yl)phenoxy)-1-oxopropan-2-yl)oxy)imino)-2-(2-((tert-butoxycarbonyl)amino)-5-chlorothiazol-4-yl)acetamido)-2,2-dimethyl-4-oxoazetidin-1-yl sulfate The procedure was the same as step G in Example 2 with the reagents (S,Z)-4-(4-(3-(tert-butoxy)-2-((((2-((tert-butoxycarbonyl)amino)-5-chlorothiazol-4-yl)(carboxy)methylene)amino)oxy)-3-oxopropoxy)phenyl)-1-(3-((tert-butoxycarbonyl)amino)propyl)-2-methyl-1H-pyrazol-2-ium iodide (0.14 g, 0.154 mmol), DCC (0.080 g, 0.386 mmol), HOBT (0.059 g, 0.386 mmol, (S)-3-amino-2,2-dimethyl-4-oxoazetidin-1-yl hydrogen sulfate (0.065 g, 0.309 mmol), sodium bicarbonate (0.065 g, 0.772 mmol) in DMF (4 ml). LC-MS [M]$^+$: m/z 971.43.

Step C: (S)-3-((Z)-2-(2-Amino-5-chlorothiazol-4-yl)-2-(((S)-2-(4-(1-(3-aminopropyl)-2-methyl-1H-pyrazol-2-ium-4-yl)phenoxy)-1-carboxyethoxy)imino)acetamido)-2,2-dimethyl-4-oxoazetidin-1-yl sulfate The procedure was the same as step H in Example 2 with the reagents 4-(4-((S)-3-(tert-butoxy)-2-(((Z)-(1-(2-((tert-butoxycarbonyl)amino)-5-chloro-thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-1-(3-((tert-butoxycarbonyl)amino)propyl)-2-methyl-1H-pyrazol-2-ium (36 mg, 0.033 mmol), CH$_2$Cl$_2$ (0.5 ml) and TFA (1 ml, 6.49 mmol). LC-MS [M]$^+$: m/z 715.22. $^1$H NMR (500 MHz, DMSO): δ$_H$ 8.77 (br s, 1H); 8.65 (br s, 1H); 7.34 (br s, 4H); 6.97 (s, 2H); 4.82 (s, 1H); 4.72 (br s, 1H); 4.57 (br s, 2H); 4.50 (br s, 2H); 4.27 (br s, 1H); 4.19 (s, 3H); 3.01 (br s, 2H); 2.21 (br s, 1H); 2.11 (br s, 1H); 1.42 (s, 3H); 1.30 (br s, 3H).

Example 12

(S)-3-((Z)-2-(5-Amino-1,2,4-thiadiazol-3-yl)-2-(((S)-2-(4-(1-(3-aminopropyl)-2-methyl-1H-pyrazol-2-ium-4-yl)phenoxy)-1-carboxyethoxy)imino)acetamido)-2,2-dimethyl-4-oxoazetidin-1-yl sulfate
(C12)

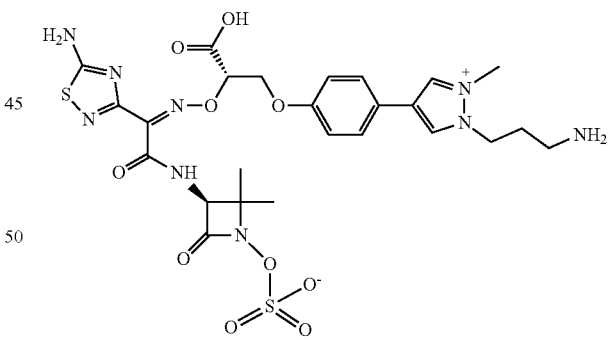

C12

Step A: (S,Z)-4-(4-(3-(tert-Butoxy)-2-((((5-((tert-butoxycarbonyl)amino)-1,2,4-thiadiazol-3-yl)(carboxy)methylene)amino)oxy)-3-oxopropoxy)phenyl)-1-(3-((tert-butoxycarbonyl)-amino)propyl)-2-methyl-1H-pyrazol-2-ium iodide The procedure was the same as step F in Example 1 with the reagents 2-(5-((tert-butoxycarbonyl)amino)-1,2,4-thiadiazol-3-yl)-2-oxoacetic acid (0.046 g, 0.170 mmol) (Intermediate 7) and (S)-4-(4-(2-(aminooxy)-3-(tert-butoxy)-3-oxopropoxy)phenyl)-1-(3-((tert-butoxycarbonyl)amino)

propyl)-2-methyl-1H-pyrazol-2-ium, iodide (0.1 g, 0.162 mmol) in EtOH (4 ml) and ClCH₂CH₂Cl (2 ml). LC-MS [M]⁺: m/z 746.31.

Step B: (S)-3-((Z)-2-(((((S)-1-(tert-Butoxy)-3-(4-(1-(3-((tert-butoxycarbonyl)amino)propyl)-2-methyl-1H-pyrazol-2-ium-4-yl)phenoxy)-1-oxopropan-2-yl)oxy)imino)-2-(5-((tert-butoxycarbonyl)amino)-1,2,4-thiadiazol-3-yl)acetamido)-2,2-dimethyl-4-oxoazetidin-1-yl sulfate The procedure was the same as step G in Example 2 with the reagents (S,Z)-4-(4-(3-(tert-butoxy)-2-(((((5-((tert-butoxycarbonyl)amino)-1,2,4-thiadiazol-3-yl)(carboxy)-methylene)amino)oxy)-3-oxopropoxy)phenyl)-1-(3-((tert-butoxycarbonyl)amino)propyl)-2-methyl-1H-pyrazol-2-ium, Iodide (0.14 g, 0.160 mmol), DCC (0.083 g, 0.401 mmol), HOBT (0.061 g, 0.401 mmol), (S)-3-amino-2,2-dimethyl-4-oxoazetidin-1-yl hydrogen sulfate (0.067 g, 0.320 mmol) and sodium bicarbonate (0.067 g, 0.801 mmol).) in DMF (4 ml). LC-MS [M]⁺: m/z 938.61.

Step C: (S)-3-((Z)-2-(5-Amino-1,2,4-thiadiazol-3-yl)-2-(((S)-2-(4-(1-(3-aminopropyl)-2-methyl-1H-pyrazol-2-ium-4-yl)phenoxy)-1-carboxyethoxy)imino)acetamido)-2,2-dimethyl-4-oxoazetidin-1-yl sulfate The procedure was the same as step H in Example 2 with the reagents 4-(4-((S)-3-(tert-butoxy)-2-(((Z)-(1-(5-((tert-butoxycarbonyl)amino)-1,2,4-thiadiazol-3-yl)-2-(((S)-2,2-dimethyl-4-oxo-1-(sulfooxy)azetidin-3-yl)amino)-2-oxoethylidene)amino)oxy)-3-oxopropoxy)phenyl)-1-(3-((tert-butoxycarbonyl)amino)propyl)-2-methyl-1H-pyrazol-2-ium (0.14 g, 0.133 mmol) in CH₂Cl₂ (0.5 ml) and TFA (0.5 ml, 6.49 mmol). LC-MS [M]⁺: m/z 682.27. ¹H NMR (500 MHz, DMSO): δ$_H$ 8.72 (s, 1H); 8.61 (s, 1H); 8.11 (s, 2H); 7.29 (s, 2H); 6.93 (d, J=8.2 Hz, 2H); 4.83 (s, 1H); 4.73 (d, J=7.6 Hz, 1H); 4.60 (br s, 1H); 4.51 (s, 2H); 4.24 (d, J=10.3 Hz, 1H); 4.20 (s, 3H); 3.02 (d, J=23.8 Hz, 2H); 2.21 (br s, 1H); 2.09 (br s, 1H); 1.44 (s, 3H); 1.30 (s, 3H).

Example 14

4-(2-(4-(4-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)phenyl)-1H-pyrazol-1-yl)ethyl)-4-methylmorpholin-4-ium 2,2,2-trifluoroacetate (C14)

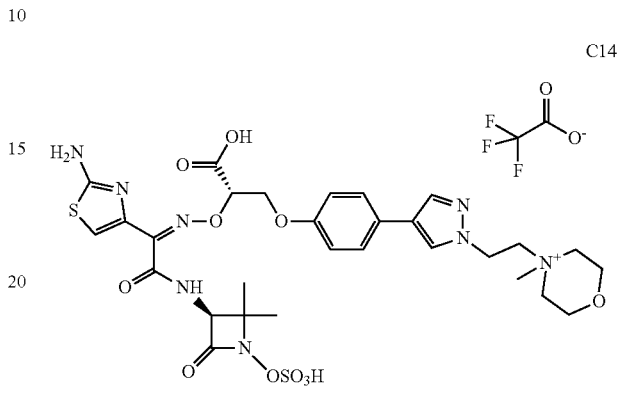

Step A: tert-butyl (R)-2-hydroxy-3-(4-(1-(2-morpholinoethyl)-1H-pyrazol-4-yl)phenoxy)propanoate To a solution of Intermediate 3 (R)-tert-butyl 3-(4-bromophenoxy)-2-hydroxypropanoate (500 mg, 1.58 mmol), 4-(2-(4-(4,4,5,5-tetramethyl-1,3,2-dioxaborolan-2-yl)-1H-pyrazol-1-yl)ethyl)morpholine (726 mg, 2.36 mmol), and 1,1'-bis(di-tert-butylphosphino)ferrocene palladium dichloride (103 mg, 0.158 mmol) in THF (10 ml) was added the 1M aqueous solution of potassium phosphate tribasic (4.73 ml, 4.73 mmol). The 20 mL microwave vial was sealed, degased (3×), and refilled with N₂, and stirred at 60° C. overnight. LC-MS indicated complete conversion. The reaction mixture was diluted with saturated NH₄Cl solution, extracted with EtOAc (2×50 mL). The organic extract were combined, dried over MgSO₄ and concentrated to dryness. The residue was purified on Flash SiO₂ column (40 g gold)

TABLE 2

By using generally the same procedure in Example 12, without step D, Example 13 was synthesized and characterized by LC/MS.

| Example | Name | Structure | LLCMS [M + 1] |
|---|---|---|---|
| 13 | 3-(4-(5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)pyridin-2-yl)-1H-pyrazol-1-yl)propan-1-aminium 2,2,2-trifluoroacetate | | 6668.24 | with MeOH in DCM (0-15%) to give the title compound. LC-MS [M+H]+: m/z 418.42.

Step B: tert-butyl (S)-2-((1,3-dioxoisoindolin-2-yl)oxy)-3-(4-(1-(2-morpholinoethyl)-1H-pyrazol-4-yl)phenoxy)propanoate The procedure was same as step C in Example 1 with the reagent of: tert-butyl (R)-2-hydroxy-3-(4-(1-(2-morpholinoethyl)-1H-pyrazol-4-yl)phenoxy)propanoate (0.480 g, 1.15 mmol), 2-hydroxyisoindoline-1,3-dione (0.225 g, 1.38 mmol), triphenylphosphine (0.362 g, 1.38 mmol), DIAD (0.272 ml, 1.380 mmol) and THF (4 ml). LC-MS [M+H]+: m/z 563.47.

Step C: (S)-4-(2-(4-(4-(3-(tert-butoxy)-2-((1,3-dioxoisoindolin-2-yl)oxy)-3-oxopropoxy)-phenyl)-1H-pyrazol-1-yl)ethyl)-4-methylmorpholin-4-ium iodide To a solution of (S)-tert-butyl 2-((1,3-dioxoisoindolin-2-yl)oxy)-3-(4-(1-(2-morpholinoethyl)-1H-pyrazol-4-yl)-phenoxy)propanoate (250 mg, 0.444 mmol) in acetonitrile (4 ml) was added iodomethane (0.167 ml, 2.67 mmol), the reaction mixture was stirred at room temperature overnight and concentrated under high vacuum to give the title compound. LC-MS [M]+: m/z 577.56.

Step D: (S)-4-(2-(4-(4-(2-(aminooxy)-3-(tert-butoxy)-3-oxopropoxy)phenyl)-1H-pyrazol-1-yl)ethyl)-4-methylmorpholin-4-ium iodide The procedure is the same as step E in Example 1 with the reagent (S)-4-(2-(4-(4-(3-(tert-butoxy)-2-((1,3-dioxoisoindolin-2-yl)oxy)-3-oxopropoxy)phenyl)-1H-pyrazol-1-yl)ethyl)-4-methylmorpholin-4-ium iodide (310 mg, 0.440 mmol), hydrazine (14.0 μl, 0.440 mmol) in EtOH (4 ml). LC-MS [M]+: m/z 447.50.

Step E: (S,Z)-4-(2-(4-(4-(3-(tert-butoxy)-2-((((2-((tert-butoxycarbonyl)amino)thiazol-4-yl)(carboxy)methylene)amino)oxy)-3-oxopropoxy)phenyl)-1H-pyrazol-1-yl)ethyl)-4-methylmorpholin-4-ium iodide The procedure was the same as step F in Example 1 with the reagents 2-(5-((tert-butoxycarbonyl)amino)-1,2,4-thiadiazol-3-yl)-2-oxoacetic acid (0.118 g, 0.435 mmol) (Intermediate 7) and (S)-4-(2-(4-(4-(2-(aminooxy)-3-(tert-butoxy)-3-oxopropoxy)phenyl)-1H-pyrazol-1-yl)ethyl)-4-methylmorpholin-4-ium iodide (0.250 g, 0.435 mmol) in EtOH (6 ml) and ClCH2CH2Cl (2 ml). LC-MS [M]+: m/z 701.00.

Step F: 4-(2-(4-(4-(((S)-3-(tert-butoxy)-2-(((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-1H-pyrazol-1-yl)ethyl)-4-methylmorpholin-4-ium iodide The procedure was the same as step F in Example 2 with the reagents (S,Z)-4-(2-(4-(4-(3-(tert-butoxy)-2-((((2-((tert-butoxycarbonyl)amino)thiazol-4-yl)(carboxy)methylene)amino)oxy)-3-oxopropoxy)phenyl)-1H-pyrazol-1-yl)ethyl)-4-methylmorpholin-4-ium iodide (0.250 g, 0.302 mmol), DCC (0.124 g, 0.603 mmol), HOBT (0.092 g, 0.603 mmol, (S)-3-amino-2,2-dimethyl-4-oxoazetidin-1-yl hydrogen sulfate (0.127 g, 0.603 mmol), sodium bicarbonate (0.101 g, 1.207 mmol) in DMF (4 ml). LC-MS [M]+: m/z 894.00.

Step G: (S)-3-((Z)-2-(2-aminothiazol-4-yl)-2-(((S)-1-carboxy-2-(4-(1-(2-(4-methyl-morpholino-4-ium)ethyl)-1H-pyrazol-4-yl)phenoxy)ethoxy)imino)acetamido)-2,2-dimethyl-4-oxoazetidin-1-yl sulfate The procedure was the same as step H in Example 2 with the reagents 4-(2-(4-(4-((S)-3-(tert-butoxy)-2-(((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)-amino)-oxy)-3-oxopropoxy)phenyl)-1H-pyrazol-1-yl)ethyl)-4-methylmorpholin-4-ium iodide (0.070 g, 0.069 mmol) in CH2Cl2 (0.5 ml) and TFA (0.5 m, 6.49 mmol). LC-MS [M+H]+: m/z 737.43.

TABLE 3

By using the same procedures as in Example 1, Examples 15-22 were synthesized and characterized by LC/MS

| Example | Name | Structure | LCMS [M]+ |
|---|---|---|---|
| 115 | 1-(3-aminopropyl)-4-(4-((S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-carboxyethoxy)-3-fluorophenyl)-2-methyl-1H-pyrazol-2-ium, TFA salt (1:1) | 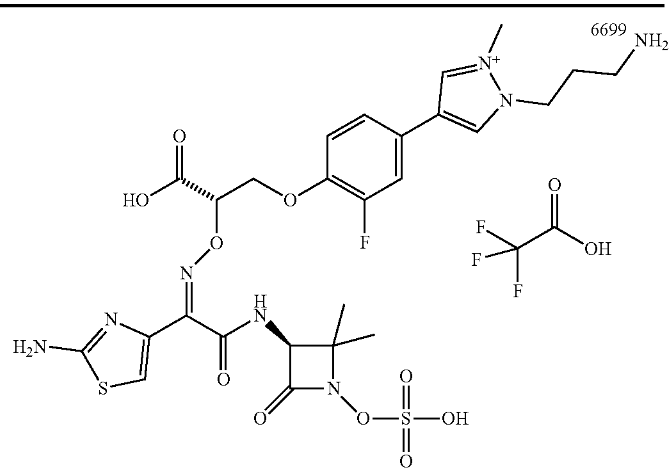 | 6699 |

TABLE 3-continued

By using the same procedures as in Example 1, Examples 15-22 were synthesized and characterized by LC/MS

| Example | Name | Structure | LCMS [M]+ |
|---------|------|-----------|-----------|
| 116 | (S)-3-((Z)-2-(2-aminothiazol-4-yl)-2-(((S)-2-(4-(1-(azetidin-3-ylmethyl)-2-methyl-1H-pyrazol-2-ium-4-yl)phenoxy)-1-carboxyethoxy)imino)acetamido)-2,2-dimethyl-4-oxoazetidin-1-yl sulfate | 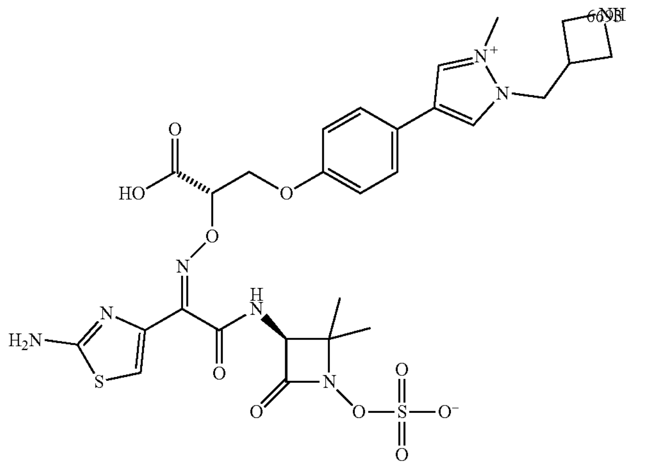 | 669 |
| 117 | (S)-3-((Z)-2-(((S)-2-(4-(1-(2-aminoethyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate | 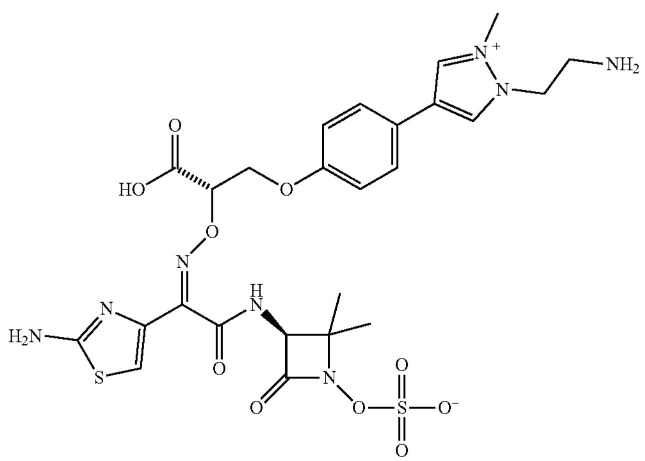 | 6667 |
| 118 | 1-(3-aminopropyl)-3-(4-((S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-carboxyethoxy)phenyl)-2-methyl-1H-pyrazol-2-ium 2,2,2-trifluoroacetate | 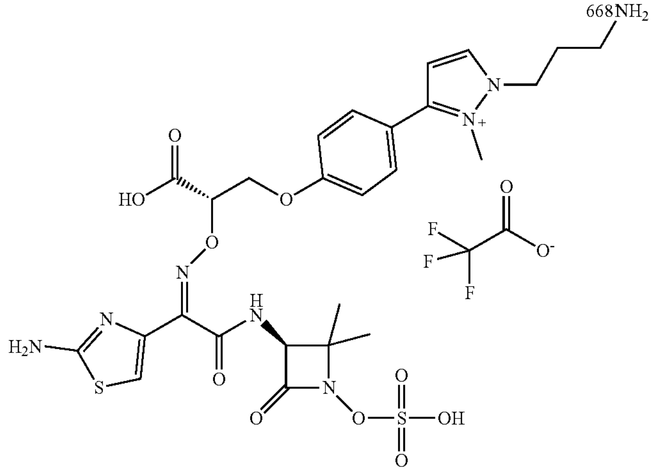 | 668 |

TABLE 3-continued

By using the same procedures as in Example 1, Examples 15-22 were synthesized and characterized by LC/MS

| Example | Name | Structure | LCMS [M]+ |
|---|---|---|---|
| 119 | 1-(3-aminopropyl)-3-(4-((S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-carboxyethoxy)phenyl)-2,4-dimethyl-1H-pyrazol-2-ium 2,2,2-trifluoroacetate | 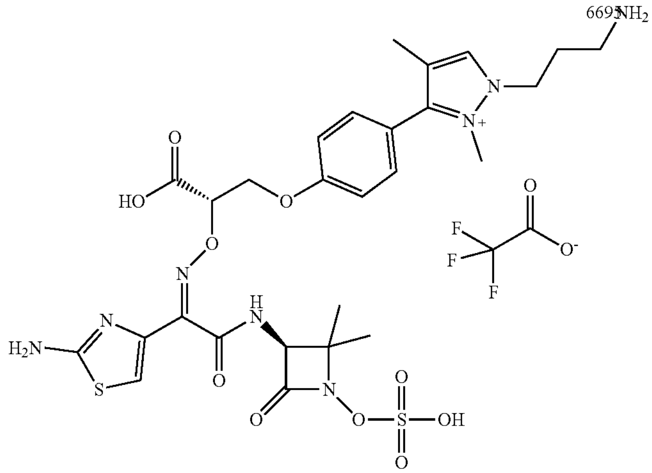 | 6695 |
| 220 | 1-(3-aminopropyl)-4-(4-((S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-carboxyethoxy)phenyl)-2,3,5-trimethyl-1H-pyrazol-2-ium 2,2,2-trifluoroacetate | 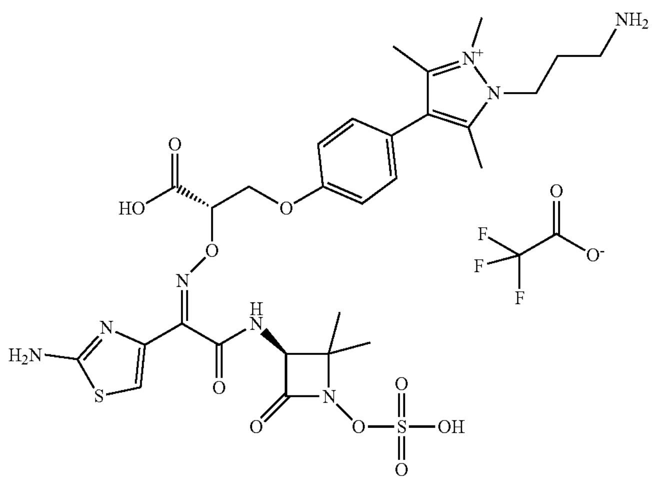 [SMILES: Cc1c(-c2ccc(OC[C@H](O/N=C(\C(=O)N[C@@H]3C(=O)N(OS(=O)(=O)O)C3(C)C)c3csc(N)n3)C(=O)O)cc2)c(C)[n+](C)n1CCCN ; O=C([O-])C(F)(F)F] | 7709 |
| 221 | 1-(3-aminopropyl)-5-(4-((S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-carboxyethoxy)phenyl)-2,3-dimethyl-1H-pyrazol-2-ium 2,2,2-trifluoroacetate | 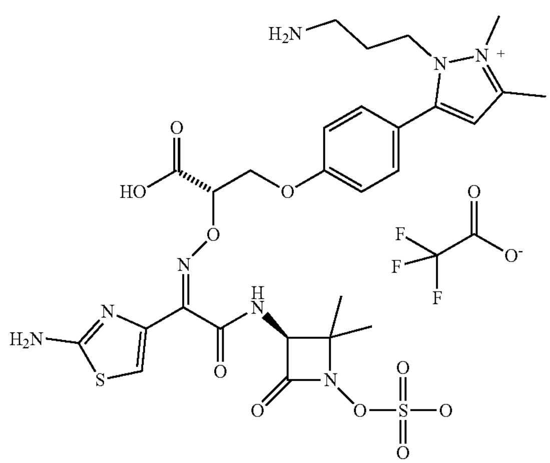 | 6695 |

TABLE 3-continued

By using the same procedures as in Example 1, Examples 15-22 were synthesized and characterized by LC/MS

| Example | Name | Structure | LCMS [M]+ |
|---|---|---|---|
| 222 | 1-(3-aminopropyl)-3-(4-((S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-carboxyethoxy)phenyl)-2,5-dimethyl-1H-pyrazol-2-ium 2,2,2-trifluoroacetate | 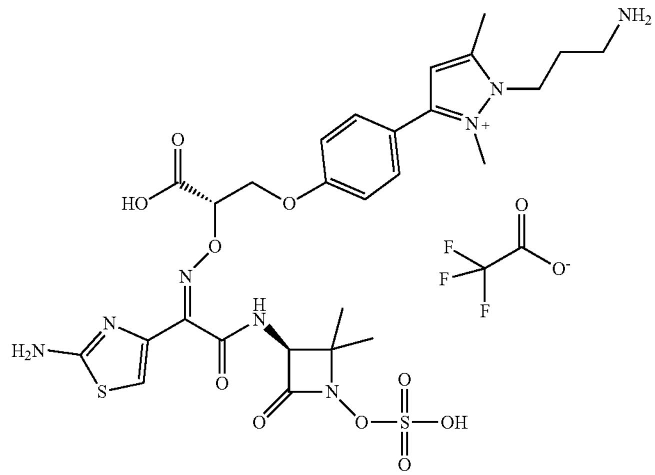 | 6695 |

Examples 23A and 23B

23A: 1-(3-aminopropyl)-4-(4-(2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxypropoxy)phenyl)-2-methyl-1H-pyrazol-2-ium 2,2,2-trifluoroacetate 23B: 1-(3-aminopropyl)-4-(4-(2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxypropoxy)phenyl)-2-methyl-1H-pyrazol-2-ium 2,2,2-trifluoroacetate

C23A

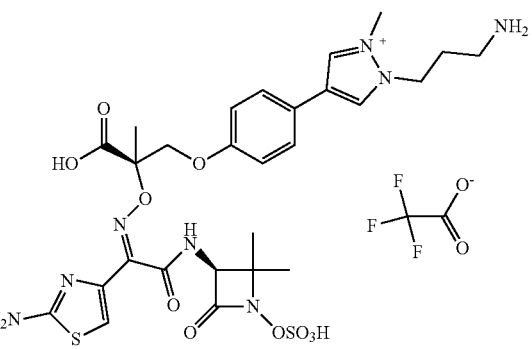

C23B

Step A: tert-butyl (3-(4-(4,4,5,5-tetramethyl-1,3,2-dioxaborolan-2-yl)-1H-pyrazol-1-yl)propyl)carbamate Cesium carbonate (12.2 g, 37.5 mmol) was added to a room temperature mixture of 4-(4,4,5,5-tetramethyl-1,3,2-dioxaborolan-2-yl)-1H-pyrazole (4.85 g, 25.00 mmol), tert-butyl (3-bromopropyl)carbamate (5.95 g, 25.0 mmol) in 40 mL of DMF and the mixture was stirred at room temperature overnight. LC-MS showed the reaction was complete. The mixture was diluted with EtOAc and water. Extracted with EtOAc. The combined organic layer was washed with brine and dried over MgSO₄. Filtered and concentrated down. The residue was purified by column chromatography on silica gel, eluting with EtOAc/isohexane (10-80% gradient) to obtain the title compound. LC-MS [M+H]+: m/z 352.33.

Step B: tert-butyl 3-(4-(1-(3-((tert-butoxycarbonyl)amino)propyl)-1H-pyrazol-4-yl)phenoxy)-2-((1,3-dioxoisoindolin-2-yl)oxy)-2-methylpropanoate To a solution of tert-butyl 2-(aminooxy)-3-(4-bromophenoxy)-2-methylpropanoate (100 mg, 0.289 mmol), tert-butyl (3-(4-(4,4,5,5-tetramethyl-1,3,2-dioxaborolan-2-yl)-1H-pyrazol-1-yl)propyl)carbamate (101 mg, 0.289 mmol), and 1,1'-bis (di-tert-butylphosphino)ferrocenepalladium dichloride (18.82 mg, 0.029 mmol) in dioxane (1 ml) was added the 1M aqueous solution of potassium phosphate (0.867 ml, 0.867 mmol). The vial was sealed, degased, and refilled with $N_2$, and stirred at 70° C. for 1 hour. LC-MS indicated complete conversion. Diluted with water. Extracted with EtOAc×2. The organic layer was dried over $MgSO_4$, filtered and concentrated down. The residue was purified by column chromatography on silica gel, eluting with $CH_2Cl_2$/MeOH (100~90%) to give the title compound. LC-MS $[M+H]^+$: m/z 491.43.

Step C: tert-butyl 3-(4-(1-(3-((tert-butoxycarbonyl)amino)propyl)-1H-pyrazol-4-yl)phenoxy)-2-((1,3-dioxoisoindolin-2-yl)oxy)-2-methylpropanoate 4-methylbenzene-sulfonic acid (12% in acetic acid) (63.2 mg, 0.044 mmol) was added to a room temperature mixture of tert-butyl 2-(aminooxy)-3-(4-(1-(3-((tert-butoxycarbonyl)amino)propyl)-1H-pyrazol-4-yl)phenoxy)-2-methylpropanoate (540 mg, 1.10 mmol), molecular sieves (200 mg) in toluene and the mixture was stirred at 100° C. for 4 hours. LC-MS showed the reaction almost completed. Filtered and concentrated down. The residue was purified by column chromatography on silica gel, eluting with $CH_2Cl_2$/MeOH (100~90%) to obtain the title compound. LC-MS $[M+H]^+$: m/z 622.56.

Step D: 4-(4-(3-(tert-butoxy)-2-((1,3-dioxoisoindolin-2-yl)oxy)-2-methyl-3-oxopropoxy)-phenyl)-1-(3-((tert-butoxycarbonyl)amino)propyl)-2-methyl-1H-pyrazol-2-ium iodide The procedure was the same as step D in Example 1 with the reagent tertbutyl 3-(4-(1-(3-((tert-butoxycarbonyl)amino)propyl)-1H-pyrazol-4-yl)phenoxy)-2-((1,3-dioxoisoindolin-2-yl)oxy)-2-methylpropanoate (0.495 g, 0.797 mmol), MeI (0.399 ml, 6.38 mmol) in MeCN (3 ml). LC-MS $[M]^+$: m/z 635.58

Step E: (Z)-4-(4-(3-(tert-butoxy)-2-((((2-((tert-butoxycarbonyl)amino)thiazol-4-yl)(carboxy)methylene)amino)oxy)-2-methyl-3-oxopropoxy)phenyl)-1-(3-((tert-butoxycarbonyl)amino)propyl)-2-methyl-1H-pyrazol-2-ium iodide Hydrazine (0.024 ml, 0.763 mmol) in 0.3 mL of DCM was added to a stirred, room temperature mixture of 4-(4-(3-(tert-butoxy)-2-((1,3-dioxoisoindolin-2-yl)oxy)-2-methyl-3-oxopropoxy)phenyl)-1-(3-((tert-butoxycarbonyl)amino)propyl)-2-methyl-1H-pyrazol-2-ium (485 mg, 0.763 mmol) in EtOH/DCM and the mixture was stirred at room temperature for 4 hours. LC-MS showed the intermediate was generated. Then 2-(2-((tert-butoxycarbonyl)amino)thiazol-4-yl)-2-oxoacetic acid (228 mg, 0.839 mmol) was added and stirred at room temperature overnight. LC-MS showed the reaction completed. The solution was filtered and the filtrate was concentrated down. The residue was purified by preparative HPLC, eluting with Acetonitrile/Water+0.05% TFA (0100%) to obtain the title compound. LC-MS $[M+H]^+$: m/z 759.58.

Step F: 4-(4-(3-(tert-butoxy)-2-((((Z)-1-(2-((tert-butoxycarbonyl)amino)thiazol-4-yl)-2-(((2R,3S)-2-methyl-4-oxo-1-sulfoazetidin-3-yl)amino)-2-oxoethylidene)amino)oxy)-2-methyl-3-oxopropoxy)phenyl)-1-(3-((tert-butoxycarbonyl)amino)propyl)-2-methyl-1H-pyrazol-2-ium To a solution of (Z)-4-(4-(3-(tert-butoxy)-2-((((2-((tert-butoxycarbonyl)amino)thiazol-4-yl)(carboxy)methylene)amino)oxy)-2-methyl-3-oxopropoxy)phenyl)-1-(3-((tert-butoxycarbonyl)amino)propyl)-2-methyl-1H-pyrazol-2-ium iodide (80 mg, 0.105 mmol) in DMF (1 ml) was added DCC (87 mg, 0.421 mmol) and HOBT (60.5 mg, 0.316 mmol). The mixture was then stirred at room temperature for 30 minutes, followed by addition of (S)-3-amino-2,2-dimethyl-4-oxoazetidin-1-yl hydrogen sulfate (76 mg, 0.421 mmol) and sodium bicarbonate (35.4 mg, 0.421 mmol). The final mixture was stirred at room temperature over night (16 hours). LC-MS indicated complete conversion. The reaction mixture was filtered and the filtrate was purified by reverse phase ISCO (130 g, 0-100%, $H_2O$/MeCN/0.05% TFA), fractions were collected and lyophilized down to obtain the title compound. LC-MS $[M+H]^+$: m/z 921.76

Step G: (S)-3-((Z)-2-(((((S)-1-(4-(1-(3-aminopropyl)-2-methyl-1H-pyrazol-2-ium-4-yl)phenoxy)-2-carboxypropan-2-yl)oxy)imino)-2-(2-(2-aminothiazol-4-yl)acetamido)-2,2-dimethyl-4-oxoazetidin-1-yl sulfate compound with 2,2,2-trifluoroacetic acid (1:1)

To a solution of 4-(4-(3-(tert-butoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-2-methyl-3-oxopropoxy)phenyl)-1-(3-((tert-butoxycarbonyl)amino)propyl)-2-methyl-1H-pyrazol-2-ium (110 mg, 0.116 mmol) in DCM was added 2 mL of TFA. The mixture was stirred at room temperature for 90 minutes. LC-MS indicated complete conversion. The mixture was concentrated to dryness under vacuum (no heat). DCM (10 ml) was added and concentrated for three times to remove TFA. The residue was washed with dry MeCN (2×2 ml) to remove impurities. The residue was dissolved in DMSO and purified on prep-HPLC with a MeCN/$H_2O$ (0.05% TFA in both) gradient 2-25% in 10 minutes. The fast eluting isomer was Compound 23A and the slower one was Compound 23B. Product fractions were collected and lyophilized to obtain the title compounds. Compound 23A: LC-MS [M+H]: m/z 695.33. Compound 23B: LC-MS [M+H]: m/z 695.16.

Example 24

(S)-3-((Z)-2-(((S)-2-(4-(1-(3-aminopropyl)-2-methyl-1H-pyrazol-2-ium-4-yl)-3-fluorophenoxy)-1-carboxyethoxy)imino)-2-(2-aminothiazol-4-yl)acetamido)-2,2-dimethyl-4-oxoazetidin-1-yl sulfate (C24)

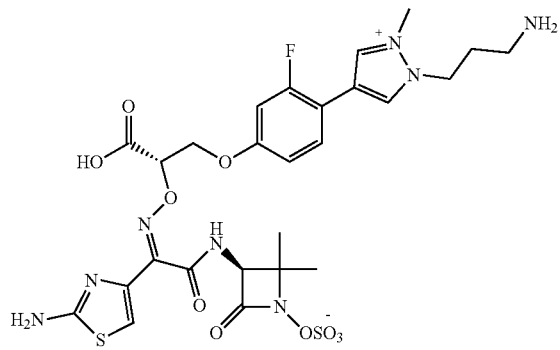

C24

Step A: tert-butyl (R)-3-(4-bromo-3-fluorophenoxy)-2-hydroxypropanoate

The procedure was the same as Intermediate 3 with the reagent of tert-butyl oxirane-2-carboxylate (4.19 g, 29.1 mmol), (R,R)—Co catalyst (0.595 g, 0.709 mmol), 4-bromo-3-fluorophenol (2.71 g, 14.19 mmol). LC-MS [M+Na]$^+$: m/z 358.92.

Step B: tert-butyl (R)-3-(4-(1-(3-((tert-butoxycarbonyl)amino)propyl)-1H-pyrazol-4-yl)-3-fluorophenoxy)-2-hydroxypropanoate The procedure was the same as Step B in Example 1 with the reagent of tert-butyl (R)-3-(4-bromo-3-fluorophenoxy)-2-hydroxypropanoate (470 mg, 1.40 mmol), tert-butyl (3-(4-(4,4,5,5-tetramethyl-1,3,2-dioxaborolan-2-yl)-1H-pyrazol-1-yl)propyl)carbamate (512 mg, 1.458 mmol), 1,1'-bis(di-tert-butylphosphino)ferrocene palladium dichloride (91 mg, 0.140 mmol), 1,4-dioxane (4 ml) and potassium phosphate (4.21 ml, 4.21 mmol, 1M aq.). LC-MS [M+H]$^+$: m/z 480.84.

Step C: tert-butyl (S)-3-(4-(1-(3-((tert-butoxycarbonyl)amino)propyl)-1H-pyrazol-4-yl)-3-fluorophenoxy)-2-((1,3-dioxoisoindolin-2-yl)oxy)propanoate The procedure was same as Step C in Example 1 with the reagent of tert-butyl (R)-3-(4-(1-(3-((tert-butoxycarbonyl)amino)propyl)-1H-pyrazol-4-yl)-3-fluorophenoxy)-2-hydroxypropanoate (0.451 g, 0.94 mmol), 2-hydroxyisoindoline-1,3-dione (0.153 g, 0.94 mmol), triphenylphosphine (0.271 g, 1.04 mmol), DEAD (0.164 ml, 1.04 mmol) and THF (4 ml). LC-MS [M+H]$^+$: m/z 625.51.

Step D: (S)-4-(4-(3-(tert-butoxy)-2-((1,3-dioxoisoindolin-2-yl)oxy)-3-oxopropoxy)-2-fluorophenyl)-1-(3-((tert-butoxycarbonyl)amino)propyl)-2-methyl-1H-pyrazol-2-ium iodide The procedure was same as step D in Example 1 with the reagent tert-butyl (S)-3-(4-(1-(3-((tert-butoxycarbonyl)amino)propyl)-1H-pyrazol-4-yl)-3-fluorophenoxy)-2-((1,3-dioxoisoindolin-2-yl)oxy)propanoate (0.576 g, 0.922 mmol), MeI (0.461 ml, 7.38 mmol) in MeCN (3 ml). LC-MS [M]$^+$: m/z 639.55

Step E: (S,Z)-4-(4-(3-(tert-butoxy)-2-((((2-((tert-butoxycarbonyl)amino)thiazol-4-yl)-(carboxy)methylene)amino)oxy)-3-oxopropoxy)-2-fluorophenyl)-1-(3-((tert-butoxy-carbonyl)amino)propyl)-2-methyl-1H-pyrazol-2-ium iodide The procedure was the same as step E in Example 1 with the reagents hydrazine (0.028 ml, 0.89 mmol), (S)-4-(4-(3-(tert-butoxy)-2-((1,3-dioxoisoindolin-2-yl)oxy)-3-oxopropoxy)-2-fluorophenyl)-1-(3-((tert-butoxycarbonyl)amino)propyl)-2-methyl-1H-pyrazol-2-ium iodide (712 mg, 0.89 mmol), 2-(2-((tert-butoxycarbonyl)amino)thiazol-4-yl)-2-oxoacetic acid (267 mg, 0.979 mmol). LC-MS [M+H]$^+$: m/z 763.53.

Step F: 4-(4-((S)-3-(tert-butoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-fluorophenyl)-1-(3-((tert-butoxycarbonyl)amino)propyl)-2-methyl-1H-pyrazol-2-ium The procedure was the same as step F in Example 1 with the reagents (S,Z)-4-(4-(3-(tert-butoxy)-2-((((2-((tert-butoxycarbonyl)amino)thiazol-4-yl)(carboxy)methylene)-amino)oxy)-3-oxopropoxy)-2-fluorophenyl)-1-(3-((tert-butoxycarbonyl)amino)propyl)-2-methyl-1H-pyrazol-2-ium iodide (0.679 g, 0.889 mmol), DCC (0.550 g, 2.67 mmol), HOBT (0.510 g, 2.67 mmol), (S)-3-amino-2,2-dimethyl-4-oxoazetidin-1-yl hydrogen sulfate (0.280 g, 1.33 mmol) and sodium bicarbonate (0.299 g, 3.56 mmol) in DMF (3 ml). LC-MS [M]$^+$: m/z 955.69.

Step G: (S)-3-((Z)-2-(((S)-2-(4-(1-(3-aminopropyl)-2-methyl-1H-pyrazol-2-ium-4-yl)-3-fluorophenoxy)-1-carboxyethoxy)imino)-2-(2-aminothiazol-4-yl)acetamido)-2,2-dimethyl-4-oxoazetidin-1-yl sulfate compound with formic acid (1:1)

The procedure was the same as step G in Example 1 with the reagents 4-(4-((S)-3-(tert-butoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-fluorophenyl)-1-(3-((tert-butoxycarbonyl)amino)propyl)-2-methyl-1H-pyrazol-2-ium (0.13 g, 0.136 mmol), TFA (2 ml, 26 mmol). LC-MS [M]$^+$: m/z 699.69

Example 25

1-(3-aminopropyl)-4-(4-((S)-2-((((Z)-1-(2-aminothiazol-4-yl)-2-(((2R,3S)-2-methyl-4-oxo-1-sulfoazetidin-3-yl)amino)-2-oxoethylidene)amino)oxy)-2-carboxypropoxy)phenyl)-2-methyl-1H-pyrazol-2-ium 2,2,2-trifluoroacetate (C25)

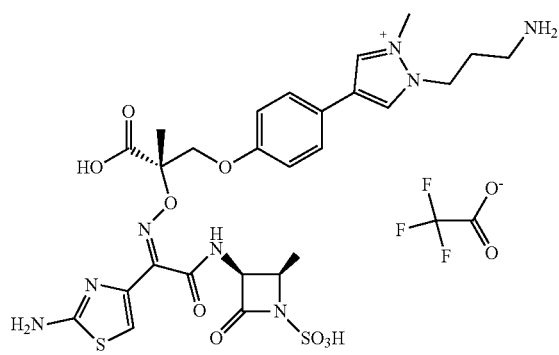

C25

Step A: 4-(4-(3-(tert-butoxy)-2-((((Z)-1-(2-((tert-butoxycarbonyl)amino)thiazol-4-yl)-2-(((2R,3S)-2-methyl-4-oxo-1-sulfoazetidin-3-yl)amino)-2-oxoethylidene)amino)oxy)-2-methyl-3-oxopropoxy)phenyl)-1-(3-((tert-butoxycarbonyl)amino)propyl)-2-methyl-1H-pyrazol-2-ium The procedure was the same as step F in Example 1 with the reagents (Z)-4-(4-(3-(tert-butoxy)-2-((((2-((tert-butoxycarbonyl)amino)thiazol-4-yl)(carboxy)methylene)amino)oxy)-2-methyl-3-oxopropoxy)phenyl)-1-(3-((tert-butoxycarbonyl)amino)propyl)-2-methyl-1H-pyrazol-2-ium (0.080 g, 0.105 mmol), DCC (0.087 g, 0.421 mmol), HOBT (0.0605 g, 0.316 mmol), (2R,3S)-3-amino-2-methyl-4-oxoazetidine-1-sulfonic acid (0.076 g, 1.05 mmol) and sodium bicarbonate (0.0354 g, 0.421 mmol). LC-MS [M]⁺: m/z 921.76.

Step B: (2R,3S)-3-((Z)-2-((((S)-1-(4-(1-(3-aminopropyl)-2-methyl-1H-pyrazol-2-ium-4-yl)phenoxy)-2-carboxypropan-2-yl)oxy)imino)-2-(2-aminothiazol-4-yl)acetamido)-2-methyl-4-oxoazetidine-1-sulfonate compound with 2,2,2-trifluoroacetic acid (1:1)

The procedure was the same as step G in Example 1 with the reagents 4-(4-(3-(tert-butoxy)-2-((((Z)-1-(2-((tert-butoxycarbonyl)amino)thiazol-4-yl)-2-(((2R,3S)-2-methyl-4-oxo-1-sulfoazetidin-3-yl)amino)-2-oxoethylidene)amino)oxy)-2-methyl-3-oxopropoxy)phenyl)-1-(3-((tert-butoxycarbonyl)amino)propyl)-2-methyl-1H-pyrazol-2-ium (0.086 g, 0.093 mmol), TFA (2.5 ml, 32.4 mmol). LC-MS [M]: m/z 665.20

Example 26

2-(1-(3-aminopropyl)-1H-pyrazol-4-yl)-5-((S)-2-((((Z)-1-(2-aminothiazol-4-yl)-2-(((S)-2,2-dimethyl-4-oxo-1-(sulfooxy)azetidin-3-yl)amino)-2-oxo-ethylidene)amino)oxy)-2-carboxyethoxy)-1-methylpyridin-1-ium 2,2,2-trifluoroacetate (C26)

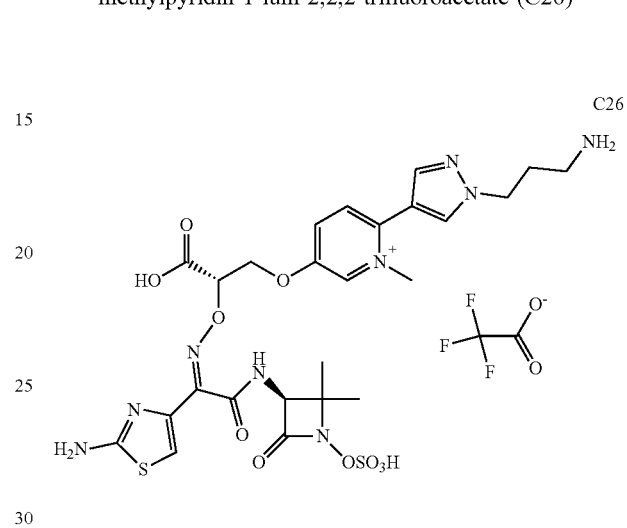

C26

Step A: tert-butyl 3-((6-bromopyridin-3-yl)oxy)-2-hydroxypropanoate

K₂CO₃ (6.35 g, 46.0 mmol) was added to a stirred, room temperature mixture of tert-butyl oxirane-2-carboxylate (6.63 g, 46.0 mmol), 6-bromopyridin-3-ol (4 g, 22.99 mmol) in acetonitrile and the mixture was stirred at 90° C. for 3 hours, cooled to room temperature and filtered. The filtrate was concentrated down. The residue was purified by column chromatography on silica gel, eluting with EtOAc/isohexane (050%) to give the title compound.

Example 26 (S)-3-((Z)-2-(((S)-2-((6-(1-(3-aminopropyl)-1H-pyrazol-4-yl)-1-methylpyridin-1-ium-3-yl)oxy)-1-carboxyethoxy)imino)-2-(2-aminothiazol-4-yl)acetamido)-2,2-dimethyl-4-oxoazetidin-1-yl sulfate compound with 2,2,2-trifluoroacetic acid (1:1) was prepared from tert-butyl 3-((6-bromopyridin-3-yl)oxy)-2-hydroxypropanoate by 6 steps. The procedures of the six steps were same as in step B, C, D, E, F, G of Example 2. LC-MS [M]⁺: m/z 682.20

Example 27

(S)-3-(4-(3-amino-1-(3-aminopropyl)-1H-pyrazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (C27)

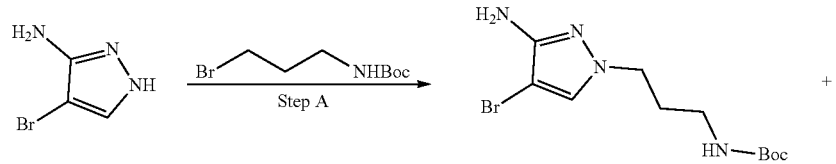

-continued
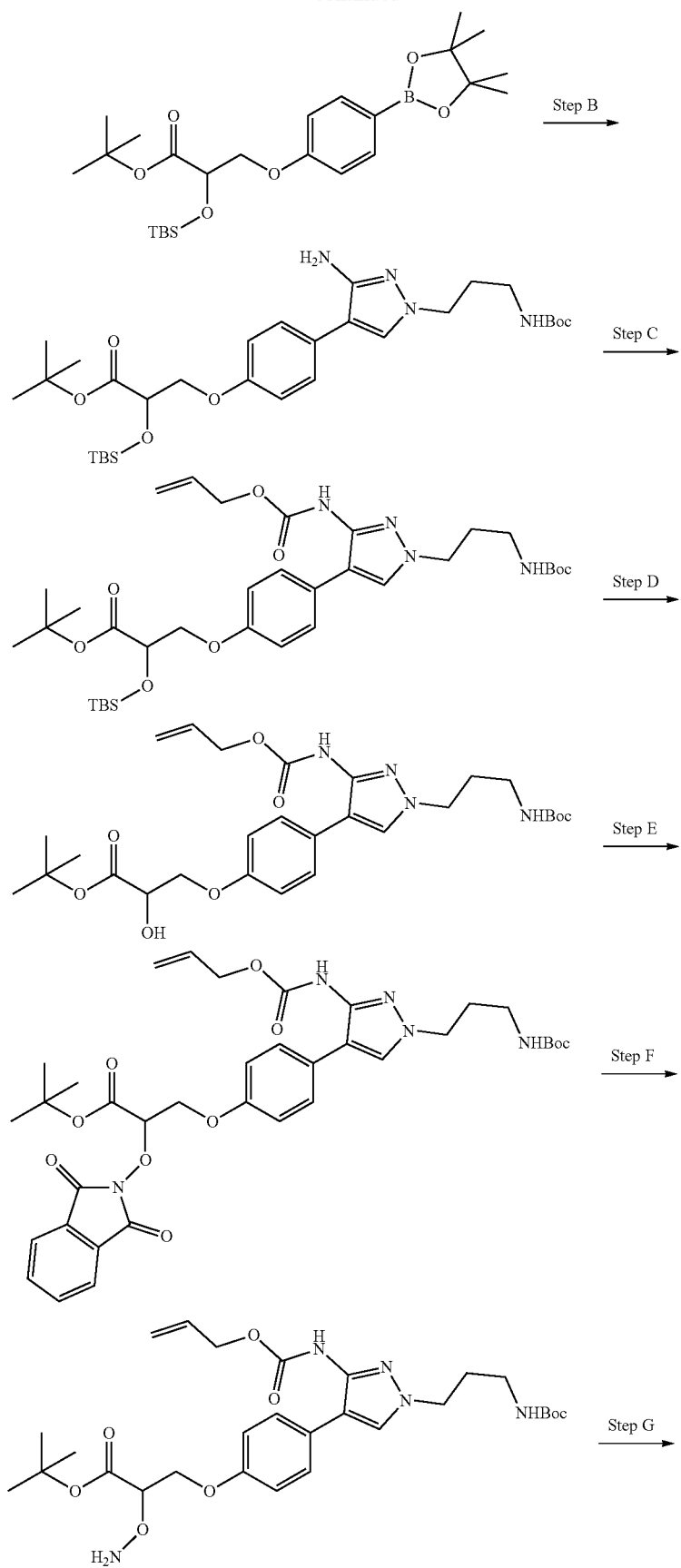

-continued
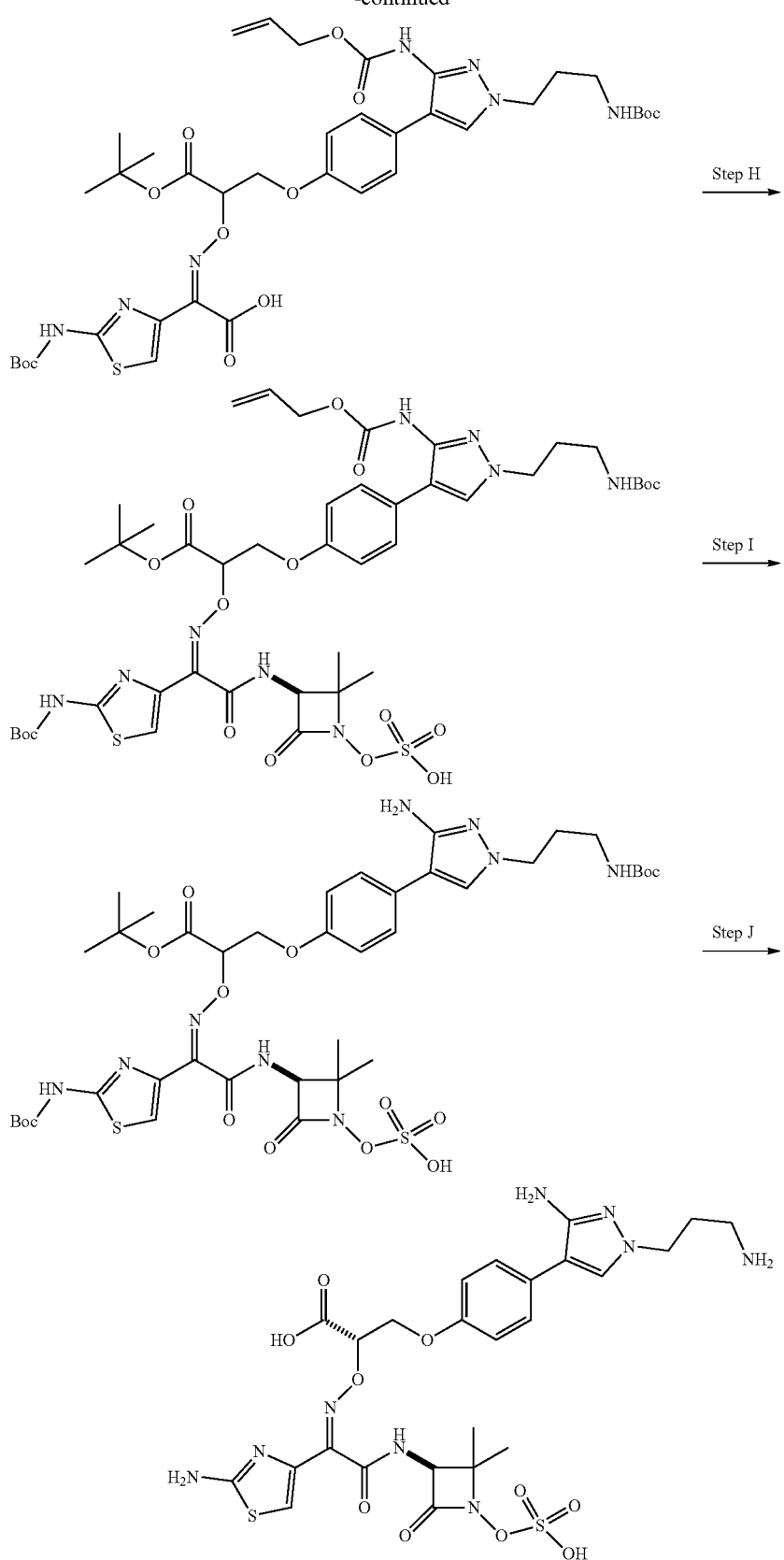

Step A: tert-Butyl (3-(3-amino-4-bromo-1H-pyrazol-1-yl)propyl)carbamate

The procedure was the same as step A in Example 1 with the reagents 4-bromo-1H-pyrazol-3-amine and tert-butyl (3-bromopropyl)carbamate.

Step B: tert-Butyl (S)-3-(4-(3-amino-1-(3-((tert-butoxycarbonyl)amino)-propyl)-1H-pyrazol-4-yl)phenoxy)-2-((tert-butyldimethylsilyl)oxy)propanoate The procedure was the same as step B in Example 1 with the reagents tert-butyl 2-((tert-butyldimethylsilyl)oxy)-3-(4-(4,4,5,5-tetramethyl-1,3,2-dioxaborolan-2-yl)phenoxy)-propanoate (0.21 g, 0.439 mmol) (Intermediate 8), tert-butyl (3-(3-amino-4-bromo-H-pyrazol-1-yl)propyl)carbamate (0.17 g, 0.533 mmol), and 1,1'-bis(di-tert-butylphosphino)-ferrocene palladium dichloride (0.029 g, 0.044 mmol) in THF (3 ml). LC-MS [M+H]$^+$: m/z 592.00

Step C: tert-Butyl 3-(4-(3-(((allyloxy)carbonyl)amino)-1-(3-((tert-butoxycarbonyl)amino) propyl)-1H-pyrazol-4-yl)phenoxy)-2-((tert-butyldimethylsilyl)oxy)propanoate To a solution of tert-butyl 3-(4-(3-amino-1-(3-((tert-butoxycarbonyl)amino)propyl)-H-pyrazol-4-yl)phenoxy)-2-((tert-butyldimethylsilyl)oxy)propanoate (0.54 g, 0.914 mmol) in CH$_2$Cl$_2$ (10 ml) was added DIPEA (0.319 ml, 1.83 mmol) followed by allyl carbonochloridate (0.194 ml, 1.828 mmol) at room temperature. The mixture was stirred for 4 hours, then the solvent was removed. The residue was purified by column chromatography on silica gel (Redi 40 g gold column), eluted with EtOAc/hexane (0-50%, 6 cv; 50%, 10 cv) to give the title compound. LC-MS [M+H]$^+$: m/z 676.71.

Step D: tert-Butyl 3-(4-(3-(((allyloxy)carbonyl)amino)-1-(3-((tert-butoxycarbonyl)-amino)propyl)-1H-pyrazol-4-yl)phenoxy)-2-hydroxypropanoate To a solution of tert-butyl 3-(4-(3-(((allyloxy)carbonyl)amino)-1-(3-((tert-butoxycarbonyl)amino)propyl)-1H-pyrazol-4-yl)phenoxy)-2-((tert-butyldimethylsilyl)oxy)propanoate (0.54 g, 0.80 mmol) was added TBAF in THF (0.80 ml, 0.80 mmol, 1M) at room temperature. The mixture was stirred for 1 hour, then the solvent was removed. The residue was purified by column chromatography on silica gel (Redi 24 g gold column), eluted with EtOAc/Hexane (0-80%, 6 cv; 80%, 10 cv) to give the title compound. LC-MS [M+H]$^+$: m/z 561.11

Step E: tert-Butyl 3-(4-(3-(((allyloxy)carbonyl)amino)-1-(3-((tert-butoxycarbonyl)-amino)propyl)-1H-pyrazol-4-yl)phenoxy)-2-((1,3-dioxoisoindolin-2-yl)oxy)propanoate The procedure was the same as step C in Example 1 with the reagents tert-butyl 3-(4-(3-(((allyloxy)carbonyl)amino)-1-(3-((tert-butoxycarbonyl)amino)propyl)-1H-pyrazol-4-yl)phenoxy)-2-hydroxypropanoate (0.3 g, 0.535 mmol), 2-hydroxyisoindoline-1,3-dione (0.096 g, 0.589 mmol), triphenylphosphine (0.168 g, 0.642 mmol), DIAD (0.125 ml, 0.642 mmol) in THF (1 mL). LC-MS [M+H]$^+$: m/z 706.

Step F: tert-Butyl 3-(4-(3-(((allyloxy)carbonyl)amino)-1-(3-((tert-butoxycarbonyl)-amino)propyl)-1H-pyrazol-4-yl)phenoxy)-2-(aminooxy)propanoate The procedure was the same as step E in Example 1 with the reagents tert-butyl 3-(4-(3-(((allyloxy)carbonyl)-amino)-1-(3-((tert-butoxycarbonyl)amino)propyl)-1H-pyrazol-4-yl)phenoxy)-2-((1,3-dioxoisoindolin-2-yl)oxy)propanoate (35 mg, 0.050 mmol) and hydrazine (3.11 µl, 0.099 mmol) in THF (2 mL). LC-MS [M+H]$^+$: m/z 576.47

Step G: (Z)-2-(((3-(4-(3-(((Allyloxy)carbonyl)amino)-1-(3-((tert-butoxycarbonyl)amino)-propyl)-1H-pyrazol-4-yl)phenoxy)-1-(tert-butoxy)-1-oxopropan-2-yl)oxy)imino)-2-(2-((tert-butoxycarbonyl)amino)thiazol-4-yl)acetic acid The procedure was the same as step F in Example 1 with the reagents 2-(2-((tert-butoxycarbonyl)amino)thiazol-4-yl)-2-oxoacetic acid (0.028 g, 0.101 mmol) and tert-butyl 3-(4-(3-(((allyloxy)carbonyl)amino)-1-(3-((tert-butoxycarbonyl)amino)propyl)-1H-pyrazol-4-yl)phenoxy)-2-(aminooxy)propanoate (0.053 g, 0.092 mmol) in EtOH (2 ml). LC-MS [M+H]$^+$: m/z 830.64

Step H: tert-Butyl 3-(4-(3-(((allyloxy)carbonyl)amino)-1-(3-((tert-butoxycarbonyl)amino)-propyl)-1H-pyrazol-4-yl)phenoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2 oxoethylidene)amino)oxy)-propanoate The procedure was the same as step G in Example 1 with the reagents (Z)-2-(((3-(4-(3-(((allyloxy)carbonyl)amino)-1-(3-((tert-butoxycarbonyl)amino)propyl)-1H-pyrazol-4-yl)phenoxy)-1-(tert-butoxy)-1-oxopropan-2-yl)oxy)imino)-2-(2-((tert-butoxycarbonyl)-amino)thiazol-4-yl)acetic acid (76 mg, 0.092 mmol), DCC (56.7 mg, 0.275 mmol), HOBT (42.1 mg, 0.275 mmol), (S)-3-amino-2,2-dimethyl-4-oxoazetidin-1-yl hydrogen sulfate (77 mg, 0.366 mmol) and sodium bicarbonate (77 mg, 0.916 mmol) in DMF (4 mL). The reaction mixture was filtered and carried over to next step without purification. LC-MS [M+H]$^+$: m/z 1023.31

Step I: tert-Butyl 3-(4-(3-amino-1-(3-((tert-butoxycarbonyl)amino)propyl)-1H-pyrazol-4-yl)phenoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate To the crude reaction mixture of tert-butyl 3-(4-(3-(((allyloxy)carbonyl)amino)-1-(3-((tert-butoxy-carbonyl)amino)propyl)-1H-pyrazol-4-yl)phenoxy)-2-(((Z)-(1-(2-((tert-butoxycarbonyl)-amino)thiazol-4-yl)-2-(((S)-2,2-dimethyl-4-oxo-1-(sulfooxy)azetidin-3-yl)amino)-2-oxoethylidene)amino)oxy)propanoate (70 mg, 0.068 mmol) in DMF (2 ml) was added Tetrakis (23.7 mg, 0.021 mmol) and phenylsilane (74.1 mg, 0.685 mmol). The mixture was stirred at room temperature for 10 minutes. The mixture was filtered and purified on RP-HPLC (Gilson) (C-18 column), eluted with ACN/Water with 0.05% TFA (20-100%, 8 min; 100% 10 min). The product fraction was lyophilized to give the title compound. LC-MS [M+H]$^+$: m/z 938.88

Step J: (S)-3-(4-(3-Amino-1-(3-aminopropyl)-1H-pyrazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid The procedure was the same as step H in Example 2 with the reagents tert-butyl 3-(4-(3-amino-1-(3-((tert-butoxycarbonyl)amino)propyl)-1H-pyrazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate, TFA-(40 mg, 0.038 mmol), TFA (0.5 ml, 6.49 mmol) in DCM (0.5 mL). LC-MS [M+H]$^+$: m/z 682.45. $^1$HNMR (500 MHz, D$_2$O) δ 7.62 (s, 1H); 7.30 (d, J=8.4 Hz, 2H); 6.96 (t, J=4.4 Hz, 3H); 4.94-4.96 (m, 1H); 4.40-4.43 (m, 2H); 4.04-4.07 (m, 2H); 2.87-2.90 (m, 2H); 2.07-2.10 (m, 2H); 1.33 (s, 3H); 1.07 (s, 3H).

Example 28

(S)-3-((Z)-2-(((S)-2-(4-(3-Amino-1-(3-aminopropyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate (C28)

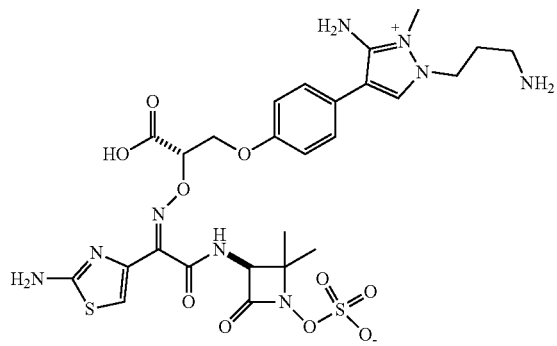

C28

Step A: (S)-3-(((Allyloxy)carbonyl)amino)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-2-methyl-1H-pyrazol-2-ium iodide The procedure was the same as step D in Example 1 with the reagents (S)-tert-butyl 3-(4-(3-(((allyloxy)carbonyl)amino)-1-(3-((tert-butoxycarbonyl)amino)propyl)-1H-pyrazol-4-yl)phenoxy)-2-((1,3-dioxoisoindolin-2-yl)oxy)propanoate (110 mg, 0.156 mmol), MeI (0.078 ml, 1.247 mmol) in CAN (1.5 mL). LC-MS [M]$^+$: m/z 720.09. The procedures of Step B-F were the same as step F-J in Example 28 to give the title compound. LC-MS [M+H]$^+$: m/z 696.41. $^1$HNMR (500 MHz, D$_2$O) δ 7.97 (1H, s), 7.38 (2H, d, J=8.3 Hz), 7.01-7.08 (3H, m), 4.99 (1H, d, J=5.8 Hz), 4.43-4.51 (2H, m), 4.33 (2H, t, J=7.2 Hz), 3.77 (3H, s), 3.06 (2H, t, J=7.9 Hz), 2.14-2.20 (2H, m), 1.44 (3H, s), 1.10 (3H, s).

Example 29

1-(3-aminopropyl)-4-(4-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-(2H-tetrazol-5-yl)ethoxy)phenyl)-2-methyl-1H-pyrazol-2-ium 2,2,2-trifluoroacetate (C29)

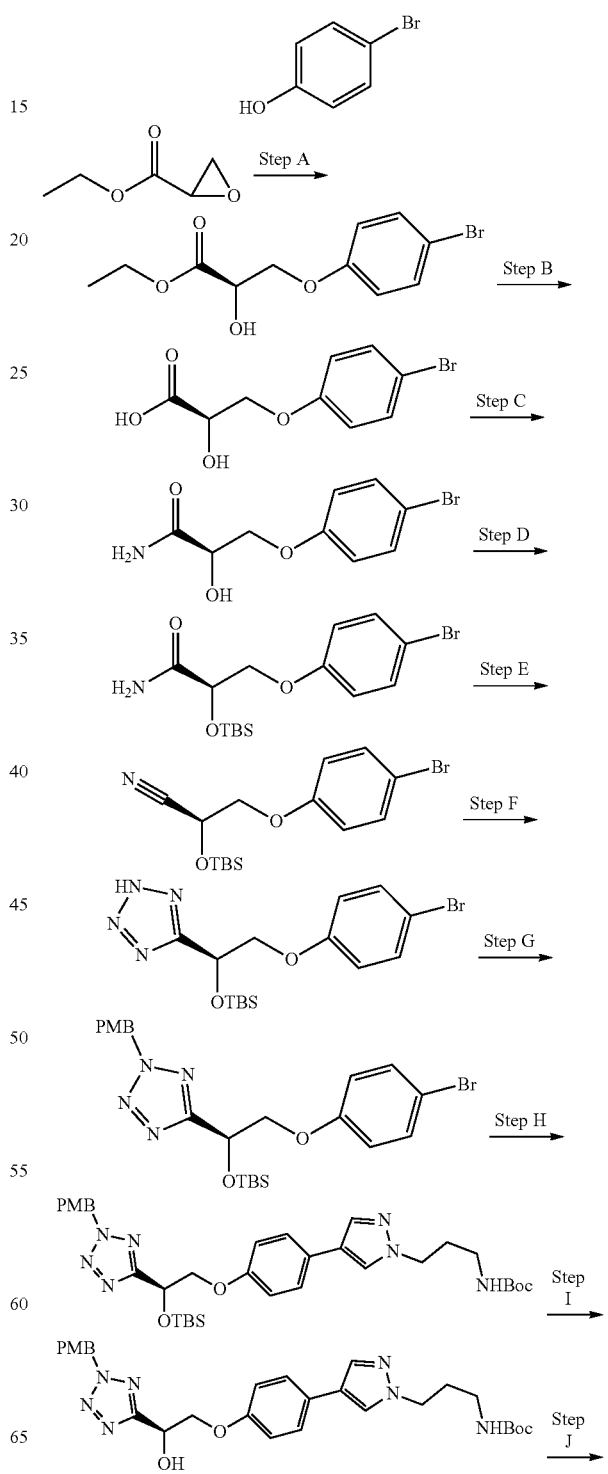

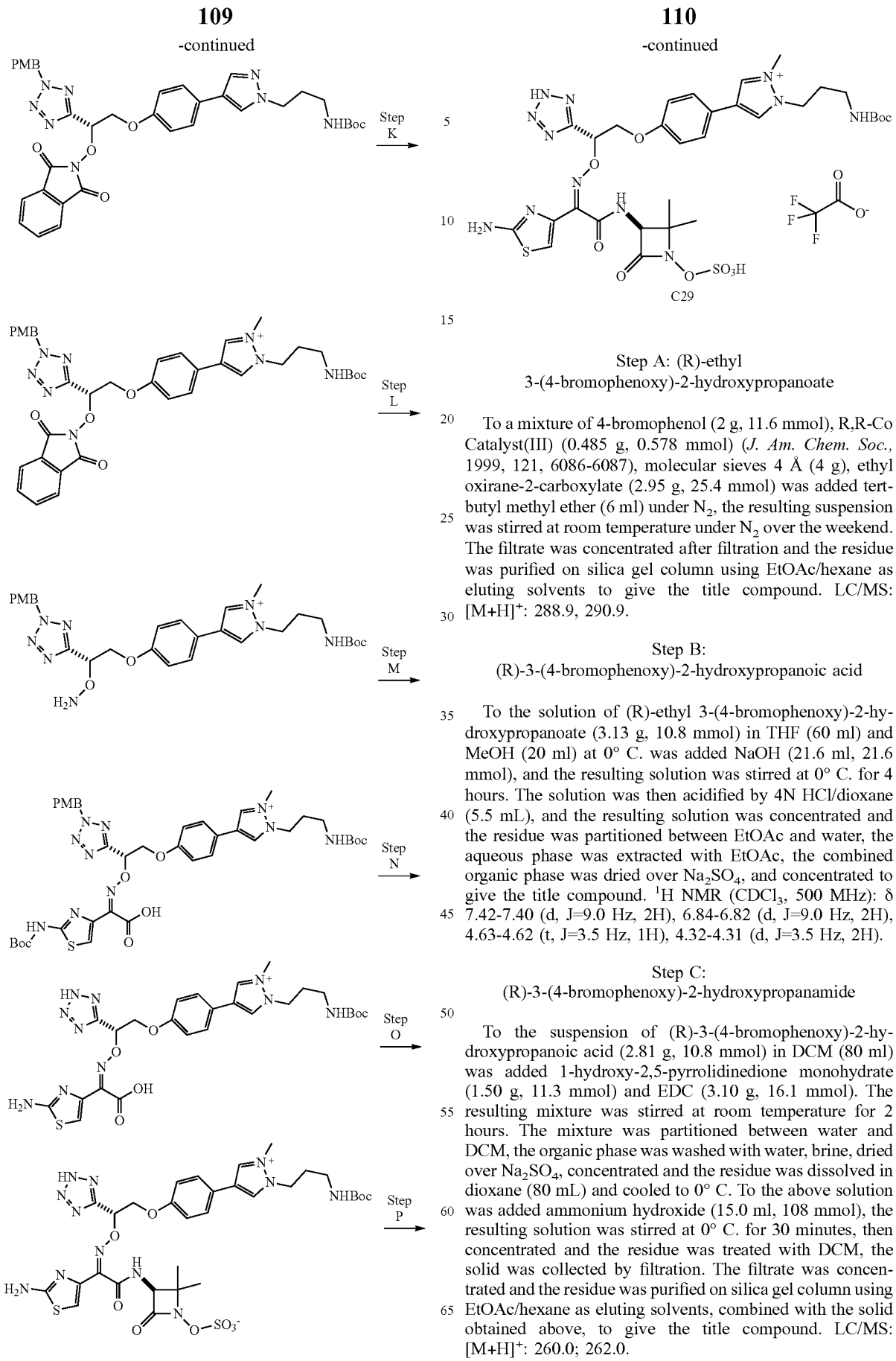

Step A: (R)-ethyl 3-(4-bromophenoxy)-2-hydroxypropanoate

To a mixture of 4-bromophenol (2 g, 11.6 mmol), R,R-Co Catalyst(III) (0.485 g, 0.578 mmol) (*J. Am. Chem. Soc.*, 1999, 121, 6086-6087), molecular sieves 4 Å (4 g), ethyl oxirane-2-carboxylate (2.95 g, 25.4 mmol) was added tert-butyl methyl ether (6 ml) under $N_2$, the resulting suspension was stirred at room temperature under $N_2$ over the weekend. The filtrate was concentrated after filtration and the residue was purified on silica gel column using EtOAc/hexane as eluting solvents to give the title compound. LC/MS: $[M+H]^+$: 288.9, 290.9.

Step B: (R)-3-(4-bromophenoxy)-2-hydroxypropanoic acid

To the solution of (R)-ethyl 3-(4-bromophenoxy)-2-hydroxypropanoate (3.13 g, 10.8 mmol) in THF (60 ml) and MeOH (20 ml) at 0° C. was added NaOH (21.6 ml, 21.6 mmol), and the resulting solution was stirred at 0° C. for 4 hours. The solution was then acidified by 4N HCl/dioxane (5.5 mL), and the resulting solution was concentrated and the residue was partitioned between EtOAc and water, the aqueous phase was extracted with EtOAc, the combined organic phase was dried over $Na_2SO_4$, and concentrated to give the title compound. $^1$H NMR (CDCl$_3$, 500 MHz): δ 7.42-7.40 (d, J=9.0 Hz, 2H), 6.84-6.82 (d, J=9.0 Hz, 2H), 4.63-4.62 (t, J=3.5 Hz, 1H), 4.32-4.31 (d, J=3.5 Hz, 2H).

Step C: (R)-3-(4-bromophenoxy)-2-hydroxypropanamide

To the suspension of (R)-3-(4-bromophenoxy)-2-hydroxypropanoic acid (2.81 g, 10.8 mmol) in DCM (80 ml) was added 1-hydroxy-2,5-pyrrolidinedione monohydrate (1.50 g, 11.3 mmol) and EDC (3.10 g, 16.1 mmol). The resulting mixture was stirred at room temperature for 2 hours. The mixture was partitioned between water and DCM, the organic phase was washed with water, brine, dried over $Na_2SO_4$, concentrated and the residue was dissolved in dioxane (80 mL) and cooled to 0° C. To the above solution was added ammonium hydroxide (15.0 ml, 108 mmol), the resulting solution was stirred at 0° C. for 30 minutes, then concentrated and the residue was treated with DCM, the solid was collected by filtration. The filtrate was concentrated and the residue was purified on silica gel column using EtOAc/hexane as eluting solvents, combined with the solid obtained above, to give the title compound. LC/MS: $[M+H]^+$: 260.0; 262.0.

Step D: (R)-3-(4-bromophenoxy)-2-((tert-butyldimethylsilyl)oxy)-propanamide

To the solution of (R)-3-(4-bromophenoxy)-2-hydroxypropanamide (1.8 g, 6.92 mmol) in acetonitrile (20 ml) was added imidazole (2.36 g, 34.6 mmol), TBS-C$_1$ (2.61 g, 17.3 mmol) and DMAP (0.085 g, 0.692 mmol). The resulting solution was stirred at room temperature for 3 hours. The reaction mixture was partitioned between EtOAc and sat. NaHCO$_3$, the aqueous phase was extracted with EtOAc three times, the combined organic phase was dried over Na$_2$SO$_4$, concentrated and the residue was purified on silica gel column using EtOAc/hexane as eluting solvents to give the title compound. LC/MS: [M+H]$^+$: 374.1; 376.1.

Step E: (S)-3-(4-bromophenoxy)-2-((tert-butyldimethylsilyl)oxy)-propanenitrile To the solution of (R)-3-(4-bromophenoxy)-2-((tert-butyldimethyl-silyl)oxy)propanamide (2.51 g, 6.71 mmol) in DMF (8 ml) at 0° C. was added cyanuric chloride (0.663 g, 3.60 mmol), the resulting solution was stirred at 0° C. for 1 hour. The mixture was quenched by addition of saturated NaHCO$_3$, the mixture was diluted in EtOAc and washed with sat. NaHCO$_3$ three times, dried over Na$_2$SO$_4$, concentrated and the residue was purified on silica gel column using EtOAC/hexane as eluting solvents to give the title compound. $^1$H NMR (CDCl$_3$, 500 MHz): δ 7.43-7.42 (d, J=8.9 Hz, 2H), 6.83-6.81 (d, J=8.9 Hz, 2H), 4.82-4.79 (dd, J=5.6 Hz, 1H), 4.18-4.15 (dd, J=5.6 Hz, 2H), 0.95 (s, 9H), 0.25 (s, 3H), 0.20 (s, 3H).

Step F: (S)-5-(2-(4-bromophenoxy)-1-((tert-butyldimethylsilyl)oxy)ethyl)-2H-tetrazole To the solution of (S)-3-(4-bromophenoxy)-2-((tert-butyldimethylsilyl)oxy)propanenitrile (1.82 g, 5.11 mmol) in toluene (30 ml) was added dibutyltin oxide (0.381 g, 1.53 mmol) and TMS-N$_3$ (2.03 ml, 15.3 mmol). The resulting mixture was heated at 110° C. overnight. After concentration, the residue was purified on silica gel column using EtOAc/hexane as eluting solvents to give the title compound. LC/MS: [M+H]$^+$: 399.1; 401.1.

Step G: (S)-5-(2-(4-bromophenoxy)-1-((tert-butyldimethylsilyl)oxy)ethyl)-2-(4-methoxybenzyl)-2H-tetrazole The mixture of K$_2$CO$_3$ (1.13 g, 8.19 mmol), tetrabutylammonium chloride, hydrate (0.162 g, 0.546 mmol), 4-methoxybenzyl chloride (0.407 ml, 3.00 mmol) and (S)-5-(2-(4-bromophenoxy)-1-((tert-butyldimethylsilyl)oxy)-ethyl)-2H-tetrazole (1.09 g, 2.73 mmol) in water (4 ml) and ClCH$_2$CH$_2$Cl (16 ml) was heated at 40° C. overnight. The mixture was partitioned between EtOAc/water, the mixture was extracted with DCM three times, the combined organic phase was dried over Na$_2$SO$_4$, concentrated and the residue was purified on silica gel column using EtOAc/hexane as eluting solvents to give the title compound. LC/MS: [M+H]$^+$: 519.2; 521.2.

Step H: (S)-tert-butyl (3-(4-(4-(2-((tert-butyldimethylsilyl)oxy)-2-(2-(4-methoxybenzyl)-2H-tetrazol-5-yl)ethoxy)phenyl)-1H-pyrazol-1-yl)propyl)carbamate To the solution of (S)-5-(2-(4-bromophenoxy)-1-((tert-butyldimethylsilyl)oxy)ethyl)-2-(4-methoxybenzyl)-2H-tetrazole (0.57 g, 1.10 mmol) and tert-butyl (3-(4-(4,4,5,5-tetramethyl-1,3,2-dioxaborolan-2-yl)-1H-pyrazol-1-yl)propyl)carbamate (0.424 g, 1.21 mmol) in dioxane (20 ml) was added Na$_2$CO$_3$ (1.646 ml, 3.29 mmol), the resulting solution was bubbled with N$_2$ for 1 hour before addition of PdCl$_2$(dppf)-CH$_2$Cl$_2$ adduct (0.090 g, 0.110 mmol). The resulting mixture was continued to bubble with N$_2$ for 20 minutes, then heated at 100° C. overnight. After filtration through Celite®, the filtrate was concentrated and the residue was purified on silica gel column using EtOAc/hexane as eluting solvents to give the title compound. LC/MS: [M+H]$^+$: 664.6.

Step I: (S)-tert-butyl (3-(4-(4-(2-hydroxy-2-(2-(4-methoxybenzyl)-2H-tetrazol-5-yl)ethoxy)phenyl)-1H-pyrazol-1-yl)propyl)carbamate To the solution of (S)-tert-butyl (3-(4-(4-(2-((tert-butyldimethylsilyl)oxy)-2-(2-(4-methoxybenzyl)-2H-tetrazol-5-yl)-ethoxy)phenyl)-1H-pyrazol-1-yl)propyl)carbamate (0.25 g, 0.377 mmol) in THF (15 ml) at 0° C. was added TBAF (1M in THF) (0.377 ml, 0.377 mmol) dropwise, the resulting solution was stirred at room temperature for 0.5 hour, the solution was concentrated and the residue was purified on silica gel column using EtOAc/hexane as eluting solvents to give the title compound. LC/MS: [M+H]$^+$: 550.5.

Step J: (R)-tert-butyl (3-(4-(4-(2-((1,3-dioxoisoindolin-2-yl)oxy)-2-(2-(4-methoxybenzyl)-2H-tetrazol-5-yl)ethoxy)phenyl)-1H-pyrazol-1-yl)propyl)carbamate To the solution of (S)-tert-butyl (3-(4-(4-(2-hydroxy-2-(2-(4-methoxybenzyl)-2H-tetrazol-5-yl)ethoxy)phenyl)-1H-pyrazol-1-yl)propyl)carbamate (0.19 g, 0.346 mmol) in THF (10 ml) was added 2-hydroxyisoindoline-1,3-dione (0.068 g, 0.415 mmol), triphenylphosphine (0.136 g, 0.519 mmol), and DEAD (0.082 ml, 0.519 mmol), the resulting solution was stirred at room temperature for 2 hours. The solution was then concentrated and the residue was purified on silica gel column using EtOAc/hexane to give the title compound. LC/MS: [M+H]$^+$: 695.5.

Step K: (R)-1-(3-((tert-butoxycarbonyl)amino)propyl)-4-(4-(2-((1,3-dioxoisoindolin-2-yl)oxy)-2-(2-(4-methoxybenzyl)-2H-tetrazol-5-yl)ethoxy)phenyl)-2-methyl-1H-pyrazol-2-ium iodide To the mixture of (R)-tert-butyl (3-(4-(4-(2-((1,3-dioxoisoindolin-2-yl)oxy)-2-(2-(4-methoxybenzyl)-2H-tetrazol-5-yl)ethoxy)phenyl)-1H-pyrazol-1-yl)propyl)carbamate (240 mg, 0.345 mmol) in acetonitrile (3 ml) was added MeI (0.108 ml, 1.73 mmol). The resulting mixture was heated at 60° C. overnight. Additional MeI (0.108 ml, 1.727 mmol) was added and the resulting solution was heated at 60° C. for 24 hours. The solution was concentrated to give the title compound. LC/MS: [M]$^+$: 709.6.

Step L: (R)-4-(4-(2-(aminooxy)-2-(2-(4-methoxybenzyl)-2H-tetrazol-5-yl)ethoxy)phenyl)-1-(3-((tert-butoxycarbonyl)amino)propyl)-2-methyl-1H-pyrazol-2-ium To the solution of (R)-1-(3-((tert-butoxycarbonyl)amino) propyl)-4-(4-(2-((1,3-dioxoisoindolin-2-yl)oxy)-2-(2-(4-methoxybenzyl)-2H-tetrazol-5-yl)ethoxy)phenyl)-2-methyl-1H-pyrazol-2-ium iodide (301 mg, 0.360 mmol) in ethanol (4 ml) and CH$_2$Cl$_2$ (4 mL) at 0° C. was added hydrazine (0.011 ml, 0.360 mmol), the resulting solution was stirred at 0° C. for 30 minutes, the solution was then concentrated to give the title compound. LC/MS: [M]$^+$: 579.5.

Step M: (R,Z)-1-(3-((tert-butoxycarbonyl)amino) propyl)-4-(4-(2-((((2-((tert-butoxy-carbonyl)amino) thiazol-4-yl)(carboxy)methylene)amino)oxy)-2-(2-(4-methoxybenzyl)-2H-tetrazol-5-yl)ethoxy)phenyl)-2-methyl-1H-pyrazol-2-ium To the suspension of (R)-4-(4-(2-(aminooxy)-2-(2-(4-methoxybenzyl)-2H-tetrazol-5-yl)ethoxy)phenyl)-1-(3-((tert-butoxycarbonyl)amino)propyl)-2-methyl-1H-pyrazol-2-ium (209 mg, 0.361 mmol) in ethanol (6 ml) and CH$_2$Cl$_2$ (6 ml) was added 2-(2-((tert-butoxycarbonyl)amino)thiazol-4-yl)-2-oxoacetic acid (196 mg, 0.721 mmol). The resulting solution was stirred at room temperature for 1 hour, after concentration the residue was purified on reverse phase MPLC using acetonitrile (0.05% TFA)/water (0.05% TFA) as mobile phase to give the title compound. LC/MS: [M]$^+$: 833.6.

Step N: (R,Z)-4-(4-(2-((((2-aminothiazol-4-yl)(carboxy)methylene)-amino)oxy)-2-(2H-tetrazol-5-yl) ethoxy)phenyl)-1-(3-((tert-butoxycarbonyl)amino) propyl)-2-methyl-1H-pyrazol-2-ium To a flask containing (R,Z)-1-(3-((tert-butoxycarbonyl)-amino)propyl)-4-(4-(2-((((2-((tert-butoxycarbonyl)amino) thiazol-4-yl)(carboxy)-methylene)amino)oxy)-2-(2-(4-methoxybenzyl)-2H-tetrazol-5-yl)ethoxy)phenyl)-2-methyl-1H-pyrazol-2-ium (230 mg, 0.276 mmol) was added TFA (4 mL, 51.9 mmol), the resulting solution was stirred at room temperature for 30 minutes, the solution was concentrated and the residue was dissolved in TFA (4 ml), the resulting solution was heated at 70° C. for 45 minutes. The solution was concentrated and the residue was dissolved in DMF (16 mL), to the resulting solution was at 0° C. added TEA (0.231 mL, 1.655 mmol), and BOC$_2$O (0.077 mL, 0.331 mmol). The resulting solution was stirred at 0° C. for 1 hour, then purified on reverse phase MPLC using acetonitrile (0.05% TFA)/water (0.05% TFA) as mobile phase to give the title compound. LC/MS: [M]$^+$: 613.5.

Step O: (S)-3-((Z)-2-(2-aminothiazol-4-yl)-2-(((R)-2-(4-(1-(3-((tert-butoxycarbonyl)-amino)propyl)-2-methyl-1H-pyrazol-2-ium-4-yl)phenoxy)-1-(2H-tetrazol-5-yl)ethoxy)-imino)acetamido)-2,2-dimethyl-4-oxoazetidin-1-yl sulfate To the solution of (R,Z)-4-(4-(2-((((2-aminothiazol-4-yl) (carboxy)methylene)amino)oxy)-2-(2H-tetrazol-5-yl) ethoxy)phenyl)-1-(3-((tert-butoxycarbonyl)amino)propyl)-2-methyl-1H-pyrazol-2-ium (47 mg, 0.077 mmol) in DMF (4 ml) was added DCC (79 mg, 0.383 mmol), and HOBT (58.6 mg, 0.383 mmol). The resulting solution was stirred at room temperature for 30 minutes, then (S)-3-amino-2,2-dimethyl-4-oxoazetidin-1-yl hydrogen sulfate (64.4 mg, 0.306 mmol) and sodium bicarbonate (77 mg, 0.919 mmol) was added. The resulting mixture was stirred at room temperature overnight. Additional DCC (79 mg, 0.383 mmol) and (S)-3-amino-2,2-dimethyl-4-oxoazetidin-1-yl hydrogen sulfate (64.4 mg, 0.306 mmol) was added and the resulting solution was stirred at room temperature for 1 hour. After filtration of the reaction mixture, the filtrate was purified on reverse phase HPLC using acetonitrile (0.05% TFA)/water (0.05% TFA) as mobile phase to give the title compound. LC/MS: [M]$^+$: 805.4.

Step P: 1-(3-aminopropyl)-4-(4-((R)-2-((((Z)-1-(2-aminothiazol-4-yl)-2-(((S)-2,2-dimethyl-4-oxo-1-(sulfooxy)azetidin-3-yl)amino)-2-oxoethylidene) amino)oxy)-2-(2H-tetrazol-5-yl)ethoxy)phenyl)-2-methyl-1H-pyrazol-2-ium 2,2,2-trifluoroacetate To the solution of (S)-3-((Z)-2-(2-aminothiazol-4-yl)-2-(((R)-2-(4-(1-(3-((tert-butoxycarbonyl)amino)propyl)-2-methyl-1H-pyrazol-2-ium-4-yl)phenoxy)-1-(2H-tetrazol-5-yl)ethoxy)imino)acetamido)-2,2-dimethyl-4-oxoazetidin-1-yl sulfate (30 mg, 0.037 mmol) in CH$_2$Cl$_2$ (2 ml) was added TFA (2 m, 26.0 mmol). The resulting solution was stirred at room temperature for 30 minutes. After concentration, the residue was purified on reverse phase HPLC using acetonitrile (0.05% TFA)/water (0.05% TFA) as mobile phase to give the title compound. LC/MS: [M]$^+$: 705.4. $^1$H NMR (DMSO-d$_6$, 500 MHz): δ 9.48-9.46 (d, J=7.7 Hz, 1H), 8.98 (s, 1H), 8.94 (s, 1H), 7.77 (s, 1H), 7.66-7.63 (d, J=8.5 Hz, 2H), 7.31 (s, 1H), 7.11-7.09 (d, J=8.6 Hz, 2H), 5.92 (s, 1H), 4.59-4.52 (m, 6H), 4.12 (s, 3H), 2.94-2.90 (m, 2H), 2.20-2.17 (m, 2H), 1.38 (s, 3H), 1.15 (s, 3H).

Example 30

1-(3-aminopropyl)-4-(4-((R)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-(2H-tetrazol-5-yl)ethoxy)phenyl)-2-methyl-1H-pyrazol-2-ium 2,2,2-trifluoroacetate (C30)

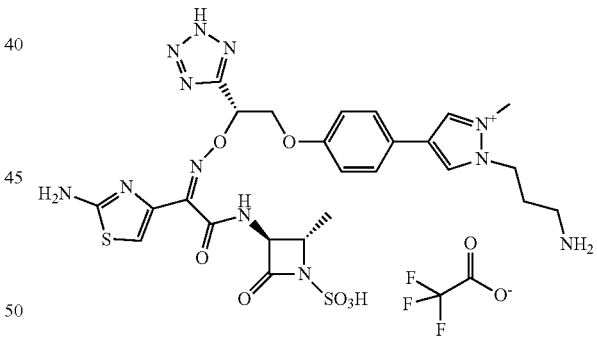

C30

Step A: 4-(4-((R)-2-(((Z)-(1-(2-aminothiazol-4-yl)-2-(((2S,3S)-2-methyl-4-oxo-1-sulfoazetidin-3-yl) amino)-2-oxoethylidene)amino)oxy)-2-(2H-tetrazol-5-yl)ethoxy)phenyl)-1-(3-((tert-butoxycarbonylamino)propyl)-2-methyl-1H-pyrazol-2-ium To the solution of (R,Z)-4-(4-(2-((((2-aminothiazol-4-yl) (carboxy)methylene)amino)oxy)-2-(2H-tetrazol-5-yl) ethoxy)phenyl)-1-(3-((tert-butoxycarbonyl)amino)propyl)-2-methyl-1H-pyrazol-2-ium (18.8 mg, 0.031 mmol) in DMF (2 ml) was added DCC (63.2 mg, 0.306 mmol), and HOBT (23.46 mg, 0.153 mmol). The resulting solution was stirred at room temperature for 30 minutes, then (2S,3S)-3-amino- 2-methyl-4-oxoazetidine-1-sulfonic acid (22.1 mg, 0.123 mmol) and sodium bicarbonate (30.9 mg, 0.368 mmol) were added. The resulting mixture was stirred at room temperature for 1 hour. After filtration of the reaction mixture, the filtrate was purified on reverse phase HPLC using acetonitrile (0.05% TFA)/water (0.05% TFA) as mobile phase to give the title compound. LC/MS: [M]+: 775.6.

Step B: 1-(3-aminopropyl)-4-(4-((R)-2-((((Z)-1-(2-aminothiazol-4-yl)-2-(((2S,3S)-2-methyl-4-oxo-1-sulfoazetidin-3-yl)amino)-2-oxoethylidene)amino)oxy)-2-(2H-tetrazol-5-yl)ethoxy)phenyl)-2-methyl-1H-pyrazol-2-ium 2,2,2-trifluoroacetate To the solution of 4-(4-((R)-2-(((Z)-(1-(2-aminothiazol-4-yl)-2-(((2S,3S)-2-methyl-4-oxo-1-sulfoazetidin-3-yl)amino)-2-oxoethylidene)amino)oxy)-2-(2H-tetrazol-5-yl)ethoxy)phenyl)-1-(3-((tert-butoxycarbonyl)amino)propyl)-2-methyl-1H-pyrazol-2-ium (11 mg, 0.014 mmol) in CH$_2$Cl$_2$ (2 ml) was added TFA (2 mL, 26.0 mmol). The resulting solution was stirred at room temperature for 30 minutes, the volatile was evaporated, and the residue was purified on reverse phase HPLC using acetonitrile (0.05% TFA)/water(0.05% TFA) as mobile phase to give the title compound. LC/MS: [M+H]+: 675.4. $^1$H NMR (DMSO-d$_6$, 500 MHz): δ 9.29-9.27 (d, J=6.7 Hz, 1H), 8.98 (s, 1H), 8.95 (s, 1H), 7.78 (m, 3H), 7.66-7.63 (d, J=10.2 Hz, 2H), 7.31 (s, 2H), 7.15-7.13 (d, J=9.6 Hz, 2H), 6.82 (s, 1H), 5.91 (t, J=7.3 Hz, 1H), 4.62-4.59 (m, 2H), 4.55-4.53 (t, J=7.0 Hz, 2H), 4.43-4.41 (d, J=9.7 Hz, 1H), 4.12 (s, 3H), 3.72-3.71 (m, 1H), 2.94-2.90 (m, 2H), 2.21-2.17 (t, J=7.8 Hz, 2H), 1.30-1.28 (d, J=6.1 Hz, 3H).

Example 31

3-(2-amino-4-(4-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)phenyl)-1H-imidazol-1-yl)propan-1-aminium 2,2,2-trifluoroacetate (C31)

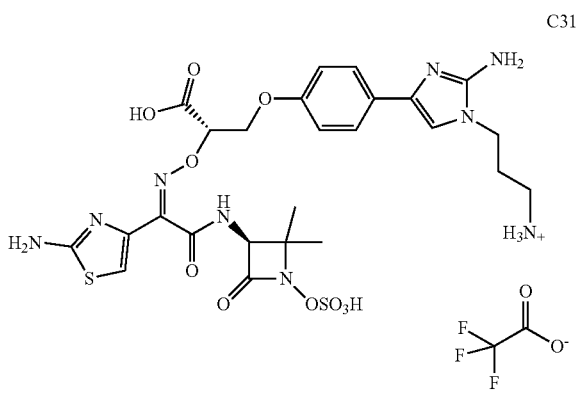

C31

Step A: tert-butyl (3-(2-nitro-1H-imidazol-1-yl)propyl)carbamate

Cesium carbonate (2240 mg, 6.88 mmol) was added to a stirred mixture of 3-(boc-amino)propyl bromide (901 mg, 3.78 mmol) and 2-nitro-1H-imidazole (389 mg, 3.44 mmol) in DMF (20 ml) and the mixture was stirred at 60° C. overnight. The mixture was diluted with ethyl acetate, washed with water three times and brine, dried over NaSO$_4$, filtered and the solvent was evaporated under reduced pressure to give crude product. The crude was purified on silica gel column using EtOAc/hexane as eluting solvents to give the title compound. LC/MS: [M+H]+: 271.1.

Step B: tert-butyl (3-(4-bromo-2-nitro-1H-imidazol-1-yl)propyl)carbamate

To the solution of tert-butyl (3-(2-nitro-1H-imidazol-1-yl)propyl)carbamate (1.17 g, 4.33 mmol) in DMF (8 ml) was added NBS (0.847 g, 4.76 mmol). The resulting solution was stirred at 60° C. for 3 hours. The solution was partitioned between EtOAc and sat. NaHCO$_3$, the organic phase was washed with saturated NaHCO$_3$ three times, dried over Na$_2$SO$_4$, concentrated and the residue was purified on silica gel column using EtOAc/hexane as eluting solvents to give the title compound. LC/MS: [M+H]+: 349.1, 351.1.

Step C: (R)-tert-butyl 3-(4-(1-(3-((tert-butoxycarbonyl)amino)propyl)-2-nitro-1H-imidazol-4-yl)phenoxy)-2-hydroxypropanoate To the solution of tert-butyl (3-(4-bromo-2-nitro-1H-imidazol-1-yl)propyl)carbamate (0.82 g, 2.348 mmol) in dioxane (20 ml) was added (R)-tert-butyl 2-hydroxy-3-(4-(4,4,5,5-tetramethyl-1,3,2-dioxaborolan-2-yl)phenoxy)propanoate (1.112 g, 3.05 mmol) and Na$_2$CO$_3$ (3.52 ml, 7.05 mmol). The resulting mixture was bubbled with N$_2$ for 20 minutes before addition of PdCl$_2$(dppf)-CH$_2$Cl$_2$ adduct (0.192 g, 0.235 mmol). The mixture was further bubbled with N$_2$ for 15 minutes, then heated at 100° C. overnight. After filtration through Celite® the filtrate was concentrated and the residue was purified on silica gel column using EtOAc/hexane as eluting solvents to give the title compound. LC/MS: [M+H]+: 507.4.

Step D: (R)-tert-butyl 3-(4-(1-(3-((tert-butoxycarbonyl)amino)propyl)-2-nitro-1H-imidazol-4-yl)phenoxy)-2-((tert-butyldimethylsilyl)oxy)propanoate To the solution of (R)-tert-butyl 3-(4-(1-(3-((tert-butoxycarbonyl)amino)propyl)-2-nitro-1H-imidazol-4-yl)phenoxy)-2-hydroxypropanoate (2460 mg, 4.86 mmol) in DMF (20 ml) was added imidazole (1653 mg, 24.28 mmol), TBS-Cl (1464 mg, 9.71 mmol) and DMAP (59.3 mg, 0.486 mmol). The resulting solution was stirred at room temperature for 1 hour, then partitioned between EtOAc and saturated NaHCO$_3$. The organic phase was washed with saturated NaHCO$_3$ three times, dried over Na$_2$SO$_4$, concentrated, and the residue was purified on silica gel column using EtOAc/hexane as eluting solvents to give the title compound. LC/MS: [M+H]+: 621.5.

Step E: (R)-tert-butyl 3-(4-(2-amino-1-(3-((tert-butoxycarbonyl)amino)propyl)-1H-imidazol-4-yl)phenoxy)-2-((tert-butyldimethylsilyl)oxy)propanoate To the solution of (R)-tert-butyl 3-(4-(1-(3-((tert-butoxycarbonyl)amino)propyl)-2-nitro-1H-imidazol-4-yl)phenoxy)-2-((tert-butyldimethylsilyl)oxy)propanoate (2.4 g, 3.87 mmol) in MeOH (50 ml) was added 10% Pd/C (0.411 g, 0.387 mmol). The resulting mixture was hydrogenated at 42 psi overnight. After filtration through Celite® the filtrate was concentrated to give the title compound. LC/MS: [M+H]+: 591.5.

Step F: (R)-tert-butyl 3-(4-(2-(bis(tert-butoxycarbonyl)amino)-1-(3-((tert-butoxycarbonyl)-amino)propyl)-1H-imidazol-4-yl)phenoxy)-2-((tert-butyldimethylsilyl)oxy)propanoate To the solution of (R)-tert-butyl 3-(4-(2-amino-1-(3-((tert-butoxycarbonyl)amino)propyl)-1H-imidazol-4-yl)phenoxy)-2-((tert-butyldimethylsilyl)oxy)propanoate (2.53 g, 4.28 mmol) in $CH_2Cl_2$ (40 ml) was added $BOC_2O$ (2.98 ml, 12.85 mmol), TEA (1.194 ml, 8.56 mmol), and DMAP (0.052 g, 0.428 mmol). The resulting solution was stirred at RT for 30 minutes. After concentration the residue was purified on silica gel column using EtOAc/hexane as eluting solvents to give the title compound. LC/MS: $[M+H]^+$: 791.6.

Step G: (R)-tert-butyl 3-(4-(2-(bis(tert-butoxycarbonyl)amino)-1-(3-((tert-butoxy-carbonyl)amino)propyl)-1H-imidazol-4-yl)phenoxy)-2-hydroxypropanoate To the solution of (R)-tert-butyl 3-(4-(2-(bis(tert-butoxycarbonyl)amino)-1-(3-((tert-butoxycarbonyl)-amino)propyl)-1H-imidazol-4-yl)phenoxy)-2-((tert-butyldimethylsilyl)oxy)propanoate (1.80 g, 2.28 mmol) in THF (20 ml) at 0° C. was added TBAF (1 M in THF) (2.275 ml, 2.275 mmol). The resulting solution was stirred at 0° C. for 30 minutes. After concentration of the solution the residue was purified on silica gel column using EtOAc/hexane as eluting solvents to give the title compound. LC/MS: $[M+H]^+$: 677.5.

Step H: (S)-tert-butyl 3-(4-(2-(bis(tert-butoxycarbonyl)amino)-1-(3-((tert-butoxy-carbonyl)amino)propyl)-1H-imidazol-4-yl)phenoxy)-2-((1,3-dioxoisoindolin-2-yl)-oxy)propanoate To the solution of (R)-tert-butyl 3-(4-(2-(bis(tert-butoxycarbonyl)amino)-1-(3-((tert-butoxycarbonyl)amino)propyl)-1H-imidazol-4-yl)phenoxy)-2-hydroxypropanoate (1.39 g, 2.05 mmol) in THF (20 ml) was added 2-hydroxyisoindoline-1,3-dione (0.402 g, 2.46 mmol), triphenylphosphine (0.808 g, 3.08 mmol), and DEAD (0.488 ml, 3.08 mmol). The resulting solution was stirred at room temperature for 1.5 hours. After concentration of the reaction solution, the residue was purified on silica gel column using EtOAc/hexane as eluting solvents to give the title compound. LC/MS: $[M+H]^+$: 822.5.

Step I: (S)-tert-butyl 2-(aminooxy)-3-(4-(2-(bis(tert-butoxycarbonyl)amino)-1-(3-((tert-butoxycarbonyl)amino)propyl)-1H-imidazol-4-yl)phenoxy)propanoate To the solution of (S)-tert-butyl 3-(4-(2-(bis(tert-butoxycarbonyl)amino)-1-(3-((tert-butoxycarbonyl)-amino)propyl)-1H-imidazol-4-yl)phenoxy)-2-((1,3-dioxoisoindolin-2-yl)oxy)propanoate (0.58 g, 0.706 mmol) in EtOH (8 ml) and $CH_2Cl_2$ (8.00 ml) was added hydrazine (0.022 ml, 0.706 mmol) at 0° C. The resulting solution was stirred at 0° C. for 0.5 hour. After concentration, the residue was dissolved in DCM (10 mL) and stirred at room temperature for 5 minutes then filtered. The filtrate was concentrated to give the title compound. LC/MS: $[M+H]^+$: 692.5.

Step J: (S,Z)-2-(((3-(4-(2-(bis(tert-butoxycarbonyl)amino)-1-(3-((tert-butoxycarbonyl)-amino)propyl)-1H-imidazol-4-yl)phenoxy)-1-(tert-butoxy)-1-oxopropan-2-yl)oxy)imino)-2-(2-((tert-butoxycarbonyl)amino)thiazol-4-yl)acetic acid To the solution of (S)-tert-butyl-2-(aminooxy)-3-(4-(2-(bis(tert-butoxycarbonyl)amino)-1-(3-((tert-butoxycarbonyl)-amino)-propyl)-1H-imidazol-4-yl)phenoxy)propanoate (0.61 g, 0.882 mmol) in ethanol (8 ml) and DCM (8 mL) was added 2-(2-((tert-butoxycarbonyl)amino)thiazol-4-yl)-2-oxoacetic acid (0.240 g, 0.882 mmol). The resulting solution was stirred at room temperature overnight. The solution was then concentrated to give the title compound. LC/MS: $[M+H]^+$: 946.6.

Step K: (S)-tert-butyl 3-(4-(2-(bis(tert-butoxycarbonyl)amino)-1-(3-((tert-butoxycarbonyl)amino)propyl)-1H-imidazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate To the solution of (S,Z)-2-(((3-(4-(2-(bis(tert-butoxycarbonyl)amino)-1-(3-((tert-butoxycarbonyl)amino)propyl)-1H-imidazol-4-yl)phenoxy)-1-(tert-butoxy)-1-oxopropan-2-yl)oxy)imino)-2-(2-((tert-butoxycarbonyl)-amino)thiazol-4-yl)acetic acid (0.42 g, 0.444 mmol) in DMF (4 ml) was added DCC (0.275 g, 1.33 mmol) and HOBT (0.204 g, 1.332 mmol). The resulting mixture was stirred at room temperature for 30 minutes before addition of (S)-3-amino-2,2-dimethyl-4-oxoazetidin-1-yl hydrogen sulfate (0.187 g, 0.888 mmol) and sodium bicarbonate (0.298 g, 3.55 mmol). The resulting mixture was stirred at room temperature for 5 hours. After filtration of the mixture, the filtrate was purified on reverse phase MPLC using acetonitrile (0.05% TFA)/water (0.05% TFA) as mobile phase to give the title compound. LC/MS: $[M+H]^+$: 1139.5.

Step L: 3-(2-amino-4-(4-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)phenyl)-1H-imidazol-1-yl)propan-1-aminium 2,2,2-trifluoroacetate To the solution of (S)-tert-butyl 3-(4-(2-(bis(tert-butoxycarbonyl)amino)-1-(3-((tert-butoxycarbonyl)amino)propyl)-1H-imidazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate (184 mg, 0.162 mmol) in $CH_2Cl_2$ (2 ml) was added TFA (4 mL, 51.9 mmol). The resulting solution was stirred at room temperature for 1 hour. After concentration of the solution on rotary evaporator at room temperature, the residue was treated with $Et_2O$ and concentrated again. The solid residue was dissolved in DMSO and purified on reverse phase HPLC using acetonitrile (0.05% TFA)/water (0.05% TFA) as mobile phase to give the title compound. LC/MS: $[M+H]^+$: 682.3. $^1H$ NMR ($D_2O$, 500 MHz): δ 7.29-7.27 (d, J=10.8 Hz, 2H), 6.99 (s, 1H), 6.89 (s, 1H), 6.89-6.87 (d, J=10.2 Hz, 2H), 5.04-5.02 (m, 1H), 4.54 (s, 1H), 4.43-4.41 (m, 2H), 3.83-3.81 (d, J=9.0 Hz), 3.00-2.98 (m, 2H), 2.08-2.04 (m, 2H), 1.33 (s, 3H), 1.02 (s, 3H).

Example 32

3-(4-(4-((S)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)-2-carboxyethoxy)phenyl)-2-imino-3-methyl-2,3-dihydro-1H-imidazol-1-yl)propan-1-aminium 2,2,2-trifluoroacetate (C32)

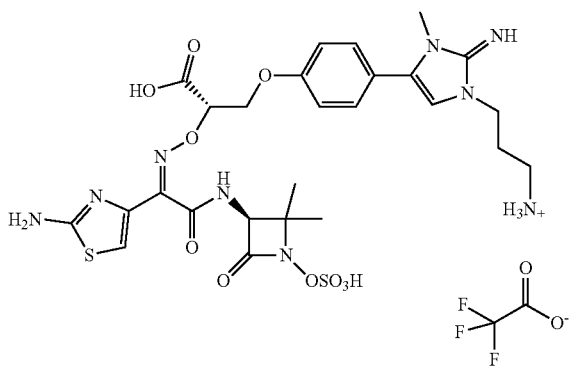

C32

Step A: (S,E)-tert-butyl 3-(4-(1-(3-((tert-butoxycarbonyl)amino)propyl)-2-((tert-butoxycarbonyl)imino)-3-methyl-2,3-dihydro-1H-imidazol-4-yl)phenoxy)-2-((1,3-dioxoisoindolin-2-yl)oxy)propanoate To the solution of (S)-tert-butyl 3-(4-(2-(bis(tert-butoxycarbonyl)amino)-1-(3-((tert-butoxycarbonyl)amino)propyl)-1H-imidazol-4-yl)phenoxy)-2-((1,3-dioxoisoindolin-2-yl)oxy)propanoate (157 mg, 0.191 mmol) in acetonitrile (2 ml) was added MeI (0.036 ml, 0.573 mmol). The resulting solution was heated at 60° C. overnight. The solution was concentrated to give the title compound. LC/MS: [M+H]$^+$: 736.5.

Step B: (S,E)-tert-butyl 2-(aminooxy)-3-(4-(1-(3-((tert-butoxycarbonyl)amino)propyl)-2-((tert-butoxycarbonyl)imino)-3-methyl-2,3-dihydro-1H-imidazol-4-yl)phenoxy)propanoate To the solution of (S,E)-tert-butyl 3-(4-(1-(3-((tert-butoxycarbonyl)amino)propyl)-2-((tert-butoxycarbonyl)imino)-3-methyl-2,3-dihydro-1H-imidazol-4-yl)phenoxy)-2-((1,3-dioxo-isoindolin-2-yl)oxy)propanoate (0.18 g, 0.245 mmol) in EtOH (4.00 ml) and CH$_2$Cl$_2$ (4 ml) at 0° C. was added hydrazine (0.015 ml, 0.489 mmol). The resulting solution was stirred at 0° C. for 2 hours then concentrated to give the title compound. LC/MS: [M+H]$^+$: 606.5.

Step C: (Z)-2-((((S)-1-(tert-butoxy)-3-(4-((E)-1-(3-((tert-butoxycarbonyl)amino)propyl)-2-((tert-butoxycarbonyl)imino)-3-methyl-2,3-dihydro-1H-imidazol-4-yl)phenoxy)-1-oxo-propan-2-yl)oxy)imino)-2-(2-((tert-butoxycarbonyl)amino)thiazol-4-yl)acetic acid To the solution of (S,E)-tert-butyl 2-(aminooxy)-3-(4-(1-(3-((tert-butoxycarbonyl)amino)propyl)-2-((tert-butoxycarbonyl)imino)-3-methyl-2,3-dihydro-1H-imidazol-4-yl)phenoxy)propanoate (126 mg, 0.208 mmol) in ethanol (8 ml) and DCM (8 mL) was added 2-(2-((tert-butoxy-carbonyl)amino)thiazol-4-yl)-2-oxoacetic acid (142 mg, 0.520 mmol). The resulting solution was stirred at room temperature for 3 hours. The solution was then concentrated, and the residue was purified on reverse phase MPLC using acetonitrile (0.05% TFA)/water (0.05% TFA) as mobile phase to give the title compound. LC/MS: [M+H]$^+$: 860.4.

Step D: (S)-tert-butyl 3-(4-((E)-1-(3-((tert-butoxycarbonyl)amino)propyl)-2-((tert-butoxycarbonyl)imino)-3-methyl-2,3-dihydro-1H-imidazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate To the solution of (Z)-2-((((S)-1-(tert-butoxy)-3-(4-((E)-1-(3-((tert-butoxycarbonyl)amino)propyl)-2-((tert-butoxycarbonyl)imino)-3-methyl-2,3-dihydro-1H-imidazol-4-yl)phenoxy)-1-oxopropan-2-yl)oxy)imino)-2-(2-((tert-butoxycarbonyl)amino)thiazol-4-yl)acetic acid (152 mg, 0.177 mmol) in DMF (5 ml) was added DCC (292 mg, 1.41 mmol) and HOBT (122 mg, 0.795 mmol). The resulting solution was stirred at room temperature for 30 minutes before addition of (S)-3-amino-2,2-dimethyl-4-oxoazetidin-1-yl hydrogen sulfate (130 mg, 0.619 mmol) and sodium bicarbonate (297 mg, 3.53 mmol). The resulting mixture was stirred at room temperature for 28 hours, then was filtered, and the filtrate was purified on reverse phase MPLC using acetonitrile (0.05% TFA)/water (0.05% TFA) as mobile phase to give the title compound. LC/MS: [M+H]$^+$: 1052.6.

Step E: 3-(4-(4-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)phenyl)-2-imino-3-methyl-2,3-dihydro-1H-imidazol-1-yl)propan-1-aminium 2,2,2-trifluoroacetate To the solution of (S)-tert-butyl 3-(4-((E)-1-(3-((tert-butoxycarbonyl)amino)propyl)-2-((tert-butoxycarbonyl)imino)-3-methyl-2,3-dihydro-1H-imidazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate (140 mg, 0.133 mmol) in CH$_2$Cl$_2$ (2 ml) was added TFA (4 mL, 51.9 mmol). The resulting solution was stirred at room temperature for 40 minutes, then concentrated and the residue was treated with Et$_2$O and concentrated again. The solid dry residue was purified on reverse phase HPLC using acetonitrile (0.05% TFA)/water (0.05% TFA) as mobile phase to give the title compound. LC/MS: [M+H]$^+$: 696.3. $^1$H NMR (D$_2$O, 500 MHz): δ 7.29-7.27 (d, J=10.3 Hz, 2H), 7.04 (s, 1H), 6.99-6.97 (d, J=10.3 Hz, 2H), 6.80 (s, 1H), 5.08 (s, 1H), 4.66 (m, 1H), 4.63 (s, 1H), 4.48-4.43 (m, 2H), 3.91-3.89 (t, J=7.1 Hz, 2H), 3.29 (s, 3H), 3.0-2.96 (m, 2H), 2.09-2.05 (m, 2H), 1.35 (s, 3H), 0.97 (s, 3H).

Example 33

1-(3-aminopropyl)-4-((5-((S)-2-((((Z)-1-(2-aminothi-azol-4-yl)-2-(((S)-2,2-dimethyl-4-oxo-1-(sulfooxy)azetidin-3-yl)amino)-2-oxoethylidene)amino)oxy)-2-carboxyethoxy)pyridin-2-yl)amino)pyridin-1-ium 2,2,2-trifluoroacetate (C33)

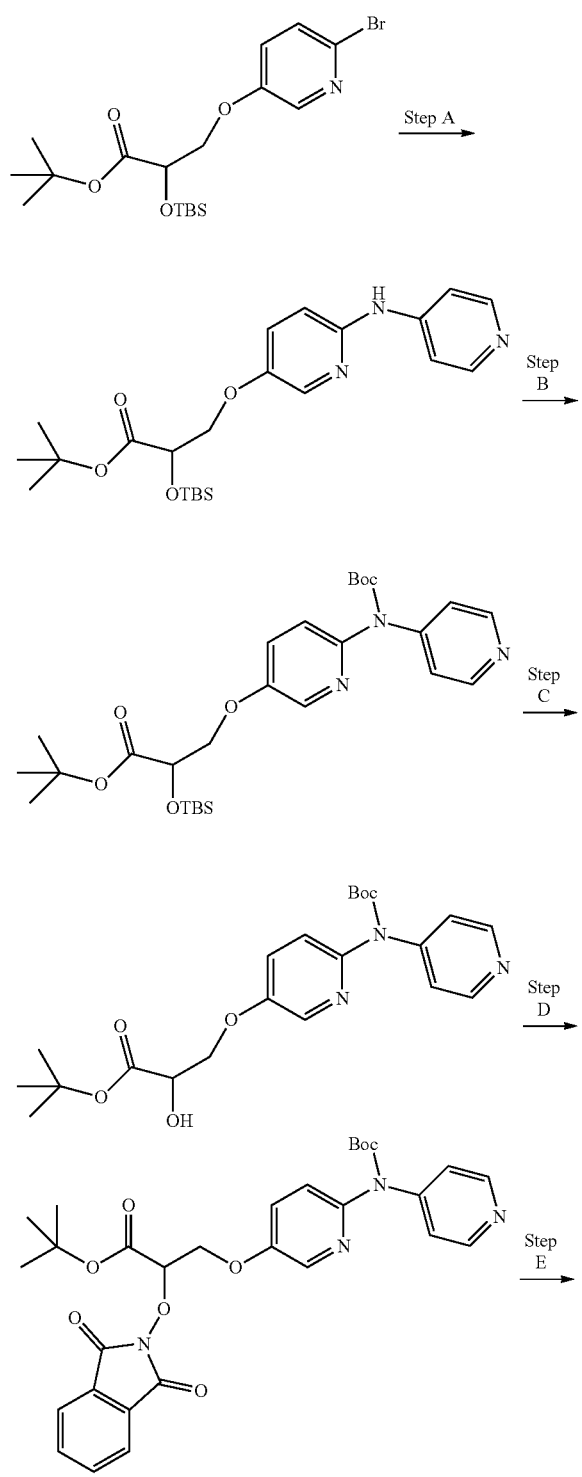

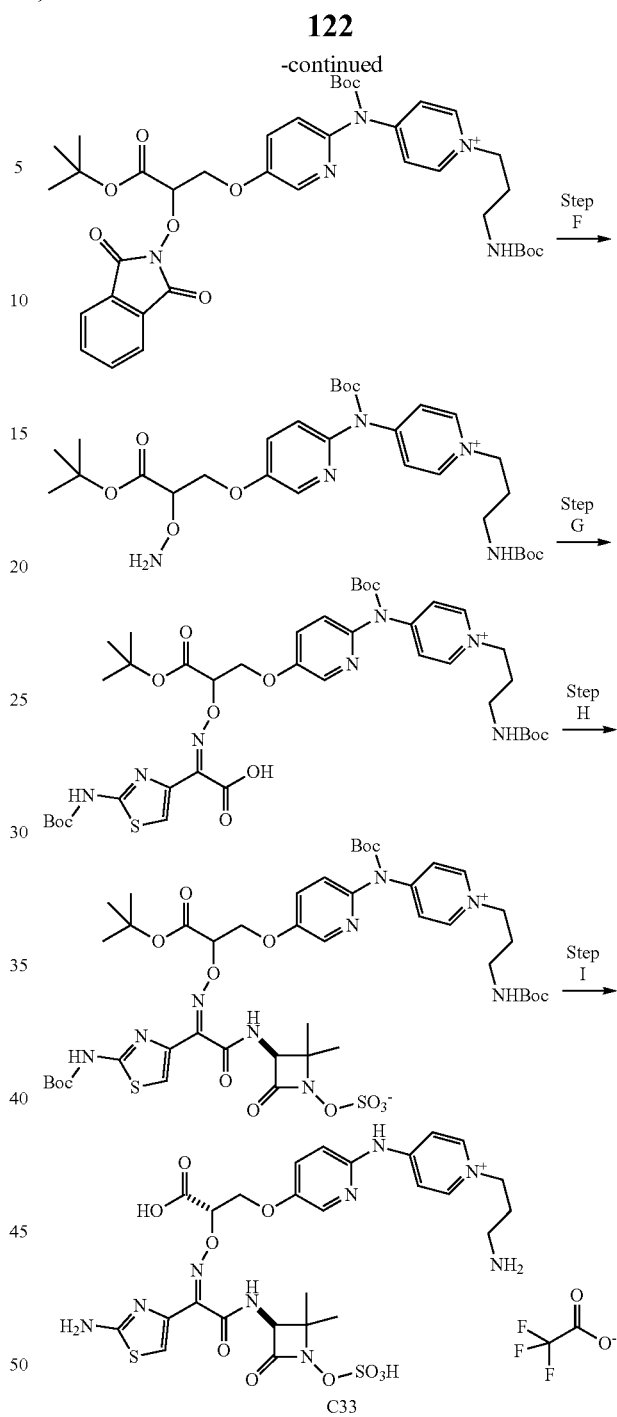

Step A: tert-butyl 2-((tert-butyldimethylsilyl)oxy)-3-((6-(Pyridin-4-ylamino)pyridin-3-yl)oxy)propanoate The mixture of J009 pre-catalyst G3 (Aldrich #88755, 250 mg, 0.27 mmol), $Cs_2CO_3$ (2.64 g, 8.12 mmol), tert-butyl 3-((6-bromopyridin-3-yl)oxy)-2-((tert-butyldimethylsilyl)oxy)propanoate (1170 mg, 2.71 mmol), and pyridin-4-amine (306 mg, 3.25 mmol) in a sealed tube was degassed by vacuum/$N_2$ refill three times before addition of dioxane (12 ml). The resulting mixture was further degassed by vacuum/$N_2$ refill three times, then was heated at 100° C. for 16 hours. The mixture was filtered through Celite®, the filtrate was concentrated, and the residue was purified on silica gel column using MeOH/DCM as eluting solvents to give the title compound. LC/MS: [M+H]⁺: 446.36.

Step B: tert-butyl 3-((6-(((tert-butoxycarbonyl)(pyridin-4-yl)amino)pyridin-3-yl)oxy)-2-((tert-butyldimethylsilyl)oxy)propanoate To the solution of tert-butyl 2-((tert-butyldimethyl-silyl)oxy)-3-((6-(pyridin-4-ylamino)pyridin-3-yl)oxy)propanoate (0.61 g, 1.37 mmol) in CH$_2$Cl$_2$ (25 ml) was added TEA (0.382 ml, 2.74 mmol), BOC$_2$O (0.381 ml, 1.64 mmol), and DMAP (0.167 g, 1.37 mmol). The resulting solution was stirred at room temperature overnight. After concentration, the residue was purified on silica gel column using EtOAc/hexane as eluting solvents to give the title compound. LC/MS: [M+H]⁺: 546.47.

Step C: tert-butyl 3-((6-(((tert-butoxycarbonyl)(pyridin-4-yl)amino)pyridin-3-yl)oxy)-2-hydroxypropanoate To the solution of tert-butyl 3-((6-(((tert-butoxycarbonyl)(pyridin-4-yl)amino)pyridin-3-yl)oxy)-2-((tert-butyldimethylsilyl)oxy)propanoate (0.28 g, 0.513 mmol) in THF (10 ml) was added TBAF (0.513 ml, 0.513 mmol) at 0° C. The resulting solution was stirred at 0° C. for 0.5 hour. After concentration, the residue was purified on silica gel column using EtOAc/hexane as eluting solvents to give the title compound. LC/MS: [M+H]⁺: 432.32.

Step D: tert-butyl 3-((6-(((tert-butoxycarbonyl)(pyridin-4-yl)amino)pyridin-3-yl)oxy)-2-((1,3-dioxoisoindolin-2-yl)oxy)propanoate To the solution of tert-butyl 3-((6-(((tert-butoxycarbonyl)(pyridin-4-yl)amino)pyridin-3-yl)oxy)-2-hydroxypropanoate (0.23 g, 0.533 mmol) in THF (6 ml) was added 2-hydroxyisoindoline-1,3-dione (0.104 g, 0.640 mmol), triphenylphosphine (0.210 g, 0.80 mmol), and DEAD (0.127 ml, 0.800 mmol). The resulting solution was stirred at room temperature for 3 hours. After concentration of the solution, the residue was purified on silica gel column using EtOAc/hexane as eluting solvents to give the title compound. LC/MS: [M+H]⁺: 577.41.

Step E: 4-((5-(3-(tert-butoxy)-2-((1,3-dioxoisoindolin-2-yl)oxy)-3-oxopropoxy)pyridin-2-yl)(tert-butoxycarbonyl)amino)-1-(3-((tert-butoxycarbonyl)amino)propyl)pyridin-1-ium To the solution of tert-butyl 3-((6-(((tert-butoxycarbonyl)(pyridin-4-yl)amino)pyridin-3-yl)oxy)-2-((1,3-dioxoisoindolin-2-yl)oxy)propanoate (0.25 g, 0.434 mmol) in acetonitrile (4 ml) was added tert-butyl (3-iodopropyl)carbamate (0.148 g, 0.520 mmol). The resulting solution was heated at 60° C. for three days. Sodium bicarbonate (0.146 g, 1.73 mmol) and additional 0.296 g of tert-butyl (3-iodopropyl)carbamate were added, and the resulting solution was further heated at 60° C. overnight. The solution was filtered, the filtrate was concentrated, and the residue was purified on reverse phase MPLC using acetonitrile (0.05% TFA)/water (0.05% TFA) as mobile phase to give the title compound. LC/MS: [M]⁺: 734.41.

Step F: 4-((5-(2-(aminooxy)-3-(tert-butoxy)-3-oxopropoxy)pyridin-2-yl)(tert-butoxy-carbonyl)amino)-1-(3-((tert-butoxycarbonyl)amino)propyl)pyridin-1-ium To the solution of 4-((5-(3-(tert-butoxy)-2-((1,3-dioxoisoindolin-2-yl)oxy)-3-oxopropoxy)pyridin-2-yl)(tert-butoxycarbonyl)amino)-1-(3-((tert-butoxycarbonyl)amino)propyl)pyridin-1-ium (110 mg, 0.150 mmol) in CH$_2$Cl$_2$ (4 ml) and Ethanol (4.00 ml) was added hydrazine (5.64 μl, 0.180 mmol) at 0° C. The resulting solution was stirred at 0° C. for 1 hour, then concentrated. The residue was treated with CH$_2$Cl$_2$ (4 ml), filtered, and the filtrate was concentrated to give the title compound. LC/MS: [M]⁺: 604.54.

Step G: (Z)-4-((5-(3-(tert-butoxy)-2-(((((2-((tert-butoxycarbonyl)amino)thiazol-4-yl)-(carboxy)methylene)amino)oxy)-3-oxopropoxy)pyridin-2-yl)(tert-butoxycarbonyl)amino)-1-(3-((tert-butoxycarbonyl)amino)propyl)pyridin-1-ium To the solution of 4-((5-(2-(aminooxy)-3-(tert-butoxy)-3-oxopropoxy)pyridin-2-yl)(tert-butoxycarbonyl)amino)-1-(3-((tert-butoxycarbonyl)amino)propyl)pyridin-1-ium (100 mg, 0.165 mmol) in ethanol (4 ml) and CH$_2$Cl$_2$ (4 mL) was added 2-(2-((tert-butoxycarbonyl)amino)thiazol-4-yl)-2-oxoacetic acid (58.5 mg, 0.215 mmol). The resulting solution was stirred at room temperature for 1 hour. The solution was concentrated and the residue was purified on reverse phase MPLC using acetonitrile (0.05% TFA)/water (0.05% TFA) as mobile phase to give the title compound. LC/MS: [M]⁺: 858.52.

Step H: 4-((5-(3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)pyridin-2-yl)(tert-butoxycarbonyl)amino)-1-(3-((tert-butoxycarbonyl)amino)-propyl)pyridin-1-ium To the solution of (Z)-4-((5-(3-(tert-butoxy)-2-(((((2-((tert-butoxycarbonyl)amino)thiazol-4-yl)(carboxy)methylene)amino)oxy)-3-oxopropoxy)pyridin-2-yl)(tert-butoxycarbonyl)amino)-1-(3-((tert-butoxycarbonyl)amino)propyl)pyridin-1-ium (16 mg, 0.019 mmol) in DMF (1 ml) was added DCC (30.7 mg, 0.149 mmol) and HOBT (11.41 mg, 0.075 mmol). The resulting solution was stirred at room temperature for 30 minutes before addition of (S)-3-amino-2,2-dimethyl-4-oxoazetidin-1-yl hydrogen sulfate (19.58 mg, 0.093 mmol) and sodium bicarbonate (31.3 mg, 0.373 mmol). The resulting solution was stirred at room temperature overnight. After filtration of the reaction mixture the residue was purified on reverse phase HPLC using acetonitrile (0.05% TFA)/water (0.05% TFA) to give the title compound. LC/MS: [M]⁺: 1050.41.

Step K: 1-(3-aminopropyl)-4-((5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-pyridin-2-yl)amino)pyridin-1-ium 2,2,2-trifluoroacetate To the solution of 4-((5-(3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)pyridin-2-yl)(tert-butoxycarbonyl)amino)-1-(3-((tert-butoxycarbonyl)amino)propyl)pyridin-1-ium (22 mg, 0.021 mmol) in CH$_2$Cl$_2$ (1 ml) was added TFA (2.5 mL, 32.4 mmol). The resulting solution was stirred at room temperature for 1.5 hours. The reaction solution was concentrated on rotary evaporated at room temperature, and the residue was further dried under high vacuum. The solid was purified on reverse phase HPLC using acetonitrile (0.05% TFA)/water (0.05% TFA) to give the title compound (the more polar diastereomer). LC/MS: [M+H]⁺: 694.17. ¹H NMR (D$_2$O, 500 MHz): δ 8.13-8.11 (d, J=8.8 Hz, 2H0, 8.01-8.00 (d, J=1.6 Hz, 1H), 7.50-7.42 (m, 3H), 7.08-7.07 (d, J=8.8 Hz, 1H), 7.02 (s, 1H), 5.05 (s, 1H), 4.66 (s, 1H), 4.48 (s, 2H), 4.27-4.24 (t, J=7.1 Hz, 2H), 2.99-2.96 (t, J=7.4 Hz, 2H), 2.21-2.18 (t, J=7.4 Hz, 2H), 1.35 (s, 3H), 1.05 (s, 3H).
Example 34
1-(3-aminopropyl)-4-((5-((S)-2-((((Z)-1-(2-aminothi-azol-4-yl)-2-(((S)-2,2-dimethyl-4-oxo-1-(sulfooxy) azetidin-3-yl)amino)-2-oxoethylidene)amino)oxy)-2-carboxyethoxy)pyridin-2-yl)oxy)pyridin-1-ium 2,2,2-trifluoroacetate (C34)
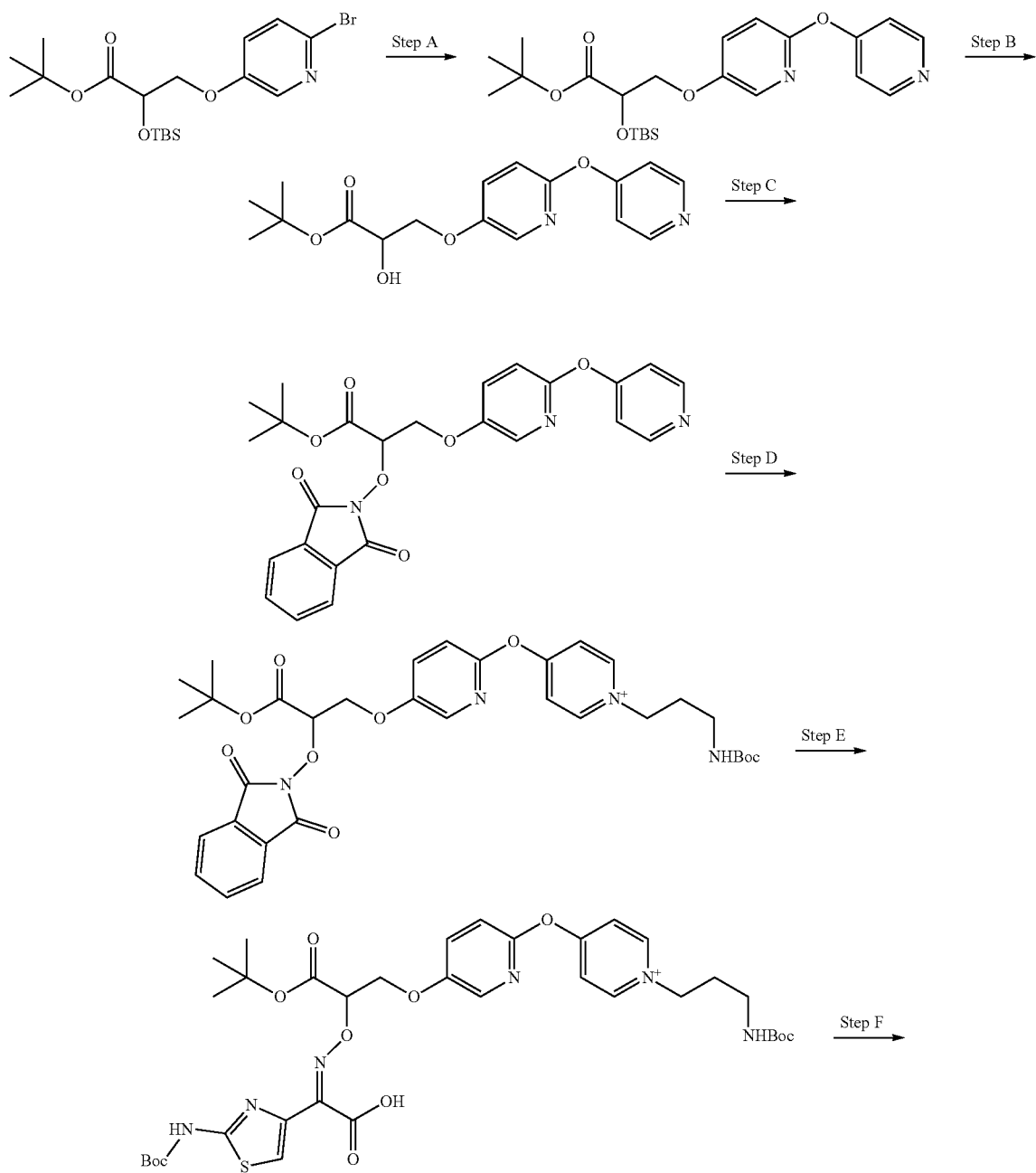

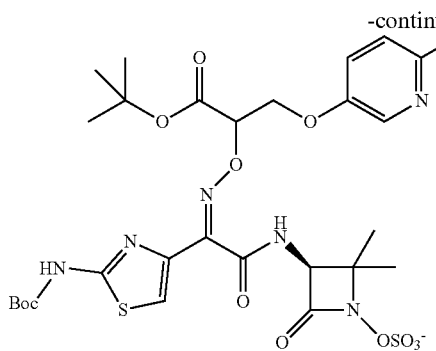

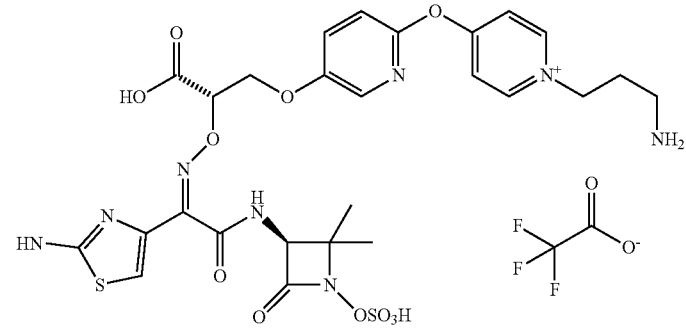

C34

Step A: tert-butyl 2-((tert-butyldimethylsilyl)oxy)-3-((6-(pyridin-4-yloxy)pyridin-3-yl)oxy)propanoate A mixture of J009 precatalyst G3 (7Aldrich #88755, 2.7 mg, 0.079 mmol), $Cs_2CO_3$ (1025 mg, 3.15 mmol), tert-butyl 3-((6-bromopyridin-3-yl)oxy)-2-((tert-butyldimethylsilyl)oxy)propanoate (680 mg, 1.57 mmol), and pyridin-4-ol (179 mg, 1.887 mmol) in a sealed tube was degassed by vacuum/$N_2$ refill three times before addition of dioxane (12 ml). The resulting mixture was further degassed by vacuum/$N_2$ refill three times, then was heated at 90° C. for 16 hours. The mixture was filtered through Celite®, the filtrate was concentrated and the residue was purified on silica gel column using EtOAc/hexane to give the title compound (the less polar regioisomer). LC/MS: [M+H]$^+$: 447.71.

Step B: tert-butyl 2-hydroxy-3-((6-(pyridin-4-yloxy)pyridin-3-yl)oxy)propanoate To the solution of tert-butyl 2-((tert-butyldimethylsilyl)oxy)-3-((6-(pyridin-4-yloxy)pyridin-3-yl)oxy)propanoate (220 mg, 0.493 mmol) in THF (6 ml) at 0° C. was added TBAF (0.493 ml, 0.493 mmol). The resulting solution was stirred at 0° C. for 30 minutes. After concentration of the solution the residue was purified on silica gel column using EtOAc/hexane as eluting solvents to give the title compound. LC/MS: [M+H]$^+$: 333.21.

Step C: tert-butyl 2-((1,3-dioxoisoindolin-2-yl)oxy)-3-((6-(pyridin-4-yloxy)pyridin-3-yl)oxy)propanoate To the solution of tert-butyl 2-hydroxy-3-((6-(pyridin-4-yloxy)pyridin-3-yl)oxy)propanoate (331 mg, 0.996 mmol) in THF (6 ml) was added 2-hydroxyisoindoline-1,3-dione (195 mg, 1.20 mmol), triphenylphosphine (392 mg, 1.49 mmol), and DEAD (0.237 ml, 1.494 mmol). The resulting solution was stirred at room temperature for 2 hours, then concentrated on rotary evaporator, the residue was purified on silica gel column using EtOAc/hexane as eluting solvents to give the title compound. LCMS [M+H]$^+$: 478.26.

Step D: 4-((5-(3-(tert-butoxy)-2-((1,3-dioxoisoindolin-2-yl)oxy)-3-oxopropoxy)pyridin-2-yl)oxy)-1-(3-((tert-butoxycarbonylamino)propyl)pyridin-1-ium To the solution of tert-butyl 2-((1,3-dioxoisoindolin-2-yl)oxy)-3-((6-(pyridin-4-yloxy)pyridin-3-yl)oxy)propanoate (0.81 g, 1.696 mmol) in acetonitrile (10 ml) was added tert-butyl (3-iodopropyl)carbamate (1.451 g, 5.09 mmol), the resulting solution was heated at 60° C. overnight. After concentration of the the reaction solution, the residue was purified on reverse phase MPLC using acetonitrile (0.05% TFA)/water(0.05% TFA) as mobile phase to give the title compound. [M]$^+$: 635.50.

Step E: (Z)-4-((5-(3-(tert-butoxy)-2-((((2-((tert-butoxycarbonyl)amino)thiazol-4-yl)-(carboxy)methylene)amino)oxy)-3-oxopropoxy)pyridin-2-yl)oxy)-1-(3-((tert-butoxy-carbonyl)amino)propyl)pyridin-1-ium To the solution of 4-((5-(3-(tert-butoxy)-2-((1,3-dioxoisoindolin-2-yl)oxy)-3-oxopropoxy)pyridin-2-yl)oxy)-1-(3-((tert-butoxycarbonyl)-amino)propyl)pyridin-1-ium (100 mg, 0.157 mmol) in $CH_2Cl_2$ (4 ml) and ethanol (4.00 ml) at 0° C. was added hydrazine (8.89 µl, 0.283 mmol). The resulting solution was stirred at 0° C. for 1 hour, then 2-(2-((tert-butoxycarbonyl)amino)thiazol-4-yl)-2-oxoacetic acid (86 mg, 0.315 mmol) was added to the above solution. The resulting solution was stirred at room temperature for 1 hour, then the mixture was concentrated and the residue was purified on reverse phase MPLC using acetonitrile (0.05% TFA)/water (0.05% TFA) as mobile phase to give the title compound. LC/MS: [M]$^+$: 759.49.

Step F: 4-((5-(3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)aminooxy)-3-oxopropoxy)pyridin-2-yl)oxy)-1-(3-((tert-butoxycarbonyl)amino)propyl)pyridin-1-ium To the solution of (Z)-4-((5-(3-(tert-butoxy)-2-(((((2-((tert-butoxycarbonyl)amino)thiazol-4-yl)(carboxy)methylene)amino)oxy)-3-oxopropoxy)pyridin-2-yl)oxy)-1-(3-((tert-butoxy-carbonyl)amino)propyl)pyridin-1-ium (28 mg, 0.037 mmol) in DMF (20 ml) was added DCC (60.8 mg, 0.295 mmol) and HOBT (22.57 mg, 0.147 mmol). The resulting solution was stirred at room temperature for 30 minutes before addition of (S)-3-amino-2,2-dimethyl-4-oxoazetidin-1-yl hydrogen sulfate (38.7 mg, 0.184 mmol) and sodium bicarbonate (61.9 mg, 0.737 mmol), the resulting solution was stirred at room temperature overnight. After filtration of the reaction mixture, the residue was purified on Gilson reverse phase HPLC using 20-100% acetonitrile (0.05% TFA) to give the title compound. LC/MS: [M]$^+$: 951.51.

Step G: 1-(3-aminopropyl)-4-((5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)-pyridin-2-yl)oxy)pyridin-1-ium 2,2,2-trifluoroacetate To the solution of 4-((5-(3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)pyridin-2-yl)oxy)-1-(3-((tert-butoxycarbonyl)amino)propyl)pyridin-1-ium (28 mg, 0.029 mmol) in CH$_2$Cl$_2$ (1 ml) was added TFA (2 mL, 26.0 mmol). The resulting solution was stirred at room temperature for 75 minutes. The solution was concentrated and the residue was treated with Et$_2$O (10 mL). The Et$_2$O was removed, and the solid residue was dried under high vacuum. The dry residue was dissolved in DMSO (2 mL) and purified on reverse phase HPLC using acetonitrile (0.05% TFA)/water (0.05% TFA) as mobile phase to give the title compound (the more polar diastereomer). LC/MS: [M+H]$^+$: 695.19. $^1$H NMR (D$_2$O, 500 MHz): δ 8.64-8.62 (d, J=7.1 Hz, 2H), 7.98-7.97 (d, J=2.4 Hz, 1H), 7.61-7.58 (m, 1H), 7.46-7.45 (d, J=7.4 Hz, 2H), 7.21-7.20 (d, J=8.3 Hz, 1H), 7.02 (s, 1H), 5.03 (s, 1H), 4.75 (s, 1H), 4.52-4.46 (m, 4H), 3.03-3.00 (t, J=7.9 Hz, 2H), 2.30-2.26 (t, J=7.9 Hz, 2H), 1.43 (s, 3H), 1.12 (s, 3H).

Example 35

(S,Z)-3-(2-((2-((6-(3-(3-aminopropyl)-1H-imidazol-3-ium-1-yl)pyridin-3-yl)oxy)ethoxy)imino)-2-(2-aminothiazol-4-yl)acetamido)-2,2-dimethyl-4-oxoazetidin-1-yl sulfate 2,2,2-trifluoroacetate (C35)

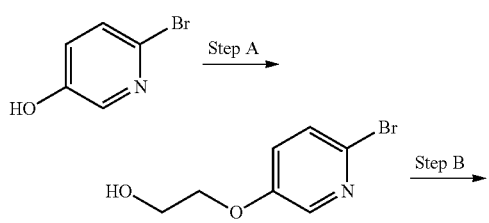
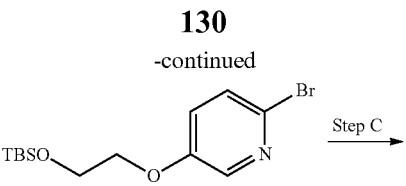
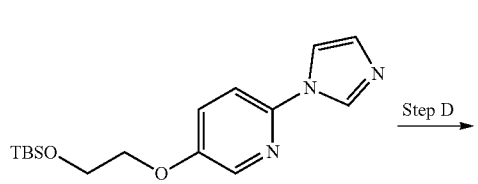
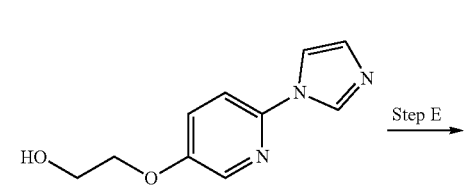
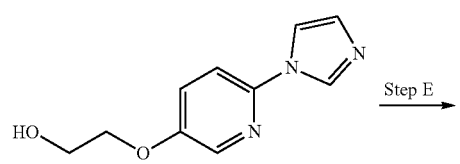
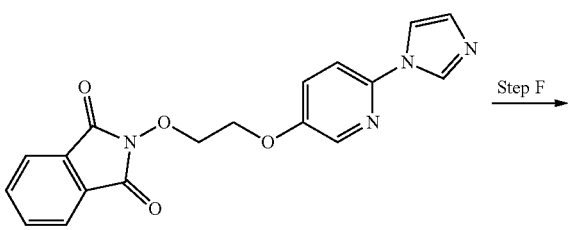
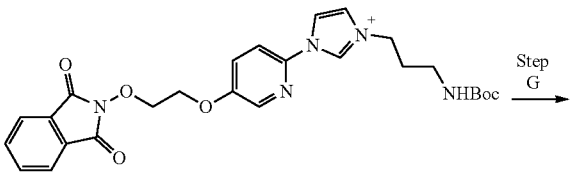
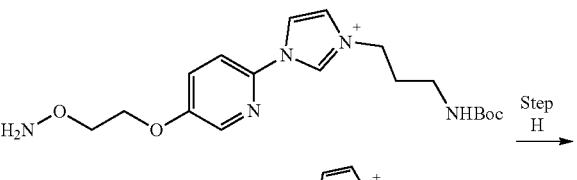
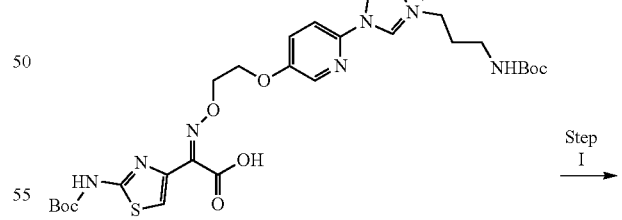
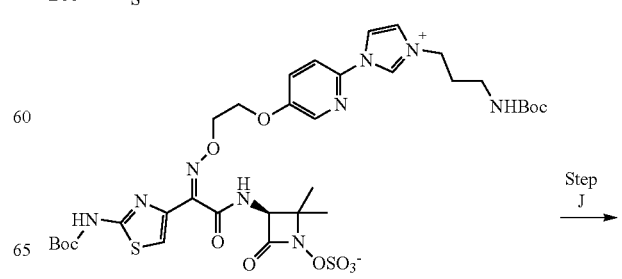

-continued

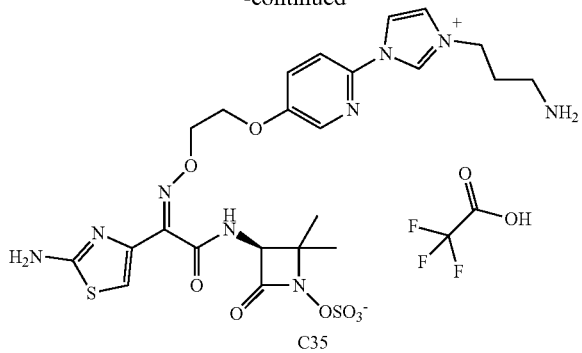

C35

Step A: 2-((6-bromopyridin-3-yl)oxy)ethan-1-ol

6-Bromopyridin-3-ol (700 mg, 4.02 mmol), 2-chloroethanol (972 mg, 12.1 mmol), and K$_2$CO$_3$ (1.39 g, 10.1 mmol), were combined and suspended in acetonitrile (18 mL). A stream of N$_2$ gas was bubbled through a septum into the solution for 10 minutes and the resultant solution was heated at 80° C. for 18 hours. After standing at ambient temperature for two days, the mixture was filtered and the filtrate concentrated in vacuo. The residue was purified by silica gel column chromatography (24 g column) using a gradient of 0-100% EtOAc/Hexanes as eluent to provide the title compound. LC-MS [M+H]$^+$: m/z 218.03. $^1$H NMR (CHCl$_3$-d, 500 MHz): δ 8.11 (1H, d, J=3.2 Hz), 7.41 (1H, d, J=8.7 Hz), 7.16 (1H, dd, J=8.7, 3.2 Hz), 4.14 (2H, t, J=4.5 Hz), 4.03-4.00 (2H, m), 2.07-2.03 (1H, m),

Step B: 2-bromo-5-(2-((tert-butyldimethylsilyl)oxy)ethoxy)pyridine

To a solution of 2-((6-bromopyridin-3-yl)oxy)ethan-1-ol (315 mg, 1.445 mmol), and imidazole (492 mg, 7.22 mmol) in acetonitrile (9 mL) was added 1M tert-butyldimethylchlorosilane in CH$_2$Cl$_2$ (3.2 mL, 3.2 mmol) followed by DMAP (17.65 mg, 0.144 mmol). After stirring for 3 hours at ambient temperature, the mixture was concentrated in vacuo. The residue was diluted with EtOAc, washed with saturated NaHCO$_3$ (aq) solution (2×), brine (1×). The organic extracts were dried over MgSO$_4$, filtered, and concentrated in vacuo. The residue was purified by silica gel column chromatography (24 g column) using a gradient of 0-40% EtOAc/Hexanes as eluent to provide the title compound. LC-MS [M+H]$^+$: m/z 332.10. $^1$H NMR (CHCl$_3$-d, 500 MHz): δ 8.09 (1H, d, J=3.1 Hz), 7.38 (1H, d, J=8.7 Hz), 7.15 (1H, dd, J=8.7, 3.2 Hz), 4.09 (2H, t, J=4.9 Hz), 3.99 (2H, t, J=4.9 Hz), 0.93 (9H, d, J=8.8 Hz), 0.12 (6H, d, J=5.7 Hz).

Step C: 5-(2-((tert-butyldimethylsilyl)oxy)ethoxy)-2-(1H-imidazol-1-yl)pyridine 2-Bromo-5-(2-((tert-butyldimethylsilyl)oxy)ethoxy)pyridine (480 mg, 1.44 mmol), imidazole (148 mg, 2.17 mmol), L-Proline (27 mg, 0.231 mmol), K$_2$CO$_3$ (399 mg, 2.89 mmol) and CuI (13.8 mg, 0.072 mmol) were combined and suspended in DMSO (3 mL). A stream of N$_2$ gas was bubbled through a septum into the solution for 10 minutes and the resultant solution was heated at 90° C. overnight. The mixture was cooled, diluted with EtOAc and washed with H$_2$O (1×) and brine (1×). The organic extracts were dried over MgSO$_4$, filtered, and concentrated in vacuo. The residue was purified by silica gel column chromatography (12 g column) using a gradient of 0-100% (3:1 EtOAc/MeOH)/Hexanes as eluent to provide the title compound. LC-MS [M+H]$^+$: m/z 320.33. $^1$H NMR (CHCl$_3$-d, 500 MHz): δ 8.24 (1H, s), 8.19 (1H, d, J=2.9 Hz), 7.58 (1H, s), 7.40 (1H, dd, J=8.8, 3.0 Hz), 7.31-7.28 (1H, m) 7.21 (1H, s), 4.15 (2H, t, J=4.9 Hz), 4.02 (2H, t, J=4.9 Hz), 0.93 (9H, s), 0.13 (6H, s)

Step D: 2-((6-(1H-imidazol-1-yl)pyridin-3-yl)oxy)ethan-1-ol

To a solution of 5-(2-((tert-butyldimethylsilyl)oxy)ethoxy)-2-(1H-imidazol-1-yl)pyridine (140 mg, 0.438 mmol) in THF (5 mL) was added a 1 M solution of TBAF in CH$_2$Cl$_2$ (0.438 mL, 0.438 mmol). After stirring at ambient temperature for 45 minutes, the mixture was concentrated in vacuo and the residue purified by silica gel column chromatography (4 g column) using a gradient of 0-100% (3:1 EtOAc/MeOH)/Hexanes as eluent to give the title compound. LC-MS [M+H]$^+$: m/z 205.90.

Step E: 2-(2-((6-(1H-imidazol-1-yl)pyridin-3-yl)oxy)ethoxyisoindoline-1,3-dione To a solution of 2-((6-(1H-imidazol-1-yl)pyridin-3-yl)oxy)ethan-1-ol (80 mg, 0.390 mmol) in THF (4 ml) was added N-hydroxyphthalimide (76 mg, 0.468 mmol) and triphenylphosphine (123 mg, 0.468 mmol). DIAD (0.091 ml, 0.468 mmol) was added dropwise and the resultant solution stirred at ambient temperature overnight. The mixture was concentrated in vacuo and the residue purified by silica gel column chromatography (12 g column) using a gradient of 0-100% (3:1 EtOAc/MeOH)/Hexanes as eluent to give the title compound. LC-MS [M+H]$^+$: m/z 350.98. $^1$H NMR (CHCl$_3$-d, 500 MHz): δ 8.24 (1H, s), 8.14 (1H, d, J=2.9 Hz), 7.89-7.86 (2H, m), 7.82-7.79 (2H, m), 7.58 (1H, s), 7.40 (1H, dd, J=8.8, 3.0 Hz), 7.33-7.30 (1H, m) 7.21 (1H, s), 4.65-4.63 (2H, m), 4.48-4.46 (2H, m).

Step F: 3-(3-((tert-butoxycarbonyl)amino)propyl)-1-(5-(2-((1,3-dioxoisoindolin-2-yl)oxy)ethoxy)pyridin-2-yl)-1H-imidazol-3-ium To a solution of 2-(2-((6-(1H-imidazol-1-yl)pyridin-3-yl)oxy)ethoxy)isoindoline-1,3-dione (131 mg, 0.374 mmol) in dioxane (3 ml) was added 3-(boc-amino)propyl bromide (214 mg, 0.89 mmol) and DMAP (5 mg, 0.041 mmol) and the mixture was stirred at 60° C. overnight. Additional DMAP (5 mg, 0.041 mmol) and a catalytic amount of sodium iodide were added, heating at 60° C. was continued for 4 hours, after which the mixture was concentrated in vacuo. The residue was triturated with EtOAc to remove starting materials and impurities, providing the title compound. LC-MS [M]$^+$: m/z 508.29.

Step G: 1-(5-(2-(aminooxy)ethoxy)pyridin-2-yl)-3-(3-((tert-butoxycarbonyl)amino)propyl)-1H-imidazol-3-ium 3-(3-((tert-butoxycarbonyl)amino)propyl)-1-(5-(2-((1,3-dioxoisoindolin-2-yl)oxy)ethoxy)pyridin-2-yl)-1H-imidazol-3-ium (0.19 g, 0.374 mmol) was suspended in MeOH (3 mL) and a 1M solution of hydrazine in MeOH (0.41 mL, 0.41 mmol) was added. After stirring at ambient temperature for 2 hours the mixture was concentrated in vacuo, removing excess hydrazine by azeotroping with MeOH followed by CH$_2$Cl$_2$. The residue was carried to the next step without further purification. LC-MS [M]$^+$: m/z 378.25.

Step H: (Z)-3-(3-((tert-butoxycarbonyl)amino)propyl)-1-(5-(2-((((2-((tert-butoxycarbonyl)amino)thiazol-4-yl)(carboxy)methylene)amino)oxy)ethoxy)pyridin-2-yl)-1H-imidazol-3-ium To a solution of 1-(5-(2-(aminooxy)ethoxy)pyridin-2-yl)-3-(3-((tert-butoxycarbonyl)amino)propyl)-1H-imidazol-3-ium (0.141 g, 0.373 mmol) in EtOH (2 mL) and ClCH$_2$CH$_2$Cl (4 mL) was added Intermediate 6 (0.107 g, 0.392 mmol). After stirring at ambient temperature overnight, the solvents were removed in vacuo and the residue carried to the next step without further purification. LC-MS [M]$^+$: m/z 632.35.

Step I: (S,Z)-3-(3-((tert-butoxycarbonyl)amino)propyl)-1-(5-(2-(((1-(2-((tert-butoxy-carbonyl)amino)thiazol-4-yl)-2-((2,2-dimethyl-4-oxo-1-(sulfooxy)azetidin-3-yl)amino)-2-oxoethylidene)amino)oxy)ethoxy)pyridin-2-yl)-1H-imidazol-3-ium To a mixture of (Z)-3-(3-((tert-butoxycarbonyl)amino)propyl)-1-(5-(2-((((2-((tert-butoxycarbonyl)amino)thiazol-4-yl)(carboxy)methylene)amino)oxy)ethoxy)pyridin-2-yl)-1H-imidazol-3-ium (237 mg, 0.374 mmol) and 4-(4,6-dimethoxy-1,3,5-triazin-2-yl)-4-methylmorpholinium chloride (176 mg, 0.636 mmol) was added (S)-3-amino-2,2-dimethyl-4-oxoazetidin-1-yl hydrogen sulfate (102 mg, 0.486 mmol) as a solution in DMF (4 mL). After stirring at ambient temperature overnight, an additional amount of (S)-3-amino-2,2-dimethyl-4-oxoazetidin-1-yl hydrogen sulfate (102 mg, 0.486 mmol) and 4-(4,6-dimethoxy-1,3,5-triazin-2-yl)-4-methylmorpholinium chloride (176 mg, 0.636 mmol) were added. After stirring at ambient temperature overnight, the mixture was diluted with H$_2$O and purified by reverse phase chromatography (Gilson SunFire C-18 30×150 mm column) using a gradient of 10-90% CH$_3$CN/H$_2$O (with 0.5% TFA) as eluent. Lyophilization provided the title compound. LC-MS [M+H]$^+$: m/z 824.78.

Step J: (S,Z)-3-(2-((2-((6-(3-(3-aminopropyl)-1H-imidazol-3-ium-1-yl)pyridin-3-yl)oxy)ethoxy)imino)-2-(2-aminothiazol-4-yl)acetamido)-2,2-dimethyl-4-oxoazetidin-1-yl sulfate 2,2,2-trifluoroacetate To a solution of (S,Z)-3-(3-((tert-butoxycarbonyl)amino)propyl)-1-(5-(2-(((1-(2-((tert-butoxycarbonyl)amino)thiazol-4-yl)-2-((2,2-dimethyl-4-oxo-1-(sulfooxy)azetidin-3-yl)amino)-2-oxoethylidene)amino)oxy)ethoxy)pyridin-2-yl)-1H-imidazol-3-ium (56 mg, 0.068 mmol) in CH$_2$Cl$_2$ (1 mL) was added TFA (1 ml, 12.98 mmol). After stirring at ambient temperature for 30 minutes the mixture was concentrated in vacuo and excess TFA was removed by azeotroping from CH$_2$Cl$_2$. After trituration with Et$_2$O the residue was purified by reverse phase chromatography (Gilson SunFire C-18 30×150 mm column) using a gradient of 5-40% CH$_3$CN/H$_2$O (with 0.5% TFA) as eluent and the product lyophilized to give the title compound. LC-MS [M+H]$^+$: m/z 624.36.

Example 36

(S)-3-((Z)-2-(((S)-2-((6-(3-(3-aminopropyl)-1H-imidazol-3-ium-1-yl)pyridin-3-yl)oxy)-1-carboxyethoxy)imino)-2-(2-aminothiazol-4-yl)acetamido)-2,2-dimethyl-4-oxoazetidin-1-yl sulfate compound with 2,2,2-trifluoroacetic acid (1:1) (C36)

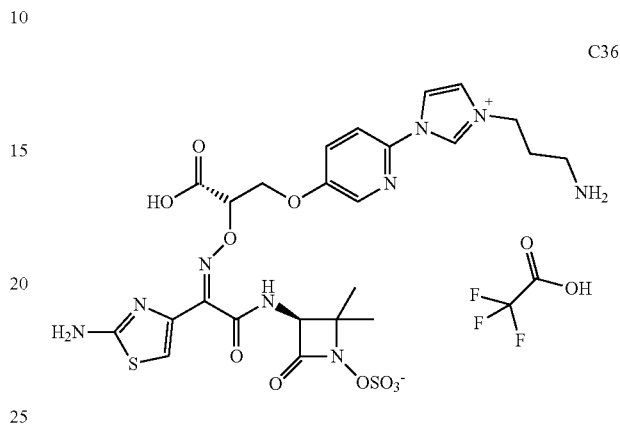

C36

Step A: Ethyl (R)-3-((6-bromopyridin-3-yl)oxy)-2-hydroxypropanoate

Ethyl oxirane-2-carboxylate (1.47 g, 12.6 mmol) was suspended in MTBE (25 mL) and 6-bromopyridin-3-ol (1.0 g, 5.75 mmol) and 4 Å molecular sieves (2 g) were added. Intermediate 2 (0.482 g, 0.575 mmol) was added and the resultant mixture stirred at ambient temperature for 3 days. Solids were removed by filtration, the filtrate was concentrated in vacuo, and the residue was purified by silica gel column chromatography (40 g column) using a gradient of 0-60% EtOAc/Hexanes as eluent to provide the title compound. LC-MS [M+H]$^+$: m/z 290.10. $^1$H NMR (CHCl$_3$-d, 500 MHz): δ 8.10 (1H, d, J=3.1 Hz), 7.40 (1H, d, J=8.7 Hz), 7.16 (1H, dd, J=8.7, 3.2 Hz), 4.53 (1H, t, J=3.2 Hz), 4.35-4.31 (4H, m), 3.24 (1H, br s), 1.32 (3H, t, J=7.1 Hz).

Step B: (R)-3-((6-bromopyridin-3-yl)oxy)-2-hydroxypropanoic acid

To a solution of ethyl (R)-3-((6-bromopyridin-3-yl)oxy)-2-hydroxypropanoate (513 mg, 1.77 mmol) in THF (14 ml) at 0° C. was added 1M NaOH (3.54 ml, 3.54 mmol). After stirring for 3 hours at 0° C., the pH was adjusted to 3 with 1N HCl and the mixture partitioned between EtOAc and water. The layers were separated and the organic phase was washed with brine (3×), dried over MgSO$_4$, filtered, and concentrated in vacuo to provide the title compound, which was used in the next step without further purification. LC-MS [M+H]$^+$: m/z 261.76.

Step C: tert-butyl (R)-3-((6-bromopyridin-3-yl)oxy)-2-hydroxypropanoate

To a solution of (R)-3-((6-bromopyridin-3-yl)oxy)-2-hydroxypropanoic acid (464 mg, 1.77 mmol) in THF (6 mL) was added 2-tert-butyl-1,3-diisopropylisourea (886 mg, 4.43 mmol) and the resultant mixture was heated at 60° C. for 2 hours and 45 minutes. The solids were removed by filtration, the filtrate was concentrated under vacuum, and the residue was purified by silica gel column chromatography (12 g column) using a gradient of 0-60% EtOAc/Hexanes as eluent to give the title compound. LC-MS [M+H]⁺: m/z 318.17. ¹H NMR (CHCl₃-d, 500 MHz): δ 8.09 (1H, d, J=3.1 Hz), 7.40 (1H, d, J=8.7 Hz), 7.16 (1H, dd, J=8.7, 3.1 Hz), 4.41 (1H, s), 4.32-4.26 (2H, m), 3.26 (1H, br s), 1.51 (9H, s).

Step D: tert-butyl (R)-3-((6-bromopyridin-3-yl)oxy)-2-((tert-butyldimethylsilyl)oxy)-propanoate To a solution of tert-butyl (R)-3-((6-bromopyridin-3-yl)oxy)-2-hydroxypropanoate (265 mg, 0.833 mmol) in CH₂Cl₂ (6 mL) at 0° C. was added triethylamine (0.348 ml, 2.50 mmol). Tert-butyldimethylsilyl trifluoromethanesulfonate (0.287 ml, 1.25 mmol) was added dropwise and after stirring at 0° C. for 30 minutes. The mixture was partitioned between CH₂Cl₂ and H₂O. The layers were separated and the organic layer was washed with brine, dried over MgSO₄, filtered, and concentrated in vacuo. The residue was purified by silica gel column chromatography (12 g column) using a gradient of 0-30% EtOAc/Hexanes as eluent to give the title compound. LC-MS [M+H]⁺: m/z 432.07. ¹H NMR (CHCl₃-d, 500 MHz): δ 8.09 (1H, d, J=3.1 Hz), 7.39 (1H, d, J=8.7 Hz), 7.15 (1H, dd, J=8.7, 3.1 Hz), 4.47 (1H, dd, J=6.8, 3.4 Hz), 4.27 (1H, dd, J=9.7, 3.4 Hz), 4.16 (1H, dd, J=9.7, 6.8 Hz), 1.50 (9H, s), 0.93 (9H, s), 0.16 (3H, s), 0.10 (3H, s).

Step E: tert-butyl (R)-3-((6-(1H-imidazol-1-yl)pyridin-3-yl)oxy)-2-((tert-butyldimethylsilyl)oxy)propanoate The procedure was the same as described for Step C, Example 35 using the reactants (R)-3-((6-bromopyridin-3-yl)oxy)-2-((tert-butyldimethylsilyl)oxy)propanoate (318 mg, 0.735 mmol), imidazole (90 mg, 1.32 mmol), L-Proline (51 mg, 0.44 mmol), K₂CO₃ (102 mg, 0.735 mmol) and CuI (42 mg, 0.22 mmol) in DMSO (3 mL). LC-MS [M+H]: m/z 420.45.

Step F: tert-butyl (R)-3-((6-(1H-imidazol-1-yl)pyridin-3-yl)oxy)-2-hydroxypropanoate The procedure is the same as described for Step D in Example 35 using reactants (R)-3-((6-(1H-imidazol-1-yl)pyridin-3-yl)oxy)-2-((tert-butyldimethylsilyl)oxy)propanoate (80 mg, 0.191 mmol) in THF (4 mL) and 1M TBAF in THF (0.191 mL, 0.191 mmol). LC-MS [M+H]⁺: m/z 306.27.

Step G: tert-butyl (S)-3-((6-(1H-imidazol-1-yl)pyridin-3-yl)oxy)-2-((1,3-dioxoisoindolin-2-yl)oxy)propanoate The procedure was the same as described for Step E in Example 35 using reactants tert-butyl (R)-3-((6-(1H-imidazol-1-yl)pyridin-3-yl)oxy)-2-hydroxypropanoate (76 mg, 0.249 mmol), N-hydroxyphthalimide (48.7 mg, 0.299 mmol), triphenylphosphine (78 mg, 0.299 mmol), and DIAD (0.058 ml, 0.299 mmol) in THF (3 mL). LC-MS [M+H]⁺: m/z 451.33.

Step H: (S)-3-(3-aminopropyl)-1-(5-(3-(tert-butoxy)-2-((1,3-dioxoisoindolin-2-yl)oxy)-3-oxopropoxy)pyridin-2-yl)-1H-imidazol-3-ium To a solution of tert-butyl (S)-3-((6-(1H-imidazol-1-yl)pyridin-3-yl)oxy)-2-((1,3-dioxoisoindolin-2-yl)oxy)propanoate (85 mg, 0.189 mmol) in dioxane (2 mL) was added 3-(boc-amino)propyl bromide (67.4 mg, 0.283 mmol) and the mixture was stirred at 60° C. overnight. Sodium iodide (10 mg, 0.067 mmol) was added and heating at 60° C. was continued for 6 hours, then additional amounts of 3-(boc-amino)propyl bromide (67.4 mg, 0.283 mmol) and sodium iodide (34 mg, 0.22 mmol) were added. Acetone (0.2 mL) was added and the mixture heated at 60° C. overnight. The mixture was concentrated in vacuo and triturated with EtOAc to give the title compound as a residue which was carried to the next step without further purification. LC-MS [M]⁺: m/z 508.39.

Step I: (S)-1-(5-(3-(tert-butoxy)-2-((1,3-dioxoisoindolin-2-yl)oxy)-3-oxopropoxy)pyridin-2-yl)-3-(3-((tert-butoxycarbonyl)amino)propyl)-1H-imidazol-3-ium To a solution of (S)-3-(3-aminopropyl)-1-(5-(3-(tert-butoxy)-2-((1,3-dioxoisoindolin-2-yl)oxy)-3-oxopropoxy)pyridin-2-yl)-1H-imidazol-3-ium (46 mg, 0.090 mmol) in CH₂Cl₂ (3 mL) was added BOC-anhydride (29.6 mg, 0.136 mmol) and N,N,N',N'-tetramethylethylenediamine (15 μL, 0.099 mmol) and the resultant mixture was stirred at ambient temperature for 3 days. After concentration in vacuo and trituration with Et₂O, the residue was lyophilized from CH₃CN/H₂O. LC-MS [M+H]⁺: m/z 608.10.

Step J: (S)-1-(5-(2-(aminooxy)-3-(tert-butoxy)-3-oxopropoxy)pyridin-2-yl)-3-(3-((tert-butoxycarbonyl)amino)propyl)-1H-imidazol-3-ium The procedure was the same as described for Step F of Example 35 using reactants (S)-1-(5-(3-(tert-butoxy)-2-((1,3-dioxoisoindolin-2-yl)oxy)-3-oxopropoxy)pyridin-2-yl)-3-(3-((tert-butoxycarbonyl)-amino)propyl)-1H-imidazol-3-ium (26 mg, 0.043 mmol) 1M hydrazine in MeOH (47 μL, 0.047 mmol) in MeOH (1 mL). LC-MS [M]⁺: m/z 478.40.

Step K: (S,Z)-1-(5-(3-(tert-butoxy)-2-((((2-((tert-butoxycarbonyl)amino)thiazol-4-yl)(carboxy)methylene)amino)oxy)-3-oxopropoxy)pyridin-2-yl)-3-(3-((tert-butoxy-carbonyl)amino)propyl)-1H-imidazol-3-ium The procedure was the same as described for Step H of Example 35 using reactants (S)-1-(5-(2-(aminooxy)-3-(tert-butoxy)-3-oxopropoxy)pyridin-2-yl)-3-(3-((tert-butoxycarbonyl)amino)propyl)-1H-imidazol-3-ium (21 mg, 0.044 mmol) and Intermediate 6 (12.6 mg, 0.046 mmol) in Ethanol (0.5 mL) and ClCH₂CH₂Cl (1 mL). LC-MS [M]⁺: m/z 732.51.

Step L: 1-(5-((S)-3-(tert-butoxy)-2-(((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)pyridin-2-yl)-3-(3-((tert-butoxycarbonyl)amino)propyl)-1H-imidazol-3-ium The procedure was the same as described for Step I of Example 35 using reactants (S,Z)-1-(5-(3-(tert-butoxy)-2-(((2-((tert-butoxycarbonyl)amino)thiazol-4-yl)(carboxy)methylene)-amino)oxy)-3-oxopropoxy)pyridin-2-yl)-3-(3-((tert-butoxycarbonyl)amino)propyl)-1H-imidazol-3-ium (32 mg, 0.044 mmol), (S)-3-amino-2,2-dimethyl-4-oxoazetidin-1-yl hydrogen sulfate (11.93 mg, 0.057 mmol), and 4-(4,6-dimethoxy-1,3,5-triazin-2-yl)-4-methylmorpholinium chloride (20.54 mg, 0.074 mmol) in DMF (1 mL). LC-MS [M+H]+: m/z 924.83.

Step M: (S)-3-((Z)-2-(((S)-2-((6-(3-(3-aminopropyl)-1H-imidazol-3-ium-1-yl)pyridin-3-yl)oxy)-1-carboxyethoxy)imino)-2-(2-aminothiazol-4-yl)acetamido)-2,2-dimethyl-4-oxoazetidin-1-yl sulfate compound with 2,2,2-trifluoroacetic acid (1:1)

The procedure was the same as described for Step J of Example 35 using reactants 1-(5-((S)-3-(tert-butoxy)-2-(((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)pyridin-2-yl)-3-(3-((tert-butoxycarbonyl)amino)propyl)-1H-imidazol-3-ium (7 mg, 7.57 µmol) and TFA (0.6 ml, 7.79 mmol) in CH2Cl2 (0.6 mL). LC-MS [M+H]+: m/z 668.37.

Example 37A and 37B 3-(2-((5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)pyridin-2-yl)amino)-1H-imidazol-1-yl) propan-1-aminium 2,2,2-trifluoroacetate (C37A) and 3-(2-((5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)pyridin-2-yl)amino)-1H-imidazol-1-yl) propan-1-aminium 2,2,2-trifluoroacetate (C37B)

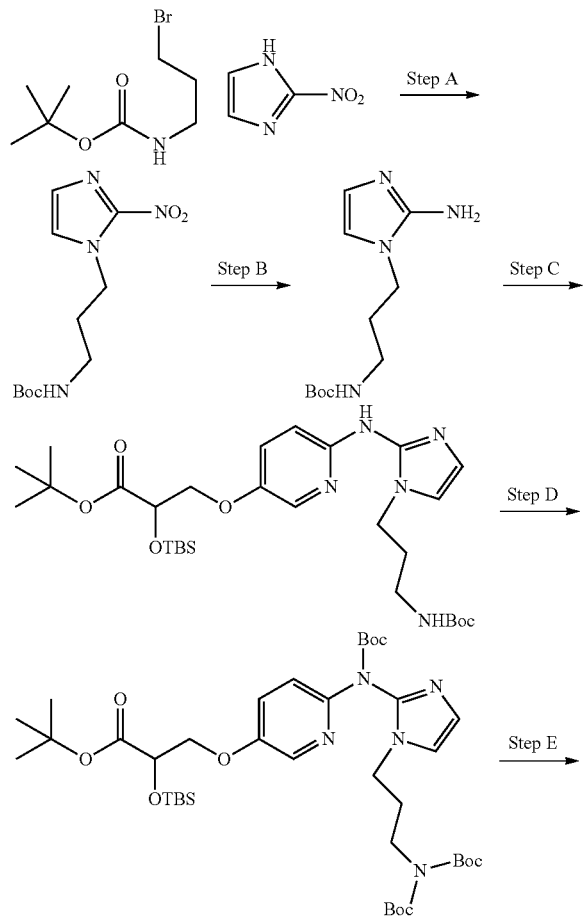

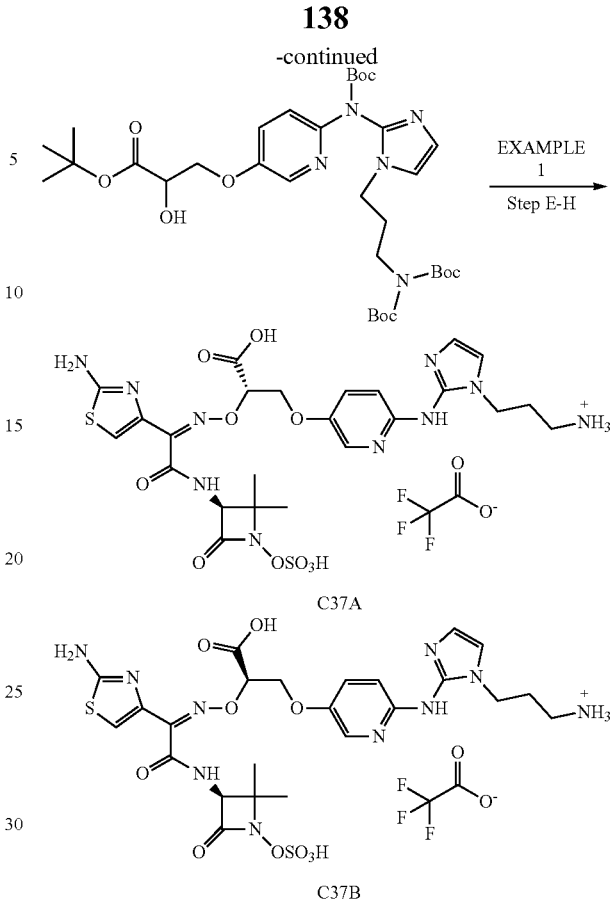

Step A: tert-butyl (3-(2-nitro-1H-imidazol-1-yl)propyl)carbamate

Cesium carbonate (576 mg, 1.77 mmol) was added to a stirred mixture of 3-(Boc-amino)propyl bromide (232 mg, 0.973 mmol) and 2-nitro-1H-imidazole (100 mg, 0.884 mmol) in DMF (2 ml) and the mixture was stirred at room temperature for 1 hour before it was stirred overnight at 60° C. The mixture was diluted with ethyl acetate, washed with water (3×) and brine, dried (MgSO4), filtered and the solvent was evaporated under reduced pressure to give crude product which was purified by ISCO (gold, 40 g) column eluting with EtOAc/hexane gradient 0-100% gradient to give the title compound. LC-MS [M+H]+: m/z 271.3.

Step B: tert-butyl (3-(2-amino-1H-imidazol-1-yl)propyl)carbamate

A mixture of tert-butyl (3-(2-nitro-1H-imidazol-1-yl)propyl)carbamate (500 mg, 1.85 mmol) and 3% Pt/0.6% V/C (100 mg, 0.015 mmol) in methanol (10 ml) was vacuumed and backfilled with H2 (3×) and stirred at room temperature for 2.5 hours. The reaction mixture was diluted with EtOAc, filtered through Celite®. The filtrate was concentrated under reduced pressure to provide the title compound, which was used as-is for the next step. LC-MS [M+H]+: m/z 241.6.

Step C: tert-butyl 3-((6-((1-(3-((tert-butoxycarbonyl)amino)propyl)-1H-imidazol-2-yl)amino)pyridin-3-yl)oxy)-2-((tert-butyldimethylsilyl)oxy)propanoate A mixture of tert-butyl 3-((6-bromopyridin-3-yl)oxy)-2-((tert-butyldimethylsilyl)oxy) propanoate (178 mg, 0.412 mmol), tert-butyl (3-(2-amino-1H-imidazol-1-yl)propyl) carbamate (90 mg, 0.375 mmol), palladium G3 precatalyst J009 and cesium carbonate (366 mg, 1.12 mmol) in dioxane (3.5 ml) was vacuum/$N_2$ exchanged 3 times before the mixture was heated at 100° C. overnight. The mixture was diluted with EtOAc and filtered through a short pad of celite and washed with EtOAc. Solvent was removed under reduced pressure to give the title compound, which was used directly for next step. LC-MS [M+H]$^+$: m/z 592.7.

Step D: tert-butyl 3-((6-((1-(3-(bis(tert-butoxycarbonyl)amino)propyl)-1H-imidazol-2-yl)(tert-butoxycarbonyl)amino)pyridin-3-yl)oxy)-2-((tert-butyldimethylsilyl)oxy)propanoate A mixture of tert-butyl 3-((6-((1-(3-((tert-butoxycarbonyl)amino)propyl)-1H-imidazol-2-yl)amino)pyridin-3-yl)oxy)-2-((tert-butyldimethylsilyl)oxy)propanoate (120 mg, 0.203 mmol) in $Boc_2O$ (0.5 ml) was stirred at 120° C. for 2.5 hours. The reaction mixture was cooled directly purified with ISCO (gold, 40 g) column eluting with EtOAc/hexane 0-100% gradient to give the title compound. LC-MS [M+H]$^+$: m/z 792.9.

Step E: tert-butyl 3-((6-((1-(3-(bis(tert-butoxycarbonyl)amino)propyl)-1H-imidazol-2-yl)(tert-butoxycarbonyl)amino)pyridin-3-yl)oxy)-2-hydroxypropanoate TBAF (1.0 M in THF, 0.606 ml, 0.606 mmol) was added to a stirred mixture of tert-butyl 3-((6-((1-(3-(bis(tert-butoxycarbonyl)amino)propyl)-1H-imidazol-2-yl)(tert-butoxycarbonyl)amino)-pyridin-3-yl)oxy)-2-((tert-butyldimethylsilyl)oxy)propanoate (320 mg, 0.404 mmol) in THF (3 ml) and the mixture was stirred at room temperature for 1 hour. Solvent was removed and the residue was purified with ISCO silica gel column (gold, 40 g) eluting with 0-100% EtOAc/hexane gradient to give the title compound. LC-MS [M+H]$^+$: m/z 678.8. The product from step E (tert-butyl 3-((6-((1-(3-(bis(tert-butoxycarbonyl)amino)propyl)-1H-imidazol-2-yl)(tert-butoxycarbonyl)amino)pyridin-3-yl)oxy)-2-hydroxypropanoate) was converted to $C_{37}A$ and $C_{37}B$ as TFA salts following a similar procedure from step C, step E to step H in Example 1.

Compound 37A: 3-(2-((5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)pyridin-2-yl)amino)-1H-imidazol-1-yl)propan-1-aminium 2,2,2-trifluoroacetate. LC-MS [M+H]$^+$: m/z 683.6. $^1$H NMR (500 MHz, Deuterium Oxide) δ 7.88 (d, J=2.9 Hz, 1H), 7.35 (d, J=8.7 Hz, 1H), 7.04-6.96 (m, 2H), 6.93 (s, 2H), 4.99 (s, 1H), 4.62 (br s, 1H), 4.47-4.34 (m, 2H), 4.04 (t, J=7.3 Hz, 2H), 2.96 (t, J=8.0 Hz, 2H), 2.08 (m, 2H), 1.31 (s, 3H), 1.00 (s, 3H). Compound 37B: 3-(2-((5-((R)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)pyridin-2-yl)amino)-1H-imidazol-1-yl)propan-1-aminium 2,2,2-trifluoroacetate. LC-MS [M+H]$^+$: m/z 683.6. $^1$H NMR (500 MHz, Deuterium Oxide) δ 7.89-7.85 (s, 1H), 7.39-7.32 (d, 1H), 7.03-6.95 (m, 2H), 6.93 (s, 2H), 4.95 (s, 1H), 4.62 (br s, 1H), 4.45-4.35 (m, 2H), 4.04 (t, J=7.3 Hz, 2H), 2.96 (t, J=8.0 Hz, 2H), 2.08 (m, 2H), 1.31 (s, 3H), 1.02 (s, 3H).

Example 38

(S)-3-((Z)-2-(((S)-2-(4-(1-(3-aminopropyl)-2-methyl-1H-pyrazol-2-ium-4-yl)-3-chlorophenoxy)-1-carboxyethoxy)imino)-2-(2-aminothiazol-4-yl)acetamido)-2,2-dimethyl-4-oxoazetidin-1-yl sulfate

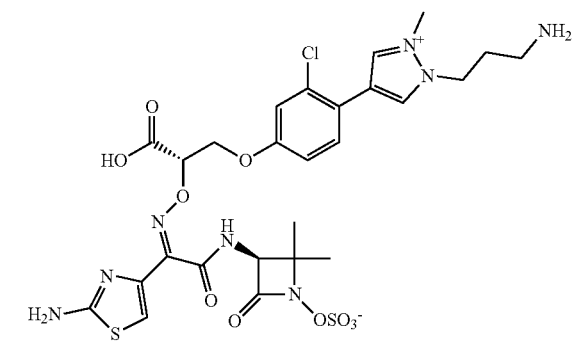

Step A: tert-butyl (R)-3-(4-bromo-3-chlorophenoxy)-2-hydroxypropanoate (R,R)—Co catalyst (0.24 g, 0.29 mmol) was added to a stirred, room temperature mixture of tert-butyl oxirane-2-carboxylate (1.7 g, 12 mmol), and 4-bromo-3-chlorophenol (1.2 g, 5.8 mmol) in t-butylmethyl ether. Then molecular sieves (2.3 g) were added, and the mixture was stirred at room temperature overnight, and filtered. The filtrate was concentrated, and the resulting residue was purified on silica gel column (80 g), eluting with EtOAc/Hexane (540%) to give the title compound.

Step B: tert-butyl (R)-3-(4-(1-(3-((tert-butoxycarbonyl)amino)propyl)-1H-pyrazol-4-yl)-3-chlorophenoxy)-2-hydroxypropanoate To a solution of (R)-tert-butyl 3-(4-bromo-3-chlorophenoxy)-2-hydroxypropanoate (0.42 g, 1.2 mmol)), tert-butyl (R)-3-(4-bromo-3-chlorophenoxy)-2-hydroxypropanoate (0.42 g, 1.2 mmol)), and 1,1'-bis(di-tert-butylphosphino) ferrocene palladium dichloride (0.078 g, 0.12 mmol)) in dioxane (1 ml) was added the 1M aqueous solution of potassium phosphate (3.6 ml, 3.6 mmol)). The reaction flask was sealed, degassed, and refilled with $N_2$. The reaction was stirred at 72° C. for 1 h, then diluted with water, and extracted with EtOAc twice. The combined organic layers were dried over $MgSO_4$, filtered and concentrated. The resulting residue was purified on a silica gel column (25 g), eluting with $CH_2C_2$/MeOH (100~90%) to give the title compound. LC-MS [M+H]$^+$: m/z 496.34.

Step C: tert-butyl (S)-3-(4-(1-(3-((tert-butoxycarbonyl)amino)propyl)-1H-pyrazol-4-yl)-3-chlorophenoxy)-2-((1,3-dioxoisoindolin-2-yl)oxy)propanoate (E)-diethyl diazene-1,2-dicarboxylate (0.20 ml, 1.3 mmol) was added to a 0° C. mixture of (R)-tert-butyl 3-(4-(1-(3-((tert-butoxycarbonyl)amino)propyl)-1H-pyrazol-4-yl)-3-chlorophenoxy)-2-hydroxypropanoate (580 mg, 1.2 mmol), 2-hydroxyisoindoline-1,3-dione (190 mg, 1.2 mmol), triphenylphosphine (340 mg, 1.3 mmol) in THF. The reaction mixture was stirred at RT for 4 h, and then concentrated. The resulting residue was purified by column chromatography on silica gel column (25 g), eluting with EtOAc/isohexane 5-50% to give the title compound. LC-MS [M+H]⁺: m/z 641.44.

Step D: (S)-4-(4-(3-(tert-butoxy)-2-((1,3-dioxoisoindolin-2-yl)oxy)-3-oxopropoxy)-2-chlorophenyl)-1-(3-((tert-butoxycarbonyl)amino)propyl)-2-methyl-1H-pyrazol-2-ium iodide MeI (610 µl, 9.8 mmol) was added to a mixture of (S)-tert-butyl 3-(4-(1-(3-((tert-butoxycarbonyl)amino)propyl)-1H-pyrazol-4-yl)-3-chlorophenoxy)-2-((1,3-dioxoisoindolin-2-yl)oxy)propanoate (625 mg, 0.98 mmol) in CH₃CN. The reaction mixture was stirred at 74° C. overnight, and then cooled to RT. The reaction mixture was concentrated to give the title compound. LC-MS [M]⁺: m/z 655.40.

Step E: (S,Z)-4-(4-(3-(tert-butoxy)-2-((((2-((tert-butoxycarbonyl)amino)thiazol-4-yl)-(carboxy)methylene)amino)oxy)-3-oxopropoxy)-2-chlorophenyl)-1-(3-((tert-butoxy-carbonyl)amino)propyl)-2-methyl-1H-pyrazol-2-ium iodide Hydrazine (28 mg, 0.86 mmol) was added to a mixture of (S)-4-(4-(3-(tert-butoxy)-2-((1,3-dioxoisoindolin-2-yl)oxy)-3-oxopropoxy)-2-chlorophenyl)-1-(3-((tert-butoxycarbonyl)amino)propyl)-2-methyl-1H-pyrazol-2-ium iodide (610 mg, 0.78 mmol) in CHCl₃/ethanol. The reaction was stirred at room temperature for 1 h, then 2-(2-((tert-butoxycarbonyl)amino)thiazol-4-yl)-2-oxoacetic acid (230 mg, 0.86 mmol) was added. The reaction was stirred at RT for 3 h, then concentrated to give the title compound. LC-MS [M]⁺: m/z 779.33.

Step F: 4-(4-((S)-3-(tert-butoxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-chlorophenyl)-1-(3-((tert-butoxycarbonyl)amino)propyl)-2-methyl-1H-pyrazol-2-ium To the solution of (S,Z)-4-(4-(3-(tert-butoxy)-2-((((2-((tert-butoxycarbonyl)-amino)thiazol-4-yl)(carboxy)methylene)amino)oxy)-3-oxopropoxy)-2-chlorophenyl)-1-(3-((tert-butoxycarbonyl)amino)propyl)-2-methyl-1H-pyrazol-2-ium (810 mg, 1.0 mmol) in DMF (1 ml) was added N,N'-methanediylidenedicyclohexanamine (DCC) (540 mg, 2.6 mmol), and 1H-benzo[d][1,2,3]triazol-1-ol hydrate (HOBt) (500 mg, 2.6 mmol). The reaction mixture was stirred at rt for 20 min, then (S)-3-amino-2,2-dimethyl-4-oxoazetidin-1-yl hydrogen sulfate (330 mg, 1.6 mmol) and sodium hydrogencarbonate (520 mg, 6.2 mmol) were added. The reaction mixture was stirred at RT for 2 h, and then filtered. The filtrate was purified on reverse phase C-18 150 g column using 075100% acetonitrile (with 0.05% TFA) over 25 min to give the title compound. LC-MS [M+H]⁺: m/z 971.27.

Step G: (S)-3-((Z)-2-(((S)-2-(4-(1-(3-aminopropyl)-2-methyl-1H-pyrazol-2-ium-4-yl)-3-chlorophenoxy)-1-carboxyethoxy)imino)-2-(2-aminothiazol-4-yl) acetamido)-2,2-dimethyl-4-oxoazetidin-1-yl sulfate TFA (2 ml, 26 mmol) was added to a stirred, room temperature mixture of 4-(4-((S)-3-(tert-butoxy)-2-(((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-chlorophenyl)-1-(3-((tert-butoxycarbonyl)amino)propyl)-2-methyl-1H-pyrazol-2-ium (175 mg, 0.18 mmol) in DCM. The reaction mixture was stirred at room temperature for 1 h 20 min, and then concentrated. The resulting crude product was dissolved in water and purified via SFC with water/acetonitrile (0.1% HCOOH) to give the title compound. LC-MS [M]⁺: m/z 715.68.

Example 39

(S)-3-((Z)-2-((((S)-1-(4-(1-(3-aminopropyl)-2-methyl-1H-pyrazol-2-ium-4-yl)phenoxy)-2-carboxypropan-2-yl)oxy)imino)-2-(2-aminothiazol-4-yl) acetamido)-2,2-dimethyl-4-oxoazetidin-1-yl sulfate

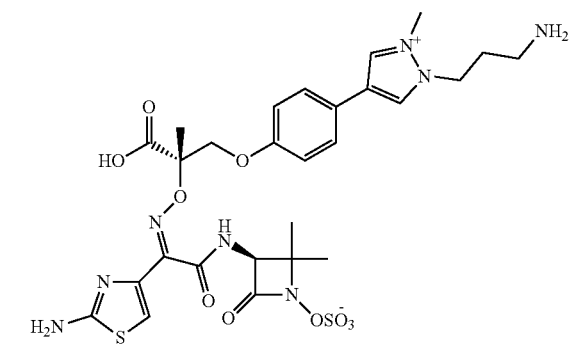

Step A: tert-butyl (3-(4-(4,4,5,5-tetramethyl-1,3,2-dioxaborolan-2-yl)-1H-pyrazol-1-yl)propyl)carbamate Cesium carbonate (12 g, 38 mmol) was added to a room temperature mixture of 4-(4,4,5,5-tetramethyl-1,3,2-dioxaborolan-2-yl)-1H-pyrazole (4.8 g, 25 mmol), tert-butyl (3-bromopropyl)carbamate (6.0 g, 25 mmol) in DMF (40 mL). The reaction mixture was stirred at RT overnight, then diluted with EtOAc and water, and extracted with EtOAc. The combined organic layers were washed with brine, dried over MgSO₄, filtered and concentrated. The resulting residue was purified by column chromatography on silica gel column, eluting with EtOAc/isohexane (1080%) to give the title compound. LC-MS [M+H]⁺: m/z 352.33.

Step B: tert-butyl 3-(4-(1-(3-((tert-butoxycarbonyl) amino)propyl)-1H-pyrazol-4-yl)-phenoxy)-2-((1,3-dioxoisoindolin-2-yl)oxy)-2-methylpropanoate To a solution of tert-butyl 2-(aminooxy)-3-(4-bromophenoxy)-2-methylpropanoate (100 mg, 0.29 mmol)), tert-butyl (3-(4-(4,4,5,5-tetramethyl-1,3,2-dioxaborolan-2-yl)-1H-pyrazol-1-yl)propyl)carbamate (100 mg, 0.29 mmol)), and 1,1-bis (di-tert-butylphosphino) ferrocene palladium dichloride (19 mg, 0.029 mmol)) in dioxane (1 ml) was added the 1M aqueous solution of potassium phosphate (0.87 ml, 0.87 mmol). The vial was sealed, degassed, refilled with N₂, and stirred at 70° C. for 1 h. Then the reaction was diluted with water, extracted with twice with ethyl acetate. The combined organic layers were dried over MgSO₄, filtered and concentrated. The resulting residue was purified by column chromatography on silica gel, eluting with CH$_2$Cl$_2$/MeOH (100~90%) to give the title compound. LC-MS [M+H]$^+$: m/z 491.43.

Step C: tert-butyl 3-(4-(1-(3-((tert-butoxycarbonyl)amino)propyl)-1H-pyrazol-4-yl)phenoxy)-2-((1,3-dioxoisoindolin-2-yl)oxy)-2-methylpropanoate 4-Methyl-benzenesulfonic acid (12% in acetic acid, 63 mg, 0.044 mmol) was added to a room temperature mixture of tert-butyl 2-(aminooxy)-3-(4-(1-(3-((tert-butoxycarbonyl)-amino)propyl)-1H-pyrazol-4-yl)phenoxy)-2-methyl-propanoate (540 mg, 1.1 mmol), and molecular sieves (200 mg) in toluene. The reaction mixture was stirred at 100° C. for 4 h, then filtered and concentrated. The resulting residue was purified by column chromatography on silica gel, eluting with CH$_2$Cl$_2$/MeOH (100~90%) to give the title compound. LC-MS [M+H]$^+$: m/z 622.56.

Step D: 4-(4-(3-(tert-butoxy)-2-((1,3-dioxoisoindolin-2-yl)oxy)-2-methyl-3-oxopropoxy)phenyl)-1-(3-((tert-butoxycarbonyl)amino)propyl)-2-methyl-1H-pyrazol-2-ium iodide The title compound was prepared according to the procedure of Example 1 Step D using tert-butyl 3-(4-(1-(3-((tert-butoxycarbonyl)amino)propyl)-1H-pyrazol-4-yl)phenoxy)-2-((1,3-dioxoisoindolin-2-yl)oxy)-2-methylpropanoate (0.50 g, 0.80 mmol), and MeI (0.40 ml, 6.4 mmol) in MeCN (3 ml). LC-MS [M]$^+$: m/z 635.58 Step E: (Z)-4-(4-(3-(tert-butoxy)-2-((((2-((tert-butoxycarbonyl)amino)thiazol-4-yl)(carboxy)methylene)amino)oxy)-2-methyl-3-oxopropoxy)phenyl)-1-(3-((tert-butoxycarbonyl)amino)propyl)-2-methyl-1H-pyrazol-2-ium iodide Hydrazine (0.024 ml, 0.76 mmol) in 0.3 mL of DCM was added to a mixture of 4-(4-(3-(tert-butoxy)-2-((1,3-dioxoisoindolin-2-yl)oxy)-2-methyl-3-oxopropoxy)phenyl)-1-(3-((tert-butoxy-carbonyl)-amino)propyl)-2-methyl-1H-pyrazol-2-ium (480 mg, 0.76 mmol) in EtOH/DCM. The mixture was stirred at room temperature for 4 h, then, 2-(2-((tert-butoxycarbonyl)-amino)thiazol-4-yl)-2-oxoacetic acid (230 mg, 0.84 mmol) was added. The reaction was stirred at RT overnight, and then filtered. The filtrate was concentrated, and the resulting residue was purified by preparative HPLC, eluting with acetonitrile/water+0.05% TFA (0~100%) to give the title compound. LC-MS [M+H]$^+$: m/z 759.58, Step F: 4-(4-(3-(tert-butoxy)-2-(((((Z)-1-(2-((tert-butoxycarbonyl)amino)thiazol-4-yl)-2-(((S)-2,2-dimethyl-4-oxo-1-sulfoazetidin-3-yl)amino)-2-oxoethylidene)amino)oxy)-2-methyl-3-oxopropoxy)phenyl)-1-(3-((tert-butoxycarbonyl)amino)propyl)-2-methyl-1H-pyrazol-2-ium To a solution of (Z)-4-(4-(3-(tert-butoxy)-2-((((2-((tert-butoxycarbonyl)amino)thiazol-4-yl)(carboxy)methylene)amino)oxy)-2-methyl-3-oxopropoxy)phenyl)-1-(3-((tert-butoxycarbonyl)amino)propyl)-2-methyl-1H-pyrazol-2-ium iodide (80 mg, 0.105 mmol) in DMF (1 ml) was added DCC (87 mg, 0.42 mmol) and HOBT (60 mg, 0.32 mmol). The reaction mixture was stirred at RT for 30 min, followed by the addition of (S)-3-amino-2,2-dimethyl-4-oxoazetidin-1-yl hydrogen sulfate (76 mg, 0.42 mmol) and sodium bicarbonate (35 mg, 0.42 mmol). Then the reaction was stirred at RT for 16 h, then filtered. The filtrate was purified by reverse phase ISCO (130 g, 0-100%, H$_2$O/MeCN/0.05% TFA) to give the title compound. LC-MS [M+H]$^+$: m/z 921.76

Step G: (S)-3-((Z)-2-((((S)-1-(4-(1-(3-aminopropyl)-2-methyl-1H-pyrazol-2-ium-4-yl)phenoxy)-2-carboxypropan-2-yl)oxy)imino)-2-(2-aminothiazol-4-yl)acetamido)-2,2-dimethyl-4-oxoazetidin-1-yl sulfate To a solution of 4-(4-(3-(tert-butoxy)-2-(((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-2-methyl-3-oxopropoxy)phenyl)-1-(3-((tert-butoxycarbonyl)amino)propyl)-2-methyl-1H-pyrazol-2-ium (110 mg, 0.12 mmol) in DCM was added 2 mL of TFA. The reaction mixture was stirred at RT for 90 min, then concentrated in vacuo without heat. DCM (10 ml) was added and the mixture was concentrated three times to remove TFA. The resulting residue was washed with dry MeCN (2×2 ml). Then the residue was dissolved in DMSO and purified on prep-HPLC with a MeCN/H$_2$O (0.05% TFA in both) gradient 2-25% in 10 min to give the title compound. LC-MS [M+H]$^+$: m/z 695.14.

Example 40

(3S)-3-((Z)-2-((2-(4-(1-(3-aminopropyl)-2-methyl-1H-pyrazol-2-ium-4-yl)phenoxy)-1-phosphonoethoxy)imino)-2-(2-aminothiazol-4-yl)acetamido)-2,2-dimethyl-4-oxoazetidin-1-yl sulfate

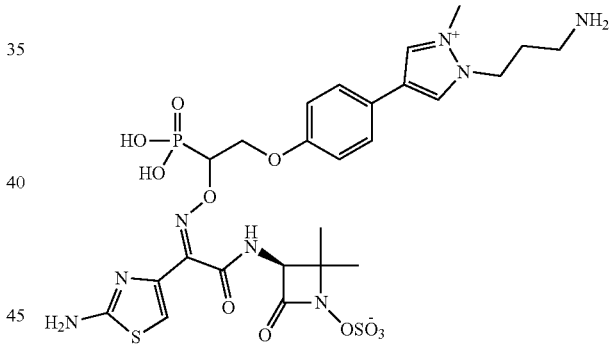

Step A: 1-bromo-4-(2,2-diethoxyethoxy)benzene

Potassium carbonate (11 g, 78 mmol) was added to a stirred, room temperature mixture of 4-bromophenol (5.4 g, 31 mmol) and 2-bromo-1,1-diethoxyethane (1.8 ml, 12 mmol) in DMF. The reaction mixture was stirred at 80° C. overnight, then cooled to room temperature and diluted with EtOAc. The mixture was washed with water and brine. The organic layer was separated, dried over MgSO$_4$, filtered and concentrated. The resulting residue was purified by column chromatography on silica gel, eluting with EtOAc/isohexane (0~40%) to give the title compound.

Step B: 2-(4-bromophenoxy)acetaldehyde

HCl (3.7 ml, 22 mmol) was added to a stirred, room temperature mixture of 1-bromo-4-(2,2-diethoxyethoxy)benzene (2.6 g, 9.0 mmol) in THF. The reaction mixture was stirred at room temperature overnight, then the mixture was extracted with ether. The organic layer was separated, washed with water and brine, dried over MgSO$_4$, filtered and concentrated to give the title compound.

Step C: dimethyl (2-(4-bromophenoxy)-1-hydroxyethyl)phosphonate

Dimethyl phosphonate (1.20 ml, 13 mmol) was added dropwise to a stirred 0° C. mixture of 2-(4-bromophenoxy)-acetaldehyde (1.2 g, 5.3 mmol), triethylamine (1.8 ml, 13 mmol) in THF. The reaction mixture was stirred at 0° C. for 1 h, and then at RT for 1 h. Then the reaction mixture was concentrated. The resulting residue was purified by column chromatography on silica gel 40 g column, eluting with CH$_2$Cl$_2$/MeOH (100~90%) to give the title compound. LC-MS [M+H]$^+$: m/z 325.00

Step D: tert-butyl (3-(4-(4-(2-(dimethoxyphosphoryl)-2-hydroxyethoxy)phenyl)-1H-pyrazol-1-yl)propylcarbamate The title compound was prepared according to the procedure of Example 38, Step B. LC-MS [M+H]$^+$: m/z 470.29

Step E: tert-butyl (3-(4-(4-(2-(dimethoxyphosphoryl)-2-((1,3-dioxoisoindolin-2-yl)oxy)-ethoxy)phenyl)-1H-pyrazol-1-yl)propyl)carbamate The title compound was prepared according to the procedure of Example 38, Step C. LC-MS [M+H]$^+$: m/z 615.29

Step F: 1-(3-((tert-butoxycarbonyl)amino)propyl)-4-(4-(2-(dimethoxyphosphoryl)-2-((1,3-dioxoisoindolin-2-yl)oxy)ethoxy)phenyl)-2-methyl-1H-pyrazol-2-ium trifluoromethanesulfonate Methyl trifluoromethanesulfonate (0.069 ml, 0.63 mmol) was added to a stirred, cooled 0° C. mixture of tert-butyl (3-(4-(4-(2-(dimethoxyphosphoryl)-2-((1,3-dioxoisoindolin-2-yl)oxy)ethoxy)phenyl)-1H-pyrazol-1-yl)propyl)carbamate (370 mg, 0.60 mmol) in CH$_3$CN. The mixture was stirred at 0° C. for 10 min, at RT overnight, and then concentrated. The resulting residue was purified by column chromatography on silica gel, eluting with CH$_2$Cl$_2$/MeOH (10080%) to give the title compound. LC-MS [M]$^+$: m/z 629.33

Step G: 1-(3-aminopropyl)-4-(4-(2-((1,3-dioxoisoindolin-2-yl)oxy)-2-phosphonoethoxy)-phenyl)-2-methyl-1H-pyrazol-2-ium trifluoromethanesulfonate Bromotrimethylsilane (0.77 ml, 5.9 mmol) was added to a stirred, room temperature mixture of 1-(3-((tert-butoxycarbonyl)amino)propyl)-4-(4-(2-(dimethoxyphosphoryl)-2-((1,3-dioxoisoindolin-2-yl)oxy)-ethoxy)phenyl)-2-methyl-1H-pyrazol-2-ium trifluoromethanesulfonate (570 mg, 0.59 mmol) in DCM. The reaction mixture was stirred at room temperature overnight, and then concentrated to give the title compound. LC-MS [M]$^+$: m/z 501.26

Step H: 1-(3-((tert-butoxycarbonyl)amino)propyl)-4-(4-(2-((1,3-dioxoisoindolin-2-yl)oxy)-2-phosphonoethoxy)phenyl)-2-methyl-1H-pyrazol-2-ium Triethylamine (0.31 ml, 2.2 mmol) was added to a stirred, cooled room temperature mixture of 1-(3-aminopropyl)-4-(4-(2-((1,3-dioxoisoindolin-2-yl)oxy)-2-phosphonoethoxy) phenyl)-2-methyl-1H-pyrazol-2-ium trifluoromethanesulfonate (0.28 g, 0.56 mmol), and di-tert-butyl dicarbonate (0.24 g, 1.12 mmol) in DMF. The reaction mixture was stirred at room temperature overnight. The mixture was purified by preparative HPLC reverse phase (C-18), eluting with 0.05% TFA in CH$_3$CN/water (2~100%) to give title compound. LC-MS [M]$^+$: m/z 601.32

Step I: 1-(3-((tert-butoxycarbonyl)amino)propyl)-4-(4-(2-((((Z)-1-(2-((tert-butoxycarbonyl)-amino)thiazol-4-yl)-2-(((S)-2,2-dimethyl-4-oxo-1-(sulfooxy)azetidin-3-yl)amino)-2-oxo-ethylidene)amino)oxy)-2-phosphonoethoxy)phenyl)-2-methyl-1H-pyrazol-2-ium Hydrazine (10 μl, 0.33 mmol) was added to a stirred, room temperature mixture of 1-(3-((tert-butoxycarbonyl)amino)propyl)-4-(4-(2-((1,3-dioxoisoindolin-2-yl)oxy)-2-phosphonoethoxy)-phenyl)-2-methyl-1H-pyrazol-2-ium in EtOH/CHCl$_3$. The reaction mixture was stirred at room temperature for 1 h, then, (S)-3-(2-(2-((tert-butoxycarbonyl) amino)thiazol-4-yl)-2-oxoacetamido)-2,2-dimethyl-4-oxoazetidin-1-yl hydrogen sulfate was added and the reaction was stirred at RT overnight. The reaction mixture was filtered and the filtrate was concentrated. The resulting residue was dissolved in DMF and purified by preparative HPLC reverse phase (C-18), eluting with Acetonitrile/Water+0.1% TFA (2100%), to give the title compound. LC-MS [M+H]$^+$: m/z 917.24

Step J: (3S)-3-((Z)-2-((2-(4-(1-(3-aminopropyl)-2-methyl-1H-pyrazol-2-ium-4-yl)phenoxy)-1-phosphonoethoxy)imino)-2-(2-aminothiazol-4-yl)acetamido)-2,2-dimethyl-4-oxoazetidin-1-yl sulfate The title compound was prepared according to the procedure of Example 2 Step G using 1-(3-((tert-butoxycarbonyl)amino)propyl)-4-(4-(2-(((((Z)-1-(2-((tert-butoxy-carbonyl)amino)thiazol-4-yl)-2-(((S)-2,2-dimethyl-4-oxo-1-(sulfooxy)azetidin-3-yl)amino)-2-oxoethylidene)amino) oxy)-2-phosphonoethoxy)phenyl)-2-methyl-1H-pyrazol-2-ium (0.13 g, 0.14 mmol), and TFA (1.5 ml, 19 mmol). LC-MS [M+H]$^+$: m/z 717.36

Example 41

(3S)-3-((Z)-2-(((1R)-2-(4-(1-(3-aminopropyl)-2-methyl-1H-pyrazol-2-ium-4-yl)phenoxy)-1-(hydroxy (methoxy)phosphoryl)ethoxy)imino)-2-(2-aminothiazol-4-yl)acetamido)-2,2-dimethyl-4-oxoazetidin-1-yl sulfate compound with 2,2,2-trifluoroacetic acid (1:1)

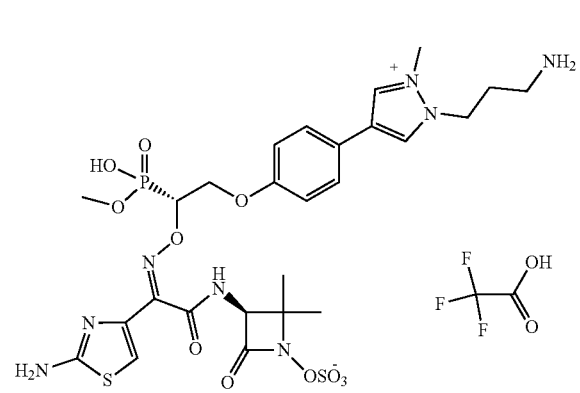

Step A: 1-(3-((tert-butoxycarbonyl)amino)propyl)-4-(4-(2-((1,3-dioxoisoindolin-2-yl)oxy)-2-(hydroxy(methoxy)phosphoryl)ethoxy)phenyl)-2-methyl-1H-pyrazol-2-ium iodide MeI (0.145 ml, 2.327 mmol) was added to a stirred, room temperature mixture of tert-butyl (3-(4-(4-(2-(dimethoxyphosphoryl)-2-((1,3-dioxoisoindolin-2-yl)oxy)ethoxy)phenyl)-1H-pyrazol-1-yl)propyl)carbamate (from Example 40 Step E, 143 mg, 0.23 mmol) in $CH_3CN$. The reaction mixture was stirred at 72° C. overnight, then concentrated to give the title compound. LC-MS [M]+: m/z 615.36

Step B: 1-(3-((tert-butoxycarbonyl)amino)propyl)-4-(4-((2R)-2-((((Z)-(2-((tert-butoxycarbonyl)amino)thiazol-4-yl)(carboxy)methylene)amino)oxy)-2-(hydroxyl-(methoxy)phosphoryl)ethoxy)phenyl)-2-methyl-1H-pyrazol-2-ium The title compound was prepared according to the procedure of Example 38 Step E. LC-MS [M]+: m/z 739.46.

Step C: 1-(3-((tert-butoxycarbonyl)amino)propyl)-4-(4-(2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-2-(hydroxy(methoxy)phosphoryl)ethoxy)phenyl)-2-methyl-1H-pyrazol-2-ium The title compound was prepared according to the procedure of Example 38 Step F. LC-MS [M]+: m/z 931.38.

Step D: (3S)-3-((Z)-2-(((1R)-2-(4-(1-(3-aminopropyl)-2-methyl-1H-pyrazol-2-ium-4-yl)phenoxy)-1-(hydroxy(methoxy)phosphoryl)ethoxy)imino)-2-(2-aminothiazol-4-yl)acetamido)-2,2-dimethyl-4-oxoazetidin-1-yl sulfate compound with 2,2,2-trifluoroacetic acid (1:1)

The title compound was prepared according to the procedure of Example 38 Step G. LC-MS [M+H]+: m/z 731.68.

Example 42

(3S)-3-((Z)-2-(((1S)-2-(4-(1-(3-amino-2-hydroxypropyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

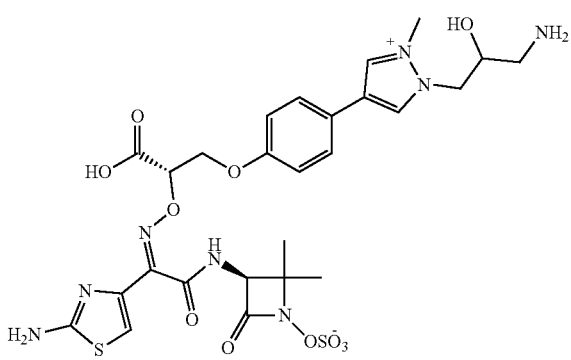

Step A: tert-butyl 2,2-dimethyl-5-((4-(4,4,5,5-tetramethyl-1,3,2-dioxaborolan-2-yl)-1H-pyrazol-1-yl)methyl)oxazolidine-3-carboxylate Cesium carbonate (3.3 g, 10.2 mmol) was added to a room temperature mixture of 4-(4,4,5,5-tetramethyl-1,3,2-dioxaborolan-2-yl)-1H-pyrazole (1.3 g, 6.8 mmol)), and tert-butyl 5-(bromomethyl)-2,2-dimethyloxazolidine-3-carboxylate (2 g, 6.8 mmol)) in DMF (10 mL). The reaction mixture was stirred at 60° C. for h, then cooled to RT, and filtered. The filtrate was diluted with EtOAc and water. The water layer was extracted with EtOAc. The combined organic layers were washed with brine, dried over $MgSO_4$, filtered and concentrated. The resulting residue was purified by column chromatography on silica gel, eluting with EtOAc/isohexane (1080%) to give the title compound. LC-MS [M+H]+: m/z 408.33.

Step B: tert-butyl 5-((4-(4-((S)-3-(tert-butoxy)-2-((1,3-dioxoisoindolin-2-yl)oxy)-3-oxopropoxy)phenyl)-1H-pyrazol-1-yl)methyl)-2,2-dimethyloxazolidine-3-carboxylate The title compound was prepared according to the procedure of Example 38 Steps A-C. LC-MS [M+H]+: m/z 663.45.

Step C: 4-(4-((S)-3-(tert-butoxy)-2-((1,3-dioxoisoindolin-2-yl)oxy)-3-oxopropoxy)phenyl)-1-((3-(tert-butoxycarbonyl)-2,2-dimethyloxazolidin-5-yl)methyl)-2-methyl-1H-pyrazol-2-ium trifluoromethanesulfonate The title compound was prepared according to the procedure of Example 40 Step D. LC-MS [M]+: m/z 677.47

Step D: 1-(3-amino-2-hydroxypropyl)-4-(4-((S)-3-(tert-butoxy)-2-((1,3-dioxoisoindolin-2-yl)oxy)-3-oxopropoxy)phenyl)-2-methyl-1H-pyrazol-2-ium trifluoromethanesulfonate DL-10-camphorsulfonic acid (0.028 g, 0.122 mmol) was added to a stirred, room temperature mixture of 4-(4-((S)-3-(tert-butoxy)-2-((1,3-dioxoisoindolin-2-yl)oxy)-3-oxopropoxy)-phenyl)-1-((3-(tert-butoxycarbonyl)-2,2-dimethyloxazolidin-5-yl)methyl)-2-methyl-1H-pyrazol-2-ium trifluoromethanesulfonate (1.0 g, 1.2 mmol) in MeOH. The reaction mixture was stirred at room temperature overnight, then concentrated to give the title compound. LC-MS [M]+: m/z 537.28.

Step E: 4-(4-((S)-3-(tert-butoxy)-2-((1,3-dioxoisoindolin-2-yl)oxy)-3-oxopropoxy)phenyl-1-(3-((tert-butoxycarbonyl)amino)-2-hydroxypropyl)-2-methyl-1H-pyrazol-2-ium 2,2,2-trifluoroacetate $Et_3N$ (170 μl, 1.2 mmol) was added to a stirred, room temperature mixture of 1-(3-amino-2-hydroxypropyl)-4-(4-((S)-3-(tert-butoxy)-2-((1,3-dioxoisoindolin-2-yl)oxy)-3-oxopropoxy)phenyl)-2-methyl-1H-pyrazol-2-ium trifluoromethanesulfonate (830 mg, 1.2 mmol), and BOC-Anhydride (225 μl, 0.97 mmol) in $CHCl_3$. The reaction mixture was stirred at room temperature overnight, then concentrated. The resulting residue was purified by column chromatography on silica gel 40 g column, eluting with $CH_2Cl_2$/MeOH (100~90%) to give a mixture. The mixture was dissolved in $CH_3CN$/water and purified by preparative HPLC Reverse phase (C-18) again, eluting with acetonitrile/water+0.1% TFA (5~80~100%), to give the title compound. LC-MS [M]+: m/z 637.33

Step E: (3S)-3-((Z)-2-(((1S)-2-(4-(1-(3-amino-2-hydroxypropyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate The title compound was prepared according to the procedure of Example 38 Steps E-G. LC-MS [M+H]+: m/z 697.24

Example 43

(S)-3-((Z)-2-(((S)-2-(4-(1-((S)-3-amino-2-hydroxypropyl)-2-methyl-1H-pyrazol-2-ium-4-yl)-3-fluorophenoxy)-1-carboxyethoxy)imino)-2-(2-aminothiazol-4-yl)acetamido)-2,2-dimethyl-4-oxoazetidin-1-yl sulfate compound with formic acid (1:1)

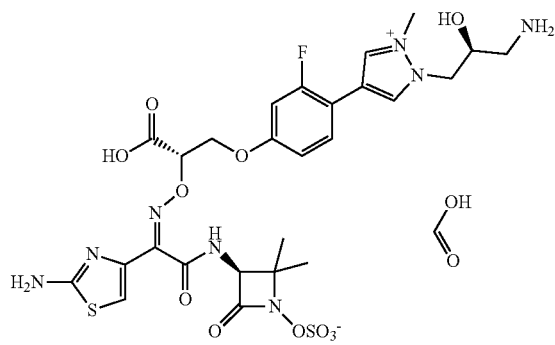

Step A: (R)-benzhydryl 3-(4-bromo-3-fluorophenoxy)-2-hydroxypropanoate

To a solution of (R)-3-(4-bromo-3-fluorophenoxy)-2-hydroxypropanoic acid (6 g, 22 mmol) and Et$_3$N (4.5 ml, 32 mmol)) in acetonitrile (40 ml) at rt was added dropwise (bromomethylene)dibenzene (6.9 g, 28 mmol)) in acetonitrile (20 ml) over 5 min. The reaction mixture was heated at 80° C. for 4 h, then concentrated. The resulting residue was partitioned between H$_2$O/DCM (75 mL/75 mL), and the aqueous layer was extracted with DCM (2×75 mL). The combined organic layers were washed with brine (200 ml), dried over MgSO$_4$, filtered, and concentrated. The resulting residue was purified by ISCO (80 g, 0-30% EtOAc/hexanes) to give the title compound. LC-MS [M+H]+: m/z 468.91

Step B: benzhydryl (R)-3-(3-fluoro-4-(4,4,5,5-tetramethyl-1,3,2-dioxaborolan-2-yl)phenoxy)-2-hydroxypropanoate Potassium acetate (3.0 g, 31 mmol) was added to a stirred, room temperature mixture of (R)-benzhydryl 3-(4-bromo-3-fluorophenoxy)-2-hydroxypropanoate (4.6 g, 9.4 mmol), 4,4,4',4',5,5,5',5'-octamethyl-2,2'-bi(1,3,2-dioxaborolane) (3.2 g, 12 mmol), and di-t-BuDPPF-PdCl$_2$ (0.34 g, 0.52 mmol) in dioxane. The reaction mixture was degassed with N$_2$ twice and stirred at 70° C. for 4 h. Then the reaction mixture was filtered and the filtrate was concentrated. The resulting residue was purified by column chromatography on silica gel 40 g column, eluting with EtOAc/isohexane (1050%) to give the title compound. LC-MS [M+H]+: m/z 493.35

Step C: benzhydryl (2R)-3-(4-(1-(3-((tert-butoxycarbonyl)amino)-2-((tert-butyldimethyl-silyl)oxy)propyl)-1H-pyrazol-4-yl)-3-fluorophenoxy)-2-hydroxypropanoate Aqueous potassium phosphate (2.6 ml, 2.6 mmol) was added to a room temperature mixture of (R)-benzhydryl 3-(3-fluoro-4-(4,4,5,5-tetramethyl-1,3,2-dioxaborolan-2-yl)phenoxy)-2-hydroxypropanoate (480 mg, 0.97 mmol), (S)-tert-butyl (3-(4-bromo-1H-pyrazol-1-yl)-2-((tert-butyldimethylsilyl)oxy)propyl)carbamate (380 mg, 0.88 mmol) and Di-t-BuDPPF-PdCl$_2$ (34 mg, 0.053 mmol) in dioxane. The reaction mixture was degassed with N$_2$ and stirred at 65° C. for 1.5 h. Then the reaction mixture was cooled to RT and extracted with EtOAc. The organic layer was washed with brine, dried over MgSO$_4$, filtered and concentrated. The resulting residue was purified by column chromatography on silica gel, eluting with EtOAc/isohexane (580%) to give the title compound. LC-MS [M+H]+: m/z 720.50

Step D: (Z)-2-((((2S)-1-(benzhydryloxy)-3-(4-(1-(3-((tert-butoxycarbonyl)amino)-2-((tert-butyldimethylsilyl)oxy)propyl)-1H-pyrazol-4-yl)-3-fluorophenoxy)-1-oxopropan-2-yl)oxy)imino)-2-(2-((tert-butoxycarbonyl)amino)thiazol-4-yl) acetic acid DEAD (0.12 ml, 0.78 mmol) was added to a stirred, cooled 0° C. mixture of benzhydryl (2R)-3-(4-(1-(3-((tert-butoxycarbonyl)amino)-2-((tert-butyldimethylsilyl)oxy)propyl)-1H-pyrazol-4-yl)-3-fluorophenoxy)-2-hydroxypropanoate (0.51 g, 0.71 mmol), 2-hydroxyisoindoline-1,3-dione (116 mg, 0.71 mmol)), and triphenylphosphine (200 mg, 0.78 mmol)) in THF. The reaction mixture was stirred at RT for 1 h, and then concentrated. The resulting residue was purified by column chromatography on silica gel [40 g Column], eluting with hexane/EtOAc (10060% to give the title compound. LC-MS [M+H]+: m/z 865.56

Step E: (Z)-2-((((S)-1-(benzhydryloxy)-3-(4-(1-((S)-3-((tert-butoxycarbonyl)amino)-2-((tert-butyldimethylsilyl)oxy)propyl)-2-methyl-1H-2l4-pyrazol-4-yl)-3-fluorophenoxy)-1-oxopropan-2-yl)oxy)imino)-2-(2-((tert-butoxycarbonyl)amino)thiazol-4-yl)acetic acid, trifluoromethanesulfonate salt The title compound was prepared according to the procedure of Example 40, Step D. LC-MS [M]+: m/z 1003.60.

Step F: 4-(4-((S)-3-(benzhydryloxy)-2-((((Z)-(2-((tert-butoxycarbonyl)amino)thiazol-4-yl)(carboxy)methylene)amino)oxy)-3-oxopropoxy)-2-fluorophenyl)-1-(3-((tert-butoxycarbonyl)amino)-2-hydroxypropyl)-2-methyl-1H-pyrazol-2-ium TBAF (0.28 g, 1.06 mmol) was added to a stirred, cooled 0° C. mixture of (Z)-2-(((((S)-1-(benzhydryloxy)-3-(4-(1-((S)-3-((tert-butoxycarbonyl)amino)-2-((tert-butyldimethylsilyl)oxy)propyl)-2-methyl-1H-2l4-pyrazol-4-yl)-3-fluorophenoxy)-1-oxopropan-2-yl)oxy)imino)-2-(2-((tert-butoxycarbonyl)amino)thiazol-4-yl)acetic acid, trifluoromethanesulfonate salt (0.80 g, 0.53 mmol) in THF. The reaction mixture was stirred at room temperature for 2 h, then diluted with EtOAc. The organic layer was washed with water and brine, dried over MgSO₄, filtered and concentrated. The resulting residue was purified by preparative Reverse phase (C-18), eluting with acetonitrile/water+0.1% TFA to give the title compound. LC-MS [M]⁺: m/z 889.45

Step G: 4-(4-((S)-3-(benzhydryloxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)-amino)oxy)-3-oxopropoxy)-2-fluorophenyl)-1-((S)-3-((tert-butoxycarbonyl)amino)-2-hydroxypropyl)-2-methyl-1H-pyrazol-2-ium To a 4-(4-((S)-3-(benzhydryloxy)-2-((((Z)-(2-((tert-butoxycarbonyl)amino)thiazol-4-yl)(carboxy)methylene)amino)oxy)-3-oxopropoxy)-2-fluorophenyl)-1-(3-((tert-butoxycarbonyl)amino)-2-hydroxypropyl)-2-methyl-1H-pyrazol-2-ium (220 mg, 0.24 mmol) and (S)-3-amino-2,2-dimethyl-4-oxoazetidin-1-yl hydrogen sulfate (102 mg, 0.48 mmol)) in acetonitrile (12 ml) at −10° C. was added pyridine (0.059 ml, 0.73 mmol) under N₂. Then N1-((ethylimino)methylene)-N3,N3-dimethylpropane-1,3-diamine hydrochloride (102 mg, 0.53 mmol) was added. The reaction was stirred at −10-0° C. for 1 h, then concentrated. The resulting residue was purified by preparative reverse phase (C-18), eluting with acetonitrile/water+0.1% TFA to give the title compound.

Step H: ((3S)-3-((Z)-2-(((1S)-2-(4-(1-(3-amino-2-hydroxypropyl)-2-methyl-1H-pyrazol-2-ium-4-yl)-3-fluorophenoxy)-1-carboxyethoxy)imino)-2-(2-aminothiazol-4-yl)acetamido)-2,2-dimethyl-4-oxoazetidin-1-yl sulfate compound with formic acid (1:1)

TFA (2 ml) was added to a stirred, room temperature mixture of 4-(4-((S)-3-(benzhydryloxy)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)-2-fluorophenyl)-1-((S)-3-((tert-butoxycarbonyl)amino)-2-hydroxypropyl)-2-methyl-1H-pyrazol-2-ium (240 mg, 0.22 mmol) in DCM. The reaction mixture was stirred at room temperature for 45 min, then concentrated and treated with ether twice. The resulting residue was dissolved in DMSO (3 mL) and ether (2 mL), and concentrated under vacuum for 5 min. The resulting solution was diluted with DMSO (4 mL) and submitted for reverse phase purification to give the title compound as a single isomer. LC-MS [M+H]⁺: m/z 715.30.

Example 44

(3S)-3-((Z)-2-(((1S)-2-(4-(1-(3-amino-2-hydroxypropyl)-2-methyl-1H-pyrazol-2-ium-4-yl)-3-fluorophenoxy)-1-carboxyethoxy)imino)-2-(2-aminothiazol-4-yl)acetamido)-2,2-dimethyl-4-oxoazetidin-1-yl sulfate compound with formic acid (1:1)

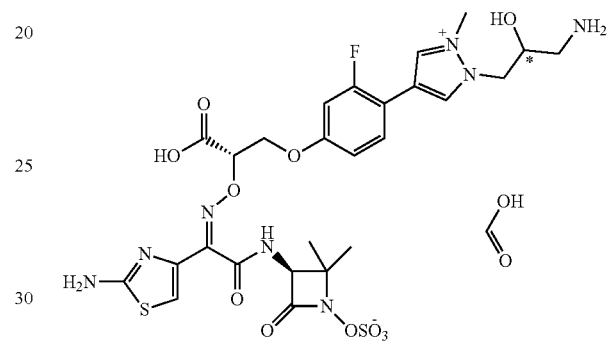

The title compound was prepared according to the procedure of Example 43 starting from the appropriate starting materials. LC-MS [M+H]⁺: m/z 715.28.

Example 45 and Example 46

(S)-3-((Z)-2-(2-aminothiazol-4-yl)-2-(((S)-1-carboxy-2-(4-(1-((R)-2,3-diaminopropyl)-2-methyl-1H-pyrazol-2-ium-4-yl)-3-fluorophenoxy)ethoxy)imino)acetamido)-2,2-dimethyl-4-oxoazetidin-1-yl sulfate (Diastereomeric at the amine)

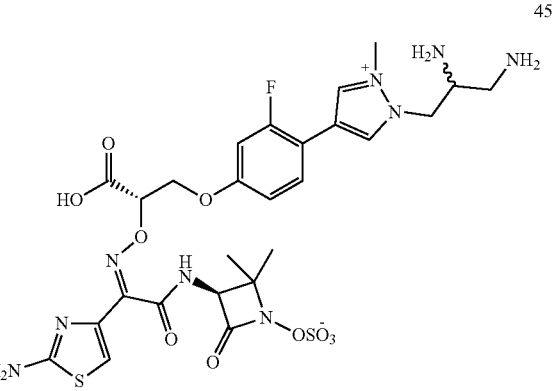

46

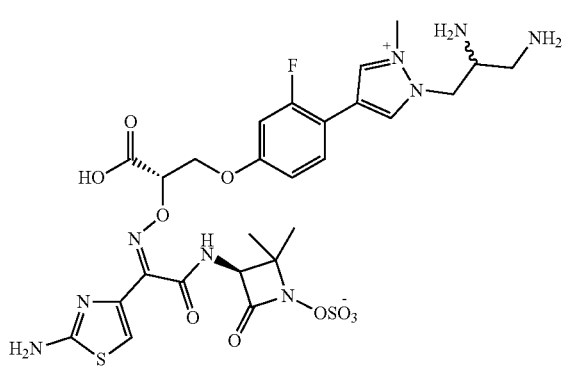

Step A: tert-butyl(2-((tert-butyldimethylsilyl)oxy)-3-(4-(4,4,5,5-tetramethyl-1,3,2-dioxaborolan-2-yl)-1H-pyrazol-1-yl)propylcarbamate Potassium acetate (3.48 g, 36 mmol) was added to a stirred, room temperature mixture of 4,4,4',4',5,5,5',5'-octamethyl-2,2'-bi(1,3,2-dioxaborolane) (3.6 g, 14 mmol), tert-butyl (3-(4-bromo-1H-pyrazol-1-yl)-2-((tert-butyldimethylsilyl)oxy)propyl)carbamate (5.1 g, 12 mmol) and di-t-BuDPPF PdCl$_2$ (0.38 g, 0.591 mmol) in dioxane. The reaction mixture was degassed with N$_2$ twice and stirred at 70° C. for 4 h. Then the reaction mixture was filtered and the filtrate was concentrated. The resulting residue was purified by column chromatography on silica gel 120 g column, eluting with EtOAc/isohexane (050%) to give the title compound. LC-MS [M+H]$^+$: m/z 482.49

Step B: tert-butyl (2-hydroxy-3-(4-(4,4,5,5-tetramethyl-1,3,2-dioxaborolan-2-yl)-1H-pyrazol-1-yl)propylcarbamate TBAF (0.61 g, 2.3 mmol) was added to a stirred, 0° C. mixture of tert-butyl (2-((tert-butyldimethylsilyl)oxy)-3-(4-(4,4,5,5-tetramethyl-1,3,2-dioxaborolan-2-yl)-1H-pyrazol-1-yl)propyl)carbamate (0.93 g, 1.9 mmol) in THF. The reaction mixture was stirred at room temperature for 2 h, then concentrated. The resulting residue was purified by column chromatography on silica gel, eluting with EtOAc/isohexane (580%) to give the title compound. LC-MS [M+H]$^+$: m/z 368.27

Step C: 1-((tert-butoxycarbonyl)amino)-3-(4-(4,4,5,5-tetramethyl-1,3,2-dioxaborolan-2-yl)-1H-pyrazol-1-yl)propan-2-yl methanesulfonate MsCl (0.104 ml, 1.33 mmol) was added in one portion to a stirred solution of tert-butyl (2-hydroxy-3-(4-(4,4,5,5-tetramethyl-1,3,2-dioxaborolan-2-yl)-1H-pyrazol-1-yl)propyl)carbamate (480 mg, 1.30 mmol) and Et$_3$N (0.24 ml, 1.7 mmol) in dichloromethane (5 mL) at 0° C. under N$_2$. The reaction mixture was stirred at 0° C. for 1 h, then concentrated in vacuo and partitioned between water (50 mL) and ethyl acetate (40 mL). The aqueous layer was separated, and extracted with ethyl acetate (2×40 mL). The combined organic layers were washed with brine (40 mL), dried (magnesium sulfate) and concentrated in vacuo to give the title compound.

Step D: tert-butyl (2-azido-3-(4-(4,4,5,5-tetramethyl-1,3,2-dioxaborolan-2-yl)-1H-pyrazol-1-yl)propyl)carbamate Sodium azide (173 mg, 2.7 mmol) was added in one portion to a stirred solution of 1-((tert-butoxycarbonyl)amino)-3-(4-(4,4,5,5-tetramethyl-1,3,2-dioxaborolan-2-yl)-1H-pyrazol-1-yl)propan-2-yl methanesulfonate (590 mg, 1.33 mmol)) in dimethyl formamide (5 mL). The reaction mixture was heated to 80° C. and stirred for 18 h, and cooled to room temperature. Then the reaction mixture was poured into water (20 mL) and extracted with ethyl acetate (2×20 mL). The combined organic layers were washed with brine (20 mL), dried (magnesium sulfate), and concentrated in vacuo to give the title compound. LC-MS [M+H]$^+$: 393.38.

Step E: tert-butyl (2-amino-3-(4-(4,4,5,5-tetramethyl-1,3,2-dioxaborolan-2-yl)-1H-pyrazol-1-yl)propyl)carbamate Pd—C (280 mg, 0.27 mmol) was added to a room temperature mixture of tert-butyl (2-azido-3-(4-(4,4,5,5-tetramethyl-1,3,2-dioxaborolan-2-yl)-1H-pyrazol-1-yl)propyl)carbamate (525 mg, 1.34 mmol) in MeOH. The reaction mixture was stirred at room temperature under H$_2$ overnight. Then the mixture was filtered and the filtrate was concentrated to dryness to give the title compound. LC-MS [M+H]$^+$: 367.24.

Step F: di-tert-butyl (3-(4-(4,4,5,5-tetramethyl-1,3,2-dioxaborolan-2-yl)-1H-pyrazol-1-yl)propane-1,2-diyl)dicarbamate BOC-Anhydride (0.34 ml, 1.5 mmol) was added to a stirred, room temperature mixture of tert-butyl (2-amino-3-(4-(4,4,5,5-tetramethyl-1,3,2-dioxaborolan-2-yl)-1H-pyrazol-1-yl)propyl)carbamate (570 mg, 1.3 mmol) in THF. The mixture was stirred at room temperature for 1 h, and then concentrated to give the title compound. LC-MS [M+H]$^+$: 467.36.

Step G: benzhydryl (2R)-3-(4-(1-(2,3-bis((tert-butoxycarbonyl)amino)propyl)-1H-pyrazol-4-yl)-3-fluorophenoxy)-2-hydroxypropanoate Aqueous potassium phosphate (4.0 ml, 4.0 mmol) was added to a room temperature mixture of (R)-benzhydryl 3-(4-bromo-3-fluorophenoxy)-2-hydroxypropanoate (590 mg, 1.3 mmol), di-tert-butyl (3-(4-(4,4,5,5-tetramethyl-1,3,2-dioxaborolan-2-yl)-1H-pyrazol-1-yl)propane-1,2-diyl)dicarbamate (630 mg, 1.3 mmol) and di-t-BuDPPF PdCl$_2$ (52 mg, 0.079 mmol) in dioxane. The reaction mixture was degassed with N$_2$ and stirred at 65° C. for 1.5 h, then cooled to RT and extracted with EtOAc. The organic layer was washed with brine. dried over MgSO$_4$, filtered and concentrated. The resulting residue was purified by column chromatography, eluting with CH$_2$Cl$_2$/MeOH (100~90%) to give the title compound as a diastereomeric mixture. LC-MS [M+H]$^+$: 705.45. The diastereomers were separated using the OJ-H column under SFC conditions to give the title compounds. Example 45 was prepared from the faster eluting isomer according to the procedure of Example 1 Steps B-H. LC-MS [M+H]$^+$: m/z 714.20. Example 46 was prepared from the slower eluting isomer according to the procedure of Example 1 Steps B-H. LC-MS [M+H]$^+$: m/z 714.36.

Example 47

(S)-3-((Z)-2-(((S)-2-(4-(3-Amino-1-(3-aminopropyl)-2-methyl-1H-pyrazol-2-ium-4-yl)-3-fluorophenoxy)-1-carboxyethoxy)imino)-2-(2-aminothiazol-4-yl)acetamido)-2,2-dimethyl-4-oxoazetidin-1-yl sulfate

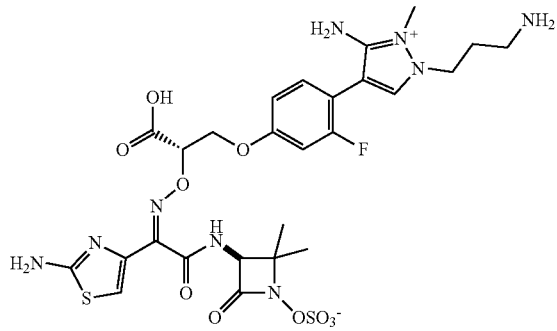

Step A: tert-Butyl (R)-3-(4-(3-amino-1-(3-((tert-butoxycarbonyl)amino)propyl)-H-pyrazol-4-yl)-3-fluorophenoxy)-2-((tert-butyldimethylsilyl)oxy)propanoate To a solution of (R)-tert-butyl 2-((tert-butyldimethylsilyl)oxy)-3-(3-fluoro-4-(4,4,5,5-tetramethyl-1,3,2-dioxaborolan-2-yl)phenoxy)propanoate (2.6 g, 5.24 mmol), tert-butyl (3-(3-amino-4-bromo-H-pyrazol-1-yl)propyl)carbamate (2.0 g, 6.3 mmol), and 1,1'-bis(di-tert-butylphosphino)ferrocene palladium dichloride (0.34 g, 0.52 mmol) in THF (15 ml) in a microwave vial was added 1M aqueous solution of potassium phosphate (7.8 ml, 7.8 mmol). The microwave vial was sealed, degassed and refilled with $N_2$(3×). The reaction was stirred at 70° C. for 2 h, then diluted with $NH_4Cl$ solution (saturated), and extracted with EtOAc. The organic layer was combined, dried over $MgSO_4$ and concentrated. The resulting residue was purified on flash chromatography $SiO_2$ column (80 g gold, eluting with EtOAc/Hexane(0-100% 3 cv, 100% 6 cv) to give the title compound. LC-MS [M+1]: m/z 609.00

Step B: tert-Butyl (R)-3-(4-(3-(((allyloxy)carbonyl)amino)-1-(3-((tert-butoxycarbonyl)amino) propyl)-1H-pyrazol-4-yl)-3-fluorophenoxy)-2-((tert-butyldimethylsilyl)oxy)propanoate To a solution of (R)-tert-butyl 3-(4-(3-amino-1-(3-((tert-butoxycarbonyl)amino)propyl)-1H-pyrazol-4-yl)-3-fluorophenoxy)-2-((tert-butyldimethylsilyl)oxy)propanoate (2.3 g, 3.8 mmol) in $CH_2Cl_2$ (100 ml) was added DIPEA (1.3 ml, 7.6 mmol) followed by addition of allyl carbonochloridate (0.80 ml, 7.6 mmol). The mixture was stirred at room temperature for 4 h, then the solvent was removed. The resulting residue was purified by column chromatography on silica gel (80 g gold), eluting with EtOAc/hexane (0-50%, 6 cv; 50%, 10 cv) to give the title compound. LC-MS [M+1]: m/z 693.48

Step C: tert-Butyl (R)-3-(4-(3-(((allyloxy)carbonyl)amino)-1-(3-((tert-butoxycarbonyl)-amino)propyl)-1H-pyrazol-4-yl)-3-fluorophenoxy)-2-hydroxypropanoate To a solution of (R)-tert-butyl 3-(4-(3-(((allyloxy)carbonyl)amino)-1-(3-((tert-butoxycarbonyl)amino)-propyl)-1H-pyrazol-4-yl)-3-fluorophenoxy)-2-((tert-butyldimethylsilyl)oxy)propanoate (2.6 g, 3.8 mmol) in THF (30 ml) was added a solution of TBAF in THF (3.75 ml, 3.75 mmol, 1M). The reaction was stirred for 1 h at room temperature, then the solvent was removed. The resulting residue was purified by column chromatography on silica gel (40 g gold), eluting with EtOAc/Hexane (0-80%, 6 cv; 80%, 10 cv) to give the title compound. LC-MS [M+1]: m/z 580.30

Step D: tert-Butyl (S)-3-(4-(3-(((allyloxy)carbonyl)amino)-1-(3-((tert-butoxycarbonyl) amino)propyl)-1H-pyrazol-4-yl)-3-fluorophenoxy)-2-((1,3-dioxoisoindolin-2-yl)oxy)-propanoate To a solution of (R)-tert-butyl 3-(4-(3-(((allyloxy)carbonyl)amino)-1-(3-((tert-butoxycarbonyl) amino)propyl)-1H-pyrazol-4-yl)-3-fluorophenoxy)-2-hydroxypropanoate (1.13 g, 2.0 mmol) in THF (5 ml) was added 2-hydroxyisoindoline-1,3-dione (0.38 g, 2.3 mmol), and triphenylphosphine (0.62 g, 2.3 mmol), followed by addition of DIAD (0.46 ml, 2.3 mmol) at room temperature. The mixture was stirred at room temperature for 3 h, then the solvent was removed. The resulting residue was purified by column chromatography on silica gel Redi 40 g gold, eluting with EtOAc/hexane (0-70%, 6 cv; 70%, 10 cv) to give the title compound. LC-MS [M+1]: m/z 725.25.

Step E: (S)-3-(((Allyloxy)carbonyl)amino)-4-(4-(2-(aminooxy)-3-(tert-butoxy)-3-oxopropoxy)-2-fluorophenyl)-1-(3-((tert-butoxycarbonyl)amino)propyl)-2-methyl-1H-pyrazol-2-ium triflate To a solution of (S)-tert-butyl 3-(4-(3-(((allyloxy)carbonyl)amino)-1-(3-((tert-butoxycarbonyl) amino)propyl)-1H-pyrazol-4-yl)-3-fluorophenoxy)-2-((1,3-dioxoisoindolin-2-yl)oxy)propanoate (0.7 g, 0.97 mmol) in acetonitrile (12 ml) at 0° C. was added methyl trifluoromethanesulfonate (0.11 ml, 0.97 mmol). The reaction was stirred at room temperature for 1 h, then a solution of ammonia in MeOH (1.4 ml, 9.7 mmol, 7M) was added. The reaction mixture was stirred at room temperature overnight, then the solvent was removed in vacuo to give the title compound. LC-MS [M+1]: m/z 608.44

Step F: (S,Z)-3-(((Allyloxy)carbonyl)amino)-4-(4-(3-(tert-butoxy)-2-(((2-((tert-butoxy-carbonyl)amino)thiazol-4-yl)(carboxy)methylene)amino)oxy)-3-oxopropoxy)-2-fluoro-phenyl)-1-(3-((tert-butoxycarbonyl)amino)propyl)-2-methyl-1H-pyrazol-2-ium triflate A solution of 2-(2-((tert-butoxycarbonyl)amino)thiazol-4-yl)-2-oxoacetic acid (0.16 g, 0.60 mmol) and (S)-3-(((allyloxy)carbonyl)amino)-4-(4-(2-(aminooxy)-3-(tert-butoxy)-3-oxopropoxy)-2-fluorophenyl)-1-(3-((tert-butoxycarbonyl)amino)propyl)-2-methyl-1H-pyrazol-2-ium triflate (0.38 g, 0.50 mmol) in EtOH (1 ml) and $CH_2ClCH_2Cl$ (0.5 ml) was stirred at room temperature overnight. Then the reaction mixture was concentrated to give the title compound. LC-MS [M+1]: m/z 862.39.

Step G: (S)-3-((Z)-2-(((S)-3-(4-(3-(((Allyloxy)carbonyl)amino)-1-(3-((tert-butoxy-carbonyl)amino)propyl)-2-methyl-1H-pyrazol-2-ium-4-yl)-3-fluorophenoxy)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate To the solution of (S,Z)-3-(((allyloxy)carbonyl)amino)-4-(4-(3-(tert-butoxy)-2-((((2-((tert-butoxycarbonyl)-amino)

thiazol-4-yl)(carboxy)-methylene)amino)oxy)-3-oxo-propoxy)-2-fluorophenyl)-1-(3-((tert-butoxycarbonyl)-amino)propyl)-2-methyl-1H-pyrazol-2-ium triflate (0.49 g, 0.50 mmol) in DMF (5 ml) was added DCC (0.31 g, 1.50 mmol), and HOBt (0.23 g, 1.50 mmol). The resulting solution was stirred at room temperature for 30 min, then (S)-3-amino-2,2-dimethyl-4-oxoazetidin-1-yl hydrogen sulfate (0.26 g, 1.25 mmol) and sodium bicarbonate (0.25 g, 3.0 mmol) were added. The reaction mixture was stirred at room temperature overnight. The resulting solid was filtered off. The filtrate was purified by RP C-18 silica gel column, eluting with ACN/water with 0.05% TFA, (20-100% 8 cv, 100% 6 cv) to give the title compound. LC-MS [M+1]: m/z 1054.77

Step H: (S)-3-((Z)-2-((((S)-3-(4-(3-Amino-1-(3-((tert-butoxycarbonyl)amino)propyl)-2-methyl-1H-pyrazol-2-ium-4-yl)-3-fluorophenoxy)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate, trifluoroacetate To a solution of (S)-3-((Z)-2-((((S)-3-(4-(3-(((allyloxy)carbonyl)amino)-1-(3-((tert-butoxycarbonyl)amino)propyl)-2-methyl-1H-pyrazol-2-ium-4-yl)-3-fluorophenoxy)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate TFA (0.5 g, 0.43 mmol) in DMF (4 ml) was added Palladium Tetrakis (0.049 g, 0.043 mmol) and phenylsilane (0.53 ml, 4.3 mmol) at 0° C. The reaction mixture was stirred for 10 min, and then filtered. The filtrate was purified on a RPHPLC (Gilson) (C-18 column) eluting with ACN/water containing 0.05% TFA (20-100%, 8 min; 100% 10 min) to give the title compound. LC-MS [M+1]: m/z 970.48

Step I: (S)-3-((Z)-2-(((S)-2-(4-(3-Amino-1-(3-aminopropyl)-2-methyl-1H-pyrazol-2-ium-4-yl)-3-fluorophenoxy)-1-carboxyethoxy)imino)-2-(2-aminothiazol-4-yl)acetamido)-2,2-dimethyl-4-oxoazetidin-1-yl sulfate To a solution of (S)-3-((Z)-2-((((S)-3-(4-(3-amino-1-(3-((tert-butoxycarbonyl)amino)propyl)-2-methyl-1H-pyrazol-2-ium-4-yl)-3-fluorophenoxy)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate TFA (170 mg, 0.16 mmol) in CH$_2$Cl$_2$ (1 ml) was added TFA (2 ml, 26 mmol). The solution was stirred at room temperature for 40 min, then the solvent was removed. The resulting residue was washed with Et$_2$O (3×) and dried under vacuum. The resulting solid was dissolved in DMSO and purified on RPHPLC (Gilson) (C-18 column), eluting with ACN/Water containing 0.05% TFA (0-40%, 12 min) to give the title compound as the TFA salt. LC-MS [M+1]: m/z 712.30. $^1$HNMR (500 MHz, D$_2$O) δ$_H$ 7.96 (1H, s), 7.31 (1H, t, J=8.6 Hz), 7.09 (1H, s), 6.85 (2H, d, J=10.8 Hz), 5.14 (1H, s), 4.51 (2H, t, J=14.7 Hz), 4.32 (2H, t, J=7.2 Hz), 3.74 (3H, s), 3.02 (2H, t, J=7.7 Hz), 2.66 (1H, s), 2.15 (2H, t, J=8.0 Hz), 1.42 (3H, s), 1.08 (3H, s).

Example 48

(S)-3-((Z)-2-(((S)-2-(4-(3-Amino-1-(3-aminopropyl)-2-methyl-1H-pyrazol-2-ium-4-yl)-3-fluorophenoxy)-1-carboxyethoxy)imino)-2-(2-amino-5-chlorothiazol-4-yl)acetamido)-2,2-dimethyl-4-oxoazetidin-1-yl sulfate

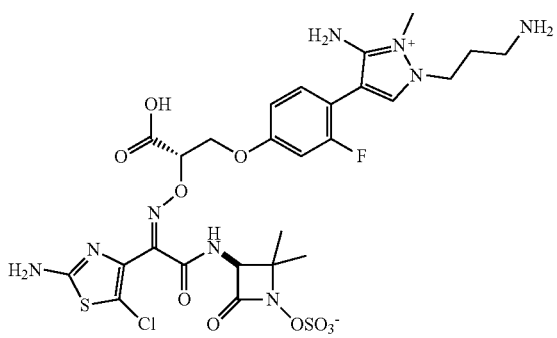

The title compound was prepared using the procedure of Example 47 using 2-(2-((tert-butoxycarbonyl)amino)-5-chlorothiazol-4-yl)-2-oxoacetic acid in Step F. LC-MS [M+1]: m/z 746.26. $^1$H NMR (D$_2$O, 500 MHz): δ$_H$ 7.97 (1H, s), 7.31 (1H, t, J=8.7 Hz), 6.84-6.87 (2H, m), 5.15 (1H, d, J=5.0 Hz), 4.44-4.53 (2H, m), 4.32 (2H, t, J=7.2 Hz), 3.75 (3H, s), 3.02 (2H, t, J=7.8 Hz), 2.15 (2H, t, J=7.9 Hz), 1.42 (3H, s), 1.07 (3H, s).

Example 49

(S)-3-((Z)-2-(((S)-2-(4-(3-Amino-1-(3-aminopropyl)-2-methyl-1H-pyrazol-2-ium-4-yl)phenoxy)-1-carboxyethoxy)imino)-2-(2-amino-5-chlorothiazol-4-yl)acetamido)-2,2-dimethyl-4-oxoazetidin-1-yl sulfate

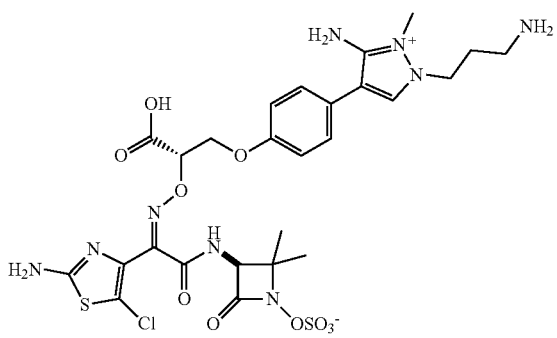

The title compound was prepared using the procedure of Example 47. LC-MS [M+1]: m/z 728.36. $^1$H NMR (D$_2$O, 500 MHz): δ$_H$ 7.93 (1H, s), 7.34 (2H, d, J=8.2 Hz), 7.02 (2H, d, J=8.2 Hz), 5.15 (1H, s), 4.29 (2H, t, J=7.2 Hz), 3.73 (3H, s), 3.02 (2H, t, J=7.7 Hz), 2.14 (2H, t, J=8.0 Hz), 1.40 (3H, s), 1.04 (3H, s).

Example 50

(S)-3-((Z)-2-(((S)-2-(4-(5-Amino-1-(3-aminopropyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

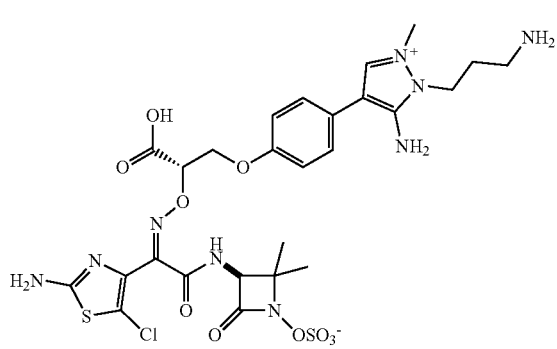

The title compound was prepared using the procedure of Example 47. LC-MS [M+1]: m/z 696.21. $^1$H NMR (D$_2$O, 500 MHz): δ$_H$ 7.88 (1H, s), 7.34 (2H, d, J=8.4 Hz), 6.97-7.04 (4H, m), 4.96 (1H, d, J=5.6 Hz), 4.42-4.47 (3H, m), 4.31 (2H, t, J=7.6 Hz), 3.81-3.83 (4H, m), 3.08 (2H, t, J=7.9 Hz), 2.67 (1H, s), 2.15 (2H, t, J=8.1 Hz), 1.42 (3H, s), 1.09 (3H, s).

Example 51A and 51B (S)-3-((Z)-2-(2-Amino-5-chlorothiazol-4-yl)-2-((((R)-1-(4-(1-(3-aminopropyl)-2-methyl-1H-pyrazol-2-ium-4-yl)phenoxy)-2-carboxypropan-2-yl)oxy)imino)acetamido)-2,2-dimethyl-4-oxoazetidin-1-yl sulfate (51A)

(S)-3-((Z)-2-(2-amino-5-chlorothiazol-4-yl)-2-((((R)-1-(4-(1-(3-aminopropyl)-2-methyl-1H-pyrazol-2-ium-4-yl)phenoxy)-2-carboxypropan-2-yl)oxy)imino)acetamido)-2,2-dimethyl-4-oxoazetidin-1-yl sulfate (51B)

51A

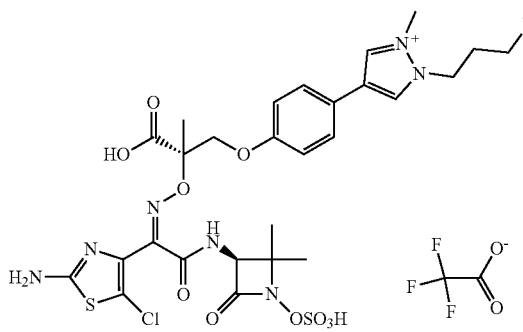

51B

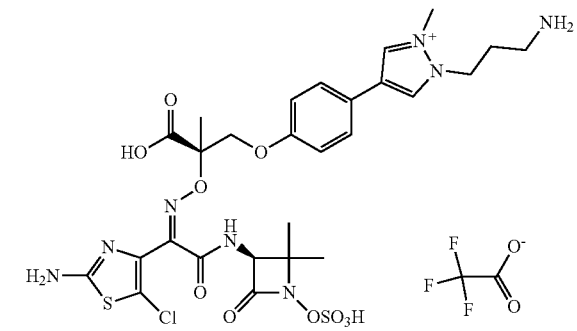

The title compounds were prepared using the procedure of Examples 23A and 23B. Example 51A: LC-MS [M+1]: m/z 727.36. $^1$HNMR (500 MHz, D$_2$O) δ$_H$ 8.49 (1H, s), 8.43 (1H, s), 7.49 (2H, d), 7.02 (2H, s), 4.57-4.53 (3H, m), 4.48 (1H, d), 4.40 (1H, d), 4.11 (3H, s), 3.12 (2H, t), 2.32 (2H, m), 1.60 (3H, s), 1.38 (3H, s), 1.17 (3H, s). Example 51B: LC-MS [M+1]: m/z 727.36. $^1$HNMR (500 MHz, D$_2$O) δ$_H$ 8.50 (1H, s), 8.44 (1H, s), 7.50 (2H, d), 7.04 (2H, s), 4.59-4.53 (4H, m), 4.37 (1H, d), 4.11 (3H, s), 3.12 (2H, t), 2.32 (2H, m), 1.61 (3H, s), 1.39 (3H, s), 1.13 (3H, s).

Example 52

(S)-3-((Z)-2-(((S)-2-(4-(1-((S)-3-Amino-2-hydroxypropyl)-2-(azetidin-3-ylmethyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

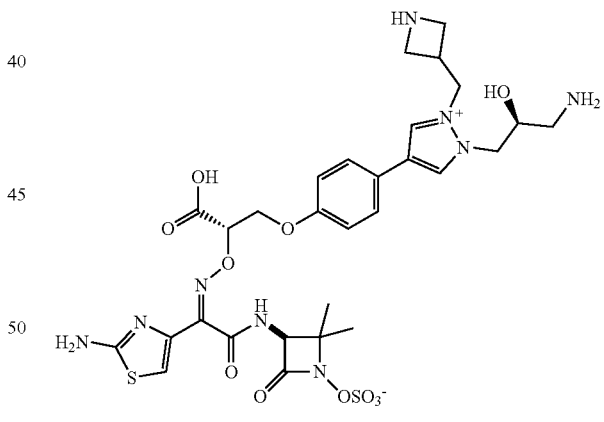

Step A: tert-Butyl (R)-3-(4-(1-((S)-3-((tert-butoxycarbonyl)amino)-2-((tert-butyl-dimethylsilyl) oxy) propyl)-1H-pyrazol-4-yl)phenoxy)-2-((tert-butyldimethylsilyl)-oxy)propanoate The mixture of tert-butyl (3-(4-bromo-H-pyrazol-1-yl)-2-((tert-butyldimethylsilyl)oxy) propyl)carbamate (0.53 g, 1.22 mmol), tert-butyl-2-hydroxy-3-(4-(4,4,5,5-tetramethyl-1,3,2-dioxaborolan-2-yl)phenoxy)propanoate (1 g, 2.8 mmol), 1,1'-bis(di-tert-butylphosphino)ferrocene palladium dichloride (0.18 g, 0.28 mmol), and potassium phosphate (4.12 ml, 8.24 mmol, 2 M aq) in THF (15 ml) was degassed and refilled with N₂ three times. The reaction mixture was heated at 60° C. for 2 h, then diluted with NH₄Cl solution (saturated), and extracted with EtOAc. The organic layers were combined, dried over MgSO₄ and concentrated. The resulting residue was purified by column chromatography on silica gel Redi 80 g gold, eluting with EtOAc/hexane (0-35%, 6 cv; 35%, cv) to give the title compound. LC-MS [M+1]: m/z 592.34.

Step B: tert-Butyl (S)-3-(4-(1-((S)-3-((tert-butoxy-carbonyl)amino)-2-((tert-butyldimethyl-silyl) oxy) propyl)-1H-pyrazol-4-yl)phenoxy)-2-((1,3-dioxoi-soindolin-2-yl)oxy)propanoate To a solution of (2R)-tert-butyl 3-(4-(1-(3-((tert-butoxy-carbonyl)amino)-2-((tert-butyl-dimethylsilyl) oxy)propyl)-1H-pyrazol-4-yl)phenoxy)-2-hydroxypropanoate (1.12 g, 1.9 mmol) in THF (10 ml) was added 2-hydroxyisoindoline-1,3-dione (0.37 g, 2.3 mmol), triphenylphosphine (0.60 g, 2.3 mmol), followed by the addition of DIAD (0.44 ml, 2.3 mmol) at room temperature. The reaction was stirred overnight, then the solvent was removed. The resulting residue was purified by column chromatography on silica gel Redi 80 g gold, eluting with EtOAc/hexane (0-50%, 5 cv, 50% 10 cv) to give the title compound. LC-MS [M+1]: m/z 737.41.

Step C: 4-(4-((S)-3-(tert-Butoxy)-2-((1,3-dioxoi-soindolin-2-yl)oxy)-3-oxopropoxy)phenyl)-1-((S)-3-((tert-butoxycarbonyl)amino)-2-((tert-butyldimethyl-silyl)oxy)propyl)-2-((1-(tert-butoxycarbonyl) azetidin-3-yl)methyl)-1H-pyrazol-2-ium, trifluoromethanesulfonate A solution of tert-butyl-3-(hydroxymethyl)azetidine-1-carboxylate (510 mg, 2.7 mmol) in CH₂Cl₂ (5 ml) was cooled to −78° C., and trifluoromethanesulfonic anhydride (0.56 ml, 3.4 mmol) and Hunig's base (0.95 ml, 5.4 mmol) was added. The reaction was stirred at −78° C. for 20 min, then quenched with water. The reaction mixture was warmed up to room temperature and partitioned between EtOAc and water. The organic layer was separated, washed with saturated NaHCO₃ and brine, dried over Na₂SO₄, and concentrated in vacuo to give an intermediate. To a vial containing the intermediate was added a solution of tert-butyl 3-(4-(1-(3-((tert-butoxycarbonyl)amino)-2-((tert-butyldimethylsi-lyl)oxy)propyl)-1H-pyrazol-4-yl)phenoxy)-2-((1,3-dioxoi-soindolin-2-yl)oxy)propanoate (500 mg, 0.68 mmol) and sodium bicarbonate (570 mg, 6.8 mmol) in anhydrous CH₃CN (10 ml). The reaction was heated at 60° C. for 1 h, then the solvent was removed. The resulting residue was triturated with Et₂O (2×15 mL), and then purified by column chromatography on silica gel Redi 24 g gold, eluting with MeOH/DCM (0-15%, 8 cv; 15%, 8 cv) to give the title compound. LC-MS [M+1]: m/z 906.9.

Step D: 4-(4-((S)-2-(Aminooxy)-3-(tert-butoxy)-3-oxopropoxy)phenyl)-1-((S)-3-((tert-butoxycarbonyl) amino)-2-((tert-butyldimethylsilyl)oxy)propyl)-2-((1-(tert-butoxy-carbonyl)azetidin-3-yl)methyl)-1H-pyrazol-2-ium trifluoromethanesulfonate To a 4-(4-((S)-3-(tert-Butoxy)-2-((1,3-dioxoisoindolin-2-yl)oxy)-3-oxopropoxy)phenyl)-1-((S)-3-((tert-butoxycarbo-nyl)amino)-2-((tert-butyldimethylsilyl)oxy)propyl)-2-((1-(tert-butoxycarbonyl)-azetidin-3-yl)methyl)-1H-pyrazol-2-ium trifluoromethanesulfonate (0.16 g, 0.18 mmol) in MeOH (1 ml) was added a solution of ammonia in MeOH (0.50 ml, 3.5 mmol, 7M). The reaction was stirred at room temperature for 5 h, then solvent was removed to give the title compound. LC-MS [M+1]: m/z 776.98.

Step E: 4-(4-((S)-3-(tert-Butoxy)-2-((((Z)-(2-((tert-butoxycarbonyl)amino)thiazol-4-yl) (carboxy)meth-ylene)amino)oxy)-3-oxopropoxy)phenyl)-1-((S)-3-((tert-butoxy carbonyl)-amino)-2-((tert-butyldimethylsilyl)oxy)propyl)-2-((1-(tert-butoxycarbonyl)azetidin-3-yl)methyl)-1H-pyrazol-2-ium trifluoromethanesulfonate To a solution of 4-(4-((S)-2-(Aminooxy)-3-(tert-butoxy)-3-oxopropoxy)phenyl)-1-((S)-3-((tert-butoxycarbonyl) amino)-2-((tert-butyldimethylsilyl)oxy)propyl)-2-((1-(tert-butoxycarbonyl) azetidin-3-yl)methyl)-1H-pyrazol-2-ium trifluoromethanesulfonate (500 mg, 0.64 mmol) in EtOH (4 ml) and ClCH₂CH₂Cl (2 mL) was added 2-(2-((tert-butoxycarbonyl)amino)thiazol-4-yl)-2-oxoacetic acid (175 mg, 0.64 mmol) at room temperature. The reaction was stirred overnight, then the solvent was removed to give the title compound. LC-MS [M+1]: m/z 1030.51.

Step F: 4-(4-((S)-3-(tert-Butoxy)-2-((((Z)-(2-((tert-butoxycarbonyl)amino)thiazol-4-yl) (carboxy)meth-ylene)amino)oxy)-3-oxopropoxy)phenyl)-1-((S)-3-((tert-butoxycarbonyl) amino)-2-hydroxypropyl)-2-((1-(tert-butoxycarbonyl)azetidin-3-yl)methyl)-1H-pyrazol-2-ium To a solution of 4-(4-((S)-3-(tert-butoxy)-2-((((Z)-(2-((tert-butoxycarbonyl)amino)-thiazol-4-yl) (carboxy)meth-ylene)amino)oxy)-3-oxopropoxy)phenyl)-1-((S)-3-((tert-butoxycarbonyl)amino)-2-((tert-butyldimethylsilyl)oxy) propyl)-2-((1-(tert-butoxycarbonyl)-azetidin-3-yl)methyl)-1H-pyrazol-2-ium trifluoromethane sulfonate (0.66 g, 0.64 mmol) in THF (2 ml) was added TBAF in THF (1.9 ml, 1.9 mmol, 1M). The reaction was stirred at room temperature overnight. Then the solvent was removed to give the title compound. LC-MS [M+1]: m/z 917.10.

Step G: (S)-3-((Z)-2-(((((S)-1-(tert-Butoxy)-3-(4-(1-((S)-3-((tert-butoxycarbonyl)amino)-2-hydroxypro-pyl)-2-((1-(tert-butoxycarbonyl)azetidin-3-yl) methyl)-1H-pyrazol-2-ium-4-yl)phenoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate To the solution of 4-(4-((S)-3-(tert-butoxy)-2-((((Z)-(2-((tert-butoxycarbonyl)amino)thiazol-4-yl) (carboxy)methyl-ene)amino)-oxy)-3-oxopropoxy)phenyl)-1-((S)-3-((tert-bu-toxycarbonyl) amino)-2-hydroxypropyl)-2-((1-(tert-butoxycarbonyl)azetidin-3-yl)methyl)-1H-pyrazol-2-ium trifluoromethane sulfonate (290 mg, 0.32 mmol) in DMF (6 mL) was added DCC (198 mg, 0.96 mmol) and HOBt (147 mg, 0.96 mmol). The reaction was stirred at room temperature for 30 min before the addition of (S)-3-amino-2,2-dimethyl-4-oxoazetidin-1-yl hydrogen sulfate (168 mg, 0.80 mmol) and sodium bicarbonate (134 mg, 1.6 mmol). The reaction mixture was stirred at room temperature overnight, then filtered. The filtrate was purified on RP-HPLC (Gilson) (C-18 column), eluting with 20-100% ACN/water containing 0.05% TFA (12 min) to give the title compound. LC-MS [M+1]: m/z 1109.52.

Step H: (S)-3-((Z)-2-(((S)-2-(4-(1-((S)-3-Amino-2-hydroxypropyl)-2-(azetidin-3-ylmethyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate 2 TFA To a solution of (S)-3-((Z)-2-((((S)-1-(tert-Butoxy)-3-(4-(1-((S)-3-((tert-butoxycarbonyl)amino)-2-hydroxypropyl)-2-((1-(tert-butoxycarbonyl)azetidin-3-yl)methyl)-1H-pyrazol-2-ium-4-yl) phenoxy)-1-oxopropan-2-yl)oxy)imino)-2-(2-((tert-butoxycarbonyl)amino)thiazol-4-yl) acetamido)-2,2-dimethyl-4-oxoazetidin-1-yl sulfate (140 mg, 0.13 mmol) in CH$_2$Cl$_2$ (0.5 ml) was added TFA (1 ml, 13 mmol). The reaction was stirred at room temperature for 1 h, then the solvent was removed. The resulting residue was washed with Et$_2$O (3 times) and then dried under vacuum to give a solid. The solid was dissolved in DMSO and purified on RP-HPLC (Gilson) (C-18 column), eluting with ACN/water containing 0.05% TFA (0-40%, 12 min) to give the title compound. LC-MS [M+1]: m/z 750.71. $^1$HNMR (500 MHz, D$_2$O) $\delta_H$ 8.59 (1H, s), 8.53 (1H, s), 7.49 (1H, d), 7.00 (1H, s), 6.97 (2H, d, J=10.8 Hz), 5.05 (1H, d), 4.83 (2H, d), 4.50 (2H, t), 4.41 (1H, m), 4.29-4.18 (2H, m), 4.04 (2H, t), 3.61 (1H, m), 3.26 (1H, m), 2.99 (1H, m), 1.32 (3H, s), 0.91 (3H, s).

Example 53

(S)-3-((Z)-2-(((S)-2-(4-(1-(3-aminopropyl)-2-(((R)-pyrrolidin-3-yl)methyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

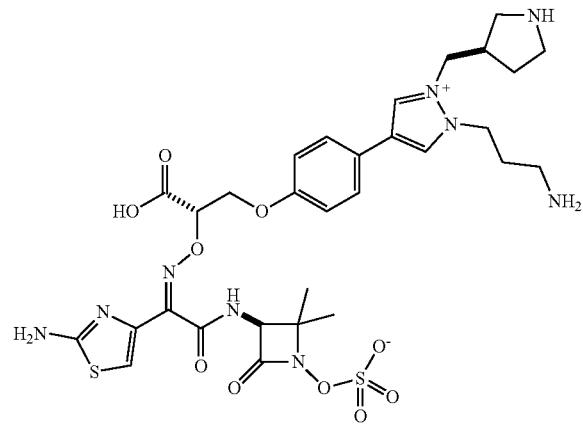

Step A: (S)-tert-butyl 3-(4-(1-(3-((tert-butoxycarbonyl)amino)propyl)-1H-pyrazol-4-yl)phenoxy)-2-((1,3-dioxoisoindolin-2-yl)oxy)propanoate To a solution of (R)-tert-butyl 3-(4-(1-(3-((tert-butoxycarbonyl)amino)propyl)-1H-pyrazol-4-yl)phenoxy)-2-hydroxypropanoate (1.77 g, 3.83 mmol) in TH (20 mL) was added 2-hydroxyisoindoline-1,3-dione (0.69 g, 4.2 mmol), triphenylphosphine (1.5 g, 5.8 mmol), and DEAD (0.91 mL, 5.8 mmol). The reaction was stirred at rt for 3 h, and then concentrated. The resulting residue was purified on silica gel using EtOAc/hexane as eluting solvents to give the title compound. LC/MS: [M+1]$^+$ m/z 607.58.

Step B: 4-(4-((S)-3-(tert-butoxy)-2-((1,3-dioxoisoindolin-2-yl)oxy)-3-oxopropoxy)phenyl)-1-(3-((tert-butoxycarbonyl)amino)propyl)-2-(((R)-1-(tert-butoxycarbonyl)pyrrolidin-3-yl)methyl)-1H-pyrazol-2-ium To a solution of (R)-tert-butyl 3-(hydroxymethyl)pyrrolidine-1-carboxylate (0.60 g, 3.0 mmol) and Hunig's Base (1.03 ml, 5.9 mmol) in CH$_2$Cl$_2$ (15 ml) at −78° C. was added trifluoromethanesulfonic anhydride (0.61 ml, 3.6 mmol) over 5 min. The reaction was stirred at −78° C. for 1 h, then quenched with saturated NaHCO$_3$. The reaction was allowed to warm to 0° C. The organic layer was separated and washed with brine. The aqueous layers were combined, and back-extracted with DCM. The organic layers were combined, dried over Na$_2$SO$_4$, and concentrated in vacuo to give (R)-tert-butyl 3-((((trifluoromethyl)sulfonyl)oxy)methyl)pyrrolidine-1-carboxylate. $^1$HNMR (500 MHz, D$_2$O): δ 4.51-4.48 (m, 2H), 3.71-3.57 (m, 2H), 3.21-3.11 (m, 2H), 2.76-2.69 (m, 1H), 2.14-2.08 (m, 1H), 1.81-1.74 (m, 1H). To a solution of (S)-tert-butyl 3-(4-(1-(3-((tert-butoxycarbonyl)amino)-propyl)-1H-pyrazol-4-yl)phenoxy)-2-((1,3-dioxoisoindolin-2-yl)oxy)propanoate (0.90 g, 1.5 mmol) and (R)-tert-butyl 3-((((trifluoromethyl)sulfonyl)-oxy)methyl)pyrrolidine-1-carboxylate (0.99 g, 3.0 mmol) in acetonitrile (15 ml) was added sodium bicarbonate (1.2 g, 15 mmol). The reaction mixture was heated at 60° C. overnight, and then filtered. The filtrate was concentrated to give the title compound. LC/MS: (M)$^+$ m/z 790.75.

Step C: 4-(4-((S)-2-(aminooxy)-3-(tert-butoxy)-3-oxopropoxy)phenyl)-1-(3-((tert-butoxycarbonyl)amino)propyl)-2-(((R)-1-(tert-butoxycarbonyl)pyrrolidin-3-yl)methyl)-1H-pyrazol-2-ium To a solution of 4-(4-((S)-3-(tert-butoxy)-2-((1,3-dioxoisoindolin-2-yl)oxy)-3-oxopropoxy)phenyl)-1-(3-((tert-butoxycarbonyl)amino)propyl)-2-(((R)-1-(tert-butoxycarbonyl)pyrrolidin-3-yl)methyl)-1H-pyrazol-2-ium (1.2 g, 1.5 mmol) in CH$_2$Cl$_2$ (10 mL) and ethanol (10 mL) at 0° C. was added hydrazine (0.056 ml, 1.8 mmol). The reaction was stirred at rt for 1 h, and then concentrated. The resulting residue was suspended in DCM (20 mL), stirred at rt for 10 min, and then filtered. The filtrate was concentrated to give the title compound. LC/MS: (M)$^+$ m/z 660.72.

Step D: 4-(4-((S)-3-(tert-butoxy)-2-(((Z)-((2-((tert-butoxycarbonyl)amino)thiazol-4-yl)(carboxy)methylene)amino)oxy)-3-oxopropoxy)phenyl)-1-(3-((tert-butoxycarbonyl)-amino)propyl)-2-(((R)-1-(tert-butoxycarbonyl)pyrrolidin-3-yl)methyl)-1H-pyrazol-2-ium To a solution of 4-(4-((S)-2-(aminooxy)-3-(tert-butoxy)-3-oxopropoxy)phenyl)-1-(3-((tert-butoxycarbonyl)amino)propyl)-2-(((R)-1-(tert-butoxycarbonyl)pyrrolidin-3-yl)methyl)-1H-pyrazol-2-ium (980 mg, 1.5 mmol) in MeOH (20 ml) and CH$_2$Cl$_2$ (20 ml) was added 2-(2-((tert-butoxycarbonyl)amino)thiazol-4-yl)-2-oxoacetic acid (520 mg, 1.9 mmol). The reaction was stirred at rt for 3 h, then concentrated. The resulting residue was purified on reverse phase MPLC using acetonitrile (0.1% formic acid)/water (0.1% formic acid) as eluting solvents to give the title compound. LC/MS: (M)$^+$ m/z 914.84.

Step E: 4-(4-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-1-(3-((tert-butoxycarbonyl)amino)propyl)-2-(((R)-1-(tert-butoxycarbonyl)pyrrolidin-3-yl)methyl)-1H-pyrazol-2-ium To a solution of 4-(4-((S)-3-(tert-butoxy)-2-(((Z)-((2-((tert-butoxycarbonyl)amino)thiazol-4-yl)(carboxy)methylene)-amino)oxy)-3-oxopropoxy)phenyl)-1-(3-((tert-butoxycarbonyl)amino)propyl)-2-(((R)-1-(tert-butoxycarbonyl)pyrrolidin-3-yl)methyl)-1H-pyrazol-2-ium (660 mg, 0.72 mmol) in acetonitrile (10 ml) at −5° C. was added pyridine (0.23 ml, 2.9 mmol), (S)-3-amino-2,2-dimethyl-4-oxoazetidin-1-yl hydrogen sulfate (300 mg, 1.4 mmol), and EDC (300 mg, 1.6 mmol). The reaction was stirred at −5° C. for 2 h, and then concentrated. The resulting residue was purified on reverse phase MPLC using acetonitrile (0.1% formic acid)/water(0.1% formic acid) as eluting solvents to give the title compound. LC/MS: (M)+ m/z 1107.25.

Step F: (S)-3-((Z)-2-(((S)-2-(4-(1-(3-aminopropyl)-2-((R)-pyrrolidin-3-ylmethyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate To a solution of 4-(4-((S)-3-(tert-butoxy)-2-(((Z)-(1-(2-((tert-butoxycarbonyl)-amino)thiazol-4-yl)-2-(((S)-2,2-dimethyl-4-oxo-1-(sulfooxy)-azetidin-3-yl)amino)-2-oxoethylidene)amino)-oxy)-3-oxopropoxy)phenyl)-1-(3-((tert-butoxycarbonyl)amino)propyl)-2-(((R)-1-(tert-butoxycarbonyl)pyrrolidin-3-yl)methyl)-1H-pyrazol-2-ium (610 mg, 0.55 mmol) in CH$_2$Cl$_2$ (3 ml) was added TFA (6 mL, 78 mmol). The reaction was stirred at rt for 55 min, and then concentrated. The resulting residue was treated with Et$_2$O (20 mL) and the resulting precipitate was collected and dried under vacuum. The precipitate was dissolved in NH$_4$OAc solution (300 mM, 2×70 mL) and stirred for 5 min, then purified on a C18 column using acetonitrile (0.1% formic acid)/water (0.1% formic acid) as eluting solvents to give crude product. The crude product was re-purified on reverse phase HPLC using acetonitrile (0.1% formic acid)/water (0.1% formic acid) to give the title compound. LC/MS: (M+1)+ m/z 750.5. $^1$HNMR (500 MHz, D$_2$O):δ 8.64-8.63 (d, J=5.7 Hz, 2H), 8.41 (s, 1H), 7.53-7.51 (d, J=8.6 Hz, 2H), 7.02-7.00 (d, J=9.2 Hz, 2H), 6.91 (s, 1H), 4.92-4.90 (m, 1H), 4.66-4.63 (m, 1H), 4.62-4.59 (t, J=6.8 Hz, 2H), 4.48-4.39 (m, 3H), 3.61-3.56 (m, 1H), 3.54-3.49 (m, 1H). 3.37-3.32 (m, 1H). 3.18-3.12 (m, 3H), 3.08-3.01 (m, 1H), 2.40-2.34 (m, 2H), 2.32-2.25 (m, 1H), 1.91-1.83 (m, 1H), 1.37 (s, 3H), 1.01 (s, 3H).

Example 54

(S)-3-((Z)-2-(2-aminothiazol-4-yl)-2-(((S)-2-(4-(1,2-bis(3-aminopropyl)-1H-pyrazol-2-ium-4-yl)phenoxy)-1-carboxyethoxy)imino)acetamido)-2,2-dimethyl-4-oxoazetidin-1-yl sulfate

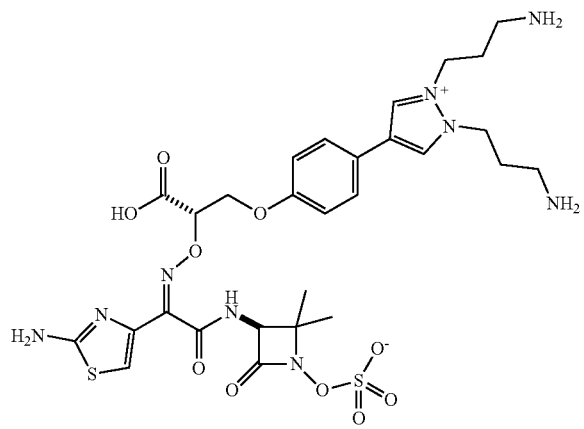

Step A: 3-azidopropyl trifluoromethanesulfonate

To a solution of 3-azidopropan-1-ol (2.7 g, 26 mmol) and Hunig's Base (9.2 ml, 52 mmol) in CH$_2$Cl$_2$ (60 ml) at −78° C. was added trifluoromethanesulfonic anhydride (5.4 ml, 32 mmol) over 5 min. The reaction was stirred at −78° C. for 1 h, quenched with saturated NaHCO$_3$, and allowed to warm to 0° C. The organic layer was separated and washed with brine. The aqueous layers were combined, back-extracted with DCM. The organic layers were combined, dried over Na$_2$SO$_4$, and concentrated in vacuo to give the title compound. $^1$HNMR (500 MHz, D$_2$O): δ 4.67-4.64 (t, J=5.8 Hz, 2H), 3.56-3.54 (t, J=5.8 Hz, 2H).

Step B: (S)-2-(3-azidopropyl)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-1H-pyrazol-2-ium The mixture of (S)-tert-butyl 3-(4-(1-(3-((tert-butoxycarbonyl)amino)propyl)-1H-pyrazol-4-yl)phenoxy)-2-((1,3-dioxoisoindolin-2-yl)oxy)propanoate (6.4 g, 11 mmol), 3-azidopropyl trifluoromethanesulfonate (5.0 g, 21 mmol), and sodium bicarbonate (8.9 g, 110 mmol) was heated at 60° C. for 3 h. Then the reaction mixture was filtered and the filtrate was concentrated to give the title compound. LC/MS: [M]+ m/z 690.6.

Step C: (S)-4-(4-(2-(aminooxy)-3-(tert-butoxy)-3-oxopropoxy)phenyl)-2-(3-azidopropyl)-1-(3-((tert-butoxycarbonyl)amino)propyl)-1H-pyrazol-2-ium To a solution of (S)-2-(3-azidopropyl)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-1H-pyrazol-2-ium (7.3 g, 11 mmol) in CH$_2$Cl$_2$ (30 ml) and EtOH (30.0 ml) at 0° C. was added hydrazine (0.40 ml, 13 mmol). The reaction was stirred at rt for 1 hr, then concentrated. The resulting residue was treated with DCM (30 mL).

The reaction was stirred at rt for 30 min, then filtered and the filtrate was concentrated to give the title compound. LC/MS: [M]+ m/z 560.6

Step D: (S,Z)-2-(3-azidopropyl)-4-(4-(3-(tert-butoxy)-2-((((2-((tert-butoxycarbonyl)-amino)thiazol-4-yl)(carboxy)methylene)amino)oxy)-3-oxopropoxy)phenyl)-1-(3-((tert-butoxycarbonyl)amino)propyl)-1H-pyrazol-2-ium To the solution of (S)-4-(4-(2-(aminooxy)-3-(tert-butoxy)-3-oxopropoxy)phenyl)-2-(3-azidopropyl)-1-(3-((tert-butoxycarbonyl)amino)propyl)-1H-pyrazol-2-ium (6.0 g, 11 mmol) in MeOH (25 ml) and CH$_2$Cl$_2$ (25 ml) was added 2-(2-((tert-butoxycarbonyl)amino)thiazol-4-yl)-2-oxoacetic acid (3.8 g, 14 mmol). The reaction was stirred at rt overnight, and concentrated. The residue was purified on reverse phase HPLC using acetonitrile (0.05% TFA)/water (0.05% TFA) as eluting solvents to give the title compound. LC/MS: [M]+ m/z 814.7.

Step E: (S,Z)-2-(3-aminopropyl)-4-(4-(3-(tert-butoxy)-2-((((2-((tert-butoxycarbonyl)amino)-thiazol-4-yl)(carboxy)methylene)amino)oxy)-3-oxopropoxy)phenyl)-1-(3-((tert-butoxy-carbonyl)amino)propyl)-1H-pyrazol-2-ium To the solution of (S,Z)-2-(3-azidopropyl)-4-(4-(3-(tert-butoxy)-2-((((2-((tert-butoxycarbonyl)amino)thiazol-4-yl)(carboxy)methylene)-amino)oxy)-3-oxopropoxy)phenyl)-1-(3-((tert-butoxycarbonyl)-amino)propyl)-1H-pyrazol-2-ium (7.8 g, 9.6 mmol) in MeOH (200 ml) was added 10% Pd/C (1.5 g, 1.4 mmol). The reaction was hydrogenated at rt for 40 min. The reaction was filtered through Celite™, and the filtrate was concentrated to give the title compound. LC/MS: [M]+ m/z 788.8

Step F: (S,Z)-4-(4-(3-(tert-butoxy)-2-((((2-((tert-butoxycarbonyl)amino)thiazol-4-yl)(carboxy)methylene)amino)oxy)-3-oxopropoxy)phenyl)-1,2-bis(3-((tert-butoxycarbonyl)amino)propyl)-1H-pyrazol-2-ium To the solution of (S,Z)-2-(3-aminopropyl)-4-(4-(3-(tert-butoxy)-2-((((2-((tert-butoxycarbonyl)amino)thiazol-4-yl)(carboxy)methylene)amino)oxy)-3-oxopropoxy)phenyl)-1-(3-((tert-butoxycarbonyl)-amino)propyl)-1H-pyrazol-2-ium (7.6 g, 9.6 mmol) in CH$_2$Cl$_2$ (200 ml) was added Boc$_2$O (2.7 ml, 12 mmol) and TEA (1.3 ml, 9.6 mmol). The reaction was stirred at rt for 1 h, and then concentrated. The resulting residue was purified on reverse phase MPLC (C18) using acetonitrile (0.05% TFA) as eluting solvents to give the title compound. LC/MS: [M]+ m/z 888.8

Step G: 4-(4-((S)-3-(tert-butoxy)-2-(((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-1,2-bis(3-((tert-butoxycarbonyl)amino)propyl)-1H-pyrazol-2-ium To a solution of (S,Z)-4-(4-(3-(tert-butoxy)-2-((((2-((tert-butoxycarbonyl)amino)thiazol-4-yl)(carboxy)methylene)amino)oxy)-3-oxopropoxy)phenyl)-1,2-bis(3-((tert-butoxycarbonyl)amino)propyl)-1H-pyrazol-2-ium (2.5 g, 2.8 mmol) in acetonitrile (30 ml) at 0° C. was added (S)-3-amino-2,2-dimethyl-4-oxoazetidin-1-yl hydrogen sulfate (1.2 g, 5.5 mmol), pyridine (0.90 ml, 11 mmol), and EDC (1.3 g, 6.9 mmol). The reaction was stirred at 0° C. for 1 h, and then concentrated in vacuo at rt. The resulting residue was purified on reverse phase MPLC using acetonitrile (0.05% TFA)/water (0.05% TFA) as eluting solvents to give the title compound. LC/MS: [M]+ m/z 1081.1.

Step H: (S)-3-((Z)-2-(2-aminothiazol-4-yl)-2-(((S)-2-(4-(1,2-bis(3-aminopropyl)-1H-pyrazol-2-ium-4-yl)phenoxy)-1-carboxyethoxy)imino)acetamido)-2,2-dimethyl-4-oxoazetidin-1-yl sulfate To a solution of 4-(4-((S)-3-(tert-butoxy)-2-(((Z)-1-(2-((tert-butoxycarbonyl)-amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-1,2-bis(3-((tert-butoxycarbonyl)-amino)propyl)-1H-pyrazol-2-ium (400 mg, 0.37 mmol) in DCM (3 ml) was added TFA (6.0 mL, 78 mmol). The reaction was stirred at rt for 50 min, and then concentrated. The resulting residue was washed with Et$_2$O (3×10 mL), dried under vacuum, and dissolved in ammonium acetate (200 mM, 80 mL, 16 mmol). The resulting solution was stirred at rt for min, and then purified on reverse phase MPLC using acetonitrile (0.1% formic acid)/water (0.1% formic acid) as eluting solvents to give a residue and a small amount of TFA. The residue was re-dissolved in 80 mL of NH$_4$OAc (200 mM, 80 mL) and the reaction was stirred at rt for 10 min, and then purified on reverse phase MPLC using acetonitrile (0.1% formic acid)/water (0.1% formic acid) as eluting solvents to give the title compound as the free base. LC/MS: [M]+ m/z 724.6. $^1$HNMR (500 MHz, D$_2$O): δ 8.57 (s, 2H), 8.41 (s, 1H), 7.49-7.48 (d, J=8.8 Hz, 2H), 6.99-6.98 (d, J=8.8 Hz, 2H), 6.90 (s, 1H), 4.91-4.89 (m, 1H), 4.59-4.56 (t, J=8.0 Hz, 4H), 4.46-4.40 (m, 4H), 3.16-3.12 (m, 4H), 2.39-2.33 (m, 4H), 1.37 (s, 3H), 1.01 (s, 3H).

Example 55

(S)-3-(4-(1-(3-amino-2-(aminomethyl)propyl)-2-imino-3-methyl-2,3-dihydro-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

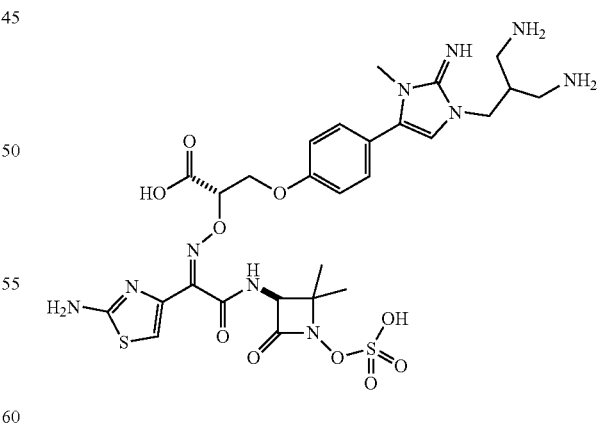

Step A: 3-((tert-butoxycarbonyl)amino)-2-(((tert-butoxycarbonyl)amino)methyl)propyl methanesulfonate To a solution of di-tert-butyl (2-(hydroxymethyl)propane-1,3-diyl)dicarbamate (1.4 g, 4.6 mmol) in DCM (anhydrous, 20 mL) at 0° C. was added TEA (1.3 mL, 9.1 mmol) and MsCl (0.43 mL, 5.5 mmol). The reaction was stirred at 0° C. for 1 h, then partitioned between DCM (100 mL) and 0.1 M HCl (ice-cold). The organic layer was washed with 0.1 M HCl (ice-cold), dried over $Na_2SO_4$, concentrated to give the title compound. LC/MS: [M+1]$^+$ m/z 383.4.

Step B: di-tert-butyl (2-((4-bromo-1H-imidazol-1-yl)methyl)propane-1,3-diyl)dicarbamate To a solution of 3-((tert-butoxycarbonyl)amino)-2-(((tert-butoxycarbonyl)amino)methyl)-propyl methanesulfonate (1.8 g, 4.7 mmol) in DMF (25 ml) was added 4-bromo-1H-imidazole (0.69 g, 4.7 mmol), and $Cs_2CO_3$ (3.1 g, 9.4 mmol). The reaction was heated at 60° C. overnight, then partitioned between EtOAc (200 mL) and saturated $NaHCO_3$ (200 mL). The organic layer was separated, washed with saturated $NaHCO_3$ and brine, dried over $Na_2SO_4$, and concentrated. The resulting residue was purified on silica gel column using EtOAc/hexane as eluting solvents to give the title compound. LC/MS: [M+1]$^+$ m/z 433.3; 435.3.

Step C: 4-bromo-1-(3-((tert-butoxycarbonyl)amino)-2-(((tert-butoxycarbonyl)-amino)methyl)propyl)-3-methyl-1H-imidazol-3-ium To a solution of di-tert-butyl (2-((4-bromo-1H-imidazol-1-yl)methyl)propane-1,3-diyl)dicarbamate (1.5 g, 3.5 mmol) in acetonitrile (10 ml) was added MeI (1.08 ml, 17 mmol). The reaction was heated at 60° C. overnight, and then concentrated. The resulting residue was purified on silica gel column using MeOH/DCM as eluting solvents to give the title compound. LC/MS: [M]$^+$ m/z 447.4; 449.4

Step D: di-tert-butyl (2-((4-bromo-2-((tert-butoxycarbonyl)imino)-3-methyl-2,3-dihydro-1H-imidazol-1-yl)methyl)propane-1,3-diyl)dicarbamate To a solution of tert-butyl carbamate (0.87 g, 7.4 mmol) in $CH_2Cl_2$ (10 ml) was added tert-butyl hypochlorite (0.97 ml, 8.4 mmol). The reaction was stirred at rt for 30 min, then cooled to 0° C. and DBU (1.52 ml, 10 mmol) was added, followed by 4-bromo-1-(3-((tert-butoxycarbonyl)amino)-2-(((tert-butoxycarbonyl)amino)methyl)propyl)-3-methyl-H-imidazol-3-ium (1.5 g, 3.4 mmol) in $CH_2Cl_2$ (16 ml). The reaction was stirred at rt for 30 min, and then concentrated. The resulting residue was purified on silica gel column using MeOH/DCM as eluting solvents to give the title compound. LC/MS: [M+1]$^+$ m/z 562.4; 564.4.

Step E: (R)-tert-butyl 3-(4-(1-(3-((tert-butoxycarbonyl)amino)-2-(((tert-butoxycarbonyl)-amino)methyl)propyl)-2-((tert-butoxycarbonyl)imino)-3-methyl-2,3-dihydro-1H-imidazol-4-yl)phenoxy)-2-hydroxypropanoate A mixture of potassium phosphate tribasic (3.6 ml, 3.6 mmol), (R)-tert-butyl 2-hydroxy-3-(4-(4,4,5,5-tetramethyl-1,3,2-dioxaborolan-2-yl)phenoxy)propanoate (0.53 g, 1.5 mmol), and tert-butyl (4-bromo-1-(3-((tert-butoxycarbonyl)amino)-2-(((tert-butoxycarbonyl)amino)methyl) propyl)-3-methyl-H-imidazol-2(3H)-ylidene)carbamate (0.68 g, 1.2 mmol) in dioxane (12 ml) was degassed by bubbling $N_2$ for 30 min, then 1,1'-bis(di-tert-butylphosphino)ferrocene palladium dichloride (0.079 g, 0.12 mmol) was added. The reaction mixture was further degassed by bubbling $N_2$ for 20 min, and then heated at 60° C. overnight. The reaction mixture was filtered through Celite™, and the filtrate was concentrated. The resulting residue was purified on silica gel column using MeOH/DCM as eluting solvents to give the title compound. LC/MS: [M+1]$^+$ m/z 720.7.

Step F: (S)-tert-butyl 3-(4-(1-(3-((tert-butoxycarbonyl)amino)-2-(((tert-butoxycarbonyl)-amino)methyl)propyl)-2-((tert-butoxycarbonyl)imino)-3-methyl-2,3-dihydro-1H-imidazol-4-yl)phenoxy)-2-((1,3-dioxoisoindolin-2-yl)oxy)propanoate To a solution of (R)-tert-butyl 3-(4-(1-(3-((tert-butoxycarbonyl)amino)-2-(((tert-butoxycarbonyl) amino)methyl)propyl)-2-((tert-butoxycarbonyl)imino)-3-methyl-2,3-dihydro-1H-imidazol-4-yl)phenoxy)-2-hydroxypropanoate (0.64 g, 0.89 mmol) in THF (15 ml) was added 2-hydroxyisoindoline-1,3-dione (0.17 g, 1.1 mmol), triphenylphosphine (0.35 g, 1.3 mmol), and DEAD (0.21 ml, 1.3 mmol). The reaction was stirred at rt for 2 h, and then concentrated. The resulting residue was purified on silica gel column using MeOH/DCM to give the title compound. LC/MS: [M+1]$^+$ m/z 865.8.

Step G: (S)-tert-butyl 2-(aminooxy)-3-(4-(1-(3-((tert-butoxycarbonyl)amino)-2-(((tert-butoxycarbonyl)amino)methyl)propyl)-2-((tert-butoxycarbonyl)imino)-3-methyl-2,3-dihydro-1H-imidazol-4-yl)phenoxy)propanoate To a solution of (S)-tert-butyl 3-(4-(1-(3-((tert-butoxycarbonyl)amino)-2-(((tert-butoxycarbonyl)amino)methyl)propyl)-2-((tert-butoxycarbonyl)imino)-3-methyl-2,3-dihydro-1H-imidazol-4-yl)phenoxy)-2-((1,3-dioxo-isoindolin-2-yl)oxy)propanoate (0.77 g, 0.89 mmol) in $CH_2Cl_2$ (5 ml) and ethanol (5 mL) at 0° C. was added hydrazine (0.033 ml, 1.1 mmol). The reaction was stirred at rt for 1 h, and then concentrated. The resulting residue was treated with DCM (10 mL), stirred at rt for 10 min, and then filtered. The filtrate was concentrated to give the title compound. LC/MS: [M+1]$^+$ m/z 735.7

Step H: (2Z)-2-((((S)-1-(tert-butoxy)-3-(4-(1-(3-((tert-butoxycarbonyl)amino)-2-(((tert-butoxycarbonyl)amino)methyl)propyl)-2-((tert-butoxycarbonyl)imino)-3-methyl-2,3-dihydro-1H-imidazol-4-yl)phenoxy)-1-oxopropan-2-yl)oxy)imino)-2-(2-((tert-butoxycarbonyl)amino)thiazol-4-yl)acetic acid To a solution of (S)-tert-butyl 2-(aminooxy)-3-(4-(1-(3-((tert-butoxycarbonyl)amino)-2-(((tert-butoxycarbonyl) amino)-methyl)propyl)-2-((tert-butoxycarbonyl)imino)-3-methyl-2,3-dihydro-1H-imidazol-4-yl)phenoxy)propanoate (0.65 g, 0.89 mmol) in $CH_2Cl_2$ (10 ml) and MeOH (10 ml) was added 2-(2-((tert-butoxycarbonyl)amino)thiazol-4-yl)-2-oxoacetic acid (0.29 g, 1.1 mmol). The reaction was stirred at rt for 2 h, and then concentrated. The resulting residue was purified on reverse phase MPLC using acetonitrile (0.05% TFA)/water (0.05% TFA) as eluting solvents to give the title compound. LC/MS: [M+1]+m/z 989.8.

Step I: (S)-tert-butyl 3-(4-(1-(3-((tert-butoxycarbonyl)amino)-2-(((tert-butoxycarbonyl)-amino)methyl)propyl)-2-((tert-butoxycarbonyl)imino)-3-methyl-2,3-dihydro-1H-imidazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate To a solution of (2Z)-2-((((S)-1-(tert-butoxy)-3-(4-(1-(3-((tert-butoxycarbonyl)amino)-2-(((tert-butoxycarbonyl)

amino)methyl)propyl)-2-((tert-butoxycarbonyl)imino)-3-methyl-2,3-dihydro-1H-imidazol-4-yl)phenoxy)-1-oxopropan-2-yl)oxy)imino)-2-(2-((tert-butoxycarbonyl)amino)thiazol-4-yl)acetic acid (550 mg, 0.55 mmol) in acetonitrile (8 ml) at 0° C. were added (S)-3-amino-2,2-dimethyl-4-oxoazetidin-1-yl hydrogen sulfate (230 mg, 1.1 mmol), pyridine (0.18 ml, 2.2 mmol), and EDC (260 mg, 1.4 mmol). The reaction was stirred at 0° C. for 2 h, and then concentrated. The resulting residue was purified on reverse phase MPLC using acetonitrile (0.05% TFA)/water (0.05% TFA) as eluting solvents to give the title compound. LC/MS: [M+1]+m/z 1182.0.

Step J: (S)-3-(4-(1-(3-amino-2-(aminomethyl)propyl)-2-imino-3-methyl-2,3-dihydro-1H-imidazol-4-yl)phenoxy)-2-(((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid To a solution of (S)-tert-butyl 3-(4-(1-(3-((tert-butoxycarbonyl)amino)-2-(((tert-butoxycarbonyl)-amino)-methyl)propyl)-2-((tert-butoxycarbonyl)imino)-3-methyl-2,3-dihydro-1H-imidazol-4-yl)phenoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate (420 mg, 0.36 mmol) in CH$_2$Cl$_2$ (2 ml) was added TFA (4 mL, 52 mmol). The reaction was stirred at rt for 50 min, then concentrated at rt. The resulting residue was treated with Et$_2$O (10 mL) to give a precipitate, which was washed with Et$_2$O three times, concentrated, and purified on reverse HPLC using acetonitrile (0.1% formic acid)/water (0.1% formic acid) as eluting solvents to give the title compound. LC/MS: [M+1]$^+$ m/z 725.7. $^1$H-NMR (500 MHz, D$_2$O): δ 7.35-7.33 (d, J=8.1 Hz, 2H), 7.04-7.02 (d, J=8.1 Hz, 2H), 6.99 (s, 1H), 6.89 (s, 1H), 4.98-4.96 (m, 1H), 4.66 (s, 1H), 4.47-4.41 (m, 2H), 4.08-4.06 (d, J=6.1 Hz, 2H), 3.35 (s, 3H), 3.25-3.19 (m, 2H), 3.14-3.09 (m, 2H), 2.73-2.67 (m, 2H), 1.42 (s, 3H), 1.03 (s, 3H).

Example 56

(2S)-3-(4-(1-(3-amino-2-hydroxypropyl)-2-imino-3-methyl-2,3-dihydro-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

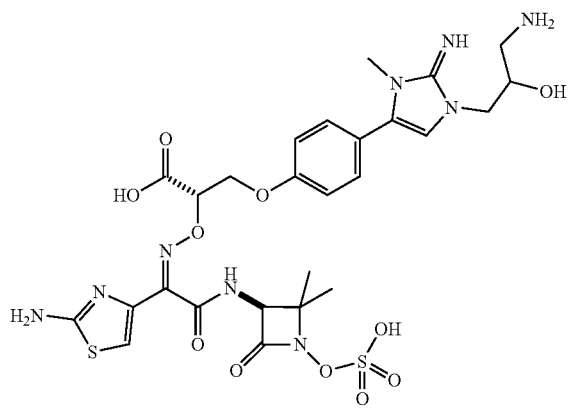 [SMILES: Cn1c(-c2ccc(OC[C@H](O/N=C(\C(=O)N[C@@H]3C(=O)N(OS(=O)(=O)O)C3(C)C)c3csc(N)n3)C(=O)O)cc2)cn(CC(O)CN)c1=N]

Step A: tert-butyl (3-(4-bromo-1H-imidazol-1-yl)-2-((tert-butyldimethylsilyl)oxy)-propyl)carbamate To a solution of 5-bromo-1H-imidazole (2.8 g, 19 mmol) and tert-butyl (3-bromo-2-((tert-butyldimethylsilyl)oxy)propyl)carbamate (7.4 g, 20 mmol) in DMF (20 ml) was added cesium carbonate (12 g, 38 mmol). The reaction mixture was heated at 60° C. overnight, and then partitioned between water (200 mL) and EtOAc (200 mL). The organic layer was washed with saturated NaHCO$_3$ twice, dried over Na$_2$SO$_4$, and concentrated. The resulting residue was purified on silica gel column using EtOAc/hexane as eluting solvents to give the title compound. LC/MS: (M+1)+m/z 434.2; 436.2.

Step B: 4-bromo-1-(3-((tert-butoxycarbonyl)amino)-2-((tert-butyldimethylsilyl)oxy)propyl)-3-methyl-1H-imidazol-3-ium To a solution of tert-butyl (3-(4-bromo-1H-imidazol-1-yl)-2-((tert-butyldimethylsilyl)oxy) propyl)carbamate (2.7 g, 6.2 mmol) in acetonitrile (10 ml) was added methyl iodide (1.9 ml, 31 mmol). The reaction was heated at 60° C. overnight, then concentrated to give the title compound. LC/MS: [M]$^+$ m/z 448.2; 450.2.

Step C: tert-butyl (3-(4-bromo-2-((tert-butoxycarbonyl)imino)-3-methyl-2,3-dihydro-1H-imidazol-1-yl)-2-((tert-butyldimethylsilyl)oxy)propyl)carbamate A solution of tert-Butyl carbamate (1.6 g, 14 mmol) in CH$_2$Cl$_2$ (20 ml) was added tert-butyl hypochlorite (1.8 ml, 16 mmol) was stirred at rt for 30 min. Then the reaction was cooled to 0° C. and DBU (2.8 ml, 19 mmol) was added, followed by the addition of 4-bromo-1-(3-((tert-butoxycarbonyl)-amino)-2-((tert-butyldimethyl-silyl)oxy)propyl)-3-methyl-1H-imidazol-3-ium (2.8 g, 6.2 mmol) in CH$_2$Cl$_2$ (16 ml). The reaction was stirred at rt for 30 min, and then concentrated. The resulting residue was purified by silica gel column using MeOH/EtOAc as eluting solvents to give the title compound. LC/MS: [M+1]$^+$ m/z 563.5; 565.5.

Step D: (2R)-tert-butyl 3-(4-(1-(3-(((tert-butoxycarbonyl)amino)-2-((tert-butyldimethyl-silyl)oxy)propyl)-2-((tert-butoxycarbonyl)imino)-3-methyl-2,3-dihydro-1H-imidazol-4-yl)phenoxy)-2-hydroxypropanoate (Peak A)

A mixture of potassium phosphate tribasic (11 ml, 11 mmol), (R)-tert-butyl 2-hydroxy-3-(4-(4,4,5,5-tetramethyl-1,3,2-dioxaborolan-2-yl)phenoxy)propanoate (1.6 g, 4.4 mmol), and tert-butyl (4-bromo-1-(3-((tert-butoxy-carbonyl)amino)-2-((tert-butyldimethylsilyl)oxy) propyl)-3-methyl-1H-imidazol-2(3H)-ylidene)carbamate (2.1 g, 3.7 mmol) in dioxane (24 ml) was degassed with bubbling N$_2$ for min, and then 1,1'-bis(di-tert-butylphosphino)ferrocene palladium dichloride (0.24 g, 0.37 mmol) was added. The reaction mixture was further degassed with bubbling N$_2$ for 20 min, and then heated at 75° C. for 3 h. The reaction mixture was filtered through Celite™, and the filtrate was concentrated. The resulting residue was purified on silica gel column using MeOH/DCM as eluting solvents to give the title compound as a mixture of diastereoisomers. LC/MS: (M+1)$^+$ m/z 721.5. The diastereomers were separated on chiral SFC (Whelk-01, 4.6×250 mm, IPA+0.1DIPA) to give the two separate diastereomers. The fast eluting diastereoisomer was carried forward in the next step.

Step H: (Z)-2-(((((2S)-1-(tert-butoxy)-3-(4-((Z)-1-(3-((tert-butoxycarbonyl)amino)-2-hydroxypropyl)-2-((tert-butoxycarbonyl)imino)-3-methyl-2,3-dihydro-1H-imidazol-4-yl)phenoxy)-1-oxopropan-2-yl)oxy)imino)-2-(2-((tert-butoxycarbonyl)amino)thiazol-4-yl)acetic acid To a solution of (2Z)-2-(((((2S)-1-(tert-butoxy)-3-(4-(1-(3-((tert-butoxy-carbonyl)amino)-2-((tert-butyldimethylsilyl)oxy)propyl)-2-((tert-butoxy-carbonyl)imino)-3-methyl-2,3-dihydro-1H-imidazol-4-yl)phenoxy)-1-oxopropan-2-yl)oxy)imino)-2-(2-((tert-butoxycarbonyl)amino)thiazol-4-yl)acetic acid (1.2 g, 1.2 mmol, prepared following steps F-H as described in Example 55) in THF (20 ml) was added TBAF (1.13 g, 4.3 mmol). The reaction was stirred at rt for 2 h, and then concentrated. The resulting residue was purified on reverse phase MPLC using acetonitrile (0.05% TFA)/water (0.05% TFA) as eluting solvents to give the title compound. LC/MS: (M+1)+ m/z 876.5.

Step I-J: (2S)-3-(4-(1-(3-amino-2-hydroxypropyl)-2-imino-3-methyl-2,3-dihydro-1H-imidazol-4-yl)phenoxy)-2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)propanoic acid The title compound was prepared from (Z)-2-(((((2S)-1-(tert-butoxy)-3-(4-((Z)-1-(3-((tert-butoxycarbonyl)amino)-2-hydroxypropyl)-2-((tert-butoxycarbonyl)imino)-3-methyl-2,3-dihydro-1H-imidazol-4-yl)phenoxy)-1-oxopropan-2-yl)oxy)imino)-2-(2-((tert-butoxy-carbonyl)amino)thiazol-4-yl)acetic acid following the procedure of Example 55 Steps I-J. LC/MS: (M+1)+ m/z 712.4. $^1$H-NMR (500 MHz, D$_2$O): δ 7.34-7.32 (d, J=8.8 Hz, 2H), 7.04-7.02 (d, J=8.8 Hz, 2H), 6.94 (s, 1H), 6.84 (s, 1H), 4.94-4.92 (m, 1H), 4.66 (s, 1H), 4.45-4.39 (m, 2H), 4.24-4.21 (m, 1H), 4.05-4.02 (d, J=4.8 Hz, 1H), 3.92-3.88 (m, 1H), 3.34 (s, 3H), 3.25-3.22 (d, J=4.8 Hz, 1H), 3.00-2.95 (t, J=10.5 Hz, 1H), 1.41 (s, 3H), 1.06 (s, 3H).

Example 57

(S)-3-(4-((Z)-2-((2-aminoethyl)imino)-1-(3-aminopropyl)-3-methyl-2,3-dihydro-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

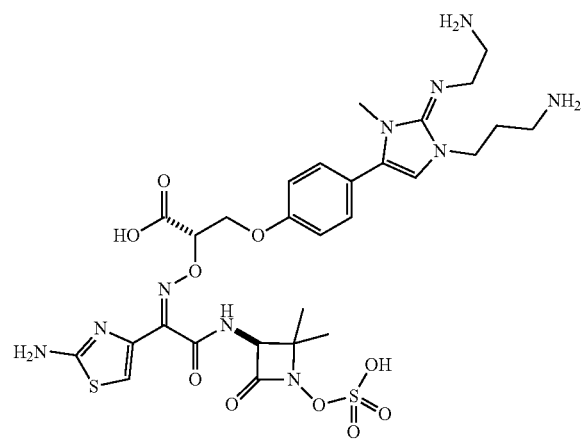 [SMILES: Cn1c(-c2ccc(OC[C@H](O/N=C(\C(=O)N[C@@H]3C(=O)N(OS(=O)(=O)O)C3(C)C)c3csc(N)n3)C(=O)O)cc2)cn(CCCN)/c1=N\CCN]

Step A: 3-(4-bromo-2-imino-3-methyl-2,3-dihydro-1H-imidazol-1-yl)propan-1-amine

To a solution of (Z)-tert-butyl (3-(4-bromo-2-((tert-butoxycarbonyl)imino)-3-methyl-2,3-dihydro-1H-imidazol-1-yl)propyl)carbamate (1.1 g, 2.5 mmol) in CH$_2$Cl$_2$ (2 ml) was added TFA (6.0 ml, 78 mmol). The reaction was stirred at rt for 1 h, and then concentrated to give the title compound. LC/MS: (M+1)+ m/z 233.1; 235.1

Step B: tert-butyl (3-(4-bromo-2-imino-3-methyl-2,3-dihydro-1H-imidazol-1-yl)propyl)-carbamate To a 3-(4-bromo-2-imino-3-methyl-2,3-dihydro-1H-imidazol-1-yl)propan-1-amine (0.59 g, 2.5 mmol) in CH$_2$Cl$_2$ (40 ml) was added TEA (1.8 ml, 13 mmol) and Boc$_2$O (0.59 ml, 2.5 mmol). The reaction was stirred at rt for 1 h, then concentrated. The resulting residue was purified on silica gel column using MeOH/DCM as eluting solvents to give the title compound. LC/MS: (M+1)+ m/z 333.1; 335.1.

Step C: tert-butyl (Z)-(3-(4-bromo-2-((2-((tert-butoxycarbonyl)amino)ethyl)imino)-3-methyl-2,3-dihydro-1H-imidazol-1-yl)propyl)carbamate To a solution of tert-butyl (3-(4-bromo-2-imino-3-methyl-2,3-dihydro-1H-imidazol-1-yl)propyl)carbamate (1.0 g, 3.0 mmol) and tert-butyl (2-bromoethyl)carbamate (1.3 g, 6.0 mmol) in acetonitrile (10 ml) was added Cs$_2$CO$_3$ (2.9 g, 9.0 mmol). The reaction was stirred at 50° C. for 6 h, then concentrated. The resulting residue was dissolved in DCM (50 mL), and filtered. The filtrate was purified on silica gel column using MeOH/DCM as eluting solvents to give the title compound. LC/MS: (M+1)+ m/z 476.0; 478.0.

Step D: (S)-3-(4-((Z)-2-((2-aminoethyl)imino)-1-(3-aminopropyl)-3-methyl-2,3-dihydro-1H-imidazol-4-yl)phenoxy)-2-(((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid The title compound was prepared from tert-butyl (Z)-(3-(4-bromo-2-((2-((tert-butoxycarbonyl)-amino)ethyl)imino)-3-methyl-2,3-dihydro-1H-imidazol-1-yl)propyl)carbamate according to the procedure of Example 55 Steps E-J. LC/MS: (M+1)+ m/z 739.4. $^1$H-NMR (500 MHz, D$_2$O): δ 7.37-7.35 (d, J=8.6 Hz, 2H), 7.15 (s, 1H), 7.06-7.04 (d, J=8.6 Hz, 2H), 6.93 (s, 1H), 4.94-4.93 (m, 1H), 4.63 (s, 1H), 4.47-4.39 (m, 2H), 4.11-4.09 (m, 2H), 3.63-3.61 (m, 2H), 3.52 (s, 3H), 3.29-3.27 (m, 2H), 3.07-3.04 (m, 2H), 2.21-2.16 (m, 2H), 1.41 (s, 3H), 1.02 (s, 3H).

Examples 58 and 59

(S)-3-(4-((S)-2-((2-aminoethyl)amino)-4,5-dihydro-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (58)

(R)-3-(4-((S)-1-amino-2-((4,5-dihydro-1H-imidazol-2-yl)amino)ethyl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (59)

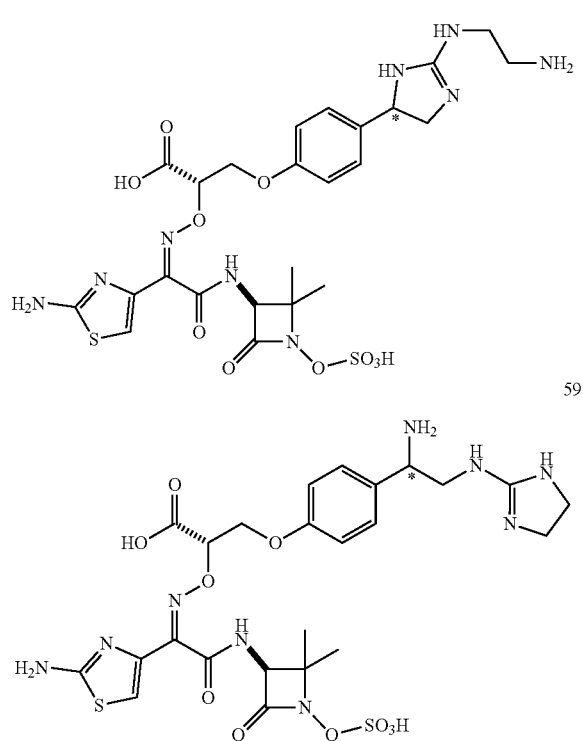

Step A: tert-butyl (R)-2-hydroxy-3-(4-vinylphenoxy)propanoate

To a solution of (R)-tert-butyl 3-(4-bromophenoxy)-2-hydroxypropanoate (2400 mg, 7.6 mmol) in EtOH (60 mL) was added potassium vinyltrifluoroborate (1520 mg, 11 mmol), Et$_3$N (1.58 mL, 11 mmol), and PdCl$_2$(dppf)-CH$_2$Cl$_2$ adduct (310 mg, 0.38 mmol). The reaction mixture was N$_2$/vacuum exchanged (3 times) and heated to reflux for overnight, then cooled to room temperature, and filtered through a short pad of Celite™ washing with CH$_2$Cl$_2$. The filtrate was concentrated and purified by ISCO column (40 g, gold), eluting with 0-50% EtOAc/hexane gradient to give the title compound. LC-MS [M+Na]$^+$: m/z 287.2.

Step B: tert-butyl (R)-2-((tert-butyldimethylsilyl)oxy)-3-(4-vinylphenoxy)propanoate To a solution of (R)-tert-butyl 2-hydroxy-3-(4-vinylphenoxy)propanoate (1580 mg, 6.0 mmol), imidazole (980 mg, 14 mmol), and TBDMS-Cl (1.1 g, 7.2 mmol) in acetonitrile (25 ml) was added DMAP (73 mg, 0.60 mmol). The resulting solution was stirred at RT overnight. Then the reaction mixture was concentrated under reduced pressure and the resulting residue was purified by ISCO Redi-Sep column (gold, 40 g) eluting with 0-30% EtOAc/hexane gradient to give the title compound.

Step C: tert-butyl (2R)-2-((tert-butyldimethylsilyl)oxy)-3-(4-(1,2-diazidoethyl)phenoxy)-propanoate (R)-tert-butyl 2-((tert-butyldimethylsilyl)oxy)-3-(4-vinylphenoxy)propanoate (1.9 g, 5.0 mmol) was added to a stirred mixture of sodium periodate (1.1 g, 5.0 mmol) and sodium azide (1.0 g, 15 mmol) in DMSO (15 ml) and acetic acid (5 ml). The reaction mixture was stirred at 75° C. for 2 h, and then cooled, diluted with ethyl acetate, washed with water (4×) and brine, dried (MgSO$_4$), and filtered. The filtrate was evaporated under reduced pressure. The resulting residue was purified by column chromatography on silica gel ISCO column (40 g gold) eluting with EtOAc/hexane gradient 0-20% to give the title compound.

Step D: tert-butyl (2R)-2-((tert-butyldimethylsilyl)oxy)-3-(4-(1,2-diaminoethyl)-phenoxy)propanoate Palladium on carbon (300 mg, 2.8 mmol) was added to a stirred mixture of (2R)-tert-butyl 2-((tert-butyldimethylsilyl)oxy)-3-(4-(1,2-diazidoethyl)-phenoxy)propanoate (1500 mg, 3.2 mmol) in methanol (30 ml) under a H$_2$ balloon. The reaction mixture was vacuum/H$_2$ exchanged 3 times, and then stirred at room temperature overnight. The reaction mixture was diluted with EtOAc and filtered through a short pad of Celite™. The filtrate was concentrated under reduced pressure to give the title compound. LC-MS [M+H]$^+$: m/z 411.6.

Step E: tert-butyl (2R)-2-((tert-butyldimethylsilyl)oxy)-3-(4-(2-thioxoimidazolidin-4-yl)phenoxy)propanoate 1,1'-Thiocarbonyldiimidazole (360 mg, 2.0 mmol) in DCM (8 ml) was slowly added dropwise over 20 minutes to a stirred mixture of (2R)-tert-butyl 2-((tert-butyldimethylsilyl)oxy)-3-(4-(1,2-diaminoethyl)phenoxy)propanoate (800 mg, 1.9 mmol) in DCM (16 ml). The reaction mixture was stirred at room temperature for 15 min, then concentrated under reduced pressure. The resulting residue was purified on a silica gel column (gold, 80 g) using 0-60% EtOAc/hexane gradient to give the title compound as a racemic mixture. This racemic mixture was separated with SFC chiral resolution (IC (2×15 cm+3×15 cm); 35% isopropanol/CO$_2$, 100 bar; 50 mL/min, 220 nm; inj vol.: 1.5 mL, 15 mg/mL ethanol:DCM) to give the title compound as two enantiomerically pure isomers. The second isomer (longer retention time) was used in the next step. LC-MS [M+H]$^+$: m/z 453.3.

Step F: tert-butyl (R)-2-((tert-butyldimethylsilyl)oxy)-3-(4-((S)-2-(methylthio)-4,5-dihydro-1H-imidazol-4-yl)phenoxy)propanoate Iodomethane (0.967 ml, 15.46 mmol) was added to a stirred mixture of (R)-tert-butyl 2-((tert-butyldimethylsilyl)oxy)-3-(4-(2-thioxoimidazolidin-4-yl)phenoxy)propanoate (1400 mg, 3.1 mmol) in MeCN (12 ml). The reaction mixture was stirred at 70° C. for 2 h, then cooled and concentrated under reduced pressure to give the title compound. LC-MS [M+H]⁺: m/z 467.3.

Step G: tert-butyl (S)-4-(4-((R)-3-(tert-butoxy)-2-((tert-butyldimethylsilyl)oxy)-3-oxo-propoxy)phenyl)-2-(methylthio)-4,5-dihydro-1H-imidazole-1-carboxylate DMAP (190 mg, 1.5 mmol) was added to a stirred mixture of Boc-anhydride (1.4 ml, 6.2 mmol), (R)-tert-butyl 2-((tert-butyldimethylsilyl)oxy)-3-(4-((S)-2-(methylthio)-4,5-dihydro-1H-imidazol-4-yl)phenoxy)propanoate (1400 mg, 3.1 mmol) and triethylamine (1.3 ml, 9.3 mmol) in CH$_2$Cl$_2$ (14 ml). The reaction mixture was stirred at room temperature for 2 h, and concentrated. The resulting residue was purified by column chromatography on silica gel (ISCO gold 80 g) eluting with 0-100% EtOAc/hexane gradient to give the title compound as a mixture of Boc regioisomers. LC-MS [M+H]⁺: m/z 567.4.

Step H: tert-butyl (S)-4-(4-((R)-3-(tert-butoxy)-2-((tert-butyldimethylsilyl)oxy)-3-oxopropoxy)phenyl)-2-((2-((tert-butoxycarbonyl)amino)ethyl)amino)-4,5-dihydro-1H-imidazole-1-carboxylate Acetic acid (0.94 ml) was added to a stirred mixture of N-Boc-ethylenediamine (420 mg, 2.6 mmol) and the mixture of Boc regioisomers from Step G (750 mg, 1.3 mmol) in EtOH (7.5 mL). The reaction mixture was stirred at 55° C. overnight, then cooled and concentrated under reduced pressure. The resulting residue was dissolved in DCM and washed with NaHCO$_3$ aqueous solution/2N NaOH (final wash aqueous pH ~10). The aqueous layer was separated and extracted with DCM 3 times. The combined organic layers were washed with brine, dried (MgSO$_4$), and filtered. The filtrate was removed under reduced pressure to give the title compound. LC-MS [M+H]⁺: m/z 679.5.

Step I: tert-butyl (S)-4-(4-((R)-3-(tert-butoxy)-2-((tert-butyldimethylsilyl)oxy)-3-oxo-propoxy)phenyl)-2-((tert-butoxycarbonyl)(2-((tert-butoxycarbonyl)amino)ethyl)amino)-4,5-dihydro-1H-imidazole-1-carboxylate Boc-anhydride (4.6 ml, 20 mmol) was added to tert-butyl (S)-4-(4-((R)-3-(tert-butoxy)-2-((tert-butyldimethylsilyl)oxy)-3-oxopropoxy)phenyl)-2-((2-((tert-butoxycarbonyl)amino)ethyl)amino)-4,5-dihydro-1H-imidazole-1-carboxylate (900 mg, 1.3 mmol) and the mixture was stirred at 100° C. for 1.5 h. Then the reaction mixture was cooled and directly loaded on a ISCO column (80 g gold) eluting with EtOAc/Hexane 0-100% gradient to give the title compound as a mixture of regioisomers. LC-MS [M+H]⁺: m/z 780.5.

Step J: tert-butyl (S)-4-(4-((R)-3-(tert-butoxy)-2-hydroxy-3-oxopropoxy)phenyl)-2-((tert-butoxycarbonyl)(2-((tert-butoxycarbonyl)amino)ethyl)amino)-4,5-dihydro-1H-imidazole-1-carboxylate TBAF (1.7 ml, 1.7 mmol) was added to a stirred mixture of (S)-tert-butyl 4-(4-((R)-3-(tert-butoxy)-2-((tert-butyldimethylsilyl)oxy)-3-oxopropoxy)phenyl)-2-((tert-butoxycarbonyl)(2-((tert-butoxycarbonyl)amino)ethyl)amino)-4,5-dihydro-1H-imidazole-1-carboxylate (900 mg, 1.155 mmol) in THF (8 ml). The reaction mixture was stirred at room temperature for 1 h, and then concentrated in vacuo. The resulting residue was purified with silica gel ISCO column (40 g gold) eluting with 0-100% EtOAc/hexane gradient to give the title compound. LC-MS [M+H]⁺: m/z 665.4.

Step K: tert-butyl (S)-4-(4-((S)-3-(tert-butoxy)-2-((1,3-dioxoisoindolin-2-yl)oxy)-3-oxopropoxy)phenyl)-2-((tert-butoxycarbonyl)(2-((tert-butoxycarbonylamino)ethyl)amino)-4,5-dihydro-1H-imidazole-1-carboxylate To a solution of (S)-tert-butyl 4-(4-((R)-3-(tert-butoxy)-2-hydroxy-3-oxopropoxy)phenyl)-2-((tert-butoxycarbonyl)(2-((tert-butoxy-carbonyl)amino)ethyl)amino)-4,5-dihydro-1H-imidazole-1-carboxylate (460 mg mixture, 0.69 mmol) in THF (5 mL) was added 2-hydroxyisoindoline-1,3-dione (135 mg, 0.83 mmol), and triphenylphosphine (254 mg, 0.97 mmol), followed with the dropwise addition of DIAD (0.19 mL, 0.97 mmol). The reaction was stirred at rt for 1 h, and then concentrated. The resulting residue was purified on silica gel column (ISCO gold 40 g) using 0-100% EtOAc/hexane gradient to give the title compound as a mixture of isomers. LC-MS [M+H]⁺: m/z 810.7.

Step L: 2-((((S)-1-(tert-butoxy)-3-(4-((S)-1-(tert-butoxycarbonyl)-2-((tert-butoxycarbonyl)(2-((tert-butoxycarbonyl)amino)ethyl)amino)-4,5-dihydro-1H-imidazol-4-yl)phenoxy)-1-oxopropan-2-yl)oxy)imino)-2-(2-((tert-butoxycarbonyl)amino)thiazol-4-yl)acetic acid To a solution of (S)-tert-butyl 4-(4-((S)-3-(tert-butoxy)-2-((1,3-dioxoisoindolin-2-yl)oxy)-3-oxopropoxy)phenyl)-2-((tert-butoxycarbonyl)(2-((tert-butoxycarbonyl)amino)ethyl)amino)-4,5-dihydro-1H-imidazole-1-carboxylate (350 mg, 0.432 mmol) in CH$_2$Cl$_2$ (2 ml) at rt was added hydrazine (0.016 ml, 0.52 mmol) in ethanol (2 m). The reaction was stirred at rt for 30 min, then 2-(2-((tert-butoxycarbonyl)amino)thiazol-4-yl)-2-oxoacetic acid (190 mg, 0.69 mmol) was added. The reaction mixture was stirred at rt for 1.5 h, then concentrated to give the title compound, which was used as is in next step. LC-MS [M+H]⁺: m/z 934.5.

Step M: (S)-tert-butyl 4-(4-((S)-3-(tert-butoxy)-2-(((Z)-(1-(2-((tert-butoxycarbonyl)-amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-2-((tert-butoxycarbonyl)(2-((tert-butoxycarbonyl)amino)ethyl)amino)-4,5-dihydro-1H-imidazole-1-carboxylate To a solution of 2-((((S)-1-(tert-butoxy)-3-(4-((S)-1-(tert-butoxycarbonyl)-2-((tert-butoxycarbonyl)(2-((tert-butoxycarbonyl)amino)ethyl)amino)-4,5-dihydro-1H-imidazol-4-yl)phenoxy)-1-oxopropan-2-yl)oxy)imino)-2-(2-((tert-butoxycarbonyl)amino)thiazol-4-yl)acetic acid (400 mg, 0.43 mmol) in DMF (3.5 ml) was added DCC (260 mg, 1.3 mmol), and HOBt (200 mg, 1.3 mmol). The resulting solution was stirred at rt for 30 min, then (S)-3-amino-2,2-dimethyl-4-oxoazetidin-1-yl hydrogen sulfate (220 mg, 1.1 mmol) and sodium bicarbonate (220 mg, 2.6 mmol) were added. The reaction was stirred at rt overnight, then filtered through a sintered syringe and washed with DMF (1.5 mL). The filtrate was purified on ISCO system with a reverse phase C-18 column (80 g) eluting with 10-100% ACN/Water with 0.05% TFA to give the title compound as a mixture of isomers. LC-MS [M+H]$^+$: m/z 1126.7.

Step N: (R)-3-(4-((S)-1-amino-2-((4,5-dihydro-1H-imidazol-2-yl)amino)ethyl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (59) and (S)-3-(4-((S)-2-((2-aminoethyl)-amino)-4,5-dihydro-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (58)

TFA (5 ml) was added to a solution of (S)-tert-butyl 4-(4-((S)-3-(tert-butoxy)-2-(((Z)-(1-(2-((tert-butoxycarbonyl)-amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-2-((tert-butoxycarbonyl)(2-((tert-butoxycarbonyl)amino)ethyl)amino)-4,5-dihydro-1H-imidazole-1-carboxylate (200 mg, 0.18 mmol, as a mixture of isomers) in CH$_2$Cl$_2$ (4 ml). The mixture was stirred at room temperature for 1.5 h, and then concentrated under reduced pressure. Ether was added to the resulting residue and the solvent was then removed under reduced pressure. To the resulting residue was added ether to crash out a solid, and then the solvent was removed. The resulting residue was dried under vacuum, dissolved in DMSO (5 mL) and purified via Gilson reverse phase separation (5-25% MeCN/water 0.05% TFA gradient) to give (2S)-3-(4-(1-amino-2-((4,5-dihydro-1H-imidazol-2-yl)amino)ethyl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (59); and (S)-3-(4-((S)-2-((2-aminoethyl)amino)-4,5-dihydro-1H-imidazol-4-yl)phenoxy)-2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)propanoic acid (58).

Example 58

LC-MS [M+H]$^+$: m/z 670.4. $^1$H-NMR (500 MHz, D$_2$O, ppm): δ 7.26 (d, J=10 Hz, 2H), 7.04 (s, 1H), 6.94 (d, J=10 Hz, 2H), 5.03 (m, 1H), 4.74 (s, 1H), 4.64 (m, 1H), 4.38 (m, 3H), 3.66 (dd, J=10, 5 Hz, 1H), 3.55 (dd, J=10, 5 Hz, 1H), 3.48 (s, 3H), 1.37 (s, 3H), 1.04 (s, 3H).).

Example 59

LC-MS [M+H]$^+$: m/z 670.0. $^1$H-NMR (500 MHz, D$_2$O, ppm): δ 7.22 (d, J=10 Hz, 2H), 7.02 (s, 1H), 6.88 (d, J=10 Hz, 2H), 5.0 (m, 2H), 4.68 (s, 1H), 4.34 (m, 2H), 3.98 (t, J=10 Hz, 1H), 3.47 (m, 3H), 3.12 (t, J=5 Hz, 2H), 1.34 (s, 3H), 0.97 (s, 3H).).

Examples 60 and 61

(2S)-3-(4-(2-((2-aminoethyl)amino)-4,5-dihydro-1H-imidazol-5-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (60)

(2S)-3-(4-(1-amino-2-((4,5-dihydro-1H-imidazol-2-yl)amino)ethyl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid (61)

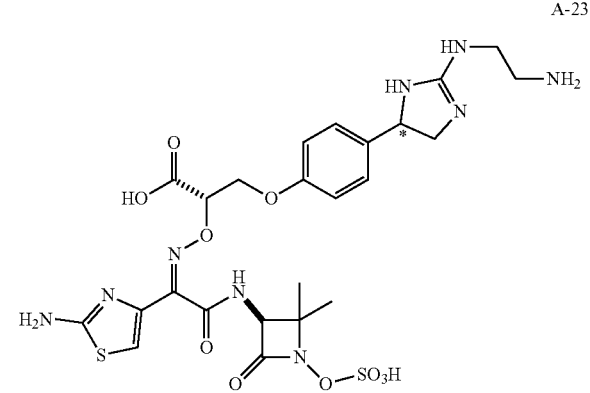

A-23

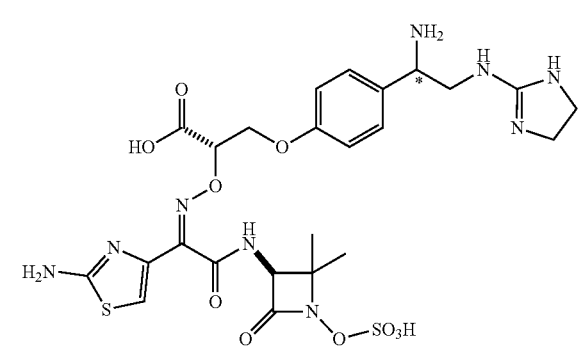

A-24

The title compounds were prepared according to the procedure of Examples 58 and 59 starting from the first isomer (shorter retention time) from Step E. Example 60: LC-MS [M+H]$^+$: m/z 670.4. Example 61: LC-MS [M+H]$^+$: m/z 670.0.

Example 62

(S)-3-((Z)-2-(((S)-2-(4-(2-((2-aminoethyl)amino)-1-methylpyridin-1-ium-4-yl)phenoxy)-1-carboxyethoxy)imino)-2-(2-aminothiazol-4-yl)acetamido)-2,2-dimethyl-4-oxoazetidin-1-yl sulfate

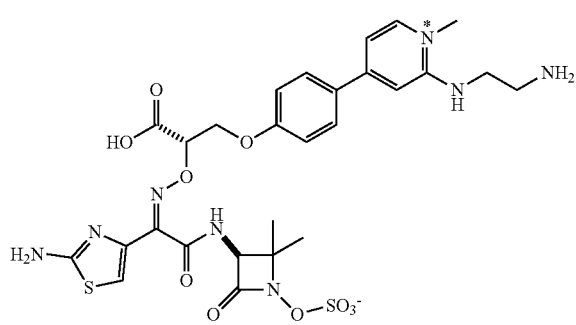

Step A: tert-butyl (2-((4-bromopyridin-2-yl)amino)ethyl)carbamate

A mixture of 4-bromopyridin-2-amine (500 mg, 2.9 mmol), 125 mg of 4 Å molecular sieves, and tert-butyl (2-oxoethyl)carbamate (510 mg, 3.2 mmol) in 1,2-dichloroethane (10 ml) was stirred at RT for 60 min, followed by the addition of sodium triacetoxyborohydride (1200 mg, 5.8 mmol). The mixture was stirred overnight, then diluted with EtOAc and washed with NaHCO$_3$ aqueous solution (3 times). The organic layer was separated, washed with water and brine, dried over Na$_2$SO$_4$, and filtered. The filtrate was concentrated under reduced pressure and the resulting residue was purified on a silica gel cartridge (ISCO gold 40 g) eluting with 0-100% EtOAc/hexane gradient to give the title compound. LC-MS [M+H]$^+$: m/z 316.2.

Step B: tert-butyl (R)-3-(4-(2-((2-((tert-butoxycarbonyl)amino)ethyl)amino)pyridin-4-yl)phenoxy)-2-hydroxypropanoate To a solution of PdCl$_2$(dppf)-CH$_2$Cl$_2$ adduct (180 mg, 0.22 mmol), tert-butyl (2-((4-bromopyridin-2-yl)amino)ethyl)carbamate (870 mg, 2.8 mmol) and (R)-tert-butyl 2-hydroxy-3-(4-(4,4,5,5-tetramethyl-1,3,2-dioxaborolan-2-yl)phenoxy)-propanoate (800 mg, 2.2 mmol) in dioxane (7.5 ml) was added Na$_2$CO$_3$ (0.70 g, 6.6 mmol) in water (2.5 ml). The reaction mixture was N$_2$/vacuum exchanged (3 times), and then heated at 100° C. under microwave reaction conditions for 1 h. Then the mixture was purified on a silica gel column (ISCO gold, 40 g) eluting with 0-100% EtOAc/hexane gradient to give the title compound. LC-MS [M+H]$^+$: m/z 474.5.

Step C: (S)-3-((Z)-2-(((S)-2-(4-(2-((2-aminoethyl)amino)-1-methylpyridin-1-ium-4-yl)phenoxy)-1-carboxyethoxy)imino)-2-(2-aminothiazol-4-yl)acetamido)-2,2-dimethyl-4-oxoazetidin-1-yl sulfate (tert-Butyl (R)-3-(4-(2-((2-((tert-butoxycarbonyl)amino)ethyl)-amino) pyridin-4-yl)phenoxy)-2-hydroxypropanoate) was converted to the title compound using a procedure similar to the procedure of Example 1 Step C to Step H. LC-MS[M+H]$^+$: m/z 694.0. $^1$H-NM/R (500 Hz, D$_2$O, ppm): δ7.83 (d, J=5 Hz, 1H), 7.64 (d, J=5 Hz, 2H), 7.13 (d, J=5 Hz, 1H), 7.07 (s, 1H), 6.99 (d, J=5 Hz, 2H), 6.96 (s, 1H), 5.01 (n, 1H), 4.49 (s, 1H), 4.43 (m, 2H), 3.75 (t, J=5 Hz, 2H), 3.72 (s, 3H), 3.22 (t, J=5 Hz, 2H), 1.28 (s, 3H), 0.96 (s, 3H).

TABLE 4

Examples 63-83 were prepared according to the procedure of Example 62.

| Example | Name | Structure | LC-MS found |
|---|---|---|---|
| 63 | (S)-3-((Z)-2-(((S)-2-(4-(2-((3-aminopropyl)amino)-1-methylpyridin-1-ium-4-yl)phenoxy)-1-carboxyethoxy)imino)-2-(2-aminothiazol-4-yl)acetamido)-2,2-dimethyl-4-oxoazetidin-1-yl sulfate | 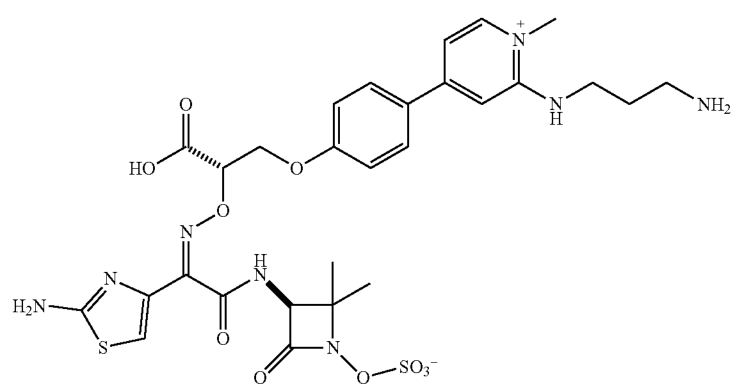 | 707.4 |

TABLE 4-continued

Examples 63-83 were prepared according to the procedure of Example 62.

| Example | Name | Structure | LC-MS found |
|---|---|---|---|
| 64 | (S)-3-((Z)-2-(((S)-2-(4-(2-((3-aminopropyl)amino)pyridin-4-yl)phenoxy)-1-carboxyethoxy)imino)-2-(2-aminothiazol-4-yl)acetamido)-2,2-dimethyl-4-oxoazetidin-1-yl sulfate | 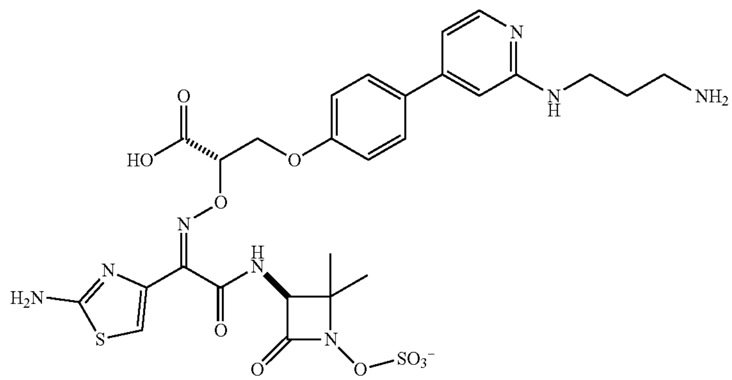 | 693.3 |
| 65 | (S)-3-((Z)-2-(2-aminothiazol-4-yl)-2-(((S)-2-(4-(2-((azetidin-3-ylmethyl)amino)-1-methylpyridin-1-ium-4-yl)phenoxy)-1-carboxy-ethoxy)imino)acetamido)-2,2-dimethyl-4-oxoazetidin-1-yl sulfate | 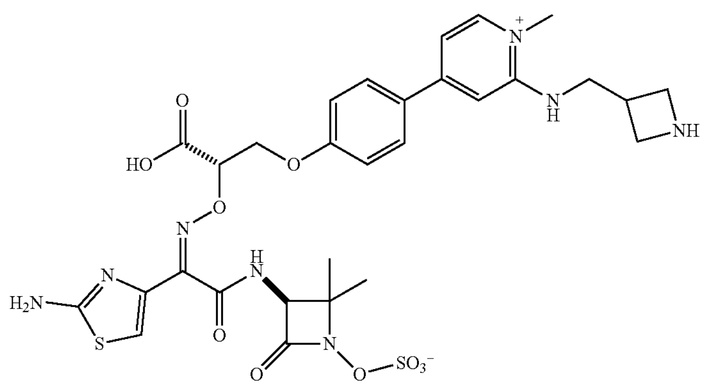 | 719.2 |
| 66 | (S)-3-((Z)-2-(((S)-2-(4-(6-((2-aminoethyl)amino)-1-methylpyridin-1-ium-3-yl)phenoxy)-1-carboxyethoxy)imino)-2-(2-aminothiazol-4-yl)acetamido)-2,2-dimethyl-4-oxoazetidin-1-yl sulfate | 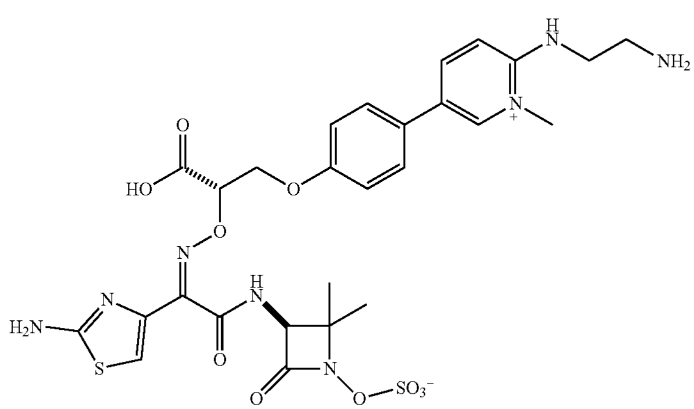 | 693.5 |

TABLE 4-continued

Examples 63-83 were prepared according to the procedure of Example 62.

| Example | Name | Structure | LC-MS found |
|---|---|---|---|
| 67 | (S)-3-((Z)-2-(2-amino-5-chlorothiazol-4-yl)-2-(((S)-2-(4-(6-((2-aminoethyl)amino)-1-methylpyridin-1-ium-3-yl)phenoxy)-1-carboxyethoxy)imino)acetamido)-2,2-dimethyl-4-oxoazetidin-1-yl sulfate | 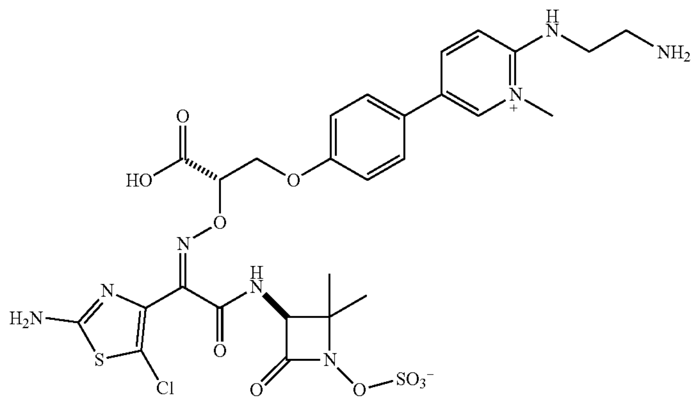 | 727.3 |
| 68 | (S)-3-((Z)-2-(((S)-2-(4-(6-((2-aminoethyl)amino)-1-methylpyridin-1-ium-3-yl)-3-fluorophenoxy)-1-carboxyethoxy)imino)-2-(2-aminothiazol-4-yl)acetamido)-2,2-dimethyl-4-oxoazetidin-1-yl sulfate | 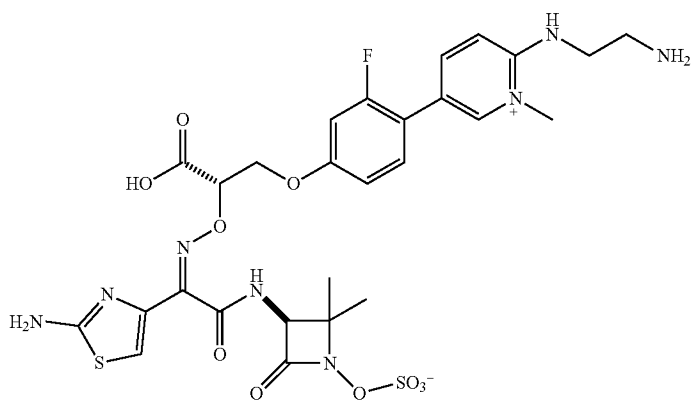 | 711.5 |
| 69 | (S)-3-((Z)-2-(2-amino-5-chlorothiazol-4-yl)-2-(((S)-2-(4-(6-((2-aminoethyl)amino)-1-methylpyridin-1-ium-3-yl)-3-fluorophenoxy)-1-carboxyethoxy)imino)acetamido)-2,2-dimethyl-4-oxoazetidin-1-yl sulfate | 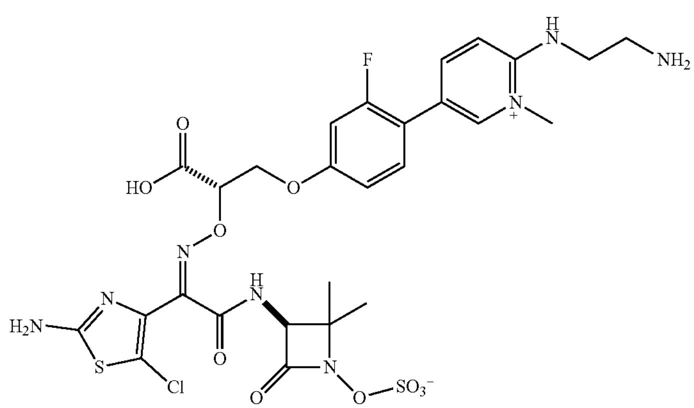 | 745.3 |

TABLE 4-continued

Examples 63-83 were prepared according to the procedure of Example 62.

| Example | Name | Structure | LC-MS found |
|---|---|---|---|
| 70 | (S)-3-(4-(2-((2-aminoethyl)amino)pyrimidin-5-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid | 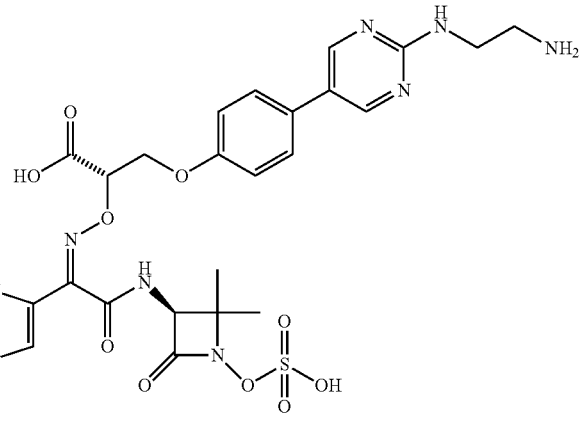 | 680.4 |
| 71 | (S)-3-((Z)-2-(2-aminothiazol-4-yl)-2-(((S)-1-carboxy-2-(4-(1-methyl-6-(piperazin-1-yl)pyridin-1-ium-3-yl)phenoxy)ethoxy)imino)acetamido)-2,2-dimethyl-4-oxoazetidin-1-yl sulfate | 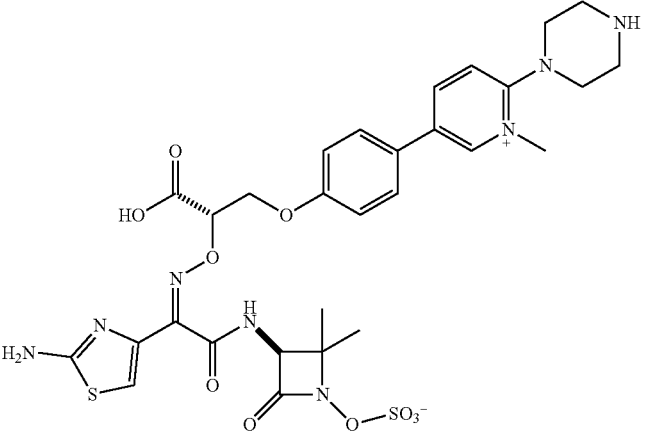 | 719.5 |
| 72 | (S)-3-((Z)-2-(((S)-2-(4-(5-((2-aminoethyl)amino)-1-methylpyridin-1-ium-2-yl)phenoxy)-1-carboxyethoxy)imino)-2-(2-aminothiazol-4-yl)acetamido)-2,2-dimethyl-4-oxoazetidin-1-yl sulfate | 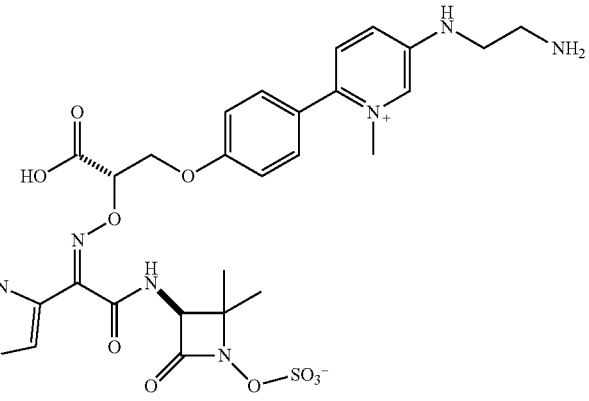 | 693.5 |

TABLE 4-continued

Examples 63-83 were prepared according to the procedure of Example 62.

| Example | Name | Structure | LC-MS found |
|---|---|---|---|
| 73 | (S)-3-((Z)-2-(2-aminothiazol-4-yl)-2-(((S)-1-carboxy-2-(4-(6-(((3-hydroxyazetidin-3-yl)methyl)amino)-1-methylpyridin-1-ium-3-yl)phenoxy)ethoxy)imino)acetamido)-2,2-dimethyl-4-oxoazetidin-1-yl sulfate | 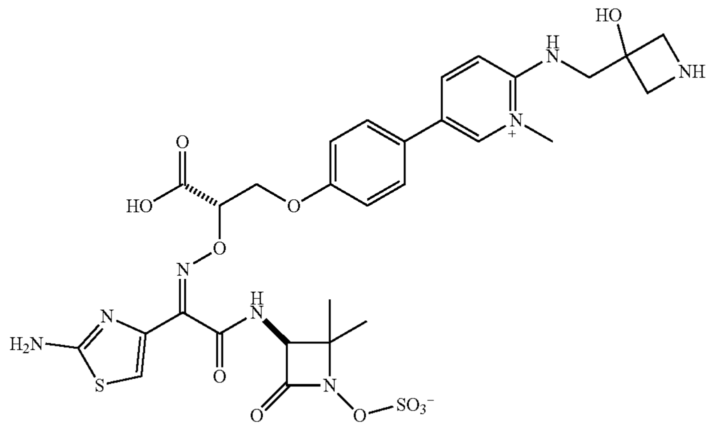 | 735.5 |
| 74 | (S)-3-((Z)-2-(((S)-2-(4-(6-(((1-aminocyclopropyl)methyl)amino)-1-methylpyridin-1-ium-3-yl)phenoxy)-1-carboxyethoxy)imino)-2-(2-aminothiazol-4-yl)acetamido)-2,2-dimethyl-4-oxoazetidin-1-yl sulfate | 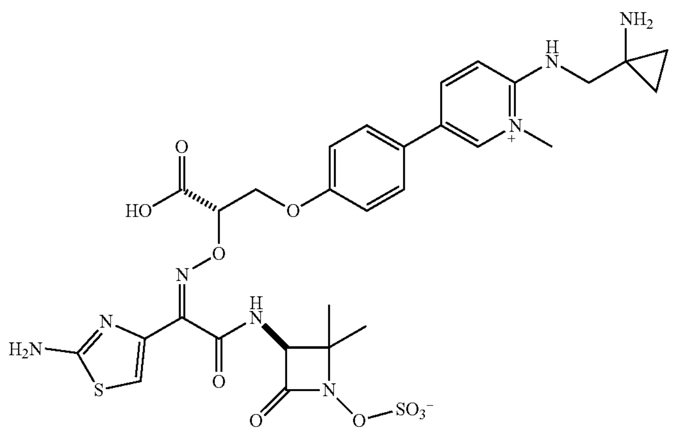 | 719.4 |
| 75 | (3S)-3-((Z)-2-(((1S)-2-(4-(6-((1-aminopropan-2-yl)amino)-1-methylpyridin-1-ium-3-yl)phenoxy)-1-carboxyethoxy)imino)-2-(2-aminothiazol-4-yl)acetamido)-2,2-dimethyl-4-oxoazetidin-1-yl sulfate | 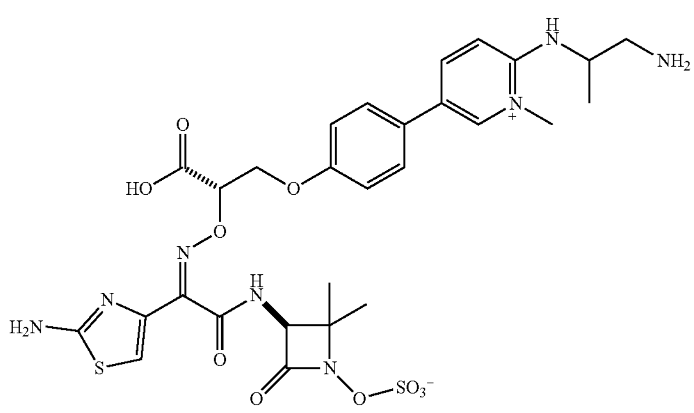 | 707.7 |

TABLE 4-continued

Examples 63-83 were prepared according to the procedure of Example 62.

| Example | Name | Structure | LC-MS found |
|---------|------|-----------|-------------|
| 76 | (3S)-3-((Z)-2-(((1S)-2-(4-(6-(((1-aminopropan-2-yl)amino)-1-methylpyridin-1-ium-3-yl)phenoxy)-1-carboxyethoxy)imino)-2-(2-aminothiazol-4-yl)acetamido)-2,2-dimethyl-4-oxoazetidin-1-yl sulfate | 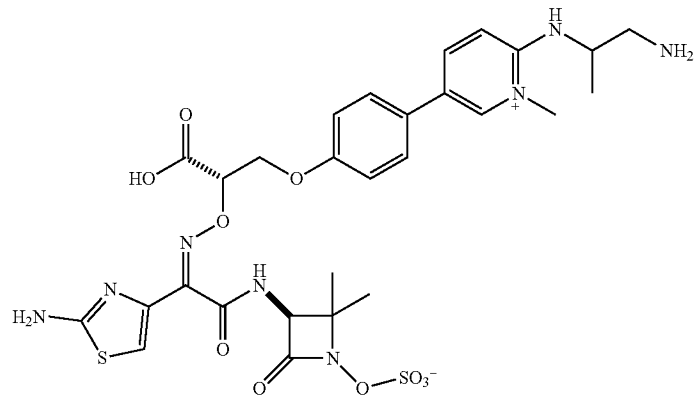 | 707.5 |
| 77 | (S)-3-((Z)-2-(((S)-2-(4-(2-((2-aminoethyl)amino)-1-methylpyrimidin-1-ium-5-yl)phenoxy)-1-carboxyethoxy)imino)-2-(2-aminothiazol-4-yl)acetamido)-2,2-dimethyl-4-oxoazetidin-1-yl sulfate | 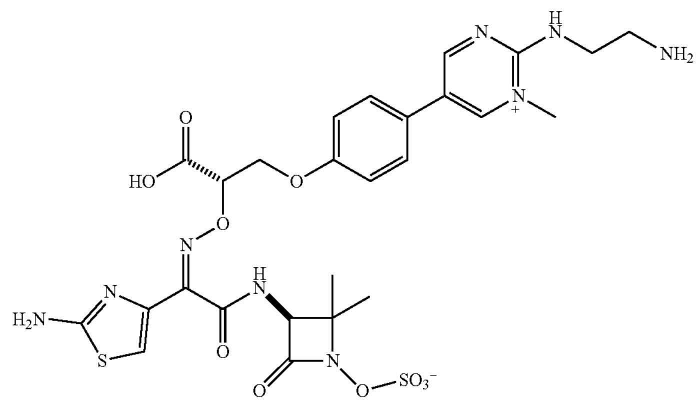 | 694.3 |
| 78 | (S)-3-((Z)-2-(((S)-2-(4-(6-(((2-aminoethyl)amino)methyl)-1-methylpyridin-1-ium-3-yl)phenoxy)-1-carboxyethoxy)imino)-2-(2-aminothiazol-4-yl)acetamido)-2,2-dimethyl-4-oxoazetidin-1-yl sulfate | 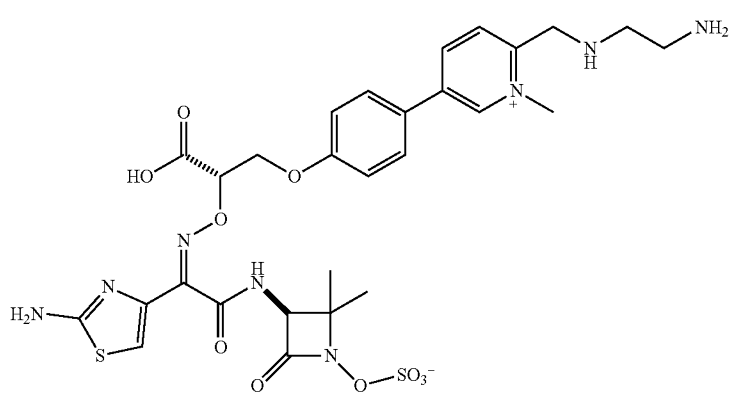 | 707.6 |

TABLE 4-continued

Examples 63-83 were prepared according to the procedure of Example 62.

| Example | Name | Structure | LC-MS found |
|---------|------|-----------|-------------|
| 79 | (S)-3-((Z)-2-(2-aminothiazol-4-yl)-2-(((S)-1-carboxy-2-(4-(6-(((1,3-diaminopropan-2-yl)amino)methyl)-1-methylpyridin-1-ium-3-yl)phenoxy)ethoxy)imino)acetamido)-2,2-dimethyl-4-oxoazetidin-1-yl sulfate | 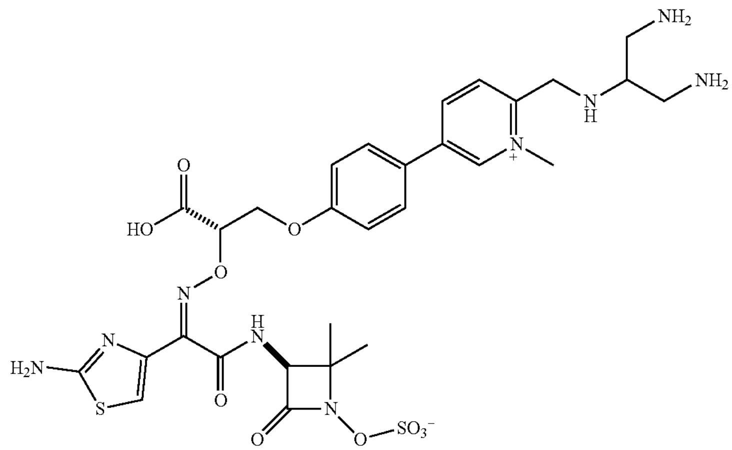 | 736.7 |
| 80 | (S)-3-((Z)-2-(2-aminothiazol-4-yl)-2-(((S)-1-carboxy-2-(4-(6-((1,3-diaminopropan-2-yl)carbamoyl)-1-methylpyridin-1-ium-3-yl)phenoxy)ethoxy)imino)acetamido)-2,2-dimethyl-4-oxoazetidin-1-yl sulfate | 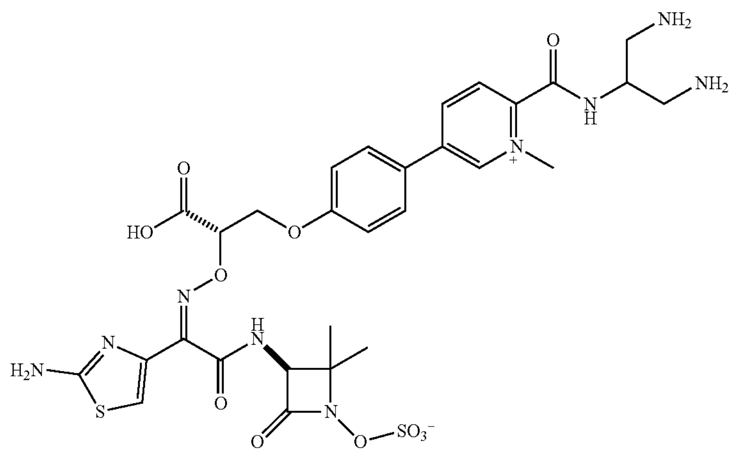 | 750.7 |
| 81 | (S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-3-(4-(6-((1,3-diaminopropan-2-yl)carbamoyl)pyridin-3-yl)phenoxy)propanoic acid | 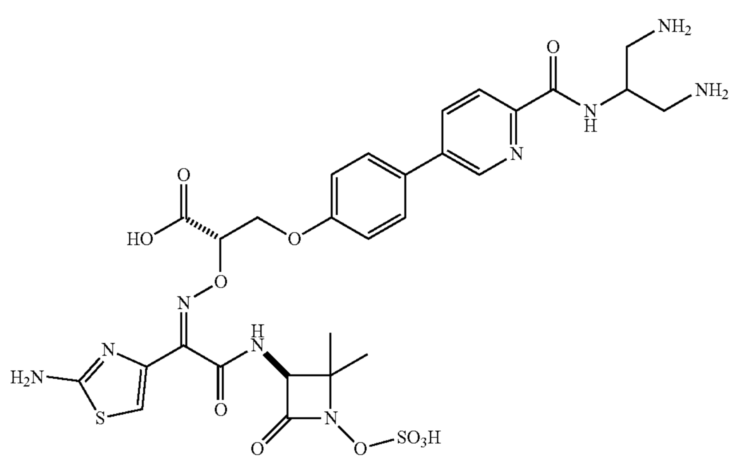 [SMILES: CC1(C)[C@H](NC(=O)/C(=N\O[C@@H](COc2ccc(-c3ccc(C(=O)NC(CN)CN)nc3)cc2)C(=O)O)c2csc(N)n2)C(=O)N1OS(=O)(=O)O] | 736.8 |

TABLE 4-continued

Examples 63-83 were prepared according to the procedure of Example 62.

| Example | Name | Structure | LC-MS found |
|---|---|---|---|
| 82 | (S)-3-((Z)-2-(2-aminothiazol-4-yl)-2-(((S)-1-carboxy-2-(4-(6-((1,3-diaminopropan-2-yl)amino)-1-methylpyridin-1-ium-3-yl)phenoxy)ethoxy)imino)acetamido)-2,2-dimethyl-4-oxoazetidin-1-yl sulfate | 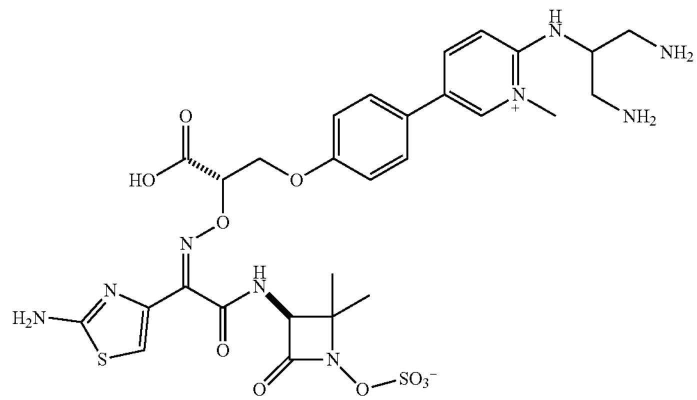 | 722.7 |
| 83 | (S)-3-((Z)-2-(((S)-2-(4-(2-((2-aminoethyl)(azetidin-3-ylmethyl)amino)-1-methylpyrimidin-1-ium-5-yl)phenoxy)-1-carboxyethoxy)imino)-2-(2-aminothiazol-4-yl)acetamido)-2,2-dimethyl-4-oxoazetidin-1-yl sulfate | 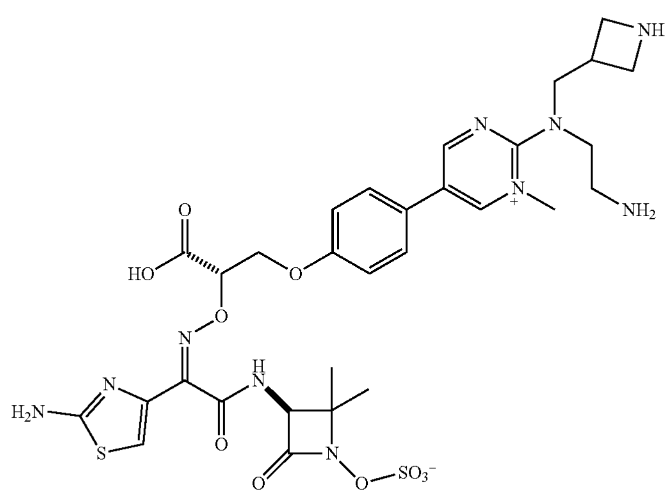 | 763.8 |

Examples 84 and 85

(3S)-3-((2-(4-(1-(3-aminopropyl)-2-methyl-1H-pyrazol-2-ium-4-yl)phenoxy)-2-carboxyethoxy)imino)-2-(2-aminothiazol-4-yl)acetamido)-2,2-dimethyl-4-oxoazetidin-1-yl sulfate (84) and (3S)-3-(2-((2-(4-(1-(3-aminopropyl)-2-methyl-1H-pyrazol-2-ium-4-yl)phenoxy)-2-carboxyethoxy)imino)-2-(2-aminothiazol-4-yl)acetamido)-2,2-dimethyl-4-oxoazetidin-1-yl sulfate (85)

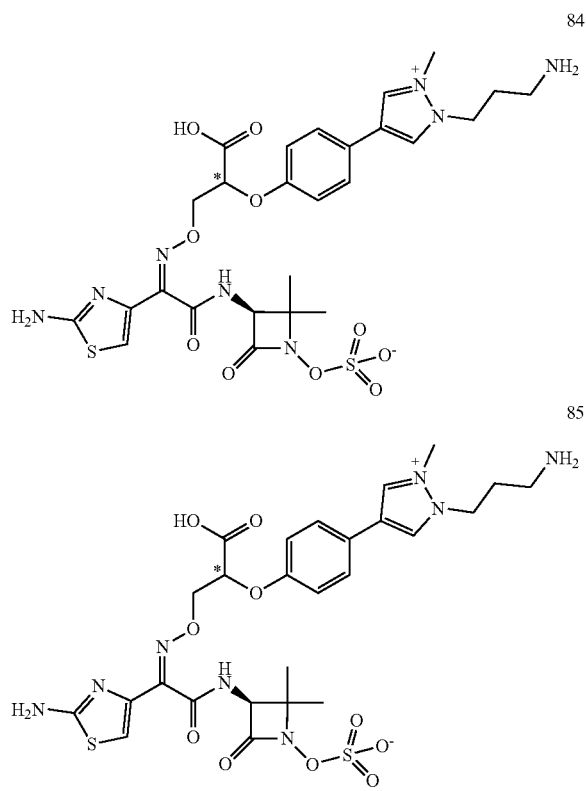

Step A: methyl 2-(4-bromophenoxy)-3-methoxypropanoate

A solution of 4-bromophenol (1.8 g, 10 mmol), methyl 2-bromo-3-methoxypropanoate (1.4 ml, 10 mmol), and lithium hydroxide (0.29 g, 12 mmol) in DMF (25.4 ml) was stirred at RT for 3 h. This reaction was partitioned between EtOAc and water. The separated organic layer was washed with water and brine, dried over MgSO$_4$, filtered and concentrated. The resulting residue was purified by ISCO silica gel column (24 g) eluting with 0-20% EA/hexane gradient to give the title compound. LC-MS [M+Na]$^+$: m/z 311.2.

Step B: methyl 2-(4-bromophenoxy)-3-hydroxypropanoate

To a stirred solution of methyl 2-(4-bromophenoxy)-3-methoxypropanoate (1.0 g, 3.6 mmol) in CHCl$_3$ (18 ml) was added TMS-I (3.0 ml, 22 mmol). This mixture was stirred at RT over the weekend. Then the reaction was quenched with MeOH, and the volatiles were removed in vacuo. The resulting residue was then taken up in EtOAc, and washed sequentially with 1N aqueous NaOH and brine, dried over MgSO$_4$, filtered and the filtrate was concentrated. The resulting residue was purified using an ISCO silica gel column (24 g) eluting with 0-30% EA/hexane gradient to give the title compound. LC-MS [M+H]$^+$: m/z 275.1.

Step C: 2-(4-(1-(3-((tert-butoxycarbonyl)amino)propyl)-1H-pyrazol-4-yl)phenoxy)-3-hydroxypropanoic acid To a solution of methyl 2-(4-bromophenoxy)-3-hydroxypropanoate (0.14 g, 0.51 mmol)), tert-butyl (3-(4-(4,4,5,5-tetramethyl-1,3,2-dioxaborolan-2-yl)-1H-pyrazol-1-yl)propyl)carbamate (0.18 g, 0.51 mmol)), and 1,1'-bis(di-tert-butylphosphino)-ferrocene palladium dichloride (0.033 g, 0.051 mmol)) in dioxane (2.5 ml) was added the 1M aqueous solution of potassium phosphate (1.5 ml, 1.5 mmol). The microwave vial was sealed, degassed, refilled with N$_2$, and stirred at 70° C. for 1 h in a microwave reactor. The mixture was filtered and the filtrate was diluted with water, and extracted with EtOAc. The aqueous layer was acidified with 1N HCl, and extracted w/EtOAc. The organic layer was dried over MgSO$_4$, filtered and concentrated to give the title compound. LC-MS [M+H]$^+$: m/z 406.5.

Step D: benzhydryl 2-(4-(1-(3-((tert-butoxycarbonyl)amino)propyl)-1H-pyrazol-4-yl)phenoxy)-3-hydroxypropanoate To the solution of 2-(4-(1-(3-((tert-butoxycarbonyl)amino)propyl)-1H-pyrazol-4-yl)phenoxy)-3-hydroxypropanoic acid (0.21 g, 0.51 mmol) in MeOH (5.1 ml) was added diphenyl diazomethane (0.50 g, 2.6 mmol). The resulting solution was stirred at RT for 1 h, and then concentrated. The resulting residue was purified on ISCO (12 g gold) using 0-100% EtOAc/hexane gradient to give the title compound. LC-MS [M+H]$^+$: m/z 572.6.

Step E: benzhydryl 2-(4-(1-(3-((tert-butoxycarbonyl)amino)propyl)-1H-pyrazol-4-yl)phenoxy)-3-((1,3-dioxoisoindolin-2-yloxy)propanoate To a solution of benzhydryl 2-(4-(1-(3-((tert-butoxycarbonyl)amino)propyl)-1H-pyrazol-4-yl)phenoxy)-3-hydroxypropanoate (0.41 g, 0.72 mmol) in THF (7.2 ml) were added 2-hydroxyisoindoline-1,3-dione (0.35 g, 2.2 mmol), triphenylphosphine (0.23 g, 0.86 mmol) and DIAD (0.17 ml, 0.86 mmol) at RT. The reaction was stirred for 2 h, and then concentrated. The resulting residue was purified by ISCO silica gel column (40 g) eluting with 0-50% EtOAc in Hexanes to give the title compound. LC-MS [M+H]$^+$: m/z 717.7.

Step F: 4-(4-((1-(benzhydryloxy)-3-((1,3-dioxoisoindolin-2-yl)oxy)-1-oxopropan-2-yl)oxy)-phenyl)-1-(3-((tert-butoxycarbonyl)amino)propyl)-2-methyl-1H-pyrazol-2-ium iodide To a solution of benzhydryl 2-(4-(1-(3-((tert-butoxycarbonyl)amino)propyl)-1H-pyrazol-4-yl)phenoxy)-3-((1,3-dioxoisoindolin-2-yl)oxy)propanoate (0.12 g, 0.17 mmol) in acetonitrile (1.7 ml) was added MeI (0.087 ml, 1.4 mmol). The reaction was stirred at 70° C. overnight. Then the mixture was cooled and concentrated to give the title compound. LC-MS [M]$^+$: m/z 731.4.

Step G: 4-(4-((1-(benzhydryloxy)-3-((((2-((tert-butoxycarbonyl)amino)thiazol-4-yl)(carboxy)methylene)amino)oxy)-1-oxopropan-2-yl)oxy)phenyl)-1-(3-((tert-butoxycarbonyl)amino)propyl)-2-methyl-1H-pyrazol-2-ium To the solution of 4-(4-((1-(benzhydryloxy)-3-((1,3-dioxoisoindolin-2-yl)oxy)-1-oxopropan-2-yl)oxy)phenyl)-1-(3-((tert-butoxycarbonyl)amino)propyl)-2-methyl-1H-pyrazol-2-ium iodide (0.15 g, 0.17 mmol) in CH$_2$Cl$_2$ (1.2 ml) at RT was added hydrazine (6.6 µl, 0.21 mmol) in ethanol (1.2 ml). The resulting solution was stirred at RT for 1.5 h. To this mixture was added 2-(2-((tert-butoxycarbonyl)amino)thiazol-4-yl)-2-oxoacetic acid (0.085 g, 0.31 mmol), and the reaction was stirred at RT for 2 h. Then the mixture was concentrated to give the title compound. LC-MS [M]$^+$: m/z 855.7.

Step H: 4-(4-((1-(benzhydryloxy)-3-(((1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-1-oxopropan-2-yl)oxy)phenyl)-1-(3-((tert-butoxycarbonyl)amino)propyl)-2-methyl-1H-pyrazol-2-ium To the solution of 4-(4-((1-(benzhydryloxy)-3-((((2-((tert-butoxycarbonyl)-amino)thiazol-4-yl)(carboxy)methylene)amino)oxy)-1-oxopropan-2-yl)oxy)phenyl)-1-(3-((tert-butoxycarbonyl)amino)propyl)-2-methyl-1H-pyrazol-2-ium (0.15 g, 0.17 mmol) in DMF (3.5 ml) was added DCC (0.090 g, 0.44 mmol), and HOBt (0.067 g, 0.44 mmol). The reaction mixture was stirred at RT for 30 min, then (S)-3-amino-2,2-dimethyl-4-oxoazetidin-1-yl hydrogen sulfate (0.073 g, 0.35 mmol) and sodium hydrogencarbonate (0.073 g, 0.87 mmol) were added. The resulting mixture was stirred at RT overnight, then filtered through a sintered syringe and washed with DMF (1.5 mL). The solution was purified on ISCO system with a reverse phase C-18 column (43 g) eluting with 10-100% ACN/water with 0.05% TFA (25 min) to give the title compound. LC-MS [M]$^+$: m/z 1048.1.

Step I: (3S)-3-(2-((2-(4-(1-(3-aminopropyl)-2-methyl-1H-pyrazol-2-ium-4-yl)phenoxy)-2-carboxyethoxy)imino)-2-(2-aminothiazol-4-yl)acetamido)-2,2-dimethyl-4-oxoazetidin-1-yl sulfate (84)

To a solution of (3S)-3-(2-((3-(benzhydryloxy)-2-(4-(1-(3-((tert-butoxy-carbonyl)amino)propyl)-2-methyl-1H-pyrazol-2-ium-4-yl)phenoxy)-3-oxopropoxy)-imino)-2-(2-((tert-butoxycarbonyl)amino)thiazol-4-yl)acetamido)-2,2-dimethyl-4-oxoazetidin-1-yl sulfate (0.10 g, 0.095 mmol) in CH$_2$Cl$_2$ (3.2 ml) was added TFA (3.2 ml). The reaction solution was stirred at RT for 1.5 h, then the solvent was removed under reduced pressure. Ether was added to the resulting residue and solvent was again removed under reduced pressure. The resulting residue was dried under vacuum, and then dissolved in 4 mL of DMSO and purified on Gilson reverse phase (5-25% MeCN/water 0.05% TFA gradient) to give the title compounds. Example 84: LC-MS [M+H]$^+$: m/z 681.5. $^1$H-NMR (500 MHz, D$_2$O, ppm): δ 8.43 (s, 1H), 8.36 (s, 1H), 7.43 (d, J=10 Hz, 2H), 6.97 (s, 1H), 6.99 (d, J=10 Hz, 2H), 4.89 (br dd, 1H), 4.63 (m, 1H), 4.59 (s, 1H), 4.55 (m, 1H), 4.47 (t, J=10 Hz, 2H), 4.03 (s, 3H), 3.03 (t, J=5 Hz, 2H), 2.24 (m, 2H), 1.34 (s, 3H), 0.98 (s, 3H). Example 85: LC-MS [M+H]$^+$: m/z 681.5.

Example 86

(S)-3-(2-(2-aminothiazol-4-yl)-2-((2-(4-(4,5,6,7-tetrahydro-3H-imidazo[4,5-c]pyridin-2-yl)phenoxy)ethoxy)imino)acetamido)-2,2-dimethyl-4-oxoazetidin-1-yl hydrogen sulfate

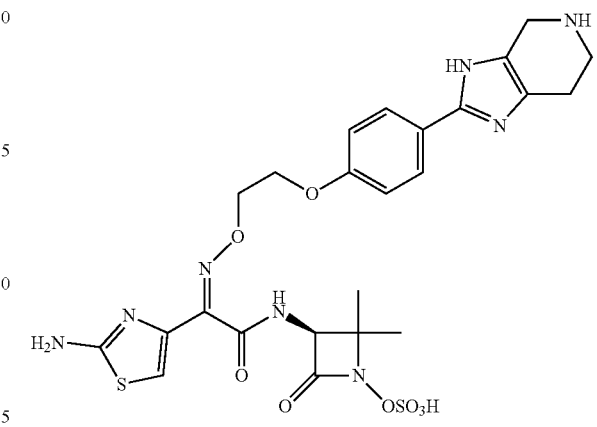

Step A: (3S,4R)-tert-butyl 3-azido-4-(((benzyloxy)carbonyl)amino)piperidine-1-carboxylate To a solution of (3R,4R)-tert-butyl 4-(((benzyloxy)carbonyl)amino)-3-hydroxypiperidine-1-carboxylate (2.0 g, 5.7 mmol) in CH$_2$Cl$_2$ (28 ml) were added TEA (1.6 ml, 11 mmol) and methanesulfonyl chloride (0.53 ml, 6.8 mmol) dropwise at 0° C. The reaction was stirred for 0.5 h, then diluted with CH$_2$Cl$_2$, washed with 1N HCl, saturated NaHCO$_3$ and brine, dried over MgSO$_4$, filtered and concentrated. The resulting residue was dissolved in DMF (28.5 ml), followed with addition of sodium azide (1.1 g, 17 mmol). The reaction mixture was stirred overnight at 80° C. Then the reaction mixture was cooled, diluted with EtOAc, washed with water and brine, dried over MgSO$_4$, filtered and concentrated. The resulting residue was purified using a ISCO silica gel column (40 g) eluting with 0-30% EA/hexane gradient to give the title compound.

Step B: (3S,4R)-tert-butyl 3,4-diaminopiperidine-1-carboxylate

To a solution of (3S,4R)-tert-butyl 3-azido-4-(((benzyloxy)carbonyl)amino)piperidine-1-carboxylate (1.5 g, 4.1 mmol) in MeOH (20 ml) was added Pd—C (0.15 g, 0.14 mmol). The reaction was stirred over the weekend at RT under a H$_2$ balloon. Then the reaction mixture was filtered through Celite™ using CH$_2$Cl$_2$, and concentrated to give the title compound.

Step C: (3aS,7aR)-tert-butyl 2-(4-(benzyloxy)phenyl)-3a,4,7,7a-tetrahydro-3H-imidazo[4,5-c]pyridine-5(6H)-carboxylate To a solution of 4-(benzyloxy)benzaldehyde (0.25 g, 1.2 mmol) in t-BuOH (12 ml), was added (3S,4R)-tert-butyl 3,4-diaminopiperidine-1-carboxylate (0.30 g, 1.4 mmol) at room temperature. The reaction was stirred for 30 min. Then Potassium carbonate (0.48 g, 3.5 mmol) and iodine (0.37 g, 1.45 mmol) were added and the reaction mixture was stirred at 70° C. for 3 h. The reaction mixture was cooled, then EtOAc was added and the mixture was washed with water and brine, dried over MgSO$_4$, filtered and concentrated to give the title compound. LC-MS [M+H]$^+$: m/z 408.5.

Step D: tert-butyl 2-(4-(benzyloxy)phenyl)-6,7-dihydro-3H-imidazo[4,5-c]pyridine-5(4H)-carboxylate To a 2M solution of oxalyl chloride (0.28 ml, 0.55 mmol) in CH$_2$Cl$_2$ under N$_2$ at −78° C. was added dropwise a solution of DMSO (0.073 ml, 1.03 mmol) in CH$_2$Cl$_2$ (0.2 ml).

The reaction was stirred for 5 min, then a solution of (3aS,7aR)-tert-butyl 2-(4-(benzyloxy)phenyl)-3a,4,7,7a-tetrahydro-3H-imidazo[4,5-c]pyridine-5(6H)-carboxylate (0.10 g, 0.24 mmol) in CH$_2$Cl$_2$ (0.5 ml) was added dropwise. The reaction was stirred for 1 h, then TEA (0.37 ml, 2.6 mmol) was added dropwise. Then the reaction mixture was allowed to warm to RT, and stirred for 2 h. Water was added and the mixture was extracted with DCM. The organic layers were combined, washed with brine and dried over MgSO$_4$, and concentrated in vacuo to give the title compound. LC-MS [M+H]$^+$: m/z 406.4.

Step E: di-tert-butyl 2-(4-(benzyloxy)phenyl)-6,7-dihydro-1H-imidazo[4,5-c]pyridine-1,5(4H)-dicarboxylate and di-tert-butyl 2-(4-(benzyloxy)phenyl)-6,7-dihydro-3H-imidazo[4,5-c]pyridine-3,5(4H)-dicarboxylate A mixture of tert-butyl 2-(4-(benzyloxy)phenyl)-6,7-dihydro-3H-imidazo[4,5-c]pyridine-5(4H)-carboxylate (0.2 g, 0.49 mmol), BOC-Anhydride (0.23 ml, 0.97 mmol), and DMAP (0.060 g, 0.49 mmol) was stirred at RT for 1.5 h. Then the mixture was concentrated and purified by ISCO silica gel column (12 g) eluting with 0-30% EA/hexane gradient to give the title compound. LC-MS [M+H]$^+$: m/z 506.5.

Step F: di-tert-butyl 2-(4-hydroxyphenyl)-6,7-dihydro-3H-imidazo[4,5-c]pyridine-3,5(4H)-dicarboxylate A mixture of di-tert-butyl 2-(4-(benzyloxy)phenyl)-6,7-dihydro-3H-imidazo[4,5-c]pyridine-3,5(4H)-dicarboxylate (0.17 g, 0.34 mmol), Pd/C (0.36 g, 0.34 mmol) and ammonium formate (0.10 g, 1.6 mmol) in MeOH (7 mL) was refluxed for 2 h. Then the mixture was filtered through Celite™ using CH$_2$C$_2$, and concentrated to give the title compound. LC-MS [M+H]$^+$: m/z 416.3.

Step G: di-tert-butyl 2-(4-(2-((1,3-dioxoisoindolin-2-yl)oxy)ethoxy)phenyl)-6,7-dihydro-3H-imidazo[4,5-c]pyridine-3,5(4H)-dicarboxylate To a solution of di-tert-butyl 2-(4-hydroxyphenyl)-6,7-dihydro-3H-imidazo[4,5-c]pyridine-3,5(4H)-dicarboxylate, 2-(2-hydroxyethoxy)isoindoline-1,3-dione (0.061 g, 0.29 mmol) and PPh$_3$ (0.085 g, 0.32 mmol) was added DEAD (0.15 ml, 0.32 mmol, 40% solution) in toluene at RT. The reaction was stirred at RT overnight. Then the mixture was concentrated and purified by ISCO silica gel column (12 g) eluting with 0-100% EA/hexane gradient to give the title compound. LC-MS [M+H]$^+$: m/z 605.4.

Step H: (3aS,7aR)-di-tert-butyl 2-(4-(2-(aminooxy)ethoxy)phenyl)-3a,4,7,7a-tetrahydro-3H-imidazo[4,5-c]pyridine-3,5(6H)-dicarboxylate To the solution of di-tert-butyl 2-(4-(2-((1,3-dioxoisoindolin-2-yl)oxy)ethoxy)phenyl)-6,7-dihydro-3H-imidazo[4,5-c]pyridine-3,5(4H)-dicarboxylate (0.18 g) in CH$_2$Cl$_2$ (1.5 ml) at RT was added hydrazine (11 µl) in EtOH (1.5 ml). The resulting solution was stirred at RT for 0.5 h, then diluted with DCM and washed with saturated NaHCO$_3$ solution 3 times. The aqueous phase was extracted with DCM once. The combined organic layers were washed with brine, dried over MgSO$_4$, filtered and concentrated under reduced pressure to give the title compound, which was used directly in the next step. LC-MS [M+H]$^+$: m/z 477.5.

Step I: 2-((2-(4-(3,5-bis(tert-butoxycarbonyl)-4,5,6,7-tetrahydro-3H-imidazo[4,5-c]pyridin-2-yl)phenoxy)ethoxy)imino)-2-(2-((tert-butoxycarbonyl)amino)thiazol-4-yl)acetic acid A solution of di-tert-butyl 2-(4-(2-(aminooxy)ethoxy)phenyl)-6,7-dihydro-3H-imidazo[4,5-c]pyridine-3,5(4H)-dicarboxylate (0.10 g, 0.22 mmol) and 2-(2-((tert-butoxycarbonyl)-amino)thiazol-4-yl)-2-oxoacetic acid (0.072 g, 0.27 mmol) in EtOH (1.5 ml) and CHCl$_3$ (0.74 ml) was stirred at RT for 1.5 h. Then the mixture was concentrated to give the title compound, which was used as is in next step. LC-MS [M+H]$^+$: m/z 729.5.

Step J: (S)-di-tert-butyl 2-(4-(2-(((1-(2-((tert-butoxycarbonyl)amino)thiazol-4-yl)-2-((2,2-dimethyl-4-oxo-1-(sulfooxy)azetidin-3-yl)amino)-2-oxoethylidene)amino)oxy)ethoxy)-phenyl)-6,7-dihydro-3H-imidazo[4,5-c]pyridine-3,5(4H)-dicarboxylate To a solution of 2-((2-(4-(3,5-bis(tert-butoxycarbonyl)-4,5,6,7-tetrahydro-3H-imidazo[4,5-c]pyridin-2-yl)phenoxy)ethoxy)imino)-2-(2-((tert-butoxycarbonyl)amino)thiazol-4-yl)acetic acid (0.16 g, 0.22 mmol) in DMF (2.2 ml) was added DCC (0.11 g, 0.55 mmol), and HOBt (0.085 g, 0.55 mmol). The resulting solution was stirred at RT for 30 min, then (S)-3-amino-2,2-dimethyl-4-oxoazetidin-1-yl hydrogen sulfate (0.093 g, 0.44 mmol) and sodium hydrogencarbonate (0.093 g, 1.1 mmol) were added. The resulting mixture was stirred at RT overnight, then filtered through a sintered syringe and washed with DMF (1.5 mL). The solution was purified using ISCO system with a reverse phase C-18 column (86 g) eluting with 10-100% ACN/water with 0.05% TFA to give the title compound. LC-MS [M-Boc]*: m/z 821.6.

Step K: (S)-3-(2-(2-aminothiazol-4-yl)-2-((2-(4-(4,5,6,7-tetrahydro-3H-imidazo[4,5-c]pyridin-2-yl)phenoxy)ethoxy)imino)acetamido)-2,2-dimethyl-4-oxoazetidin-1-yl hydrogen sulfate To a solution of (S)-di-tert-butyl 2-(4-(2-(((1-(2-((tert-butoxycarbonyl)amino)-thiazol-4-yl)-2-((2,2-dimethyl-4-oxo-1-(sulfooxy)azetidin-3-yl)amino)-2-oxoethylidene)-amino)oxy)ethoxy)phenyl)-6,7-dihydro-3H-imidazo[4,5-c]pyridine-3,5(4H)-dicarboxylate (0.075 g, 0.081 mmol) in CH$_2$Cl$_2$ (1.357 ml) was added TFA (1.4 ml). The reaction mixture was stirred at RT for 1.5 h, then the solvent was removed under reduced pressure. The resulting residue was dried in vacuo, then dissolved in 4 mL of DMSO and purified by Gilson reverse phase separation (5-25% MeCN/ water 0.05% TFA gradient) to give the title compound. LC-MS [M+H]⁺: m/z 621.4. ¹H-NMR (500 MHz, D₂O, ppm): δ 7.66 (d, J=10 Hz, 2H), 7.05 (d, J=10 Hz, 2H), 6.91 (s, 1H), 4.63 (s, 1H), 4.50 (m, 2H), 4.35 (s, 2H), 4.33 (m, 2H), 3.55 (t, J=5 Hz, 2H), 3.00 (t, J=5 Hz, 2H), 2.24 (m, 2H), 1.34 (s, 3H), 0.98 (s, 3H).

Example 87

(S)-3-((Z)-2-((((S)-1-(4-(6-((2-aminoethyl)amino)-1-methylpyridin-1-ium-3-yl)phenoxy)-2-carboxypropan-2-yl)oxy)imino)-2-(2-aminothiazol-4-yl)acetamido)-2,2-dimethyl-4-oxoazetidin-1-yl sulfate

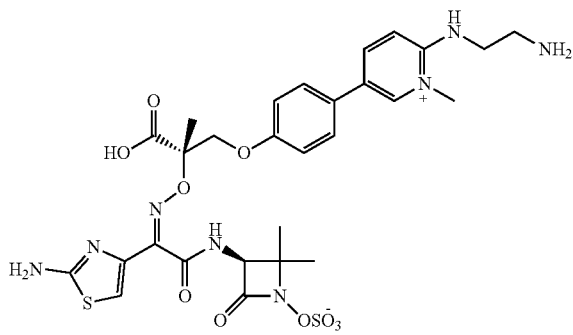

Step A: (S)-tert-butyl 2-(aminooxy)-3-(4-(6-((2-((tert-butoxycarbonyl)amino)ethyl) amino)pyridin-3-yl)phenoxy)-2-methylpropanoate A mixture of (S)-tert-butyl 2-(aminooxy)-3-(4-bromophenoxy)-2-methylpropanoate (0.5 g, 1.4 mmol), bis(pinacolato)-diboron (0.38 g, 1.5 mmol), potassium acetate (0.42 g, 4.3 mmol), and 1,1'-bis(di-tert-butylphosphino)ferrocene palladium dichloride (0.14 g, 0.22 mmol) in dioxane (7.2 ml) was degassed three times via vacuum/N₂ refills. The reaction was heated at 70° C. overnight. Then the reaction mixture was cooled, and 1,1'-bis(di-tert-butylphosphino)ferrocene palladium dichloride (0.094 g, 0.1 eq), tert-butyl (2-((5-bromopyridin-2-yl)amino)ethyl)-carbamate (first eluent from chiral SFC separation of intermediate 10 using OD-H, 4.6×250 mm, 20% MeOH/CO₂, 2.5 m/min, 100 bar, 35° C.) (0.50 g, 1.6 mmol), and 1M solution of potassium phosphate tribasic (4.3 ml, 4.3 mmol) in water were added. The mixture was degassed three times by vacuum/N₂ refills, then heated at 70° C. for 5 h. Then the reaction mixture was filtered through Celite™, and the filtrate was concentrated. The resulting residue was purified by ISCO (40 g) using 0-100% EA/hex to give the product, which was purified again by ISCO (40 g) using 0-30% 3:1 EA; EtOH/hex to give the title compound. LC-MS [M+H]⁺: m/z 503.6.

Step B: (S)-tert-butyl 3-(4-(6-((2-((tert-butoxycarbonyl)amino)ethyl)amino)pyridin-3-yl)phenoxy)-2-((1,3-dioxoisoindolin-2-yl)oxy)-2-methylpropanoate A mixture of (S)-tert-butyl 2-(aminooxy)-3-(4-(6-((2-((tert-butoxycarbonyl)amino)ethyl)amino)pyridin-3-yl)phenoxy)-2-methylpropanoate (0.25 g, 0.50 mmol), isobenzofuran-1,3-dione (0.074 g, 0.50 mmol), and TEA (0.069 ml, 0.50 mmol) in toluene (4.97 ml) was heated at 120° C. for 1.5 h. Then the mixture was cooled to RT and concentrated.

The resulting residue was purified by ISCO silica gel column (24 g) eluting with 0-100% EA/hexane gradient to give the title compound. LC-MS [M+H]⁺: m/z 633.4.

Step C: (S)-5-(4-(3-(tert-butoxy)-2-((1,3-dioxoisoindolin-2-yl)oxy)-2-methyl-3-oxo-propoxy)phenyl)-2-((2-((tert-butoxycarbonyl)amino)ethyl)amino)-1-methylpyridin-1-ium iodide To a solution of (S)-tert-butyl 3-(4-(6-((2-((tert-butoxycarbonyl)amino)ethyl)-amino)pyridin-3-yl)phenoxy)-2-((1,3-dioxoisoindolin-2-yl)oxy)-2-methylpropanoate (0.13 g, 0.20 mmol) in acetonitrile (2.0 ml) was added MeI (0.102 ml, 1.6 mmol). The reaction was stirred at 75° C. for 3 h, then concentrated to give the title compound. LC-MS [M]⁺: m/z 648.4.

Step D: (S)-3-((Z)-2-((((S)-1-(4-(6-((2-aminoethyl)amino)-1-methylpyridin-1-ium-3-yl)phenoxy)-2-carboxypropan-2-yl)oxy)imino)-2-(2-aminothiazol-4-yl)acetamido)-2,2-dimethyl-4-oxoazetidin-1-yl sulfate (S)-5-(4-(3-(tert-butoxy)-2-((1,3-dioxoisoindolin-2-yl)oxy)-2-methyl-3-oxopropoxy)phenyl)-2-((2-((tert-butoxycarbonyl)amino)ethyl)amino)-1-methylpyridin-1-ium iodide was converted to the title compound following a procedure similar to the procedure from Example 1 Step E through Step H. H-NMR (500 MHz, D₂O, ppm): δ 8.15 (d, J=10 Hz, 1H), 8.11 (s, 1H), 7.40 (d, J=10 Hz, 2H), 7.15 (d, J=10 Hz, 1 H), 6.97 (d, J=10 Hz, 2H), 6.90 (s, 1H), 4.50 (s, 1H), 4.44 (d, J=15 Hz, 1H), 4.30 (d, J=15 Hz, 1H), 3.80 (s, 3H), 3.73 (t, J=5 Hz, 2H), 3.20 (t, J=5 Hz, 2H), 1.54 (s, 3H), 1.31 (s, 3H), 1.10 (s, 3H). LC-MS [M+H]⁺: m/z 707.4.

Example 88

(S)-3-((Z)-2-(((S)-2-(4-(6-(3-aminopropyl)-1-methylpyridin-1-ium-3-yl)phenoxy)-1-carboxyethoxy)imino)-2-(2-aminothiazol-4-yl)acetamido)-2,2-dimethyl-4-oxoazetidin-1-yl sulfate

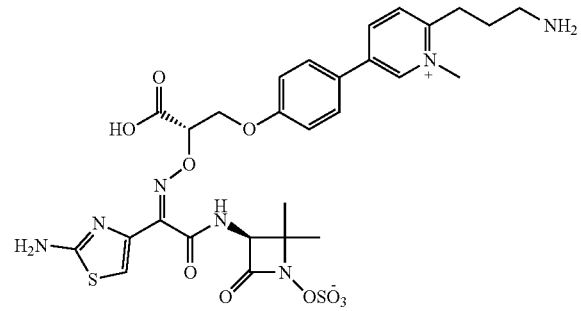

Step A: tert-butyl (3-(5-bromopyridin-2-yl)prop-2-yn-1-yl)carbamate

A mixture of 2,5-dibromopyridine (0.76 g, 3.2 mmol), tert-butyl prop-2-yn-1-ylcarbamate (0.5 g, 3.2 mmol), palladium dichloride diphenylphosphine (0.045 g, 0.064 mmol) and copper(I) iodide (0.012 g, 0.064 mmol) in TEA (10 ml, 72 mmol) was cooled in an ice bath for 1 h. Then the reaction was stirred at RT for 1 h. The reaction mixture was diluted with $Et_2O$, washed with water (4×), brine, dried over $MgSO_4$, filtered and concentrated. The resulting residue was purified by ISCO 40 g (0-30% EA/hex) to give the title compound.

Step B: (R)-tert-butyl 3-(4-(6-(3-((tert-butoxycarbonyl)amino)prop-1-yn-1-yl)pyridin-3-yl)phenoxy)-2-hydroxypropanoate To a solution of (R)-tert-butyl 2-hydroxy-3-(4-(4,4,5,5-tetramethyl-1,3,2-dioxaborolan-2-yl)phenoxy)propanoate (0.4 g, 1.1 mmol), tert-butyl (3-(5-bromopyridin-2-yl)prop-2-yn-1-yl)carbamate (0.38 g), and 1,1'-bis(di-tert-butylphosphino)-ferrocene palladium dichloride (0.072 g, 0.11 mmol) in THF (5.5 ml) in a microwave vial was added the 1M aqueous solution of potassium phosphate (3.3 ml, 3.3 mmol). The microwave vial was sealed, degassed (3×), refilled with $N_2$, and stirred at 70° C. for 3 h. Then the reaction mixture was diluted with saturated $NH_4Cl$ solution, and extracted with EtOAc. The organic layers were combined, dried over $MgSO_4$ and concentrated to dryness. The resulting residue was purified by ISCO silica gel column (24 g) eluting with EtOAc/Hexane gradient (0-60%) to give the title compound. LC-MS $[M-Boc]^+$: m/z 413.3.

Step C: (R)-tert-butyl 3-(4-(6-(3-((tert-butoxycarbonyl)amino)propyl)pyridin-3-yl)phenoxy)-2-hydroxypropanoate A mixture of (R)-tert-butyl 3-(4-(6-(3-((tert-butoxycarbonyl)-amino)prop-1-yn-1-yl)pyridin-3-yl)phenoxy)-2-hydroxypropanoate (0.33 g, 0.71 mmol) and Pd—C (0.067 g, 0.63 mmol) in MeOH (3.6 ml) was stirred at RT under a $H_2$ balloon overnight. The reaction mixture was filtered through Celite™ using $CH_2Cl_2$, and the filtrate was concentrated to give the title compound. LC-MS $[M+H]^+$: m/z 473.0.

Step D: (S)-3-((Z)-2-(((S)-2-(4-(6-(3-aminopropyl)-1-methylpyridin-1-ium-3-yl)phenoxy)-1-carboxyethoxy)imino)-2-(2-aminothiazol-4-yl)acetamido)-2,2-dimethyl-4-oxoazetidin-1-yl sulfate (R)-tert-butyl 3-(4-(6-(3-((tert-butoxycarbonyl)amino) propyl)pyridin-3-yl)phenoxy)-2-hydroxypropanoate was converted to the title compound following a procedure similar to the procedure from Example 1 Step C through Step H. $^1$H-NMR (500 MHz, $D_2O$, ppm): δ 8.85 (s, 1H), 8.49 (d, J=5 Hz, 1H), 7.82 (d, J=5 Hz, 1H), 7.56 (d, J=10 Hz, 2H), 7.02 (d, J=10 Hz, 2H), 6.98 (s, 1H), 5.01 (s, 1H), 4.47 (m, 3H), 4.19 (s, 3H), 3.10 (m, 4H), 2.09 (m, 2H), 1.31 (s, 3H), 0.92 (s, 3H). LC-MS $[M+H]^+$: m/z 692.5.

Example 89

(S)-3-((Z)-2-((((R)-1-(4-(6-((2-aminoethyl)amino)-1-methylpyridin-1-ium-3-yl)phenoxy)-3-hydroxypropan-2-yl)oxy)imino)-2-(2-aminothiazol-4-yl)acetamido)-2,2-dimethyl-4-oxoazetidin-1-yl sulfate

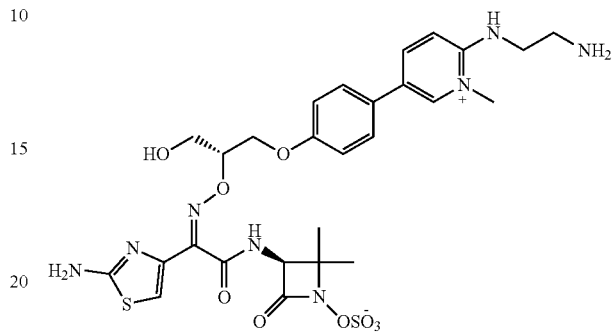

Step A: (R)-4-((4-bromophenoxy)methyl)-2,2-dimethyl-1,3-dioxolane

To a solution of (R)-(2,2-dimethyl-1,3-dioxolan-4-yl) methanol (5.0 g, 38 mmol), triphenylphosphine (13 g, 49 mmol) and 4-bromophenol (15 g, 87 mmol) in toluene (200 mL), was added DEAD (6.0 mL, 38 mmol). The reaction was warmed to 70° C. and stirred for 18 h. Then the reaction mixture was evaporated and purified by silica-gel chromatography ($SiO_2$, EA:PE=0% to 5%) to give the title compound.

Step B: (S)-3-(4-bromophenoxy)propane-1,2-diol

To a solution of (R)-4-((4-bromophenoxy)methyl)-2,2-dimethyl-1,3-dioxolane (9 g, 31 mmol) in MeOH (150 mL) was added Amberlyst-15 (660 mg). The reaction was stirred for 24 h at 25° C., then the Amberlyst-15 was filtered off, and the filtrate was concentrated. The resulting residue was purified by silica-gel chromatography ($SiO_2$, EtOAc/hexane 2:1 to 4:1) to give the title compound.

Step C: (R)-1-(4-bromophenoxy)-3-(trityloxy)propan-2-ol

To a solution of (S)-3-(4-bromophenoxy)propane-1,2-diol (5 g, 20 mmol) and TBAI (2.2 g, 6.1 mmol) in $CH_2Cl_2$ (100 mL) was added DIPEA (11 mL, 61 mmol). Then (chloro methanetriyl)tribenzene (6.2 g, 22 mmol) was added at 25° C., and the reaction mixture was stirred for 18 h at 25° C. The reaction was quenched by the addition of 3M aqueous HCl (50 mL). The organic layer was separated, washed with saturated $NaHCO_3$ (50 mL) and saturated brine (50 mL), dried over $Na_2SO_4$ and filtered. The filtrate was concentrate, and the resulting residue was purified by silica-gel chromatography ($SiO_2$, EtOAc/PE 1:10 to 1:4) to give the title compound.

Step D: (R)-1-(4-(4,4,5,5-tetramethyl-1,3,2-dioxaborolan-2-yl)phenoxy)-3-(trityloxy)propan-2-ol To a solution of (R)-1-(4-bromophenoxy)-3-(trityloxy) propan-2-ol (3 g, 6.1 mmol) in DMF (50 mL) was added 4,4,4',4',5,5,5',5'-octamethyl-2,2'-bi(1,3,2-dioxaborolane) (1.7 g, 6.7 mmol), potassium acetate (1.8 g, 18 mmol, 3 eq.) and PdCl$_2$(dppf) (0.31 g, 0.43 mmol).

The reaction was purged with nitrogen and heated for 10 h at 90° C. Then the reaction mixture was diluted with 500 mL EtOAc and filtered. The filtrate was washed with 2×300 mL water. The organic layer was separated, dried over sodium sulfate, filtered and concentrated. The resulting residue was purified by silica-gel chromatography (SiO$_2$, EA:PE=0% to 20%) to give the title compound. LC-MS [M+H]$^+$: m/z 359.2.

Step E: (R)-tert-butyl (2-((5-(4-(2-hydroxy-3-(trityloxy)propoxy)phenyl)pyridin-2-yl)amino)ethyl)carbamate To the solution of PdCl$_2$(dppf)-CH$_2$Cl$_2$ (78 mg, 0.095 mmol), tert-butyl (2-((5-bromopyridin-2-yl)amino)ethyl) carbamate (300 mg) and (R)-1-(4-(4,4,5,5-tetramethyl-1,3,2-dioxaborolan-2-yl)phenoxy)-3-(trityloxy)propan-2-ol (510 mg, 0.95 mmol) in dioxane (4.5 ml) was added Na$_2$CO$_3$ (300 mg, 2.8 mmol) in water (1.5 ml). The resulting mixture was N$_2$/vacuum exchanged 3 times, then heated at 100° C. under microwave reaction conditions for 1 h. Then the reaction mixture was cooled and diluted with EtOAc, dried (MgSO$_4$), filtered, and concentrated. The resulting residue was purified on silica gel column (ISCO gold, 80 g) using 0-100% EtOAc/hexane to give the title compound. LC-MS [M+H]$^+$: m/z 646.6.

Step F: (S)-3-((Z)-2-((((R)-1-(4-(6-((2-aminoethyl)amino)-1-methylpyridin-1-ium-3-yl)phenoxy)-3-hydroxypropan-2-yl)oxy)imino)-2-(2-aminothiazol-4-yl)acetamido)-2,2-dimethyl-4-oxoazetidin-1-yl sulfate (R)-tert-butyl (2-((5-(4-(2-hydroxy-3-(trityloxy)-propoxy) phenyl)pyridin-2-yl)amino)ethyl)carbamate was converted to the title compound as a TFA salt following a procedure similar to the procedure of Example 1 Step C through Step H. LC-MS [M+H]$^+$: m/z 679.6. $^1$H-NMR (500 MHz, D$_2$O, ppm): δ 8.15 (d, J=10 Hz, 1H), 8.11 (s, 1H), 7.41 (d, J=10 Hz, 2H), 7.14 (d, J=10 Hz, 1H), 6.96 (d, J=10 Hz, 2H), 6.82 (s, 1H), 4.55 (s, 1H), 4.33 (d, J=10 Hz, 1H), 4.17 (dd, J=10, 5 Hz, 1H), 3.82 (m, 2H), 3.80 (s, 3H), 3.71 (t, J=5 Hz, 2H), 3.19 (t, J=5 Hz, 2H), 1.33 (s, 3H), 0.95 (s, 3H).

Example 90

(S)-3-((Z)-2-((((S)-1-(4-(6-((2-aminoethyl)amino)-1-methylpyridin-1-ium-3-yl)phenoxy)propan-2-yl)oxy) imino)-2-(2-aminothiazol-4-yl)acetamido)-2,2-dimethyl-4-oxoazetidin-1-yl sulfate

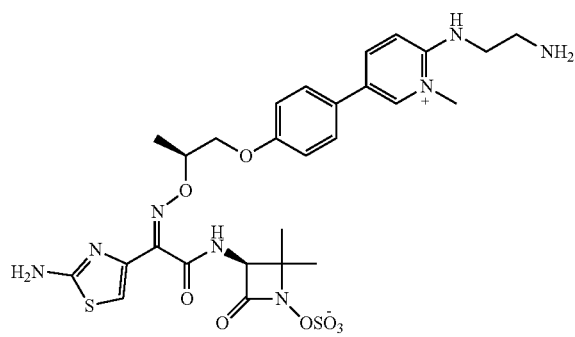

Step A: (R)-1-(4-bromophenoxy)propan-2-ol

To a solution of 4-bromophenol (1.8 g, 11 mmol) in DMF (25 ml) was added K$_2$CO$_3$ (2.9 g, 21 mmol) and (R)-1-chloropropan-2-ol (2.0 g, 21 mmol). The reaction was stirred and heated at 140° C. for 48 hours. TLC showed a new spot formed. The reaction mixture was diluted with water (80 mL), and extracted with EtOAc (100 mL*3). The combined organic layers were dried over Na$_2$SO$_4$, filtered, concentrated in vacuum. The resulting residue was purified by column chromatography (SiO$_2$, EtOAc/PE=0% to 15%) to give the title compound Step B: (R)-1-(4-(4,4,5,5-tetramethyl-1,3,2-dioxaborolan-2-yl)phenoxy)propan-2-ol (R)-1-(4-bromophenoxy)propan-2-ol was converted to (R)-1-(4-(4,4,5,5-tetramethyl-1,3,2-dioxaborolan-2-yl)phenoxy)propan-2-ol following the same procedure as the procedure of Example 89 Step D.

Step C: (R)-tert-butyl (2-((5-(4-(2-hydroxypropoxy) phenyl)pyridin-2-yl)amino)ethyl)-carbamate To the solution of PdCl$_2$(dppf)-CH$_2$Cl$_2$ adduct (88 mg, 0.11 mmol), tert-butyl (2-((5-bromopyridin-2-yl)amino) ethyl)carbamate (340 mg) and (R)-1-(4-(4,4,5,5-tetramethyl-1,3,2-dioxaborolan-2-yl)phenoxy)propan-2-ol (300 mg, 1.1 mmol) in dioxane (4.5 ml) was added Na$_2$CO$_3$ (340 mg, 3.2 mmol) in water (1.5 ml). The resulting mixture was N$_2$/vacuum exchanged 3 times, then heated at 100° C. under microwave reaction conditions for 1 h. Then the reaction was cooled and diluted with EtOAc, dried (MgSO$_4$), filtered, and concentrated. The resulting residue was purified on silica gel column (ISCO gold, 80 g) using 0-100% EtOAc/hexane to give the title compound. LC-MS [M+H]$^+$: m/z 388.4.

Step D: (S)-tert-butyl (2-((5-(4-(2-((1,3-dioxoisoindolin-2-yl)oxy)propoxy)phenyl)pyridin-2-yl)amino) ethyl)carbamate To a solution of (R)-tert-butyl (2-((5-(4-(2-hydroxypropoxy)-phenyl)pyridin-2-yl)amino)ethyl)carbamate (210 mg, 0.54 mmol) in THF (4 ml) was added 2-hydroxyisoindoline-1,3-dione (106 mg, 0.65 mmol), triphenylphosphine (200 mg, 0.76 mmol), followed by the dropwise addition of DIAD (0.15 ml, 0.76 mmol). The resulting solution was stirred at rt for 1 h, then concentration. The resulting residue was purified on silica gel column (ISCO gold 80 g) using 0-100% EtOAc/hexane gradient to give the title compound. LC-MS [M+H]$^+$: m/z 533.3.

Step E: (S)-3-((Z)-2-((((S)-1-(4-(6-((2-aminoethyl) amino)-1-methylpyridin-1-ium-3-yl)phenoxy)propan-2-yl)oxy)imino)-2-(2-aminothiazol-4-yl)acetamido)-2,2-dimethyl-4-oxoazetidin-1-yl sulfate (S)-tert-butyl (2-((5-(4-(2-((1,3-dioxoisoindolin-2-yl) oxy)-propoxy)phenyl)pyridin-2-yl)amino)ethyl)carbamate was converted to the title compound as a formic acid salt following a procedure similar to the procedure of Example 1 Step D through Step H. $^1$H-NMR (500 MHz, D$_2$O, ppm): δ 8.06 (d, J=10 Hz, 1H), 8.00 (s, 1H), 7.33 (d, J=10 Hz, 2H), 7.06 (d, J=10 Hz, 1H), 6.95 (d, J=10 Hz, 2H), 6.67 (s, 1H), 4.51 (m, 1H), 4.47 (s, 1H), 4.08 (d, J=10 Hz, 1H), 3.95 (dd, J=10, 5 Hz, 1H), 3.73 (s, 3H), 3.68 (t, J=5 Hz, 2H), 3.17 (t, J=5 Hz, 2H), 1.21 (s, 3H), 1.18 (d, J=5 Hz, 3H), 0.92 (s, 3H). LC-MS [M+H]⁺: m/z 663.6.

Example 91

(3S)-3-(2-((2-((4-(1-(3-aminopropyl)-2-methyl-1H-pyrazol-2-ium-4-yl)phenyl)amino)-1-carboxyethoxy)imino)-2-(2-aminothiazol-4-yl)acetamido)-2,2-dimethyl-4-oxoazetidin-1-yl sulfate

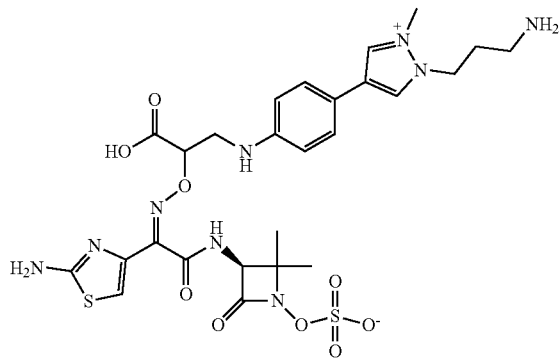

Step A: tert-butyl oxirane-2-carboxylate

To a mixture of tert-butyl acrylate (10 g, 78 mmol) in DCM (100 mL) was added 80% m-CPBA (30 g, 140 mmol) in DCM (140 mL). The reaction mixture was stirred at 40° C. for 48 h. Then the reaction was cooled to 0° C. and saturated aqueous Na₂SO₃ solution (300 mL) was added dropwise. The organic layer was separated, washed with saturated aqueous NaHCO₃ (2×200 mL) and saturated brine (200 mL), dried over Na₂SO₄, filtered and concentrated in vacuo to give the title compound, which was used directly in the next step without purification Step B: tert-butyl 3-((4-bromophenyl)amino)-2-hydroxypropanoate To a mixture of 4-bromoaniline (4.0 g, 23 mmol) in acetonitrile (80 mL) was added tert-butyl oxirane-2-carboxylate (5.0 g, 35 mmol) and lithium trifluoro methanesulfonate (5.4 g, 35 mmol). The reaction mixture was stirred at 60° C. under N₂ for 15 h, then the reaction was diluted with EtOAc (100 mL) and water (120 mL). The aqueous layer was separated and extracted with EtOAc (3×50 mL). The combined organic layers were dried over Na₂SO₄, filtered and concentrated in vacuo. The resulting residue was purified by column chromatography (SiO₂, PE:EtOAc=100:1 to 5:1) to give the title compound. LC-MS [M+H]⁺: m/z 316.2.

Step C: tert-butyl 3-((4-bromophenyl)amino)-2-((tert-butyldimethylsilyl)oxy)propanoate To a solution of tert-butyl 3-((4-bromophenyl)amino)-2-hydroxypropanoate (3.3 g, 10 mmol) and DBU (3.2 mL, 21 mmol) in CH₃CN (50 mL) was added tert-butylchlorodimethylsilane (2.4 g, 16 mmol). The reaction mixture was stirred at 25° C. for 2 h, then concentrated in vacuo. The resulting residue was purified by column chromatography (SiO₂, PE:EtOAc=100:1 to 10:1) to give the title compound. LC-MS [M+H]⁺: m/z 430.0.

Step D: tert-butyl 3-((4-bromophenyl)(tert-butoxycarbonyl)amino)-2-((tert-butyldimethylsilyl)-oxy)propanoate A solution of tert-butyl 3-((4-bromophenyl)amino)-2-((tert-butyldimethyl-silyl)oxy) propanoate (4.4 g, 10 mmol) in (Boc)₂O (50 mL) was stirred at 125° C. for 1 h. The reaction mixture was cooled and the solvent was removed. The resulting residue was purified by column chromatography (SiO₂, PE:EtOAc=100:1 to 10:1) to give the title compound. LC-MS [M+H]⁺: m/z 554.1.

Step E: tert-butyl 3-((tert-butoxycarbonyl)(4-(1-(3-((tert-butoxycarbonyl)amino)propyl)-1H-pyrazol-4-yl)phenyl)amino)-2-((tert-butyldimethylsilyl)oxy) propanoate To a solution of tert-butyl 3-((4-bromophenyl)(tert-butoxycarbonyl)amino)-2-((tert-butyldimethylsilyl)-oxy)propanoate (0.50 g, 0.94 mmol)), tert-butyl (3-(4-(4,4,5,5-tetramethyl-1,3,2-dioxaborolan-2-yl)-1H-pyrazol-1-yl)propyl)carbamate (0.33 g, 0.94 mmol)), and 1,1'-bis(di-tert-butylphosphino)ferrocene palladium dichloride (0.061 g, 0.094 mmol)) in dioxane (4.71 ml) in a microwave vial was added the 1 M aqueous solution of potassium phosphate (2.8 ml, 2.8 mmol). The microwave vial was sealed, degassed, filled with N₂, and stirred at 70° C. overnight. Then the reaction mixture was filtered and the filtrate was diluted with water, and extracted with EtOAc. The organic layer was dried over MgSO₄, filtered and concentrated. The resulting residue was purified by ISCO silica gel column (12 g) eluting with 0-100% EA/hexane gradient to give the title compound. LC-MS [M+H]⁺: m/z 675.9.

Step F: tert-butyl 3-((tert-butoxycarbonyl)(4-(1-(3-((tert-butoxycarbonyl)amino)propyl)-1H-pyrazol-4-yl)phenyl)amino)-2-hydroxypropanoate To a solution of tert-butyl 3-((tert-butoxycarbonyl)(4-(1-(3-((tert-butoxycarbonyl)amino)propyl)-1H-pyrazol-4-yl)phenyl)amino)-2-((tert-butyldimethylsilyl)oxy)propanoate (0.57 g, 0.85 mmol) in THF (4.25 ml) was added 1M TBAF (0.85 ml, 0.85 mmol, THF solution). The reaction was stirred at RT for 1 h, and then concentrated. The resulting residue was purified by ISCO silica gel column (12 g) eluting with 0-100% EA/hexane gradient to give the title compound. LC-MS [M+H]⁺: m/z 561.5.

Step G: tert-butyl 3-((tert-butoxycarbonyl)(4-(1-(3-((tert-butoxycarbonyl)amino)propyl)-1H-pyrazol-4-yl)phenyl)amino)-2-((1,3-dioxoisoindolin-2-yl)oxy)propanoate To a solution of tert-butyl 3-((tert-butoxycarbonyl)(4-(1-(3-((tert-butoxycarbonyl)amino)propyl)-1H-pyrazol-4-yl)phenyl)amino)-2-hydroxypropanoate (0.36 g, 0.65 mmol) in THF (6.5 ml) were added 2-hydroxyisoindoline-1,3-dione (0.12 g, 0.71 mmol), triphenylphosphine (0.20 g, 0.78 mmol) and DIAD (0.15 ml, 0.78 mmol). The reaction was stirred at RT for 2 h, then concentrated and purified by ISCO silica gel column (12 g) eluting with 0-100% EtOAc in Hexanes to give the title compound. LC-MS [M+H]⁺: m/z 706.6.

Step H: (3S)-3-(2-((2-((4-(1-(3-aminopropyl)-2-methyl-1H-pyrazol-2-ium-4-yl)phenyl)amino)-1-carboxyethoxy)imino)-2-(2-aminothiazol-4-yl)acetamido)-2,2-dimethyl-4-oxoazetidin-1-yl sulfate tert-butyl 3-((tert-butoxycarbonyl)(4-(1-(3-((tert-butoxycarbonyl)amino)propyl)-1H-pyrazol-4-yl)phenyl)amino)-2-((1,3-dioxoisoindolin-2-yl)oxy)propanoate was converted to the title compound as a TFA salt following a procedure similar to the procedure of Example 1 Step D through Step H. $^1$H-NMR (500 MHz, D$_2$O, ppm): δ 8.39 (s, 1H), 8.35 (s, 1H), 7.35 (d, J=10 Hz, 2H), 6.88 (s, 1H), 6.76 (d, J=10 Hz, 2H), 4.78 (m, 1H), 4.67 (s, 1H), 4.46 (t, J=5 Hz, 2H), 4.03 (s, 3H), 3.61 (m, 2H), 3.03 (t, J=5 Hz, 2H), 2.24 (m, 2H), 1.28 (s, 3H), 1.05 (s, 3H). LC-MS [M+H]$^+$: m/z 680.6.

Example 92

(3S)-3-(2-((2-((4-(1-(3-aminopropyl)-2-methyl-1H-pyrazol-2-ium-4-yl)phenyl)(methyl)amino)-1-carboxyethoxy)imino)-2-(2-aminothiazol-4-yl)acetamido)-2,2-dimethyl-4-oxoazetidin-1-yl sulfate

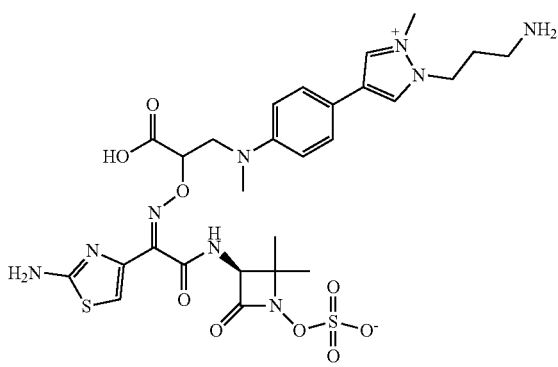

Step A: 4-bromo-N-methylaniline

To a mixture of 4-bromoaniline (5.0 g, 29 mmol) and Cs$_2$CO$_3$ (9.5 g, 29 mmol) in DMF (60 mL) was added CH$_3$I (2.7 mL, 44 mmol). The reaction mixture was stirred at 25° C. for 2 h, then diluted with EtOAc (100 mL) and water (200 mL). The aqueous layer was extracted with EtOAc (3×50 mL). The combined organic layers were dried over Na$_2$SO$_4$, filtered and concentrated in vacuo. The resulting residue was purified by column chromatography (SiO$_2$, PE:EtOAc=100:1 to 10:1) to give the title compound. LC-MS [M+H]$^+$: m/z 186.0.

Step B: tert-butyl 3-((4-bromophenyl)(methyl)amino)-2-hydroxypropanoate

To a mixture of 4-bromo-N-methylaniline (2.2 g, 12 mmol) in CH$_3$CN (50 mL) was added tert-butyl oxirane-2-carboxylate (2.6 g, 18 mmol) and lithium trifluoromethanesulfonate (2.8 g, 18 mmol). The reaction mixture was stirred at 65° C. under N$_2$ for 15 h, then diluted with EtOAc (30 mL) and water (50 mL). The aqueous layer was extracted with EtOAc (3×30 mL). The combined organic layers were dried over Na$_2$SO$_4$, filtered and concentrated in vacuo. The resulting residue was purified by column chromatography (SiO$_2$, PE:EtOAc=100:1 to 5:1) to give the title compound. LC-MS [M+H]$^+$: m/z 330.0.

Step C: tert-butyl 3-((4-bromophenyl)(methyl)amino)-2-((tert-butyldimethylsilyl)oxy)-propanoate To a solution of tert-butyl 3-((4-bromophenyl)(methyl)amino)-2-hydroxypropanoate (3.8 g, 11.51 mmol) and DBU (2.081 mL, 13.81 mmol) in CH$_3$CN (50 mL) was added tert-butylchlorodimethylsilane (2.60 g, 17.26 mmol). The reaction mixture was stirred at 25° C. for 2 h, then concentrated in vacuo. The resulting residue was purified by column chromatography (SiO$_2$, PE:EtOAc=100:1 to 10:1) to give the title compound. LC-MS [M+H]$^+$: m/z 444.1.

Step D: (3S)-3-(2-((2-((4-(1-(3-aminopropyl)-2-methyl-1H-pyrazol-2-ium-4-yl)phenyl)(methyl)amino)-1-carboxyethoxy)imino)-2-(2-aminothiazol-4-yl)acetamido)-2,2-dimethyl-4-oxoazetidin-1-yl sulfate tert-Butyl 3-((4-bromophenyl)(methyl)amino)-2-((tert-butyldimethylsilyl)oxy)-propanoate was converted to the title compound as a TFA salt following a procedure similar to the procedure of Example 91. $^1$H-NMR (500 MHz, D$_2$O, ppm): δ 8.44 (s, 1H), 8.40 (s, 1H), 7.42 (d, J=10 Hz, 2H), 6.92 (d, J=10 Hz, 2H), 6.80 (s, 1H), 4.86 (m, 1H), 4.48 (t, J=5 Hz, 2H), 4.04 (s, 3H), 4.02 (dd, J=10.5 Hz, 1H), 3.83 (s, 1H), 3.72 (d, J=10 Hz, 1H), 3.05 (t, J=5 Hz, 2H), 2.89 (s, 3H), 2.26 (m, 2H), 1.28 (s, 3H), 1.05 (s, 3H). LC-MS [M+H]$^+$: m/z 694.5.

Example 93

(3S)-3-(2-((3-(4-(1-(3-aminopropyl)-2-methyl-1H-pyrazol-2-ium-4-yl)phenyl)-1-carboxypropoxy)imino)-2-(2-aminothiazol-4-yl)acetamido)-2,2-dimethyl-4-oxoazetidin-1-yl sulfate

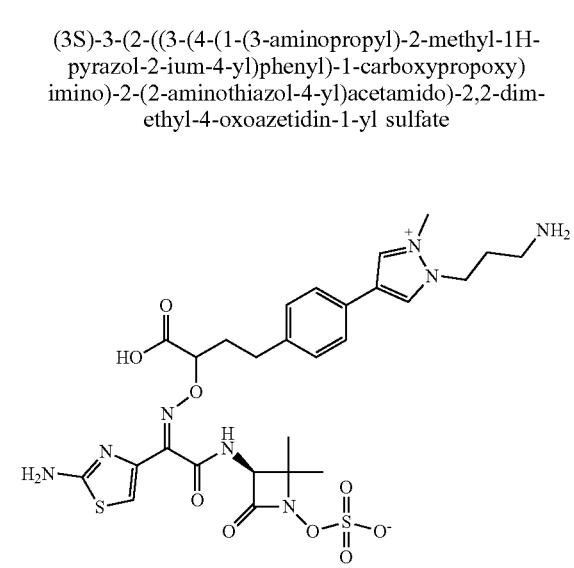

Step A: 4-(4-bromophenyl)-2-hydroxybutanoic acid

The mixture of (4-bromophenyl)-methanol (10 g, 54 mmol)), 2-hydroxypropanoic acid (5.8 g, 64 mmol), KOH (5.4 g, 96 mmol), nickel(II) acetate tetrahydrate (6.6 g, 27 mmol) and triphenylphosphine (14 g, 54 mmol) was stirred at 160° C. for 7.5 h under N$_2$. Then the mixture was cooled to 25° C., and H$_2$O (40 mL) and 1N HCl were added until the mixture pH was pH<3. The mixture was extracted with EtOAc (3*50 mL). The combined organic layers was dried with sodium sulfate, filtered and concentrated under reduced pressure. The resulting residue was purified by column chromatography (SiO$_2$, PE:EtOAC=28:72) to afford the title compound.

Step B: benzhydryl 4-(4-bromophenyl)-2-hydroxybutanoate

To a mixture of 4-(4-bromophenyl)-2-hydroxybutanoic acid (3.5 g, 6.8 mmol) in THF (40 ml) was added 3,3-diphenyl-3H-diazirine (1.3 g, 6.8 mmol). The reaction mixture was stirred at 25° C. for 16 h, then concentrated in vacuo. The resulting residue was purified by preparative HPLC to give the title compound.

Step C: benzhydryl 4-(4-bromophenyl)-2-hydroxybutanoate

Benzhydryl 4-(4-bromophenyl)-2-hydroxybutanoate (4.5 g, 11 mmol) was separated by SFC (Column: OJ (250 mm*50 mm, 10 μm) Mobile phase: A: CO$_2$ B: 0.1% NH$_3$H$_2$O EtOH Gradient: from 40% to 40% of B Flow rate: 200 mL/min Wavelength: 220 nm) to afford first isomer benzhydryl 4-(4-bromophenyl)-2-hydroxybutanoate, and the 2$^{nd}$ isomer benzhydryl 4-(4-bromophenyl)-2-hydroxybutanoate.

Step D: benzhydryl 4-(4-bromophenyl)-2-((tert-butyldimethylsilyl)oxy)butanoate To a mixture of benzhydryl 4-(4-bromophenyl)-2-hydroxybutanoate (2$^{nd}$ isomer from Step 3, 2.2 g, 5.2 mmol) in DMF (15 ml) was added 1H-imidazole (0.70 g, 10 mmol) and tert-butylchlorodimethylsilane (1.9 g, 13 mmol). The reaction mixture was stirred at 25° C. for 16 h under N$_2$. Then the solvent was removed in vacuo and the resulting residue was purified by column chromatography (SiO$_2$, PE:EtOAc=20:1-5:1) to give the title compound.

Step E: benzhydryl 4-(4-(1-(3-((tert-butoxycarbonyl)amino)propyl)-1H-pyrazol-4-yl)phenyl)-2-((tert-butyldimethylsilyl)oxy)butanoate To a solution of benzhydryl 4-(4-bromophenyl)-2-((tert-butyldimethylsilyl)oxy)butanoate, peak 2 (0.68 g, 1.3 mmol)), tert-butyl (3-(4-(4,4,5,5-tetramethyl-1,3,2-dioxaborolan-2-yl)-1H-pyrazol-1-yl)propyl)carbamate (0.45 g, 1.3 mmol), and 1,1'-bis(di-tert-butylphosphino)ferrocene palladium dichloride (0.082 g, 0.13 mmol) in dioxane (6.3 ml) was added the 1 M aqueous solution of potassium phosphate (3.8 ml, 3.8 mmol). The microwave vial was sealed, degassed, and refilled with N$_2$, and stirred at 70° C. overnight. Then the mixture was filtered and the filtrate was diluted with water, and extracted with EtOAc. The organic layer was dried over MgSO$_4$, filtered and concentrated. The resulting crude product was purified using an ISCO silica gel column (24 g) eluting with 0-50% EA/hexane gradient to give the title compound. LC-MS [M+H]$^+$: m/z 684.7.

Step F: benzhydryl 4-(4-(1-(3-((tert-butoxycarbonyl)amino)propyl)-1H-pyrazol-4-yl)phenyl)-2-hydroxybutanoate To a solution of benzhydryl 4-(4-(1-(3-((tert-butoxycarbonyl)amino)-propyl)-1H-pyrazol-4-yl)phenyl)-2-((tert-butyldimethylsilyl)oxy)butanoate (0.70 g, 1.03 mmol) in THF (5.1 ml) was added 1M TBAF (1.03 ml, 1.03 mmol) THF solution. The reaction was stirred at RT for 1 h, then concentrated and purified by ISCO silica gel column (24 g) eluting with 0-100% EA/hexane gradient to give the title compound. LC-MS [M+H]$^+$: m/z 570.6.

Step G: benzhydryl 4-(4-(1-(3-((tert-butoxycarbonyl)amino)propyl)-1H-pyrazol-4-yl)phenyl)-2-((1,3-dioxoisoindolin-2-yloxy)butanoate To a solution of benzhydryl 4-(4-(1-(3-((tert-butoxycarbonyl)amino)propyl)-1H-pyrazol-4-yl)phenyl)-2-hydroxybutanoate (0.41 g, 0.72 mmol) in THF (7.2 ml) were added 2-hydroxyisoindoline-1,3-dione (0.13 g, 0.79 mmol), triphenylphosphine (0.23 g, 0.86 mmol) and DIAD (0.17 ml, 0.86 mmol) at RT. The reaction was stirred for 1 h, then the mixture was concentrated and purified by ISCO silica gel column (24 g) eluting with 0-100% EA/hexane gradient to give the title compound. LC-MS [M+H]$^+$: m/z 715.5.

Step H: 4-(4-(4-(benzhydryloxy)-3-((1,3-dioxoisoindolin-2-yl)oxy)-4-oxobutyl)phenyl)-1-(3-((tert-butoxycarbonyl)amino)propyl)-2-methyl-1H-pyrazol-2-ium iodide To a solution of benzhydryl 4-(4-(1-(3-((tert-butoxycarbonyl)amino)propyl)-1H-pyrazol-4-yl)phenyl)-2-((1,3-dioxoisoindolin-2-yl)oxy)butanoate (0.51 g, 0.71 mmol) in acetonitrile (7.1 ml) was added MeI (0.36 ml, 5.7 mmol). The reaction was stirred at 70° C. overnight. Then the mixture was cooled and concentrated to give the title compound. LC-MS [M+H]$^+$: m/z 730.4.

Step I: (3S)-3-(2-((3-(4-(1-(3-aminopropyl)-2-methyl-1H-pyrazol-2-ium-4-yl)phenyl)-1-carboxypropoxy)imino)-2-(2-aminothiazol-4-yl)acetamido)-2,2-dimethyl-4-oxoazetidin-1-yl sulfate 4-(4-(4-(benzhydryloxy)-3-((1,3-dioxoisoindolin-2-yl)oxy)-4-oxobutyl)phenyl)-1-(3-((tert-butoxycarbonyl)amino)propyl)-2-methyl-1H-pyrazol-2-ium iodide was converted to the title compound as a TFA salt following a procedure similar to the procedure of Step E to Step H in Example 1. $^1$H-NMR (500 MHz, D$_2$O, ppm): δ 8.52 (s, 1H), 8.47 (s, 1H), 7.44 (d, J=10 Hz, 2H), 7.26 (d, J=10 Hz, 2H), 6.95 (s, 1H), 4.70 (m, 2H), 4.49 (t, J=5 Hz, 2H), 4.08 (s, 3H), 3.06 (t, J=5 Hz, 2H), 2.73-2.60 (m, 2H), 2.27 (t, J=5 Hz, 2H), 2.27-2.15 (m, 2H) 1.43 (s, 3H), 1.22 (s, 3H). LC-MS [M+H]$^+$: m/z 679.5.

Example 94

(2S)-3-(4-(2-((2-aminoethyl)amino)-1,4,5,6-tetrahydropyrimidin-5-yl)phenoxy)-2-(((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

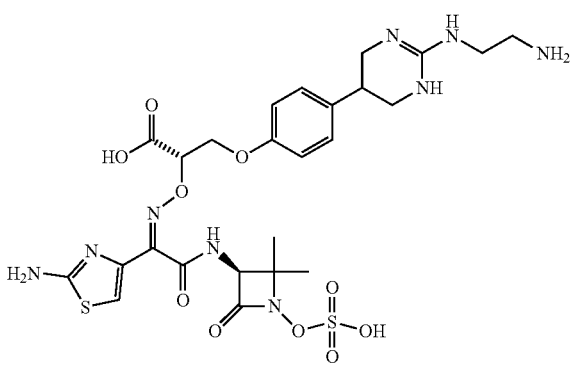 [SMILES: CC1(C)[C@H](NC(=O)/C(=N\O[C@@H](COc2ccc(C3CN=C(NCCN)NC3)cc2)C(=O)O)c2csc(N)n2)C(=O)N1OS(=O)(=O)O]

Step A: 4-(1,3-dinitropropan-2-yl)phenol

To a solution of 4-hydroxybenzaldehyde (5 g, 41 mmol), bis(triphenylphosphine)nickel(II) bromide (6.1 g, 8.2 mmol), $K_2CO_3$ (23 g, 164 mmol) and triphenylphosphine (13 g, 49 mmol) in $CH_3NO_2$ (500 ml) was added zinc (11 g, 164 mmol). The mixture was stirred at 80° C. for 20 h, then the mixture was filtered and concentrated under reduced pressure. The resulting residue was purified by column chromatography ($SiO_2$, PE:EtOAc=45:55) to give the title compound.

Step B: (R)-tert-butyl 3-(4-(1,3-dinitropropan-2-yl)phenoxy)-2-hydroxypropanoate To the mixture of 4-(1,3-dinitropropan-2-yl)phenol (4 g, 18 mmol) and molecular sieves (4 Å, 4 g) in tert-butyl oxirane-2-carboxylate (10 g, 71 mmol) was added Co-catalyst (CAS: 240489-45-6) (1.2 g, 1.4 mmol) under $N_2$. The resulting suspension was stirred at 25° C. under $N_2$ for 48 h, then the mixture was filtered and the filtrate was purified by column chromatography ($SiO_2$, PE:EtOAc=45:55) to give the title compound.

Step C: (R)-tert-butyl 2-((tert-butyldimethylsilyl)oxy)-3-(4-(1,3-dinitropropan-2-yl)phenoxy)propanoate To a solution of (R)-tert-butyl 3-(4-(1,3-dinitropropan-2-yl)phenoxy)-2-hydroxypropanoate (4 g, 11 mmol) in DMF (30 ml) was added imidazole (2.2 g, 32 mmol) and tert-butylchlorodimethylsilane (3.3 g, 22 mmol) at 0° C. The mixture was warmed to 25° C. and stirred at 25° C. for 3 h. Then the mixture was added to EtOAc (50 ml) and washed with water (3*50 ml) and brine (3*50 ml). The organic layer was dried over anhydrous $Na_2SO_4$, filtered and concentrated under reduced pressure to give the title compound, which was used for the next step without further purification.

Step D: (R)-tert-butyl 3-(4-(1,3-diaminopropan-2-yl)phenoxy)-2-hydroxypropanoate A solution of (R)-tert-butyl 2-((tert-butyldimethylsilyl)oxy)-3-(4-(1,3-dinitropropan-2-yl) phenoxy) propanoate (4 g, 8.25 mmol) in EtOH (150 ml) was added platinum (II) oxide (0.35 g, 1.7 mmol). The mixture was stirred under $H_2$ (50 psi) at 25° C. for 16 h. Then the mixture was filtered and concentrated under reduced pressure to afford the crude (R)-tert-butyl 2-((tert-butyldimethylsilyl)oxy)-3-(4-(1,3-dinitropropan-2-yl)phenoxy)propanoate which was de-silylated during freezing-dry process after acidic pre-HPLC purification.

Step E: (R)-tert-butyl 2-hydroxy-3-(4-(2-thioxohexahydropyrimidin-5-yl)phenoxy)propanoate 1,1'-thiocarbonyldiimidazole (362 mg, 2.03 mmol) was added in 5 portions over 10 minutes to a stirred mixture of (R)-tert-butyl 3-(4-(1,3-diaminopropan-2-yl)phenoxy)-2-hydroxypropanoate (600 mg, 1.93 mmol) in DCM (30 ml). The mixture was stirred at room temperature for 2 h, then the solvent was removed under reduced pressure. The resulting residue was purified on silica gel column (80 g) using 0-60% EtOAc/Hexane to give the title compound. LC-MS $[M+H]^+$: m/z 353.5.

Step F: (R)-tert-butyl 2-((tert-butyldimethylsilyl)oxy)-3-(4-(2-thioxohexahydropyrimidin-5-yl)phenoxy)propanoate To a solution of (R)-tert-butyl 2-hydroxy-3-(4-(2-thioxohexahydropyrimidin-5-yl)phenoxy)propanoate (200 mg, 0.57 mmol), imidazole (93 mg, 1.36 mmol), and TBDMS-Cl (100 mg, 0.68 mmol) in acetonitrile (4 ml) was added DMAP (6.9 mg, 0.057 mmol). The resulting mixture was stirred at rt overnight. Then the reaction mixture was concentrated. The resulting residue was purified by ISCO Combi-flash on 40 g gold column, eluting with 0-100% EtOAc/hexane to give the title compound. LC-MS $[M+H]^+$: m/z 467.5.

Step G: (2R)-tert-butyl 2-((tert-butyldimethylsilyl)oxy)-3-(4-(2-(methylthio)-1,4,5,6-tetrahydropyrimidin-5-yl)phenoxy)propanoate Iodomethane (0.17 ml, 2.8 mmol) was added to a stirred mixture of (R)-tert-butyl 2-((tert-butyldimethylsilyl)oxy)-3-(4-(2-thioxohexahydropyrimidin-5-yl)phenoxy)propanoate (260 mg, 0.55 mmol) in MeCN (3 ml). The mixture was stirred at 70° C. for 2 h, then cooled and the solvent was evaporated under reduced pressure to give the title compound. LC-MS $[M+H]^+$: m/z 481.0.

Step H: tert-butyl (2R)-3-(4-(2-((2-((tert-butoxycarbonyl)amino)ethyl)amino)-1,4,5,6-tetrahydropyrimidin-5-yl)phenoxy)-2-((tert-butyldimethylsilyl)oxy)propanoate Hunig's Base (0.19 ml, 1.1 mmol) was added to a stirred mixture of N-Boc-ethylenediamine (130 mg, 0.83 mmol) and (2R)-tert-butyl 2-((tert-butyldimethylsilyl)oxy)-3-(4-(2-(methylthio)-1,4,5,6-tetrahydropyrimidin-5-yl)phenoxy)propanoate (260 mg, 0.55 mmol) in dioxane (3 ml). The mixture was stirred at 70° C. for 24 h, then the solvent was removed under reduced pressure to give the title compound, which was used directly in the next step. LC-MS $[M+H]^+$: m/z 593.5.

Step I: tert-butyl 5-(4-((R)-3-(tert-butoxy)-2-((tert-butyldimethylsilyl)oxy)-3-oxopropoxy)-phenyl)-2-((tert-butoxycarbonyl)(2-((tert-butoxycarbonyl)amino)ethyl)amino)-5,6-dihydropyrimidine-1(4H)-carboxylate Boc-anhydride (2100 µl, 9.3 mmol) was added to (2R)-tert-butyl 3-(4-(2-((2-((tert-butoxycarbonyl)amino)ethyl)

amino)-1,4,5,6-tetra-hydropyrimidin-5-yl)phenoxy)-2-((tert-butyldimethylsilyl)oxy)propanoate (275 mg, 0.46 mmol) and the mixture was stirred at 100° C. for 6 h. Then the reaction mixture was cooled and directly loaded onto a ISCO column (40 g gold) eluting with EtOAc/Hexane 0-100% gradient to give the title compound. LC-MS [M+H]$^+$: m/z 793.6.

Step J: tert-butyl 5-(4-((R)-3-(tert-butoxy)-2-hydroxy-3-oxopropoxy)phenyl)-2-((tert-butoxycarbonyl)(2-((tert-butoxycarbonyl)amino)ethyl)amino)-5,6-dihydropyrimidine-1(4H)-carboxylate TBAF (0.79 ml, 0.79 mmol) was added to a stirred mixture of tert-butyl 5-(4-((R)-3-(tert-butoxy)-2-((tert-butyldimethylsilyl)oxy)-3-oxopropoxy)phenyl)-2-((tert-butoxycarbonyl)(2-((tert-butoxycarbonyl)amino)ethyl)amino)-5,6-dihydropyrimidine-1(4H)-carboxylate (420 mg, 0.53 mmol) in THF (5 ml). The mixture was stirred at room temperature for 1 h, then the solvent was removed. The resulting residue was purified using a silica gel ISCO column (40 g gold) eluting with 0-100% EtOAc/hexane gradient to give the title compound. LC-MS [M+H]$^+$: m/z 679.5.

Step K: tert-butyl 5-(4-((S)-3-(tert-butoxy)-2-((1,3-dioxoisoindolin-2-yl)oxy)-3-oxopropoxy)phenyl)-2-((tert-butoxycarbonyl)(2-((tert-butoxycarbonyl)amino)ethyl)amino)-5,6-dihydropyrimidine-1(4H)-carboxylate To a solution of tert-butyl 5-(4-((R)-3-(tert-butoxy)-2-hydroxy-3-oxopropoxy)phenyl)-2-((tert-butoxycarbonyl)(2-((tert-butoxycarbonyl)amino)ethyl)amino)-5,6-dihydropyrimidine-1(4H)-carboxylate (360 mg, 0.53 mmol) in THF (5 ml) was added 2-hydroxyisoindoline-1,3-dione (104 mg, 0.64 mmol), triphenylphosphine (195 mg, 0.74 mmol), followed by the dropwise addition of DIAD (0.144 ml, 0.74 mmol). The resulting solution was stirred at rt for 1 h, then concentrated. The resulting residue was purified on a silica gel column (ISCO gold 40 g) using 0-100% EtOAc/hexane gradient to give the title compound. LC-MS [M+H]$^+$: m/z 824.8.

Step L: (2S)-3-(4-(2-((2-aminoethyl)amino)-1,4,5,6-tetrahydropyrimidin-5-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid tert-butyl 5-(4-((S)-3-(tert-butoxy)-2-((1,3-dioxoisoindolin-2-yl)oxy)-3-oxopropoxy)phenyl)-2-((tert-butoxycarbonyl)(2-((tert-butoxycarbonyl)amino)ethyl)amino)-5,6-dihydropyrimidine-1(4H)-carboxylate was converted to the title compound as a formic acid salt following a procedure similar to the procedure of Step E to Step H of Example 1. $^1$H-NMR (500 MHz, D$_2$O, ppm): δ 7.13 (d, J=10 Hz, 2H), 7.02 (s, 1H), 6.85 (d, J=10 Hz, 2H), 5.05 (m, 1H), 4.68 (s, 1H), 4.36 (m, 2H), 3.45 (dd, J=15, 5 Hz, 2H), 3.38 (t, J=5 Hz, 2H), 3.32 (dd, J=10, 5 Hz, 2H), 3.11 (m, 1H), 3.06 (t, J=5 Hz, 2H), 1.34 (s, 3H), 0.95 (s, 3H). LC-MS [M+H]$^+$: m/z 684.4.

Example 95

(2S)-3-(4-(2-((2-aminoethyl)amino)-1,4,5,6-tetrahydropyrimidin-5-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-methylpropanoic acid

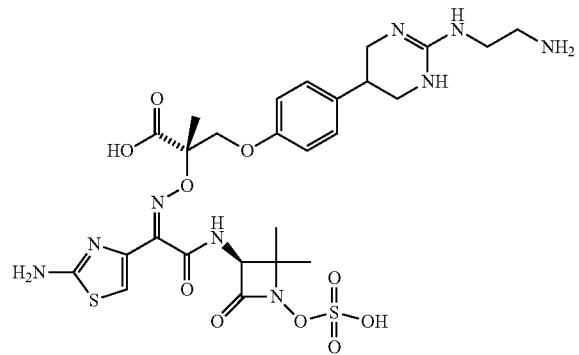 [SMILES: CC1(C)[C@H](NC(=O)/C(=N\O[C@@](C)(COc2ccc(C3CN=C(NCCN)NC3)cc2)C(=O)O)c2csc(N)n2)C(=O)N1OS(=O)(=O)O]

Step A: tert-butyl (2-((5-(4,4,5,5-tetramethyl-1,3,2-dioxaborolan-2-yl)pyrimidin-2-yl)amino)ethyl)carbamate To a solution of tert-butyl (2-((5-bromopyrimidin-2-yl)amino)ethyl)carbamate (700 mg, 2.2 mmol), 4,4,4',4,5,5,5',5'-octamethyl-2,2'-bi(1,3,2-dioxaborolane) (840 mg, 3.3 mmol), and 1,1'-bis(diphenylphosphino)ferrocene-palladium(ii)dichloride dichloromethane complex (180 mg, 0.22 mmol) in 1,4-dioxane (10 mL) was added potassium acetate (650 mg, 6.6 mmol). The mixture was degassed and refilled with nitrogen and heated at 85° C. for 4 h. Then the mixture was filtered and concentrated to dryness under vacuum and purified via ISCO column (40 g gold, 0-100% EtOAc/hexane gradient) to give the title compound.

Step B: (S)-tert-butyl 3-(4-bromophenoxy)-2-(((tert-butoxycarbonyl)amino)oxy)-2-methylpropanoate Boc-anhydride (8.38 ml, 36.1 mmol) was added to a stirred mixture of (S)-tert-butyl 2-(aminooxy)-3-(4-bromophenoxy)-2-methylpropanoate (5 g, 14.44 mmol) in DCM (10 ml) and the mixture was stirred at 50° C. overnight. Then the mixture was cooled and directly purified by ISCO (120 g gold), eluting with 0-30% EtOAc/isohexane gradient, to give the title compound. LC-MS [M+Na]$^+$: m/z 468.2.

Step C: (S)-tert-butyl 3-(4-(2-((2-((tert-butoxycarbonyl)amino)ethyl)amino)pyrimidin-5-yl)phenoxy)-2-(((tert-butoxycarbonyl)amino)oxy)-2-methylpropanoate To the solution of PdCl$_2$(dppf)-CH$_2$Cl$_2$ (75 mg, 0.092 mmol), tert-butyl (2-((5-(4,4,5,5-tetramethyl-1,3,2-dioxaborolan-2-yl)pyrimidin-2-yl)amino)ethyl)carbamate (350 mg, 0.96 mmol) and (S)-tert-butyl 3-(4-bromophenoxy)-2-(((tert-butoxycarbonyl)amino)oxy)-2-methylpropanoate (410 mg, 0.92 mmol) in dioxane (4.5 ml) was added Na$_2$CO$_3$ (290 mg, 2.8 mmol) in water (1.5 ml). The resulting mixture was N$_2$/vacuum exchanged for 3 times before it was heated at 100° C. under microwave reaction conditions for 1 h.

Then the mixture was cooled and diluted with EtOAc, dried (MgSO$_4$), filtered, and concentrated. The resulting residue was purified on silica gel column (ISCO gold, 80 g) using 0-100% EtOAc/hexane to give the title compound. LC-MS [M+H]$^+$: m/z 604.5.

Step D: (2S)-tert-butyl 3-(4-(2-((2-(((tert-butoxycarbonyl)amino)ethyl)amino)-1,4,5,6-tetrahydropyrimidin-5-yl)phenoxy)-2-(((tert-butoxycarbonyl)amino)oxy)-2-methylpropanoate Palladium on carbon (20 mg, 0.19 mmol) was added to a stirred mixture of (S)-tert-butyl 3-(4-(2-((2-(((tert-butoxycarbonyl)amino)ethyl)amino)pyrimidin-5-yl)-phenoxy)-2-(((tert-butoxycarbonyl)amino)oxy)-2-methylpropanoate (100 mg, 0.17 mmol) in MeOH (5 ml) and hydrochloric acid (0.83 ml, 0.83 mmol). The mixture was vacuum/H$_2$ exchanged 3 times and stirred under a hydrogen balloon at room temperature for 2.5 h. Then the mixture was diluted with DCM and filtered through a sintered funnel. The filtrate was diluted with DCM and washed with 1N aqueous NaOH solution (~5 mL). The aqueous phase was extracted with DCM (2×). The combined organic phases were washed with brine, dried (MgSO$_4$), filtered and concentrated to give the title compound. LC-MS [M+H]$^+$: m/z 608.5.

Step E: (2S)-tert-butyl 3-(4-(2-((2-aminoethyl)amino)-1,4,5,6-tetrahydropyrimidin-5-yl)phenoxy)-2-(aminooxy)-2-methylpropanoate TFA (1 ml) was added to a solution of (2S)-tert-butyl 3-(4-(2-((2-((tert-butoxycarbonyl)amino)ethyl)amino)-1,4,5,6-tetrahydropyrimidin-5-yl)phenoxy)-2-(((tert-butoxycarbonyl)amino)oxy)-2-methylpropanoate (120 mg, 0.20 mmol) in CH$_2$Cl$_2$ (1 ml) and the mixture was stirred at room temperature for 40 min. Then the reaction was stopped by removing the solvent under reduced pressure. Ether was added to the residue and solvent was removed under reduced pressure. To the resulting residue was added ether to crash out a solid, then the solvent was removed via pipette. The solid residue was dried under vacuum to give the title compound. LC-MS [M+H]$^+$: m/z 408.4.

Step F: (2S)-tert-butyl 3-(4-(2-((2-aminoethyl)amino)-1,4,5,6-tetrahydropyrimidin-5-yl)-phenoxy)-2-(((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-2-methylpropanoate To a solution of (2S)-tert-butyl 3-(4-(2-((2-aminoethyl)amino)-1,4,5,6-tetrahydropyrimidin-5-yl)phenoxy)-2-(aminooxy)-2-methylpropanoate (148 mg, 0.20 mmol) in methanol (2.5 ml) at rt was added (S)-3-(2-(2-((tert-butoxycarbonyl)amino)thiazol-4-yl)-2-oxoacetamido)-2,2-dimethyl-4-oxoazetidin-1-yl hydrogen sulfate (110 mg, 0.24 mmol). The resulting solution was stirred at rt for 4 h, then concentrated to give the title compound. LC-MS [M+H]$^+$: m/z 854.5.

Step G: (2S)-3-(4-(2-((2-aminoethyl)amino)-1,4,5,6-tetrahydropyrimidin-5-yl)phenoxy)-2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)-2-methylpropanoic acid TFA (2 ml) was added to a solution of (2S)-tert-butyl-3-(4-(2-((2-aminoethyl)amino)-1,4,5,6-tetrahydropyrimidin-5-yl)phenoxy)-2-(((Z)-(1-(2-((tert-butoxycarbonyl)amino)thiazol-4-yl)-2-(((S)-2,2-dimethyl-4-oxo-1-(sulfo-oxy)azetidin-3-yl)amino)-2-oxoethylidene)amino)oxy)-2-methylpropanoate (160 mg, 0.19 mmol) in CH$_2$Cl$_2$ (1 ml) and the mixture was stirred at room temperature for 45 min. Then the reaction was stopped by removing solvent under reduced pressure. Ether was added to the residue and solvent was again removed under reduced pressure. To the resulting residue was added ether to crash out a solid, and the solvent was removed with a pipette. The solid residue was dried under vacuum, and then dissolved in 5 mL of DMSO for HTP purification with standard formic acid conditions to give the title compound as the formic acid salt. $^1$H-NMR (500 MHz, D$_2$O, ppm): δ 7.10 (d, J=10 Hz, 2H), 6.94 (s, 1H), 6.85 (d, J=10 Hz, 2H), 4.47 (s, 1H), 4.40 (d, J=10 Hz, 1H), 4.22 (d, J=10, 5 Hz, 1H), 3.42 (dd, J=10, 5 Hz, 2H), 3.37 (t, J=5 Hz, 2H), 3.27 (dd, J=15, 5 Hz, 2H), 3.06 (t, J=5 Hz, 2H), 1.53 (s, 3H), 1.36 (s, 3H), 1.12 (s, 3H). LC-MS [M+H]$^+$: m/z 698.7.

Example 96

(S)-3-(4-(1-(3-aminopropyl)-2-imino-3-methyl-2,3-dihydro-1H-imidazol-4-yl)-3-fluorophenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

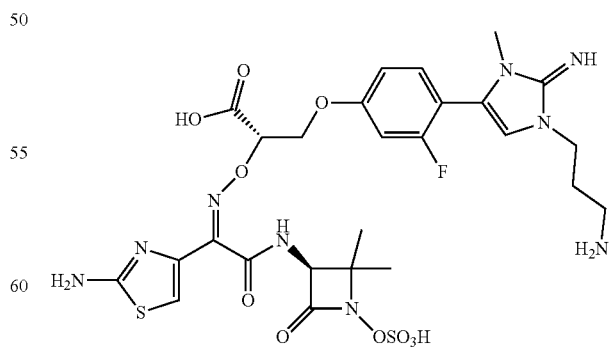

The title compound was prepared following the same procedure as Example 32 using the appropriate starting material. LC-MS [M+H]$^+$: m/z 714.4

Example 97

(S)-3-((Z)-2-(((S)-2-(4-(1-(3-aminopropyl)-2-(azetidin-3-ylmethyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

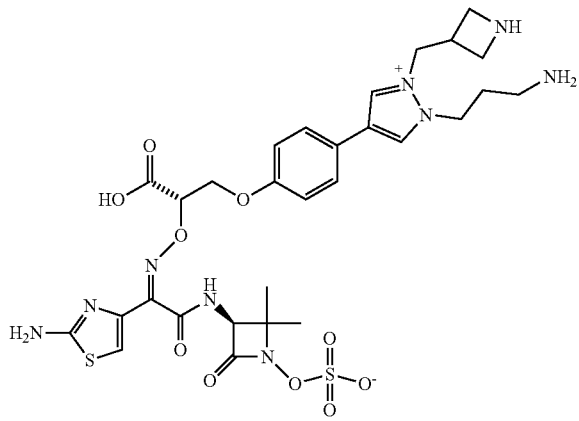

Step A: tert-butyl 3-(((((trifluoromethyl)sulfonyl)oxy)methyl)azetidine-1-carboxylate To a solution of tert-butyl 3-(hydroxymethyl)azetidine-1-carboxylate (1.32 g, 7.1 mmol, Example 1 Step C) and Hunig's base (3.1 ml, 18 mmol) in $CH_2Cl_2$ (35.4 ml) at −78° C. was added trifluoromethanesulfonic anhydride (1.8 ml, 11 mmol) over 5 min. The internal temperature was maintained between −75° C. to −65° C. during the addition of $Tf_2O$. After 30 min, the reaction was quenched with saturated $NaHCO_3$ solution (30 mL) and allowed to warm to 0° C. The resulting mixture was partitioned and the organic layer was washed with brine (10 mL). The aqueous layers were back-extracted with $CH_2Cl_2$ (15 mL) and the organic layers were combined, dried over $Na_2SO_4$, filtered, and concentrated in vacuo to give the title compound, which was used immediately without further purification.

Step B: (S)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-2-((1-(tert-butoxycarbonyl)azetidin-3-yl)methyl)-1H-pyrazol-2-ium To a vial containing tert-butyl 3-(((((trifluoromethyl)sulfonyl)oxy)methyl) azetidine-1-carboxylate (2.3 g, 7.1 mmol) was added a solution of tert-Butyl (S)-3-(4-(1-(3-((tert-butoxycarbonyl)amino)propyl)-1H-pyrazol-4-yl)phenoxy)-2-((1,3-dioxoisoindolin-2-yl)oxy)propanoate (3.03 g, 4.30 mmol) from Example 1, Step C in anhydrous $CH_3CN$ (43 mL), followed by the addition of solid sodium bicarbonate (3.6 g, 43 mmol). The resulting mixture was heated to 60° C. for 2.5 h. Then the solid $NaHCO_3$ was removed by filtration, and the filtrate was concentrated in vacuo. The resulting residue was purified by $SiO_2$ flash chromatography and eluted with hexanes/(3:1 EtOAc/EtOH) 0-100% to obtain the title compound. LC-MS [M+H]: m/z 776.6

Step C: (S)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-2-((1-(tert-butoxycarbonyl)azetidin-3-yl)methyl)-1H-pyrazol-2-ium To a solution of (S)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-2-((1-(tert-butoxycarbonyl) azetidin-3-yl)methyl)-1H-pyrazol-2-ium (1.24 g, 1.6 mmol) in anhydrous MeOH (6.4 ml) was added 7N ammonia solution in MeOH (1.8 ml, 12.8 mmol) at ambient temperature. The reaction was stirred for 23 h and then concentrated in vacuo to give the title compound, which was used immediately in the next reaction. LC-MS [M+H]: m/z 647.5

Step D: 4-(4-((S)-3-(tert-butoxy)-2-(((Z)-(1-(2-((tert-butoxycarbonyl)amino)thiazol-4-yl)-2-(((R)-2,2-dimethyl-4-oxo-1-(sulfooxy)azetidin-3-yl)amino)-2-oxoethylidene)amino)oxy)-3-oxopropoxy)phenyl)-1-(3-((tert-butoxycarbonyl)amino)propyl)-2-((1-(tert-butoxycarbonyl)-azetidin-3-yl)methyl)-1H-pyrazol-2-ium To a mixture of (S)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-2-((1-(tert-butoxycarbonyl) azetidin-3-yl)methyl)-1H-pyrazol-2-ium (0.12 g, 0.085 mmol) and (S)-3-(2-(2-((tert-butoxycarbonyl)amino)thiazol-4-yl)-2-oxoacetamido)-2,2-dimethyl-4-oxoazetidin-1-yl hydrogen sulfate (Intermediate 22, 0.071 g, 0.13 mmol) in anhydrous DCE (0.36 ml) and anhydrous MeOH (0.36 ml) was added benzenesulfonic acid (4.0 mg, 0.025 mmol). The resulting mixture was stirred at ambient temperature. After 3 h, the reaction was concentrated in vacuo. The resulting residue was purified by reverse phase ISCO C18 column (130 g) and eluted with $H_2O$/AcCN (0-100%). The fractions were collected and lyophilized to afford the title compound. LC-MS [M+H]: m/z 1093. $^1$H NMR (500 MHz, DMSO-d6) δ 9.49 (d, J=7.9 Hz, 1H), 9.01 (s, 1H), 8.90 (s, 1H), 7.78-7.62 (m, 2H), 7.34 (s, 1H), 7.10-7.03 (m, 2H), 6.99 (s, 1H), 4.96 (dd, J=4.6, 3.0 Hz, 1H), 4.71 (d, J=7.7 Hz, 2H), 4.62 (dd, J=8.1, 2.3 Hz, 1H), 4.46 (t, J=7.1 Hz, 2H), 4.41 (dd, J=10.8, 4.7 Hz, 1H), 4.33 (dd, J=10.7, 3.0 Hz, 1H), 4.02 (bs, 2H), 3.71 (bs, 2H), 3.29-3.12 (m, 1H), 3.06 (d, J=6.5 Hz, 2H), 2.06 (dd, J=12.3, 5.4 Hz, 2H), 1.38-1.48 (multiple s, 35H), 1.14 (s, 3H).

Step E: (S)-3-((Z)-2-(((S)-2-(4-(1-(3-aminopropyl)-2-(azetidin-3-ylmethyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate To a solution of 4-(4-((S)-3-(tert-butoxy)-2-(((Z)-(1-(2-((tert-butoxycarbonyl)amino)thiazol-4-yl)-2-(((R)-2,2-dimethyl-4-oxo-1-(sulfooxy)azetidin-3-yl)amino)-2-oxoethylidene)amino)oxy)-3-oxopropoxy)phenyl)-1-(3-((tert-butoxy-carbonyl)amino)propyl)-2-((1-(tert-butoxycarbonyl) azetidin-3-yl)methyl)-1H-pyrazol-2-ium (1.51 g, 1.4 mmol) in anhydrous $CH_2Cl_2$ (3.5 ml) at an internal temperature of 10° C. (dry ice/dioxane bath) was added dropwise trifluoroacetic acid (5.3 ml, 69 mmol) over 5 minutes. The internal temperature was maintained below 11° C. during the addition. The bath was removed and the reaction was stirred at ambient temperature. After 2 h, the reaction was cooled to 0° C. and pipetted dropwise into a cold stirring solution of MTBE (−5° C., 35 mL). The resulting solid was collected by vacuum filtration and washed with 35 mL of MTBE divided into 3 portions. The solids were dried under a stream of $N_2$ for 1.5 h. Then the crude solid was purified 2× by reverse-phase chromatography using Waters CSH column (50×250 mm, 5 micron, flow rate=100 mL/min., eluted with $H_2O$+8% formic acid/AcCN+8% formic acid (0%-8% gradient)). The desired fractions were lyophilized to give the title compound. LC-MS [M+H]: m/z 736.3 ¹H NMR (500 MHz, Deuterium Oxide) δ 8.62 (s, 1H), 8.51 (s, 1H), 8.40 (d, J=1.1 Hz, 1H), 7.49 (d, J=8.4 Hz, 2H), 7.00 (d, J=8.5 Hz, 2H), 6.89 (d, J=1.1 Hz, 1H), 4.90 (dd, J=6.3, 2.2 Hz, 1H), 4.82 (d, J=7.6 Hz, 2H), 4.56 (t, J=7.5 Hz, 2H), 4.47 (dd, J=11.7, 2.3 Hz, 1H), 4.44-4.36 (m, 2H), 4.29 (dd, J=9.6, 5.8 Hz, 2H), 4.11 (ddd, J=10.9, 7.3, 2.3 Hz, 2H), 3.64 (p, J=8.0 Hz, 1H), 3.17-3.06 (m, 2H), 2.35 (p, J=7.6 Hz, 2H), 1.36 (s, 3H), 0.99 (s, 3H).

Example 98

(S)-3-((Z)-2-(((S)-2-(4-(6-((2-aminoethyl)amino)-1-(azetidin-3-ylmethyl)pyridin-1-ium-3-yl)phenoxy)-1-carboxyethoxy)imino)-2-(2-aminothiazol-4-yl)acetamido)-2,2-dimethyl-4-oxoazetidin-1-yl sulfate

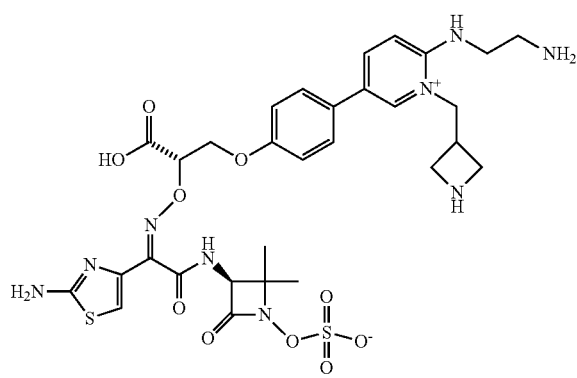 [SMILES: CC1(C)[C@H](NC(=O)/C(=N\O[C@@H](COc2ccc(-c3ccc(NCCN)[n+](CC4CNC4)c3)cc2)C(=O)O)c2csc(N)n2)C(=O)N1OS(=O)(=O)[O-]]

The title compound was prepared following the same procedure as Example 97. LC-MS [M+H]: m/z 748.7

Example 99

(S)-3-((Z)-2-(((S)-2-(4-(2-((2-aminoethyl)amino)-1-(azetidin-3-ylmethyl)pyrimidin-1-ium-5-yl)phenoxy)-1-carboxyethoxy)imino)-2-(2-aminothiazol-4-yl)acetamido)-2,2-dimethyl-4-oxoazetidin-1-yl sulfate

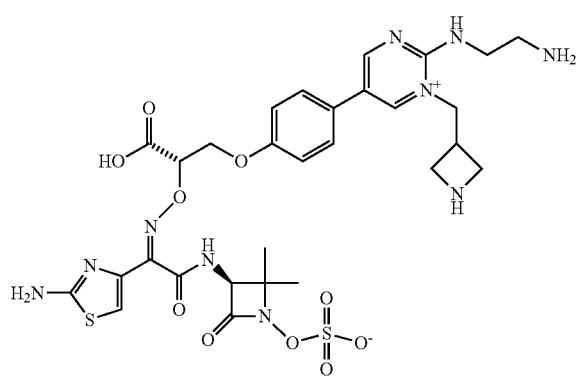 [SMILES: CC1(C)[C@H](NC(=O)/C(=N\O[C@@H](COc2ccc(-c3cnc(NCCN)[n+](CC4CNC4)c3)cc2)C(=O)O)c2csc(N)n2)C(=O)N1OS(=O)(=O)[O-]]

The title compound was prepared following the same procedure as Example 97. LC-MS [M+H]: m/z 749.7

Example 100

(S)-3-((Z)-2-(((S)-2-(4-(2-(2-aminoethyl)-1-(3-aminopropyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

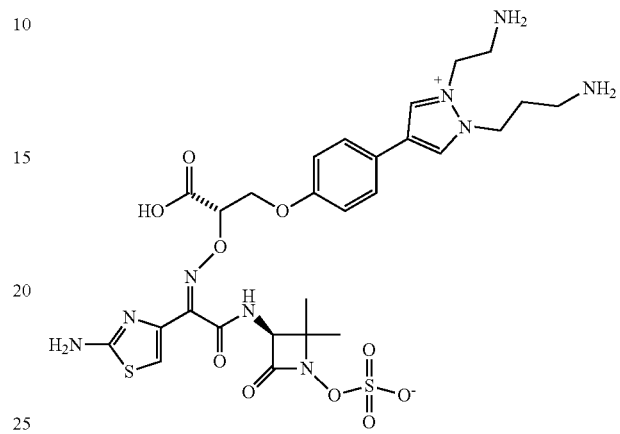

Step A: 2-bromoethyl trifluoromethanesulfonate

Utilizing the procedure described in Example 97 Step A, 2-bromoethanol (0.41 g, 3.3 mmol) was converted to the corresponding triflate, which was used without further purification.

Step B: (S)-2-(2-bromoethyl)-4-(4-(3-(tert-butoxy)-2-((1,3-dioxoisoindolin-2-yl)oxy)-3-oxopropoxy) phenyl)-1-(3-((tert-butoxycarbonyl)amino)propyl)-1H-pyrazol-2-ium Utilizing the procedure described in Example 97 Step B, tert-Butyl (S)-3-(4-(1-(3-((tert-butoxycarbonyl)amino)propyl)-1H-pyrazol-4-yl)phenoxy)-2-((1,3-dioxoisoindolin-2-yl)oxy)propanoate (0.43 g, 0.61 mmol) from Example 1 Step C was alkylated with 2-bromoethyl trifluoromethanesulfonate to afford the title compound. LC-MS [M+H]: m/z 715.04

Step C: (S)-2-(2-azidoethyl)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-1H-pyrazol-2-ium A flask equipped with a stirrer was charged with (S)-2-(2-bromoethyl)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-1H-pyrazol-2-ium (0.47 g, 0.66 mmol), sodium azide (0.15 g, 2.4 mmol) and anhydrous DMF (3.3 mL). The reaction was heated conventionally in a heating block at 50° C. for 1 h. Then the reaction was quenched with addition of brine, and extracted with EtOAc (2×). The combined organic layers were dried over Na₂SO₄, filtered, and concentrated in vacuo. The resulting residue was purified by reverse phase ISCO C18 column (86 g) eluted with H₂O/MeCN (0-100%). The desired fractions were collected and partitioned between EtOAc and brine. The aqueous layer was back-extracted with EtOAc (2×). The organic layers were combined, dried over Na₂SO₄, filtered and concentrated in vacuo to give the title compound. LC-MS [M+H]: m/z 677.3 $^1$H NMR (500 MHz, Chloroform-d) δ 8.71 (s, 1H), 8.55 (s, 1H), 7.88 (dd, J=5.4, 3.1 Hz, 2H), 7.80 (dd, J=5.5, 3.1 Hz, 2H), 7.55-7.49 (m, 2H), 6.96 (d, J=8.6 Hz, 2H), 5.38 (s, 1H), 5.08 (dd, J=5.4, 3.5 Hz, 1H), 4.77 (t, J=5.2 Hz, 2H), 4.63 (t, J=6.9 Hz, 2H), 4.60-4.45 (m, 2H), 4.00 (t, J=5.2 Hz, 2H), 3.29 (s, 2H), 2.21 (q, J=6.5 Hz, 2H), 1.53 (s, 9H), 1.44 (s, 9H).

Step D: (S)-4-(4-(2-(aminooxy)-3-(tert-butoxy)-3-oxopropoxy)phenyl)-2-(2-azidoethyl)-1-(3-((tert-butoxycarbonyl)amino)propyl)-1H-pyrazol-2-ium The title compound was prepared from S)-2-(2-azidoethyl)-4-(4-(3-(tert-butoxy)-2-((1,3-dioxoisoindolin-2-yl)oxy)-3-oxopropoxy)phenyl)-1-(3-((tert-butoxycarbonyl)amino)propyl)-1H-pyrazol-2-ium (0.31 g, 0.45 mmol) utilizing the procedure described in Example 97 Step C. LC-MS [M+H]: m/z 547.2

Step E: (S,Z)-2-(2-azidoethyl)-4-(4-(3-(tert-butoxy)-2-((((2-((tert-butoxycarbonyl)-amino)thiazol-4-yl)(carboxy)methylene)amino)oxy)-3-oxopropoxy)phenyl)-1-(3-((tert-butoxycarbonyl)amino)propyl)-1H-pyrazol-2-ium To a solution of (S)-4-(4-(2-(aminooxy)-3-(tert-butoxy)-3-oxopropoxy)phenyl)-2-(2-azidoethyl)-1-(3-((tert-butoxycarbonyl)-amino)propyl)-1H-pyrazol-2-ium (0.25 g, 0.45 mmol) in anhydrous DCE (1.8 ml) and anhydrous MeOH (1.8 ml) was added 2-(2-((tert-butoxycarbonyl)amino)thiazol-4-yl)-2-oxoacetic acid (0.25 g, 0.90 mmol, Intermediate 5). The reaction was stirred at ambient temperature for 21 h. Then the reaction was concentrated in vacuo and purified by reverse phase ISCO C$_{18}$ column (130 g), eluting with H$_2$O/MeCN (0-100%). The desired fractions were collected and lyophilized to afford the title compound. LC-MS [M+H]: m/z 800.4

Step F: (S,Z)-4-(4-(3-(tert-butoxy)-2-((((2-((tert-butoxycarbonyl)amino)thiazol-4-yl)(carboxy)methylene)amino)oxy)-3-oxopropoxy)phenyl)-2-(2-((tert-butoxycarbonyl)-amino)ethyl)-1-(3-((tert-butoxycarbonylaminopropyl)-1H-pyrazol-2-ium To a solution of (S,Z)-2-(2-azidoethyl)-4-(4-(3-(tert-butoxy)-2-((((2-((tert-butoxycarbonyl)amino)thiazol-4-yl)(carboxy)methylene)amino)oxy)-3-oxopropoxy)phenyl)-1-(3-((tert-butoxycarbonyl)-amino)propyl)-1H-pyrazol-2-ium (0.19 g, 0.24 mmol) and BOC$_2$O (0.052 g, 0.24 mmol) in THF (2.4 mL) was added 10% Pd/C (0.038 g). The mixture was hydrogenated under atmospheric H$_2$ for 1 h. Then the catalyst was removed by filtering through Celite™ and the Celite™ pad was rinsed well with EtOAc. The filtrate was concentrated in vacuo to give the title compound, which was used in the next step without further purification. LC-MS [M+H]: m/z 875.5

Step G: 4-(4-((S)-3-(tert-butoxy)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-2-(2-((tert-butoxycarbonyl)amino)ethyl)-1-(3-((tert-butoxycarbonyl)-amino)propyl)-1H-pyrazol-2-ium To a mixture of (S,Z)-4-(4-(3-(tert-butoxy)-2-((((2-((tert-butoxycarbonyl)amino)thiazol-4-yl)(carboxy)methylene)amino)oxy)-3-oxopropoxy)phenyl)-2-(2-((tert-butoxycarbonyl)amino)ethyl)-1-(3-((tert-butoxycarbonyl)amino)propyl)-1H-pyrazol-2-ium (0.21 g, 0.24 mmol) in anhydrous MeCN (2.1 ml) was added (S)-3-amino-2,2-dimethyl-4-oxoazetidin-1-yl hydrogen sulfate (0.093 g, 0.36 mmol, commercial sources CAS: 102507-49-3) and pyridine (0.048 ml, 0.59 mmol) under N$_2$ at ambient temperature. The reaction was cooled to 0° C. and EDC-HCl (0.091 g, 0.47 mmol) was added in one portion. After 1 h, the reaction was partitioned between EtOAc and a 1:1 mixture of 0.5 M citric acid aqueous solution and brine. The aqueous layer was back-extracted with EtOAc. The organic layers were combined, dried over Na$_2$SO$_4$, filtered, and concentrated in vacuo. The resulting residue was purified by reverse phase ISCO C18 column (86 g) and eluted with H$_2$O/MeCN (0-100%). The desired fractions were collected and concentrated in vacuo. The resulting wet residue was partitioned between EtOAc/AcCN (4:1) and brine containing solid NaCl. The aqueous layer was back-extracted with EtOAc. The organic layers were combined, dried over Na$_2$SO$_4$, filtered and concentrated in vacuo to give the title compound. LC-MS [M+H]: m/z 1066.9

Step H: 2-(2-aminoethyl)-1-(3-aminopropyl)-4-(4-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)phenyl)-1H-pyrazol-2-ium Utilizing the procedure described in Example 97 Step E, a mixture of 1:2 DCM/TFA (1.66 mL) was used and the reaction was stirred for 1 h at ambient temperature. 4-(4-((S)-3-(tert-butoxy)-2-(((Z)-(1-(2-((tert-butoxycarbonyl)-amino)thiazol-4-yl)-2-(((S)-2,2-dimethyl-4-oxo-1-(sulfooxy)azetidin-3-yl)amino)-2-oxoethylidene)amino)oxy)-3-oxopropoxy)phenyl)-2-(2-((tert-butoxycarbonyl)amino)ethyl)-1-(3-((tert-butoxycarbonyl)amino)propyl)-1H-pyrazol-2-ium (0.179 g, 0.168 mmol) was elaborated to the final product, followed by purification using reverse-phase chromatography using Waters CSH column (50×250 mm, 5 micron, flow rate=100 mL/min., eluting with H$_2$O+8% Formic acid/AcCN+8% Formic acid (0%-10% gradient)) to give the title compound. LC-MS [M+1]: m/z 710.2 $^1$H NMR (500 MHz, Deuterium Oxide) δ 8.67 (dd, J=14.9, 1.2 Hz, 2H), 8.38 (s, 1H), 7.52 (d, J=8.5 Hz, 2H), 7.00 (d, J=8.6 Hz, 2H), 6.91 (s, 1H), 4.88 (dt, J=13.2, 5.9 Hz, 3H), 4.60 (t, J=7.5 Hz, 2H), 4.50-4.31 (m, 3H), 3.61 (t, J=6.5 Hz, 2H), 3.22-3.06 (m, 2H), 2.39 (p, J=7.6 Hz, 2H), 1.38 (s, 3H), 1.00 (s, 3H).

Example 101

(S)-3-((E)-2-(2-aminothiazol-4-yl)-2-(((S)-1-carboxy-2-(4-(1-(3-(((S)-2,3-dihydroxypropyl)amino)propyl)-2-methyl-1H-pyrazol-2-ium-4-yl)phenoxy)ethoxy)imino)acetamido)-2,2-dimethyl-4-oxoazetidin-1-yl sulfate

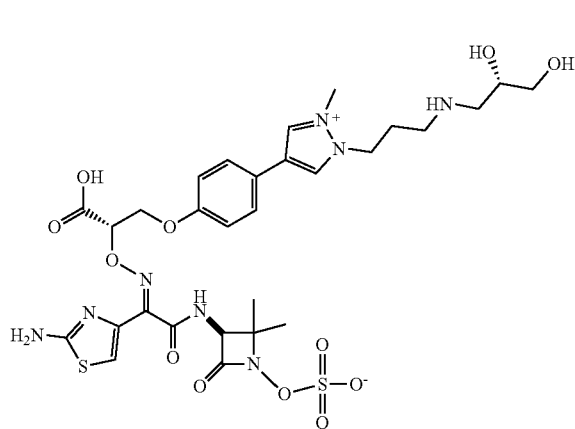

To a solution of (S)-3-((E)-2-(((S)-2-(4-(1-(3-aminopropyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate (50 mg, 0.073 mmol, Example 1) in DMSO (1 ml) was added (R)-2,3-dihydroxypropanal (9.9 mg, 0.11 mmol). The mixture was stirred at RT for 1 h, and then sodium triacetoxyborohyride (23 mg, 0.11 mmol) was added. The mixture was stirred at RT overnight. The DMSO solution was then injected directly into prep-HPLC for separation (Gilson, Water/MeCN/0.05% TFA, 0-40% in 10 min.) The first peak collected was combined, and freeze-dried to give the title compound. LC-MS [M+H]: m/z 755.10. $^1$HNMR (500 MHz, D$_2$O) δ 8.52 (s, 1H); 8.48 (s, 1H); 7.48 (d, J=6.8 Hz, 2H); 6.98 (s, 1H); 6.94 (d, J=6.8, 2H); 5.01 (s, 1H); 4.48 (m, 2H); 4.38 (m, 2H); 4.02 (s, 3H); 3.06-3.65 (m, 7H); 2.39 (m, 2H); 1.25 (s, 3H); 0.98 (s, 3H).

Example 102

(S)-3-((E)-2-(((S)-2-(4-(1-(3-((2-aminoethyl)amino)propyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

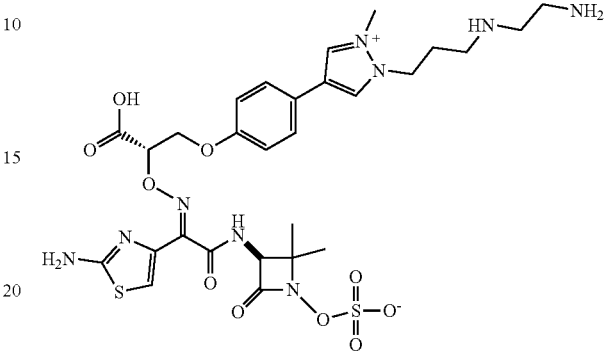

To a solution of Example 1 (50 mg, 0.073 mmol) in DMSO (1 ml) was added tert-butyl (2-oxoethyl)carbamate (18 mg, 0.11 mmol) and TFA (0.1 ml). The mixture was stirred at rt for 1 h, then sodium triacetoxyborohydride (17 mg, 0.081 mmol) was added. The resulting mixture was stirred at rt overnight. The DMSO solution was then injected directly into prep-HPLC for separation (Gilson, Water/MeCN/0.05% TFA, 0-40% in 10 min.). The first peak collected was freeze-dried to give a crude product, which was dissolved in DCM (1 ml) with 0.2 ml of TFA. The resulting mixture was stirred at room temperature for 30 min and then concentrated to dryness. The resulting residue was re-dissolved in 0.5 mL of DMSO and injected into Prep-HPLC for separation (Gilson, water/MeCN/0.05% TFA, 0-40% in 10 min). The product peak was collected and freeze dried to obtain the title compound as a TFA salt. LC-MS [M+H]: m/z 724.08. $^1$HNMR (500 MHz, D$_2$O) δ 8.55 (s, 1H); 8.52 (s, 1H); 7.42 (d, J=8, 2H); 7.07 (s, 2H); 7.00 (d, J=8, 2H); 5.15 (s, 1H); 4.56 (m, 4H); 4.19 (s, 3H); 3.46 (m, 6H); 2.46 (m, 2H); 1.53 (s, 3H); 1.29 (s, 3H).

TABLE 5

Examples 103 and 104 were prepared according to the procedure of Example 101.

| Example | Name | Structure | LCMS [M + H] |
|---------|------|-----------|--------------|
| 103 | (S)-3-((E)-2-(2-aminothiazol-4-yl)-2-(((S)-2-(4-(1-(3-((azetidin-3-ylmethyl)amino)propyl)-2-methyl-1H-pyrazol-2-ium-4-yl)phenoxy)-1-carboxyethoxy)imino)acetamido)-2,2-dimethyl-4-oxoazetidin-1-yl sulfate, 3TFA | 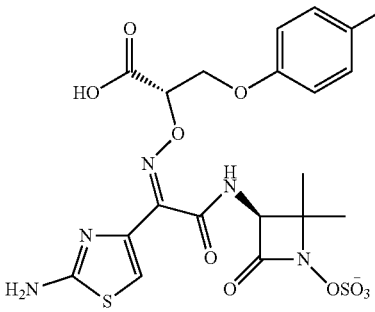 | 750.35 |

TABLE 5-continued

Examples 103 and 104 were prepared according to the procedure of Example 101.

| Example | Name | Structure | LCMS [M + H] |
|---|---|---|---|
| 104 | (S)-3-((E)-2-(((S)-2-(4-(1-(3-((3-aminopropyl)amino)-propyl)-2-methyl-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate, 3TFA | 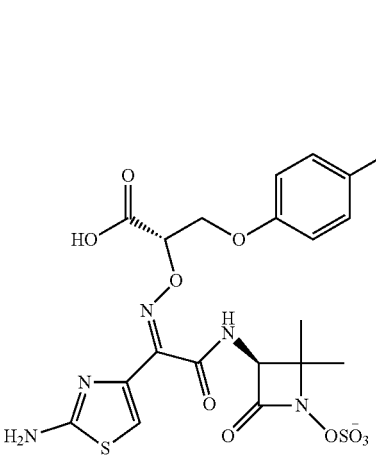 | 738.13 |

Example 105

(S)-3-((Z)-2-((((Sn-1-(4-(1-(3-aminopropyl)-2-methyl-1H-pyrazol-2-ium-4-yl)-3-fluorophenoxy)-2-carboxypropan-2-yl)oxy)imino)-2-(2-aminothiazol-4-yl)acetamido)-2,2-dimethyl-4-oxoazetidin-1-yl sulfate

Example 106

(S)-3-((Z)-2-(((S)-2-((6-(1-(3-aminopropyl)-2-methyl-1H-pyrazol-2-ium-4-yl)pyridazin-3-yl)oxy)-1-carboxyethoxy)imino)-2-(2-aminothiazol-4-yl)acetamido)-2,2-dimethyl-4-oxoazetidin-1-yl sulfate

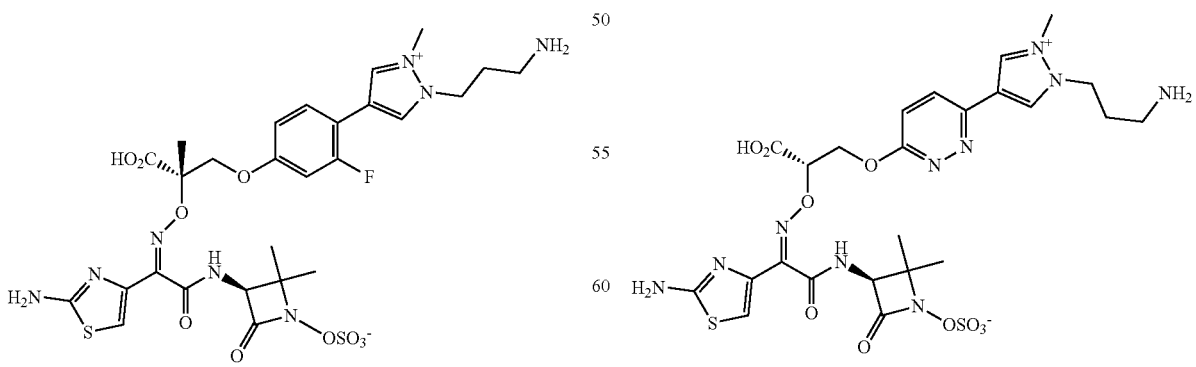

The title compound was prepared following procedures similar to those described in Example 39 starting from Intermediate 14. LC-MS [M+H]: m/z 713.5.

The title compound was prepared following procedures similar to those described in Example 1 starting from Intermediate 12. LC-MS [M+H]: m/z 683.3.

Example 107

(S)-3-((Z)-2-((((S)-1-(4-(1-(3-aminopropyl)-2-imino-3-methyl-2,3-dihydro-1H-imidazol-4-yl)phenoxy)-2-carboxypropan-2-yl)oxy)imino)-2-(2-aminothiazol-4-yl)acetamido)-2,2-dimethyl-4-oxoazetidin-1-yl sulfate The title compound was prepared following procedures similar to those described in Example 39 starting from Intermediate 10. LC-MS [M+H]: m/z 728.3.

Example 108

(S)-3-((Z)-2-(2-aminothiazol-4-yl)-2-(((S)-2-((6-((1-(azetidin-3-ylmethyl)pyridin-1-ium-4-yl)amino)pyridin-3-yl)oxy)-1-carboxyethoxy)imino)acetamido)-2,2-dimethyl-4-oxoazetidin-1-yl sulfate

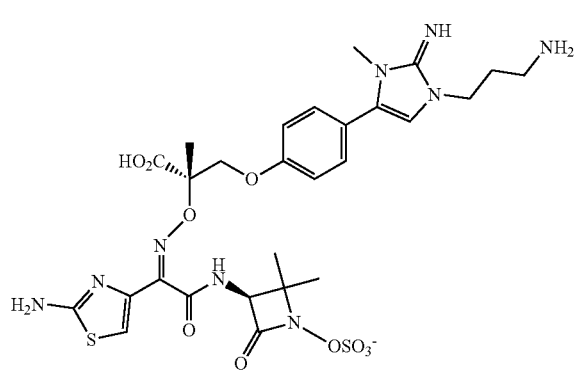

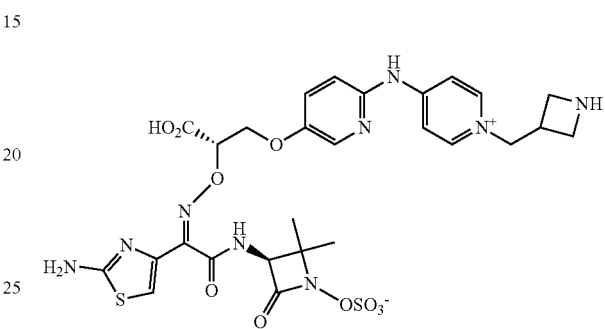

The title compound was prepared following procedures similar to Example 33. LC-MS[M+H]: m/z 706.6.

TABLE 6

Examples 109-112 were prepared using procedures similar to the procedures used for the synthesis of Example 36

| Example | Name | Structure | LC-MS: [M + H]+ |
|---|---|---|---|
| 109 | (S)-3-((Z)-2-(2-aminothiazol-4-yl)-2-(((S)-2-((6-(3-(azetidin-3-ylmethyl)-1H-imidazol-3-ium-1-yl)pyridin-3-yl)oxy)-1-carboxyethoxy)imino)acetamido)-2,2-dimethyl-4-oxoazetidin-1-yl sulfate | 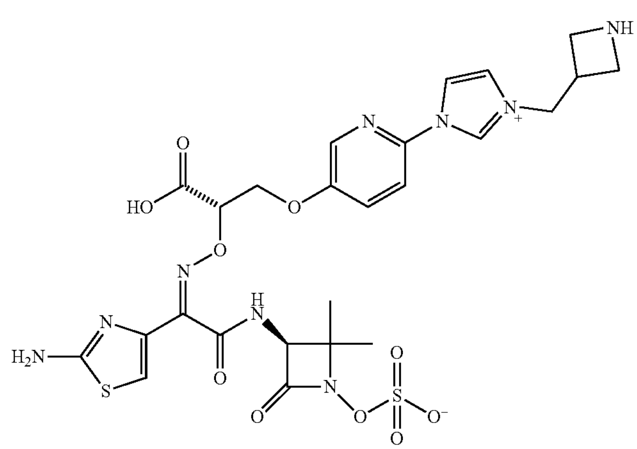 | 680.4 |

TABLE 6-continued

Examples 109-112 were prepared using procedures similar to the procedures used for the synthesis of Example 36

| Example | Name | Structure | LC-MS: [M + H]+ |
|---|---|---|---|
| 110 | (S)-3-((Z)-2-(2-aminothiazol-4-yl)-2-(((S)-1-carboxy-2-((6-(3-(3-(trimethylammonio)propyl)-1H-imidazol-3-ium-1-yl)pyridin-3-yl)oxy)ethoxy)imino)acetamido)-2,2-dimethyl-4-oxoazetidin-1-yl sulfate | 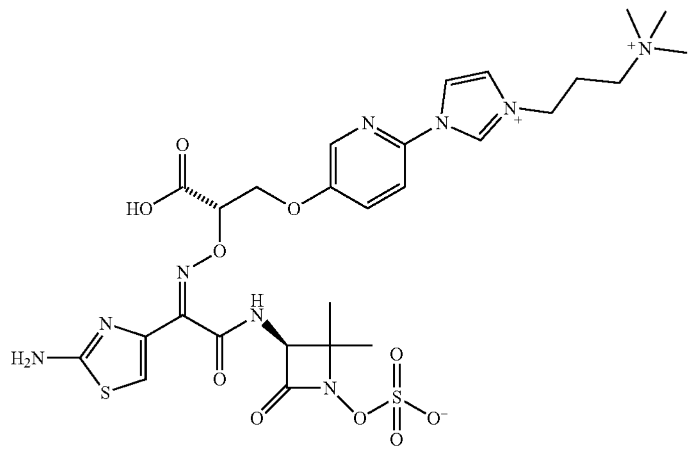 | 710.2 |
| 111 | (S)-3-((Z)-2-(((S)-2-((2-(3-(3-aminopropyl)-1H-imidazol-3-ium-1-yl)pyrimidin-5-yl)oxy)-1-carboxyethoxy)imino)-2-(2-aminothiazol-4-yl)acetamido)-2,2-dimethyl-4-oxoazetidin-1-yl sulfate | 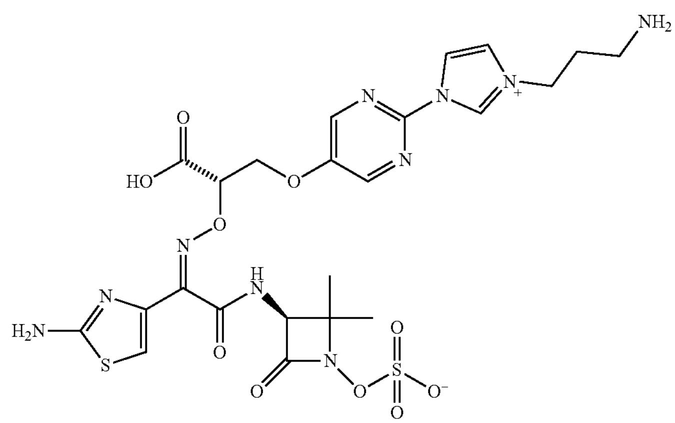 | 669.1 |
| 112 | (S)-3-((Z)-2-(((S)-2-((6-(3-(3-aminopropyl)-1H-imidazol-3-ium-1-yl)pyridin-3-yl)oxy)-1-carboxyethoxy)imino)-2-(2-aminothiazol-4-yl)acetamido)-2,2-dimethyl-4-oxoazetidin-1-yl sulfate | 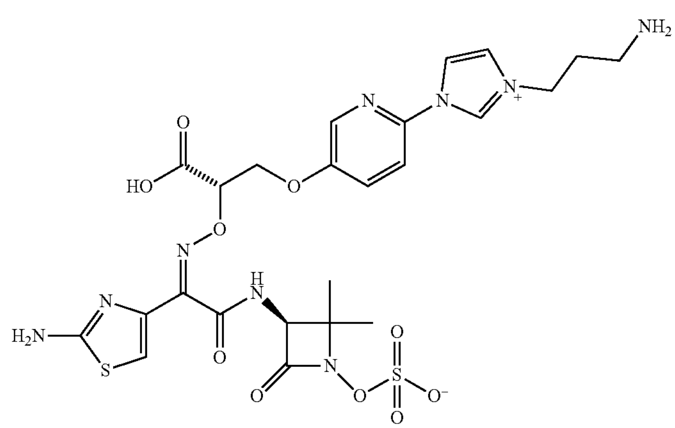 | 668.37 |

Example 113

(S)-3-((Z)-2-((((S)-1-((6-(3-(3-aminopropyl)-1H-imidazol-3-ium-1-yl)pyridin-3-yloxy)-2-carboxypropan-2-yl)oxy)imino)-2-(2-aminothiazol-4-yl)acetamido)-2,2-dimethyl-4-oxoazetidin-1-yl sulfate

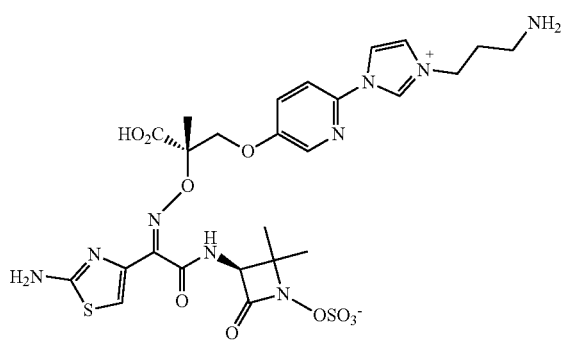

Step A: tert-butyl (S)-3-((6-bromopyridin-3-yl)oxy)-2-hydroxy-2-methylpropanoate tert-Butyl N,N'-diisopropylcarbammidate (380 μL, 1.63 mmol) was added to a stirred solution of (S)-3-((6-bromopyridin-3-yl)oxy)-2-hydroxy-2-methylpropanoic acid (180 mg, 0.65 mmol) in THF (6.5 mL). The resulting mixture was heated to 60° C. for 1 h, then the reaction was cooled to rt and concentrated in vacuo. Purification of the resulting crude residue via column chromatography on silica gel (0-50% EtOAc in hexanes as eluent) afforded the title compound. LC-MS [M+H]: m/z 332.1.

Step B: tert-butyl (S)-3-((6-(1H-imidazol-1-yl)pyridin-3-yl)oxy)-2-hydroxy-2-methylpropanoate The title compound was prepared following procedures similar to those from Example 36, Step E. LC-MS [M+H]: m/z 320.2.

Step C: tert-butyl (S)-3-((6-(1H-imidazol-1-yl)pyridin-3-yl)oxy)-2-(aminooxy)-2-methylpropanoate To a stirred solution of tert-butyl (S)-3-((6-(1H-imidazol-1-yl)pyridin-3-yl)oxy)-2-hydroxy-2-methylpropanoate (100 mg, 0.313 mmol) in THF (3.1 mL) at 0° C. was added NaH (22.5 mg of a 60% dispersion in mineral oil, 0.56 mmol) in one portion. The resulting mixture was allowed to stir at 0° C. for 15 min, at which time, O-(mesitylsulfonyl)-hydroxylamine (74 mg, 0.344 mmol) was added, and the mixture was stirred at 0° C. for 1 h. Then the reaction mixture was partitioned between EtOAc and water. The layers were separated, and the organic layer was washed with water and brine. The organic layers were further dried ($Na_2SO_4$), filtered and concentrated in vacuo to afford a crude residue that was purified by column chromatography on silica gel (0-10% $CH_3OH$ in DCM as eluent) to afford the title compound. LC-MS [M+H]: m/z 335.2.

Step D: tert-butyl (S)-3-((6-(1H-imidazol-1-yl)pyridin-3-yl)oxy)-2-((1,3-dioxoisoindolin-2-yl)oxy)-2-methylpropanoate To a stirred solution of tert-butyl (S)-3-((6-(1H-imidazol-1-yl)pyridin-3-yl)oxy)-2-(aminooxy)-2-methylpropanoate (62 mg, 0.185 mmol) in toluene (1.9 mL) was added phthalic anhydride (33 mg, 0.223 mmol), followed by a small amount of 3 Å molecular sieves. p-Toluenesulfonic acid polymer (16 mg of 2-3 mmol/g beads, 0.032-0.048 mmol) was added, and the resulting mixture was heated to 100° C. After 2 h, the reaction mixture was cooled to rt and concentrated in vacuo to afford a slurry that was purified by column chromatography on silica gel (0-10% $CH_3OH$ in DCM as eluent) to give the title compound. LC-MS [M+H]: m/z 465.3.

Step E: (S)-1-(5-(3-(tert-butoxy)-2-((1,3-dioxoisoindolin-2-yl)oxy)-2-methyl-3-oxo-propoxy)pyridin-2-yl)-3-(3-((tert-butoxycarbonyl)amino)propyl)-1H-imidazol-3-ium The title compound was prepared following procedures similar to those from Example 35, Step F. LC-MS [M+H]: m/z 509.2.

Step F (S)-3-((Z)-2-((((S)-1-((6-(3-(3-aminopropyl)-1H-imidazol-3-ium-1-yl)pyridin-3-yl)oxy)-2-carboxypropan-2-yl)oxy)imino)-2-(2-aminothiazol-4-yl)acetamido)-2,2-dimethyl-4-oxoazetidin-1-yl sulfate was prepared from (S)-1-(5-(3-(tert-butoxy)-2-((1,3-dioxoisoindolin-2-yl)oxy)-2-methyl-3-oxopropoxy)pyridin-2-yl)-3-(3-((tert-butoxycarbonyl)amino)propyl)-1H-imidazol-3-ium following procedures similar to those described in Example 36, Steps G-J. LC-MS [M+H]: m/z 682.2.

Example 114

(S)-3-((Z)-2-((((S)-1-amino-3-(4-(1-(3-aminopropyl)-2-imino-3-methyl-2,3-dihydro-1H-imidazol-4-yl)phenoxy)-1-oxopropan-2-yl)oxy)imino)-2-(2-aminothiazol-4-yl)acetamido)-2,2-dimethyl-4-oxoazetidin-1-yl sulfate

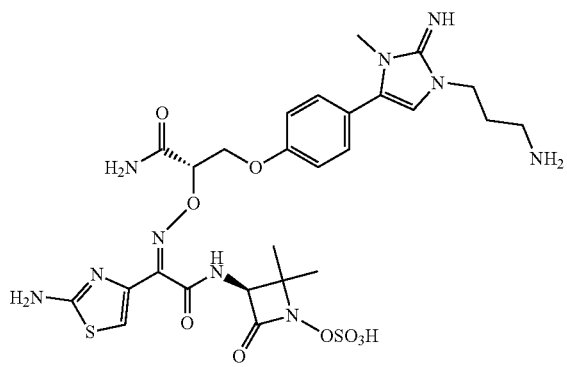

Step A: ethyl (R,E)-3-(4-(1-(3-((tert-butoxycarbonyl)amino)propyl)-2-((tert-butoxycarbonyl)imino)-3-methyl-2,3-dihydro-1H-imidazol-4-yl)phenoxy)-2-hydroxypropanoate The title compound was prepared following procedures similar to those described in Example 1, Step B. LC-MS [M+H]: m/z 563.6.

Step B: ethyl (S,Z)-3-(4-(1-(3-((tert-butoxycarbonyl)amino)propyl)-2-((tert-butoxycarbonyl)imino)-3-methyl-2,3-dihydro-1H-imidazol-4-yl)phenoxy)-2-((1,3-dioxoisoindolin-2-yl)oxy)propanoate The title compound was prepared following procedures similar to those described in Example 1, Step C. LC-MS [M+H]: m/z 708.4.

Step C: tert-butyl (S,Z)-(4-(4-(3-amino-2-(aminooxy)-3-oxopropoxy)phenyl)-1-(3-((tert-butoxycarbonyl)amino)propyl)-3-methyl-1,3-dihydro-2H-imidazol-2-ylidene)carbamate Ammonia (0.65 mL of a 7.0 M CH₃OH solution, 4.54 mmol) was added to a stirred solution of ethyl (S,Z)-3-(4-(1-(3-((tert-butoxycarbonyl)amino)propyl)-2-((tert-butoxycarbonyl)-imino)-3-methyl-2,3-dihydro-1H-imidazol-4-yl)phenoxy)-2-((1,3-dioxoisoindolin-2-yl)oxy)propanoate (107 mg, 0.151 mmol) in CH₃OH (2.0 mL). The reaction was sealed and allowed to stir at rt overnight. Then the reaction mixture was concentrated in vacuo, and the resulting crude residue was purified by reverse phase chromatography on C-18 silica (0-100% CH₃CN in water as eluent) to give the title compound. LC-MS [M+H]: m/z 549.3.

Step D: (S)-3-((Z)-2-((((S)-1-amino-3-(4-(1-(3-aminopropyl)-2-imino-3-methyl-2,3-dihydro-1H-imidazol-4-yl)phenoxy)-1-oxopropan-2-yl)oxy)imino)-2-(2-aminothiazol-4-yl)-acetamido)-2,2-dimethyl-4-oxoazetidin-1-yl sulfate The title compound was prepared from tert-butyl (S,Z)-(4-(4-(3-amino-2-(aminooxy)-3-oxopropoxy)phenyl)-1-(3-((tert-butoxycarbonyl)amino)propyl)-3-methyl-1,3-dihydro-2H-imidazol-2-ylidene)carbamate following procedures described in Example 1, Steps F-H. LC-MS [M+H]: m/z 695.7.

Example 115

(S)-3-((Z)-2-((((S)-3-(4-(1-(3-aminopropyl)-2-methyl-1H-pyrazol-2-ium-4-yl)phenoxy)-1-ethoxy-1-oxopropan-2-yl)oxy)imino)-2-(2-aminothiazol-4-yl)acetamido)-2,2-dimethyl-4-oxoazetidin-1-yl sulfate

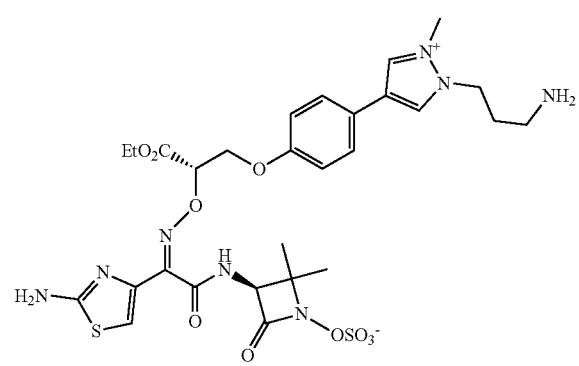

The title compound was prepared from intermediate 11 following procedures described in Example 1, Steps B-H. LC-MS [M+H]: m/z 709.5.

Example 116

Ethyl (S)-3-(4-(1-(3-aminopropyl)-2-imino-3-methyl-2,3-dihydro-1H-imidazol-4-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoate

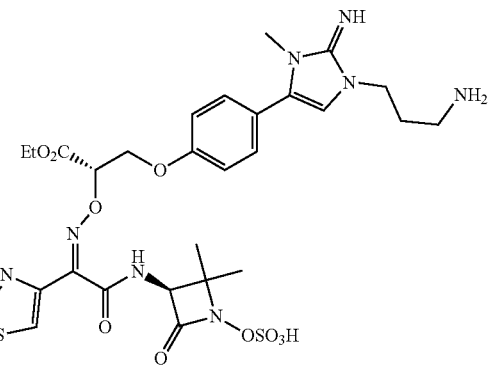

The title compound was prepared from intermediate 13 following procedures similar to those described in Example 114, Steps A-B, and Example 1, Steps F-H. LC-MS [M+H]: m/z 724.6.

Example 117

(S)-3-((Z)-2-((((S)-3-(4-(1-(3-aminopropyl)-2-methyl-1H-pyrazol-2-ium-4-yl)phenoxy)-1-methoxy-1-oxopropan-2-yl)oxy)imino)-2-(2-aminothiazol-4-yl)acetamido)-2,2-dimethyl-4-oxoazetidin-1-yl sulfate

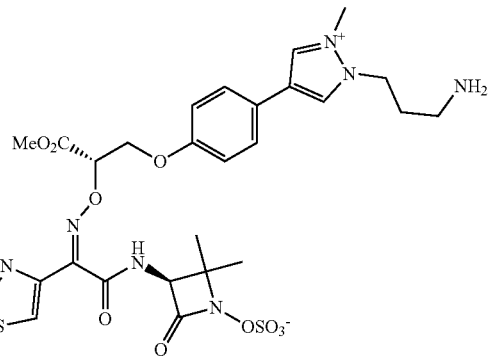

The title compound was prepared from Intermediate 15 following procedures described in Example 1, Steps B-H. LC-MS [M+H]: m/z 695.4.

Example 118

(S)-3-((6-(3-(3-aminopropyl)-2-imino-2,3-dihydro-1H-imidazol-1-yl)pyridin-3-yl)oxy)-2-(((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

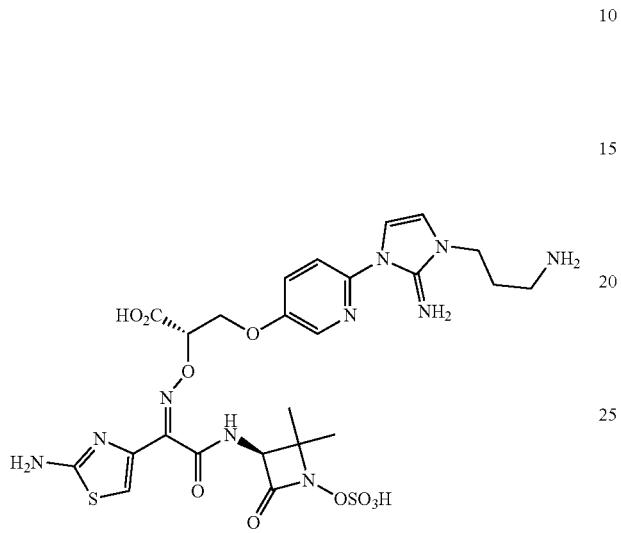

Step A: tert-butyl (S,E)-3-((6-(3-(3-((tert-butoxycarbonyl)amino)propyl)-2-((tert-butoxycarbonyl)imino)-2,3-dihydro-1H-imidazol-1-yl)pyridin-3-yl)oxy)-2-((1,3-dioxoisoindolin-2-yl)oxy)propanoate tert-Butyl hypochlorite (250 µL, 2.22 mmol) was added to a mixture of tert-butyl carbamate (229 mg, 1.95 mmol) in DCM (6.0 mL). The resulting mixture was stirred at rt for 30 min, then the mixture was cooled to 0° C., and DBU (402 µL, 2.66 mmol) was added. To this stirred mixture was added a solution of (S)-1-(5-(3-(tert-butoxy)-2-((1,3-dioxoisoindolin-2-yl)oxy)-3-oxopropoxy)pyridin-2-yl)-3-(3-((tert-butoxycarbonyl)amino)propyl)-1H-imidazol-3-ium (541 mg, 0.888 mmol from Example 36 Step F) in DCM (6.0 mL). The reaction mixture was stirred at 0° C. for 1 h, then the mixture was suspended in benzene. The resulting mixture was loaded onto a silica column and purified by column chromatography (0-7% CH₃OH in DCM as eluent) to afford the title compound. LC-MS [M+H]: m/z 723.6.

Steps B-E: (S)-3-((6-(3-(3-aminopropyl)-2-imino-2,3-dihydro-1H-imidazol-1-yl)pyridin-3-yl)oxy)-2-(((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid The title compound was prepared following procedures similar to those described in Example 36, Steps G-J. LC-MS [M+H]: m/z 683.4.

Example 119

(S)-3-((Z)-2-(((S)-2-(4-(1-(3-aminopropyl)-2-((3-fluoroazetidin-3-yl)methyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

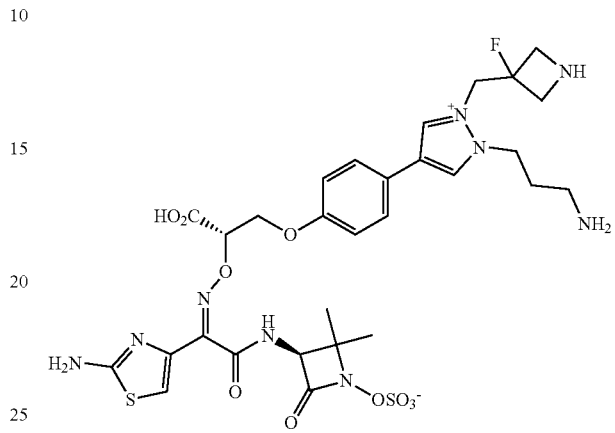

Step A: tert-butyl (R)-3-((4-(4-(3-(tert-butoxy)-2-hydroxy-3-oxopropoxy) phenyl)-1H-pyrazol-1-yl)methyl)-3-fluoroazetidine-1-carboxylate The title compound was prepared from Intermediate 4 following procedures similar to those described in Example 1, Step B, substituting Intermediate 13 for tert-butyl (3-(4-bromo-1H-pyrazol-1-yl)propyl)carbamate Intermediate 16. LC-MS [M+H]: m/z 492.5.

Step B: tert-butyl (S)-3-((4-(4-(3-(tert-butoxy)-2-((1,3-dioxoisoindolin-2-yl)oxy)-3-oxopropoxy)phenyl)-1H-pyrazol-1-yl)methyl)-3-fluoroazetidine-1-carboxylate The title compound was prepared following procedures similar to those described in Example 1, Step C. LC-MS [M+H]: m/z 637.6.

Step C: (S)-2-(3-azidopropyl)-4-(4-(3-(tert-butoxy)-2-((1,3-dioxoisoindolin-2-yl)oxy)-3-oxopropoxy)phenyl)-1-((1-(tert-butoxycarbonyl)-3-fluoroazetidin-3-yl)methyl)-1H-pyrazol-2-ium Intermediate 17 (406 mg, 1.74 mmol) was added to a stirred solution of tert-butyl (S)-3-((4-(4-(3-(tert-butoxy)-2-((1,3-dioxoisoindolin-2-yl)oxy)-3-oxopropoxy)phenyl)-1H-pyrazol-1-yl)methyl)-3-fluoroazetidine-1-carboxylate (300 mg, 0.471 mmol) and sodium bicarbonate (396 mg, 4.71 mmol) in acetonitrile (5.0 mL). The resulting suspension was heated to 60° C., and after 30 min, the reaction mixture was filtered through a pad of Celite™ The column was washed with acetonitrile, and the combined organic layers were concentrated in vacuo. The resulting crude residue was triturated with DCM and ether, and purified by column chromatography on silica gel (0-100% (3:1 EtOAc:EtOH) in hexanes as eluent) to afford the title compound. LC-MS [M]⁺: m/z 720.6.

Steps D-F: (S)-3-((Z)-2-(((((S)-3-(4-(1-(3-azidopropyl)-2-((1-(tert-butoxycarbonyl)-3-fluoroazetidin-3-yl)methyl)-1H-pyrazol-2-ium-4-yl)phenoxy)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate The title compound was prepared following procedures described in Example 1, Steps E-G. LC-MS [M+Na]: m/z 1059.8.

Step G: (S)-3-((Z)-2-(((((S)-3-(4-(1-(3-aminopropyl)-2-((1-(tert-butoxycarbonyl)-3-fluoroazetidin-3-yl)methyl)-1H-pyrazol-2-ium-4-yl)phenoxy)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate A stirred solution of (S)-3-((Z)-2-(((((S)-3-(4-(1-(3-azidopropyl)-2-((1-(tert-butoxycarbonyl)-3-fluoroazetidin-3-yl)methyl)-1H-pyrazol-2-ium-4-yl)phenoxy)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate (50 mg, 0.048 mmol) in 2,2,2-trifluoroethanol (2.0 mL) was degassed thrice under house vacuum, backfilling with nitrogen gas in each iteration. To this mixture was added 10% Palladium on carbon (5.0 mg, 4.70 µmol), and the resulting mixture was degassed as described above, backfilling with hydrogen gas. After 2 h, the reaction mixture was filtered through a pad of Celite™, washing the column with $CH_3OH$. The combined organic layers were concentrated in vacuo to afford the title compound, which was carried on without purification. LC-MS [M+]: m/z 1010.9.

Step H: (S)-3-((Z)-2-(((S)-2-(4-(1-(3-aminopropyl)-2-((3-fluoroazetidin-3-yl)methyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate The title compound was prepared following procedures described in Example 1, Step H. LC-MS [M+H]: m/z 755.2

Example 120

(S)-3-((Z)-2-(((S)-2-(4-(2-(3-amino-2-fluoro-2-((3-propyl)-1-(3-aminopropyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate Step A: tert-butyl (2R)-3-(4-(1-(3-((tert-butoxycarbonyl)amino)-2-fluoropropyl)-1H-pyrazol-4-yl)phenoxy)-2-hydroxypropanoate The title compound was prepared as a mixture of stereoisomers from Intermediate 4 following procedures similar to those described in Example 1, Step B, substituting Intermediate 15 for tert-butyl (3-(4-bromo-1H-pyrazol-1-yl)propyl)carbamate. LC-MS [M+H]: m/z 480.4.

Step B: Separation of stereoisomers of tert-butyl (2R)-3-(4-(1-(3-((tert-butoxycarbonyl)amino)-2-fluoropropyl)-1H-pyrazol-4-yl)phenoxy)-2-hydroxypropanoate The stereoisomers of tert-butyl (2R)-3-(4-(1-(3-((tert-butoxycarbonyl)amino)-2-fluoropropyl)-1H-pyrazol-4-yl)phenoxy)-2-hydroxypropanoate were separated using preparative supercritical fluid chromatography. A solution of tert-butyl (2R)-3-(4-(1-(3-((tert-butoxycarbonyl)amino)-2-fluoropropyl)-1H-pyrazol-4-yl)phenoxy)-2-hydroxypropanoate (260 mg) in methanol (20 mL) was injected (40×0.5 mL) onto a Chiralpak® AD-H (available from Chiral Technologies, Inc., Exton, Pa.) semi-preparative (250×21 mm) HPLC column (eluting with 40% (EtOH+0.2% diisopropylamine)/$CO_2$ at 70 mL/min, 120 bar outlet pressure with UV detection at 215 nm) to give a faster eluting enantiomer B-1 (retention time=2.4 min) and a slower eluting enantiomer B-2 (retention time=3.1 min) using analytical chiral HPLC conditions: Chiralpak© AD-H (available from Chiral Technologies, Inc., Exton, Pa.) semi-preparative (250×4.6 mm) HPLC column (eluting with 40% (EtOH+0.1% diisopropylamine)/$CO_2$ at 120 bar outlet pressure with UV detection at 254 nm).

Step C: (S)-3-((Z)-2-(((S)-2-(4-(2-(3-amino-2-fluoro-2$\lambda^3$-propyl)-1-(3-aminopropyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate The title compound was prepared from intermediate B-2 of Step B, following procedures similar to those described in Example 1, Steps C-H. LC-MS [M+H]: m/z 754.5.

Example 121

(S)-3-((Z)-2-(((S)-2-(4-(2-(3-amino-2-fluoro-2$\lambda^3$-propyl)-1-(azetidin-3-ylmethyl)-1H-pyrazol-2-ium-4-yl)phenoxy)-1-carboxyethoxy)imino)-2-(2-aminothiazol-4-yl)acetamido)-2,2-dimethyl-4-oxoazetidin-1-yl sulfate

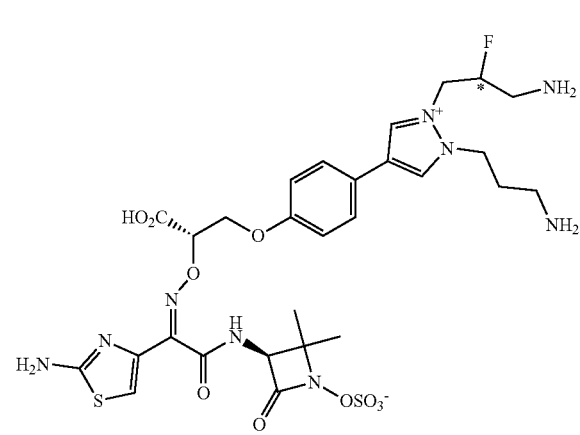

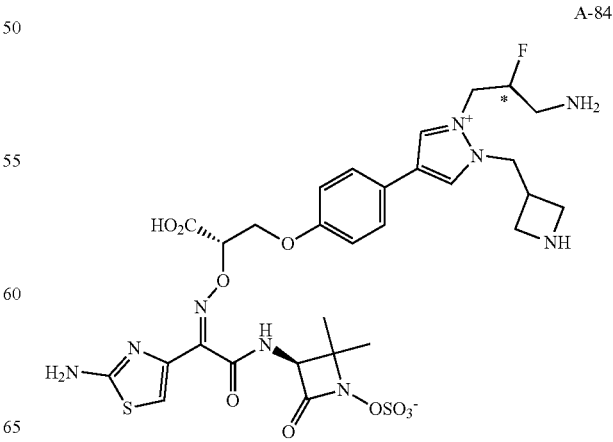

A-84

The title compound was prepared from Intermediate 20, following procedures similar to those described in Example 119 Steps B-H. LC-MS [M+H]: m/z 742.7.

Examples 122 and 123

(S)-3-((Z)-2-(((S)-2-(4-(3-((3-aminopropyl)amino)-1-methylpyridazin-1-ium-6-yl)phenoxy)-1-carboxyethoxy)imino)-2-(2-aminothiazol-4-yl)acetamido)-2,2-dimethyl-4-oxoazetidin-1-yl sulfate (122) and
(S)-3-((Z)-2-(((S)-2-(4-(6-((3-aminopropyl)amino)-1-methylpyridazin-1-ium-3-yl)phenoxy)-1-carboxyethoxy)imino)-2-(2-aminothiazol-4-yl)acetamido)-2,2-dimethyl-4-oxoazetidin-1-yl sulfate (123)

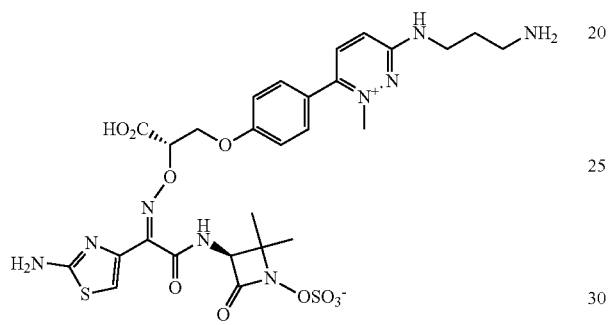

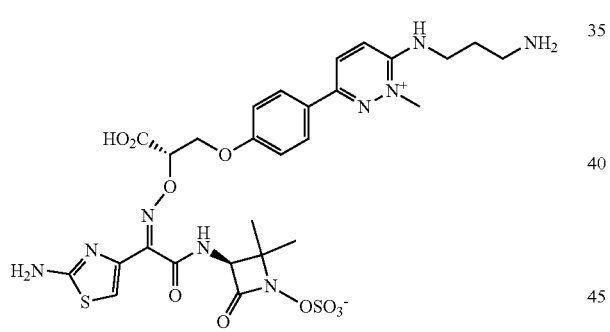

Step A: tert-butyl (R)-3-(4-(6-((3-((tert-butoxycarbonyl)amino)propyl) amino)pyridazin-3-yl)phenoxy)-2-hydroxypropanoate The title compound was prepared from Intermediate 4, following procedures similar to those described in Example 1, Step B. LC-MS [M+H]: m/z 489.5.

Step B: tert-butyl (R)-3-(4-(6-((3-((tert-butoxycarbonyl)amino) propyl)amino)pyridazin-3-yl)phenoxy)-2-((1,3-dioxoisoindolin-2-yl)oxy)propanoate The title compound was prepared from tert-butyl (R)-3-(4-(6-((3-((tert-butoxycarbonyl)amino)propyl) amino) pyridazin-3-yl)phenoxy)-2-hydroxypropanoate following procedures similar to those described in Example 1, Step C. LC-MS [M+H]: m/z 634.7.

Step C: (R)-6-(4-(3-(tert-butoxy)-2-((1,3-dioxoisoindolin-2-yl)oxy)-3-oxopropoxy)phenyl)-3-((3-((tert-butoxycarbonyl)amino)propyl)amino)-1-methylpyridazin-1-ium (C-1); and (R)-3-(4-(3-(tert-butoxy)-2-((1,3-dioxoisoindolin-2-yl)oxy)-3-oxopropoxy)phenyl)-6-((3-((tert-butoxycarbonyl)amino)propyl)amino)-1-methylpyridazin-1-ium (C-2)

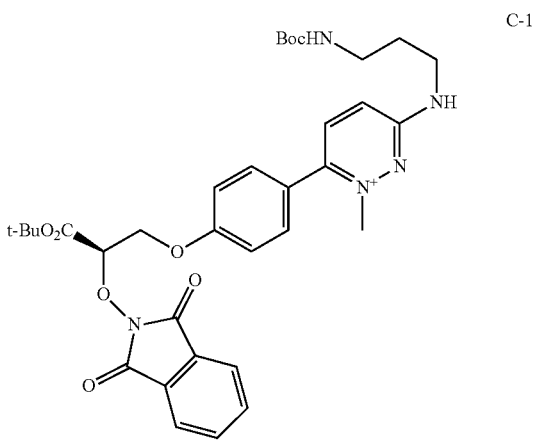

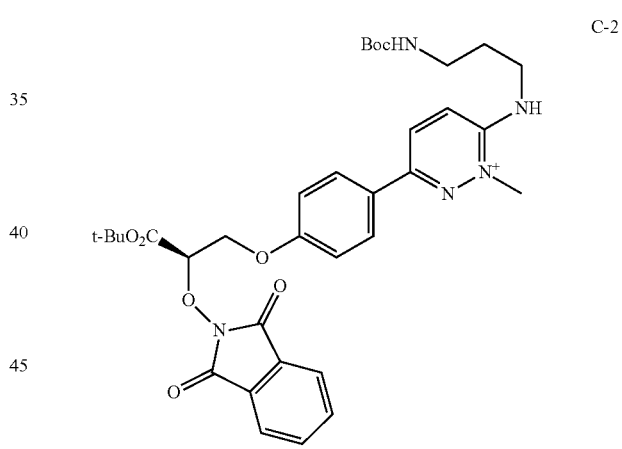

The title compounds were prepared as a mixture of regioisomers from tert-butyl (R)-3-(4-(6-((3-((tert-butoxycarbonyl)amino)propyl)amino)pyridazin-3-yl)phenoxy)-2-((1,3-dioxo-isoindolin-2-yl)oxy)propanoate, following procedures similar to those described in Example 1, Step D. The crude mixture of regioisomers was separated by column chromatography on silica gel (0-5% $CH_3OH$ in DCM as eluent) to afford intermediates $H_1$ and $H_2$. $H_1$: LC-MS [M+H]: m/z 648.8. $H_2$: LC-MS [M+H]: m/z 648.8.

(S)-3-((Z)-2-(((S)-2-(4-(3-((3-aminopropyl)amino)-1-methylpyridazin-1-ium-6-yl)phenoxy)-1-carboxyethoxy)imino)-2-(2-aminothiazol-4-yl)acetamido)-2,2-dimethyl-4-oxoazetidin-1-yl sulfate (122)

The title compound was prepared from compound H1, following procedures described in Example 1, Steps E-H. LC-MS [M+H]: m/z 708.8.

(S)-3-((Z)-2-(((S)-2-(4-(6-((3-aminopropyl)amino)-1-methylpyridazin-1-ium-3-yl)phenoxy)-1-carboxyethoxy)imino)-2-(2-aminothiazol-4-yl)acetamido)-2,2-dimethyl-4-oxoazetidin-1-yl sulfate (123)

The title compound was prepared from compound H2, following procedures described in Example 1, Steps E-H. LC-MS [M+H]: m/z 708.7.

Example 124

(S)-3-((Z)-2-(((S)-2-((6-(4-(3-aminopropyl)-3-((3-fluoroazetidin-3-yl)methyl)-1H-imidazol-3-ium-1-yl)pyridin-3-yl)oxy)-1-carboxyethoxy)imino)-2-(2-aminothiazol-4-yl)acetamido)-2,2-dimethyl-4-oxoazetidin-1-yl sulfate

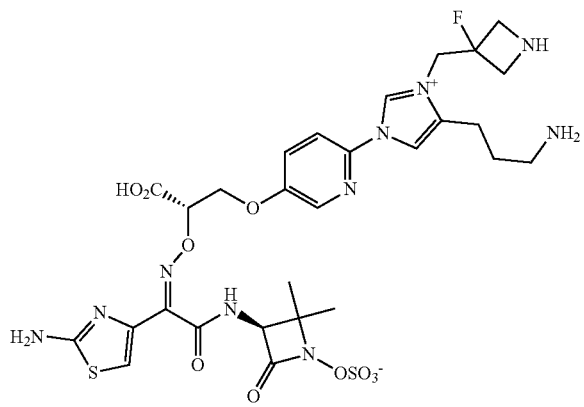

Step A: tert-butyl (R)-3-((6-(4-(3-((tert-butoxycarbonyl)amino)propyl)-1H-imidazol-1-yl)pyridin-3-yl)oxy)-2-((tert-butyldimethylsilyl)oxy)propanoate The title compound was prepared from tert-butyl (R)-3-((6-bromopyridin-3-yl)oxy)-2-((tert-butyldimethylsilyl)oxy)propanoate (Example 36, step D) following procedures similar to those described in Example 35, Step C. LC-MS [M+H]: m/z 577.6.

Steps B-C: tert-butyl (S)-3-((6-(4-(3-((tert-butoxycarbonyl)amino)propyl)-1H-imidazol-1-yl)pyridin-3-yl)oxy)-2-((1,3-dioxoisoindolin-2-yl)oxy)propanoate The title compound was prepared from tert-butyl (R)-3-((6-(4-(3-((tert-butoxycarbonyl)amino)propyl)-1H-imidazol-1-yl)pyridin-3-yl)oxy)-2-((tert-butyldimethylsilyl)oxy)propanoate following procedures similar to those described in Example 36, Steps F and G. LC-MS [M+H]: m/z 608.3.

Step D: (S)-1-(5-(3-(tert-butoxy)-2-((1,3-dioxoisoindolin-2-yl)oxy)-3-oxopropoxy)pyridin-2-yl)-3-((1-(tert-butoxycarbonyl)-3-fluoroazetidin-3-yl)methyl)-4-(3-((tert-butoxycarbonyl)-amino)propyl)-1H-imidazol-3-ium The title compound was prepared from tert-butyl (S)-3-((6-(4-(3-((tert-butoxycarbonyl)amino)propyl)-1H-imidazol-1-yl)pyridin-3-yl)oxy)-2-((1,3-dioxoisoindolin-2-yl)oxy)propanoate following procedures similar to those described in Example 36, Step H. LC-MS [M+]: m/z 795.8.

4-(3-aminopropyl)-1-(5-((S)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-2-carboxyethoxy)pyridin-2-yl)-3-((3-fluoroazetidin-3-yl)methyl)-1H-imidazol-3-ium The title compound was prepared from (S)-1-(5-(3-(tert-butoxy)-2-((1,3-dioxoisoindolin-2-yl)oxy)-3-oxopropoxy)pyridin-2-yl)-3-((1-(tert-butoxycarbonyl)-3-fluoroazetidin-3-yl)methyl)-4-(3-((tert-butoxycarbonyl)amino)propyl)-1H-imidazol-3-ium following procedures similar to those described in Example 1, Steps E-H. LC-MS [M+]: m/z 755.5.

Example 125

(S)-3-(4-(5-(((2-Aminoethyl)amino)methyl)-1-(3-aminopropyl)-1H-pyrazol-3-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

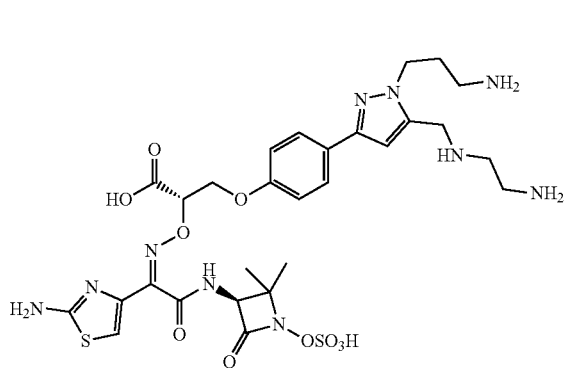

Step A: Methyl (R)-4-(3-(tert-butoxy)-2-hydroxy-3-oxopropoxy) benzoate

A mixture of tert-butyl oxirane-2-carboxylate (2.1 g, 14.5 mmol), methyl 4-hydroxybenzoate (1 g, 6.6 mmol), molecular sieves (0.1 g), and Co-catalyst (R, R) (0.28 g, 0.33 mmol) in t-BuOMe (2.2 ml) was stirred at rt for 4 days. Then the reaction mixture was filtered through Celite™, the filtrate was concentrated and the resulting residue was purified on a silica gel column (220 g) using 0-30% EtOAc/hexane to give the title compound. LC/MS: m/e 319.34 [M+Na]+.

Step B: Methyl (R)-4-(3-(tert-butoxy)-2-((tert-butyldimethylsilyl)oxy)-3-oxopropoxy)-benzoate To a solution of (R)-methyl 4-(3-(tert-butoxy)-2-hydroxy-3-oxopropoxy)benzoate (1.38 g, 4.7 mmol) and imidazole (0.79 g, 11.6 mmol) in DCM (47 ml) was added TBDMS-Cl (0.84 g, 5.6 mmol) at RT. The reaction was stirred at RT overnight, and then partitioned between EtOAc and water. The organic layer was separated, washed with brine, dried over MgSO4, filtered, and concentrated. The resulting residue was purified on silica gel column (220 g) using 0-10% EtOAc/hexane to give the title compound. LC/MS: m/e 433.21 [M+Na]+.

Step C: tert-Butyl (R)-2-((tert-butyldimethylsilyl)oxy)-3-(4-(methoxy(methyl)carbamoyl)-phenoxy)propanoate To a 0° C. solution of (R)-methyl 4-(3-(tert-butoxy)-2-((tert-butyl-dimethylsilyl)oxy)-3-oxopropoxy)benzoate (1.9 g, 4.7 mmol) and Weinreb amide (0.96 g, 9.9 mmol) in THF (47 ml) was added dropwise iPrMgCl solution (6.5 ml, 19 mmol, 2.9 M) while keeping the internal temperature below 5° C. The reaction mixture was stirred at 0° C. for 3 h and then quenched with aqueous $NH_4Cl$. The reaction mixture was extracted with EtOAc (3×), dried over $MgSO_4$, filtered, and concentrated. The resulting residue was purified on silica gel column (80 g) using 0-30% EtOAc/hexane to give the title compound. LC/MS: m/e 440.23 $[M+H]^+$.

Step D: tert-Butyl (R)-3-(4-(4-(benzyloxy) but-2-ynoyl)phenoxy)-2-((tert-butyldimethylsilyl)oxy) propanoate To a solution of ((prop-2-yn-1-yloxy)methyl)benzene (1.87 g, 12.8 mmol) in THF (12 ml) at −78° C. was added butyllithium (4.26 ml, 10.6 mmol) (2.5M/hexane). The reaction mixture was stirred at −78° C. for 1 hr, then added dropwise via syringe to a solution of (R)-tert-butyl 2-((tert-butyldimethylsilyl)oxy)-3-(4-(methoxy-(methyl)carbamoyl) phenoxy)propanoate (1.56 g, 3.6 mmol) in THF (5 ml) at −78° C. The reaction mixture was stirred at −78° C. for 30 min, and at 0° C. for 30 min. Then the reaction was quenched with saturated $NH_4Cl$ solution, and extracted with EtOAc (3×). The combined organic layers were washed with brine, dried over $MgSO_4$, filtered, and concentrated. The resulting residue was and purified on a silica gel column (40 g) using 0-30% EtOAc/hexane to give the title compound. LC/MS: m/e 525.23 $[M+H]^+$.

Step E: tert-Butyl (R)-3-(4-(5-((benzyloxy)methyl)-1H-pyrazol-3-yl)phenoxy)-2-((tert-butyldimethylsilyl)oxy)propanoate A solution of (R)-tert-butyl 3-(4-(4-(benzyloxy) but-2-ynoyl)phenoxy)-2-((tert-butyldimethylsilyl)oxy) propanoate (1.16 g, 2.2 mmol) and hydrazine (0.35 ml, 11 mmol) in EtOH (22 ml) was heated at 80° C. for 1 h. Then the reaction mixture was concentrated to dryness and purified on silica gel column (80 g) using 0-30% EtOAc/hexane to give the title compound. LC/MS: m/e 539.25 $[M+H]^+$.

Step F: tert-Butyl (R)-3-(4-(5-((benzyloxy)methyl)-1-(3-((tert-butoxycarbonyl)amino)-propyl)-1H-pyrazol-3-yl)phenoxy)-2-((tert-butyldimethylsilyloxy) propanoate A solution of (R)-tert-butyl 3-(4-(5-((benzyloxy)methyl)-1H-pyrazol-3-yl)phenoxy)-2-((tert-butyldimethylsilyl)oxy) propanoate (1.11 g, 2.1 mmol), tert-butyl (3-bromopropyl) carbamate (0.49 g, 2.1 mmol), and $Cs_2CO_3$ (1.0 g, 3.1 mmol) in DMF (4.12 ml) was stirred at RT overnight. Then the reaction mixture was diluted with water and extracted with EtOAc (3×). The combined organic layers were washed with brine (3×), dried over $MgSO_4$ and concentrated. The resulting residue was purified on silica gel column (120 g) using 0-30% EtOAc/hexane to give the title compound. LC/MS: m/e 696.37 $[M+H]^+$.

Step G: tert-Butyl (R)-3-(4-(1-(3-((tert-butoxycarbonyl)amino)propyl)-5-(hydroxymethyl)-1H-pyrazol-3-yl)phenoxy)-2-((tert-butyldimethylsilyl)oxy)propanoate A mixture of (R)-tert-butyl 3-(4-(5-((benzyloxy)methyl)-1-(3-((tert-butoxycarbonyl)amino)propyl)-1H-pyrazol-3-yl) phenoxy)-2-((tert-butyldimethylsilyl)oxy)propanoate (810 mg, 1.16 mmol) and Pd/C (82 mg, 0.077 mmol) in MeOH (5.8 mL) was stirred under $H_2$ balloon at rt overnight. TLC showed reaction complete. It was filtered through a pack of Celite™, and concentrated to dryness to give the title compound. LC/MS: m/e 606.32 $[M+H]^+$.

Step H: tert-Butyl (R)-3-(4-(1-(3-((tert-butoxycarbonyl)amino)propyl)-5-formyl-1H-pyrazol-3-yl)phenoxy)-2-((tert-butyldimethylsilyl)oxy)propanoate To a solution of (R)-tert-butyl 3-(4-(1-(3-((tert-butoxycarbonyl)amino)propyl)-5-(hydroxymethyl)-1H-pyrazol-3-yl) phenoxy)-2-((tert-butyldimethylsilyl)oxy)propanoate (590 mg, 0.97 mmol) in DCM (9.7 ml) at 0° C. was added Dess-martin periodinane (434 mg, 1.02 mmol). After addition, the reaction mixture was warmed to RT and stirred for approx. 2 hrs. The reaction mixture was quenched with 5% $Na_2S_2O_3$ solution. The mixture was extracted with EtOAc (3×), and the combined organic layers were washed with sat $NaHCO_3$ and brine, dried over $MgSO_4$, concentrated in vacuum and purified on silica gel column (40 g) using 0-30% EtOAc/hexane to give the title compound. LC/MS: m/e 604.30 $[M+H]^+$.

Step I: tert-Butyl (R)-3-(4-(5-(((2-((tert-butoxycarbonyl)amino)ethyl)amino)methyl)-1-(3-((tert-butoxycarbonyl)amino)propyl)-1H-pyrazol-3-yl)phenoxy)-2-((tert-butyldimethylsilyl)-oxy)propanoate To a solution of (R)-tert-butyl 3-(4-(1-(3-((tert-butoxycarbonyl)amino)-propyl)-5-formyl-1H-pyrazol-3-yl)phenoxy)-2-((tert-butyldimethylsilyl)oxy)propanoate (203 mg, 0.34 mmol) and N-boc-ethylenediamine hydrochloride (99 mg, 0.50 mmol) in THF (1.7 ml) at RT was added triethylamine (70 µl, 0.50 mmol) and $MgSO_4$. The reaction was stirred at rt for 16 hrs, filtered and concentrated. The resulting residue was redissolved in MeOH (1.7 ml), then sodium borohydride (12.7 mg, 0.34 mmol) was added, and the reaction was stirred at rt for 2 hr. The reaction mixture was partitioned between EtOAc and $H_2O$. Then the aqueous layer was extracted with EtOAc(3×), washed with brine, dried over $MgSO_4$, and concentrated in vacuum. The resulting residue was purified on silica gel column (24 g) using 0-100% EtOAc/hexane to give the title compound. LC/MS: m/e 748.46 $[M+H]^+$.

Step J: tert-Butyl (R)-3-(4-(5-(((tert-butoxycarbonyl)(2-((tert-butoxycarbonyl)amino)-ethyl)amino) methyl)-1-(3-((tert-butoxycarbonyl)amino)propyl)-1H-pyrazol-3-yl)phenoxy)-2-((tert-butyldimethylsilyl)oxy)propanoate The solution of (R)-tert-butyl 3-(4-(5-(((2-((tert-butoxycarbonyl)amino)ethyl)amino)methyl)-1-(3-((tert-butoxycarbonyl)amino)propyl)-1H-pyrazol-3-yl)phenoxy)-2-((tert-butyldimethylsilyl)oxy)propanoate (290 mg, 0.39 mmol), $BOC_2O$ (0.18 ml, 0.78 mmol) and TEA (0.16 ml, 1.16 mmol) in THF (10 ml) was stirred at rt overnight, diluted with $H_2O$, extracted with EtOAc(3×), washed with brine, dried over $MgSO_4$, filtered, concentrated and purified on silica gel column (40 g) using 0-80% EtOAc/hexane to give the title compound. LC/MS: m/e 848.47 $[M+H]^+$.

Step K: tert-Butyl (R)-3-(4-(5-(((tert-butoxycarbonyl)(2-((tert-butoxycarbonyl)amino-ethyl)-amino) methyl)-1-(3-((tert-butoxycarbonyl)amino)propyl)-1H-pyrazol-3-yl)phenoxy)-2-hydroxypropanoate To a solution of (R)-tert-butyl 3-(4-(5-(((tert-butoxycarbonyl)(2-((tert-butoxycarbonyl)amino)ethyl)amino)

methyl)-1-(3-((tert-butoxycarbonyl)amino)propyl)-1H-pyrazol-3-yl)phenoxy)-2-((tert-butyldimethylsilyl) oxy)propanoate (305 mg, 0.36 mmol) in THF (3.6 ml) at RT was added TBAF (430 µl, 0.43 mmol). The reaction was stirred at rt for 3 hr, and then concentrated and purified on silica gel column (40 g) using 0-75% EtOAc/hexane to give the title compound. LC/MS: m/e 734.42 (M+H)$^+$.

Step L: (S)-3-(4-(5-(((2-Aminoethyl)amino)methyl)-1-(3-aminopropyl)-1H-pyrazol-3-yl)phenoxy)-2-((((Z)-1-(2-aminothiazol-4-yl)-2-(((S)-2,2-dimethyl-4-oxo-1-(sulfooxy)-azetidin-3-yl)amino)-2-oxoethylidene)amino)oxy)propanoic acid The title compound was prepared according to the procedure of Example 1 Step C to Step H starting from tert-Butyl (R)-3-(4-(5-(((tert-butoxycarbonyl)(2-((tert-butoxycarbonyl)amino)ethyl)amino)methyl)-1-(3-((tert-butoxycarbonyl)amino)propyl)-1H-pyrazol-3-yl)phenoxy)-2-hydroxypropanoate. LC/MS: m/e 739.18 [M+H]$^+$. $^1$H NMR (500 MHz, Deuterium Oxide) δ (ppm) 7.59 (d, J=8.4 Hz, 2H), 7.02-6.86 (m, 3H), 6.74 (s, 1H), 5.07-4.92 (m, 1H), 4.54-4.28 (m, 5H), 4.22 (t, J=6.9 Hz, 2H), 3.43 (t, J=6.9 Hz, 2H), 3.32 (t, J=7.0 Hz, 2H), 2.93 (t, J=7.9 Hz, 2H), 2.10 (p, J=6.8 Hz, 2H), 1.23 (s, 3H), 0.96 (s, 3H).

Example 126

(S)-3-(4-(5-(Aminomethyl)-1-(3-aminopropyl)-1H-pyrazol-3-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid

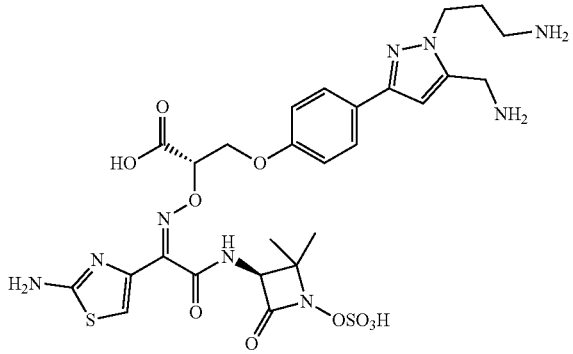

Step A: Potassium bis(tert-butoxycarbonyl)amide

To a solution of di-tert-butyl-iminodicarboxylate (20 g, 92 mmol) in EtOH (20 m) at rt was added KOH (5.4 g, 97 mmol) in EtOH (20 ml). The reaction was stirred at rt for 40 min, and then Et$_2$O was added. The mixture was filtered, and washed with Et$_2$O to give the title compound, which was used in the next step without further purification.

Step B: tert-Butyl (R)-3-(4-(1-(3-((tert-butoxycarbonyl)amino)propyl)-5-(chloromethyl)-1H-pyrazol-3-yl)phenoxy)-2-((tert-butyldimethylsilyl)oxy)propanoate To a solution of (R)-tert-butyl 3-(4-(1-(3-((tert-butoxycarbonyl)amino)propyl)-5-(hydroxymethyl)-1H-pyrazol-3-yl)phenoxy)-2-((tert-butyldimethylsilyl)oxy)propanoate (100 mg, 0.16 mmol) in DCM (825 µl) at 0° C. was added TEA (23 µl, 0.16 mmol), followed by methanesulfonyl chloride (13 µl, 0.16 mmol). The reaction mixture was stirred at 0° C. for 1 h, then additional TEA (23.01 µl, 0.165 mmol), and methanesulfonyl chloride (12.86 µl, 0.165 mmol)) were added. The reaction mixture was warmed up to rt and stirred for 2 h, then partitioned between DCM and water. The organic layer was separated, dried over MgSO$_4$, concentrated and purified on a silica gel column (40 g) using 0-30-60% EtOAc/hexane to give the title compound. LC/MS: m/e 624.74 [M+H]$^+$.

Step C: tert-Butyl (R)-3-(4-(5-((bis(tert-butoxycarbonyl)amino)methyl)-1-(3-((tert-butoxycarbonyl)amino)propyl)-1H-pyrazol-3-yl)phenoxy)-2-((tert-butyldimethylsilyl)-oxy)propanoate To a solution of (R)-tert-butyl 3-(4-(1-(3-((tert-butoxycarbonyl)amino)-propyl)-5-(chloromethyl)-1H-pyrazol-3-yl)phenoxy)-2-((tert-butyldimethylsilyl)-oxy)-propanoate (70 mg, 0.112 mmol) in DMF (1 ml) at RT was added potassium bis(tert-butoxycarbonyl)amide (32 mg, 0.123 mmol). The reaction mixture was stirred at RT overnight. Additional potassium bis(tert-butoxycarbonyl)amide (10 mg) was added and the reaction was stirred at RT for 1 h, then diluted with H$_2$O, extracted with EtOAc (3×). The combined organic layers were washed with brine (3×), dried over MgSO$_4$, filtered, and concentrated. The resulting residue was purified on silica gel column (24 g) using 0-30% EtOAc/hexane to give the title compound. LC/MS: m/e 805.45 [M+H]$^+$.

Step D: tert-butyl (R)-3-(4-(5-((bis(tert-butoxycarbonyl)amino)methyl)-1-(3-((tert-butoxy-carbonyl)amino)propyl)-1H-pyrazol-3-yl)phenoxy)-2-hydroxypropanoate To a solution of (R)-tert-butyl 3-(4-(5-((bis(tert-butoxycarbonyl)amino)methyl)-1-(3-((tert-butoxycarbonyl)-amino)propyl)-1H-pyrazol-3-yl)phenoxy)-2-((tert-butyldimethylsilyl)oxy)propanoate (76 mg, 0.094 mmol) in THF (944 µl) at RT was added TBAF (113 µl, 0.113 mmol). The reaction mixture was stirred at RT for 30 min, and then concentrated. The resulting residue was purified by ISCO (12 g, 0-60% EtOAc/hexanes) to give the title compound. LC/MS: m/e 691.39 [M+H]$^+$.

Step F: (S)-3-(4-(5-(Aminomethyl)-1-(3-aminopropyl)-1H-pyrazol-3-yl)phenoxy)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic acid The title compound was prepared according to the procedure of Example 1 Step C-Step H starting from (R)-tert-butyl 3-(4-(5-((bis(tert-butoxycarbonyl)amino)methyl)-1-(3-((tert-butoxycarbonyl)amino)propyl)-1H-pyrazol-3-yl)phenoxy)-2-hydroxypropanoate. LC/MS: m/e 696.27 [M+H]$^+$. $^1$H NMR (500 MHz, D$_2$O): δ (ppm) 7.58 (d, J=8.4 Hz, 2H); 6.93 (d, J=8.3 Hz, 2H); 6.81 (s, 1H); 6.65 (s, 1H); 4.81 (s, 1H); 4.40 (s, 1H); 4.35-4.36 (m, 2H); 4.23 (s, 2H); 4.18 (t, J=6.9 Hz, 2H); 2.94 (t, J=7.8 Hz, 2H); 2.10 (t, J=7.8 Hz, 2H); 1.25 (s, 3H); 1.02 (s, 3H).

Biological Assays

Antibiotic Activity: Determination of Growth Inhibitory Concentration

The concentrations of compounds required to inhibit the growth of various strains of bacteria were determined in an assay that assessed bacterial growth by measuring optical density at 600 nm (OD600). The bacterial strains tested included the clinical strains *Escherichia coli* expressing NDM-1 (CLB30016), *Klebsiella pneumoniae* expressing KPC-1 (CL6569), *Acinetobacter baumannii* expressing TEM-1, AmpC, and Oxa-24/40 (CL6188) and *Pseudomonas aeruginosa* expressing AmpC (CL5701). All compounds were tested in the presence of a β lactamase inhibitor (BLi, Relebactam) in 384-well microplates. The clinical strains were stored as frozen single use stocks, thawed and diluted into 1.1× cation-adjusted Mueller-Hinton II broth to achieve approximately $2 \times 10^5$ CFU/mL. Test compounds were dissolved in DMSO and diluted 1:50 in the assay, resulting in a final concentration range of 100 μM to 0.098 μM. On the day of the assay, 1 μL of test compound was added to the plate followed by 4 μL of 50 μg/mL BLi in MOPS buffer and 45 μL of diluted bacteria. Plates were centrifuged at 1000 rpm for 30 seconds, shaken at approximately 800 rpm for 1 minute, and incubated at 35±2° C. for 22 hours. The concentration of BLi used in the assay was 4 μg/mL. At the end of the incubation, absorbance at 600 nm was determined using a spectrophotometer. Inhibition was quantitated by identifying the lowest concentration of test compound that was required to inhibit 95% of the growth of the bacteria. The results for Examples 1-126 are reported in Table I, expressed as the concentration of compound that inhibited 95% of bacterial growth (Minimum Inhibitory Threshold Concentration; MITC95).

Representative compounds of the present invention display a growth inhibitory effect. For example, representative compounds of Examples 1-126 were determined to inhibit growth at concentrations of 100 μM or less.

TABLE I

Antibacterial activity of Examples 1-126

| Examples # | AB_CL6188 MITC95 (μM) | EC_CLB30016 MITC95 (μM) | KP_CL6569 MITC95 (μM) | PA_CL5701 MITC95 (μM) |
|---|---|---|---|---|
| 1 | 2.734 | 4.688 | 0.3906 | 3.125 |
| 2 | 1.563 | 12.5 | 0.3906 | 3.125 |
| 3 | 6.25 | 3.13 | 0.39 | 6.25 |
| 4 | 6.25 | 12.5 | 1.281 | 25 |
| 5 | 25 | 100 | 6.25 | 50 |
| 6 | 100 | 100 | 12.5 | 100 |
| 7 | 25 | 25 | 1.563 | 12.5 |
| 8 | 100 | 100 | 3.125 | 25 |
| 9 | 12.5 | 12.5 | 0.3906 | 6.25 |
| 10 | 12.5 | 6.25 | 0.3906 | 6.25 |
| 11 | 3.125 | 6.25 | 0.7813 | 3.125 |
| 12 | 6.25 | 100 | 0.3906 | 3.125 |
| 13 | 25 | 12.5 | 0.7813 | 12.5 |
| 14 | 50 | 12.5 | 0.7813 | 12.5 |
| 15 | 3.125 | 6.25 | 0.3906 | 6.25 |
| 16 | 3.125 | 6.25 | 0.3906 | 3.125 |
| 17 | 12.5 | 6.25 | 0.3906 | 6.25 |
| 18 | 3.125 | 6.25 | 0.3906 | 6.25 |
| 19 | 12.5 | 6.25 | 0.7813 | 12.5 |
| 20 | 6.25 | 6.25 | 0.3906 | 6.25 |
| 21 | 3.125 | 6.25 | 0.3906 | 12.5 |
| 22 | 12.5 | 12.5 | 0.7813 | 25 |
| 23A | 6.25 | 12.5 | 0.3906 | 3.125 |
| 23B | 12.5 | 100 | 3.125 | 25 |
| 24 | 1.563 | 3.125 | 0.3906 | 3.125 |
| 25 | 50 | 6.25 | 0.3906 | 3.125 |
| 26 | 12.5 | 100 | 1.563 | 50 |
| 27 | 12.5 | 12.5 | 0.7813 | 6.25 |
| 28 | 3.13 | 6.25 | 0.2 | 3.13 |
| 29 | 3.125 | 25 | 1.563 | 6.25 |
| 30 | 25 | 25 | 3.125 | 6.25 |
| 31 | 3.125 | 6.25 | 0.3906 | 3.125 |
| 32 | 3.125 | 3.125 | 0.1953 | 3.125 |
| 33 | 3.125 | 6.25 | 0.3906 | 6.25 |
| 34 | 12.5 | 25 | 0.78 | 25 |
| 35 | 6.25 | 25 | 1.281 | 50 |
| 36 | 3.125 | 12.5 | 0.7813 | 6.25 |
| 37A | 12.5 | 12.5 | 0.78 | 3.13 |
| 37B | 50 | 100 | 6.25 | 25 |
| 38 | 6.25 | 6.25 | 0.3906 | 6.25 |
| 39 | 7.292 | 12.5 | 0.3255 | 3.125 |
| 40 | 50 | 50 | 3.125 | 50 |
| 41 | 12.5 | 25 | 1.563 | 25 |
| 42 | 1.563 | 3.125 | 0.3906 | 3.125 |
| 43 | 3.125 | 6.25 | 0.1953 | 3.125 |
| 44 | 1.563 | 3.125 | 0.1953 | 3.125 |
| 45 | 3.125 | 6.25 | 0.3906 | 6.25 |
| 46 | 3.125 | 6.25 | 0.3906 | 6.25 |
| 47 | 3.125 | 3.125 | 0.3906 | 3.125 |
| 48 | 12.5 | 12.5 | 0.7813 | 6.25 |
| 49 | 3.125 | 12.5 | 0.7813 | 6.25 |
| 50 | 3.125 | 6.25 | 0.3906 | 6.25 |
| 51A | 6.25 | 12.5 | 0.7813 | 3.125 |
| 51B | 25 | 100 | 6.25 | 25 |
| 52 | 1.563 | 6.25 | 0.1953 | 1.563 |
| 53 | 1.563 | 3.125 | 0.09766 | 1.563 |
| 54 | 1.563 | 3.125 | 0.09766 | 1.563 |
| 55 | 3.125 | 1.563 | 0.1953 | 1.563 |
| 56 | 3.125 | 3.125 | 0.3906 | 3.125 |
| 57 | 3.125 | 3.125 | 0.1953 | 3.125 |
| 58 | 3.125 | 25 | 0.3906 | 3.125 |
| 59 | 12.5 | 50 | 3.125 | 12.5 |
| 60 | 3.125 | 12.5 | 0.3906 | 3.125 |
| 61 | 25 | 50 | 1.563 | 12.5 |
| 62 | 2.9 | 1.9 | 0.36 | 5.8 |
| 63 | 3.125 | 1.563 | 0.3906 | 6.25 |
| 64 | 50 | 12.5 | 1.563 | 12.5 |
| 65 | 3.125 | 1.563 | 0.3906 | 12.5 |
| 66 | 1.708 | 1.708 | 0.2135 | 1.708 |
| 67 | 3.125 | 6.25 | 0.7813 | 6.25 |
| 68 | 3.125 | 3.125 | 0.1953 | 3.125 |
| 69 | 3.125 | 6.25 | 0.3906 | 3.125 |
| 70 | 12.5 | 6.25 | 0.7813 | 6.25 |
| 71 | 3.125 | 3.125 | 0.1953 | 6.25 |
| 72 | 3.125 | 6.25 | 0.3906 | 6.25 |
| 73 | 1.563 | 3.125 | 0.1953 | 3.125 |
| 74 | 6.25 | 1.563 | 0.1953 | 6.25 |
| 75 | 1.563 | 3.125 | 0.1953 | 3.125 |
| 76 | 0.7813 | 3.125 | 0.1953 | 3.125 |
| 77 | 1.563 | 3.125 | 0.3906 | 3.125 |
| 78 | 6.25 | 12.5 | 0.7813 | 12.5 |
| 79 | 3.125 | 6.25 | 0.3906 | 6.25 |
| 80 | 1.563 | 6.25 | 0.1953 | 3.125 |
| 81 | 3.125 | 3.125 | 0.1953 | 3.125 |
| 82 | 1.563 | 1.563 | 0.1953 | 3.125 |
| 83 | 1.563 | 3.125 | 0.1953 | 1.563 |
| 84 | 10 | 40 | 2.5 | 40 |
| 85 | 10 | 40 | 2.5 | 40 |
| 86 | 6.25 | 12.5 | 1.281 | 25 |
| 87 | 6.25 | 25 | 0.1953 | 3.125 |
| 88 | 1.563 | 3.125 | 0.3906 | 3.125 |
| 89 | 6.25 | 12.5 | 1.563 | 50 |
| 90 | 6.25 | 25 | 1.563 | 25 |
| 91 | 6.25 | 25 | 0.7813 | 12.5 |
| 92 | 25 | 100 | 6.25 | 100 |
| 93 | 6.25 | 1.563 | 0.1953 | 6.25 |
| 94 | 0.7813 | 6.25 | 0.1953 | 3.125 |
| 95 | 12.5 | 25 | 0.3906 | 3.125 |
| 96 | 6.25 | 12.5 | 0.3906 | 6.25 |

TABLE I-continued

Antibacterial activity of Examples 1-126

| Examples # | AB_CL6188 MITC95 (μM) | EC_CLB30016 MITC95 (μM) | KP_CL6569 MITC95 (μM) | PA_CL5701 MITC95 (μM) |
|---|---|---|---|---|
| 97 | 1.391 | 2.563 | 0.125 | 1.781 |
| 98 | 1.563 | 1.563 | 0.09766 | 1.563 |
| 99 | 1.563 | 6.25 | 0.1953 | 3.125 |
| 100 | 3.125 | 3.125 | 0.39 | 3.125 |
| 101 | 6.25 | 6.25 | 0.7813 | 12.5 |
| 102 | 1.781 | 1.781 | 0.125 | 3.125 |
| 103 | 1.563 | 3.125 | 0.09766 | 3.125 |
| 104 | 1.563 | 1.563 | 0.1953 | 6.25 |
| 105 | 6.25 | 12.5 | 0.3906 | 3.125 |
| 106 | 100 | 100 | 50 | 100 |
| 107 | 12.5 | 100 | 6.25 | 50 |
| 108 | 6.25 | 12.5 | 0.7813 | 12.5 |
| 109 | 6.25 | 12.5 | 0.7813 | 12.5 |
| 110 | 12.5 | 50 | 1.563 | 50 |
| 111 | 25 | 50 | 1.563 | 50 |
| 112 | 5.208 | 20.83 | 0.7813 | 10.42 |
| 113 | 12.5 | 25 | 0.7813 | 12.5 |
| 114 | 6.25 | 6.25 | 1.563 | 50 |
| 115 | 25 | 100 | 12.5 | 100 |
| 116 | 6.25 | 50 | 6.25 | 50 |
| 117 | 6.25 | 50 | 3.125 | 25 |
| 118 | 6.25 | 6.25 | 0.3906 | 6.25 |
| 119 | 6.25 | 6.25 | 0.3906 | 6.25 |
| 120 | 1.563 | 1.563 | 0.1953 | 3.125 |
| 121 | 1.563 | 6.25 | 0.1953 | 1.563 |
| 122 | 3.125 | 3.125 | 0.1953 | 3.125 |
| 123 | 3.125 | 3.125 | 0.3906 | 12.5 |
| 124 | 12.5 | 12.5 | 0.7813 | 12.5 |
| 125 | 3.125 | 3.125 | 0.39 | 3.125 |
| 126 | 6.25 | 3.125 | 0.39 | 3.125 |

What is claimed:
1. A compound of Formula I

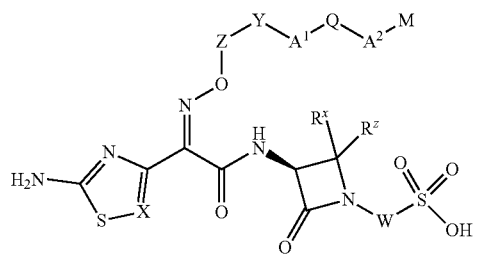

(I)

or a pharmaceutically acceptable salt thereof, wherein:
W is a bond or O;
$R^X$ and $R^Z$ are independently hydrogen, —$SC_1$-$C_3$alkyl, $C_1$-$C_3$ alkyl, —($C_1$-$C_3$alkylene)$_n$O$C_1$-$C_3$alkyl, or —($C_1$-$C_3$alkylene)$_n$N$C_1$-$C_3$alkyl, wherein the —$SC_1$-$C_3$alkyl, the $C_1$-$C_3$ alkyl, the —($C_1$-$C_3$alkylene)$_n$O$C_1$-$C_3$alkyl and the —($C_1$-$C_3$alkylene)$_n$N$C_1$-$C_3$alkyl are optionally substituted with one to seven fluorines;
or, alternatively, $R^X$ and $R^Z$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and said $C_4$-$C_7$ heterocycloalkyl are optionally substituted with one to three substituents independently selected from —F, —OH and —O$C_1$-$C_3$alkyl;
X is N or $CR^1$;
$R^1$ is hydrogen, $C_1$-$C_3$ alkyl, or halogen; wherein said $C_1$-$C_3$ alkyl is optionally substituted with one to three $R^a$;
each occurrence of $R^a$ is independently hydrogen, halogen, $C_1$-$C_3$alkyl, —NR$^c$R$^d$ or —OR$^e$;
Z is $C_1$-$C_3$ alkylene, optionally substituted with one to three $R^b$;
each occurrence of $R^b$ is independently —$C_1$-$C_8$ alkyl, —$C_3$-$C_7$ cycloalkyl, —C(O)OR$^e$, —C(O)NR$^c$R$^d$, tetrazolyl, oxadiazolonyl, HetA, AryA, —S(O)$_m$R$^e$, —S(O)$_m$NR$^c$R$^d$, or —P(O)(R$^e$)$_p$ wherein said —$C_1$-$C_8$ alkyl and said —$C_3$-$C_7$ cycloalkyl are optionally substituted with one to three $R^a$;
HetA is a 4- to 6-membered saturated or monounsaturated monocyclic ring with 1, 2, or 3 heteroatom ring atoms independently selected from N, N as a quaternary salt, O and S, optionally substituted with one to four $R^4$;
AryA is a 5- to 6-membered monocyclic aromatic ring with 0, 1, 2, or 3 ring atoms independently selected from N, N as a quaternary salt, O and S, optionally substituted with one to four $R^4$;
Y is a bond, O, NR$^2$, S, or CH$_2$;
$R^2$ is hydrogen, —$C_1$-$C_3$ alkyl, —C(O)R$^e$, —C(O)NR$^c$R$^d$, —S(O)$_m$R$^e$, or —S(O)$_m$NR$^c$R$^d$, wherein said —$C_1$-$C_3$ alkyl is optionally substituted with one to three $R^a$;
$A^1$ is AryA;
$A^2$ is:

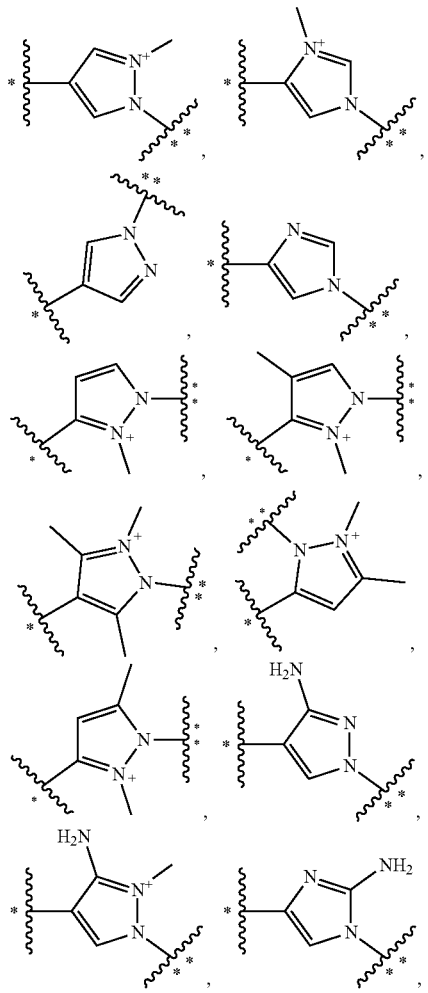

-continued

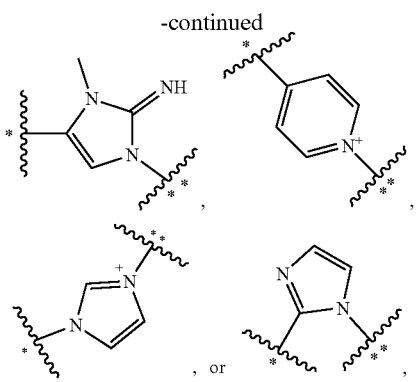

wherein * indicates attachment to Q and ** indicates attachment to M;

each occurrence of $R^4$ is independently: —$C_1$-$C_8$ alkyl, —$C_2$-$C_8$ alkenyl, —$C_2$-$C_8$ alkynyl, halogen, —$OR^e$, —$S(O)_mR^e$, —$S(O)_mNR^cR^d$, —$C(O)R^e$, —$OC(O)R^e$, —$C(O)OR^e$, —CN, —$C(O)NR^cR^d$, —$NR^cR^d$, —$(CH_2)_nNR^cR^d$; —$NR^cC(O)R^e$, —$NR^cC(O)OR^e$, —$NR^cC(O)NR^cR^d$, —$NR^cS(O)_mR^e$, —NH, —$CF_3$, —$OCF_3$, —$OCHF_2$, —$C_3$-$C_6$ cycloalkyl, —O—$C_3$-$C_6$cycloalkyl, —$C_1$-$C_{10}$alkylene-$C_3$-$C_6$cycloalkyl, —O—$C_1$-$C_{10}$ alkylene-$C_3$-$C_6$cycloalkyl, HetB, —O-HetB, —$C_1$-$C_{10}$alkylene-HetB, —O—$C_1$-$C_{10}$ alkylene-HetB, AryA, —O-AryA, —$C_1$-$C_{10}$ alkylene-AryA, or —O—$C_1$-$C_{10}$alkylene-AryA, wherein each $R^4$ is unsubstituted or substituted with one to four substituents selected from halogen, —$C_1$-$C_6$ alkyl and —$(CH_2)_nNR^cR^d$, or wherein $R^4$ and M, together with the atoms to which they are attached, form a 4- to 7-membered cycloheteroalkyl optionally containing one to two additional heteroatoms independently selected from O, S and —$NR^g$;

HetB is a 3- to 6-membered saturated or monounsaturated monocyclic ring with 1, 2, or 3 heteroatom ring atoms independently selected from N, N as a quaternary salt, O and S, optionally substituted with one to three $R^a$;

Q is a bond, $CH_2$, O, S, —$(CH_2)_nNR^3$—, or —$NR^3(CH_2)_n$—, wherein each $CH_2$ is unsubstituted or substituted with one to two substituents selected from halogen, —$C_1$-$C_6$ alkyl, $OR^e$ and —$(CH_2)_nNR^cR^d$;

$R^3$ is hydrogen or —$C_1$-$C_3$ alkyl, wherein said —$C_1$-$C_3$ alkyl is optionally substituted with one to three $R^a$;

M is $R^5$, —$NHR^5$, —$N(R^5)_2$, —$OR^5$, —$(CH_2)_nR^5$, —$C(O)R^5$, —$CH(NH)R^5$, or —$S(O)_mR^5$;

$R^5$ is H, $C_2$-$C_{10}$ alkyl, $C_3$-$C_7$ cycloalkyl, $C_1$-$C_6$ alkyl-$C_3$-$C_7$ cycloalkyl, HetB, AryB, or —$NH(C_1$-$C_6$ alkyl), wherein said $C_1$-$C_6$ alkyl, said $C_2$-$C_{10}$ alkyl and said $C_3$-$C_7$ cycloalkyl are optionally substituted with one to four $R^6$;

AryB is a 5- to 6-membered monocyclic aromatic ring with 0, 1, 2, or 3 ring atoms independently selected from N, O and S, optionally substituted with one to four $R^4$;

each occurrence of $R^6$ is independently selected from the group consisting of: halogen, —$OR^e$, —$S(O)_mR^e$, —$S(O)_mNR^cR^d$, —$C(O)R^e$, —$OC(O)R^e$, —$C(O)OR^e$, —CN, —$C(O)NR^cR^d$, —$C(NH)NR^cR^d$, —$NR^cR^d$, —$(CH_2)_nNR^cR^d$, —$N(R^c)(C(O)R^e)$, —$N(R^c)(C(O)OR^e)$, —$N(R^c)(C(O)NR^cR^d)$, —$N(R^c)(S(O)_mR^e)$, and HetB;

each occurrence of $R^c$ and $R^d$ is independently: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, or, alternatively, $R^c$ and $R^d$ together with the nitrogen atom to which they are attached, form a 4- to 7-membered cycloheteroalkyl optionally containing one to two additional heteroatoms independently selected from O, S and —$NR^g$, and wherein each $R^c$ and $R^d$ is optionally substituted with one to three $R^f$;

each occurrence of $R^e$ is independently: hydrogen, —$C_1$-$C_{10}$alkyl, —$C_2$-$C_{10}$ alkenyl, —OH, —$OC_1$-$C_4$ alkyl, —$C_3$-$C_6$ cycloalkyl, —$C_1$-$C_{10}$ alkylene-$C_3$-$C_6$ cycloalkyl, HetB, —$C_1$-$C_{10}$ alkylene-HetB, AryB, —$C_1$-$C_{10}$ alkylene-AryB, or —$C_1$-$C_{10}$ alkylene-HetB; wherein each $R^e$ is optionally substituted with one to three $R^h$;

each occurrence of $R^f$ is independently: halogen, —$C_1$-$C_{10}$ alkyl, —OH, —$OC_1$-$C_4$ alkyl, —$S(O)_mC_1$-$C_4$ alkyl, —CN, —$CF_3$, —$OCHF_2$, —$OCF_3$, or $NH_2$, wherein said —$C_1$-$C_{10}$ alkyl is optionally substituted with one to three substituents independently selected from: —OH, halogen, cyano, and —$S(O)_2CH_3$;

each occurrence of $R^g$ is independently: hydrogen, —$C(O)R^e$, and or —$C_1$-$C_{10}$ alkyl, wherein said —$C_1$-$C_{10}$alkyl is optionally substituted with one to five fluorines;

each occurrence of $R^h$ is independently: halogen, —$C_1$-$C_{10}$alkyl, —OH, —$OC_1$-$C_4$ alkyl, —$S(O)_mC_1$-$C_4$ alkyl, —CN, —$CF_3$, —$OCHF_2$, or —$OCF_3$; wherein said —$C_1$-$C_{10}$ alkyl is optionally substituted with one to three substituents independently selected from: —OH, halogen, cyano, or —$S(O)_2CH_3$;

each n is independently 0, 1, 2, 3 or 4;

each m is independently 0, 1 or 2, and each p is independently 1 or 2.

2. The compound of formula (I) of claim 1

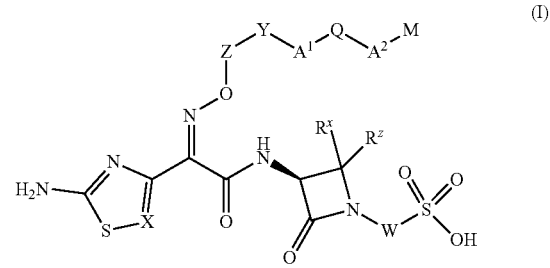

(I)

or a pharmaceutically acceptable salt thereof, wherein:

W is a bond or O;

$R^X$ and $R^Z$ are independently hydrogen, —$SC_1$-$C_3$alkyl, $C_1$-$C_3$ alkyl, —$(C_1$-$C_3$alkylene$)_nOC_1$-$C_3$alkyl, or —$(C_1$-$C_3$alkylene$)_nNC_1$-$C_3$alkyl, wherein the —$SC_1$-$C_3$alkyl, the $C_1$-$C_3$ alkyl, the —$(C_1$-$C_3$alkylene$)_nOC_1$-$C_3$alkyl and the —$(C_1$-$C_3$alkylene$)_nNC_1$-$C_3$alkyl are optionally substituted with one to seven fluorines;

or, alternatively, $R^X$ and $R^Z$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein said $C_4$-$C_7$ cycloalkyl and said $C_4$-$C_7$ heterocycloalkyl are optionally substituted with one to three substituents independently selected from —F, —OH and —$OC_1$-$C_3$alkyl;

X is N or CR¹;

R¹ is hydrogen, $C_1$-$C_3$ alkyl, or halogen; wherein said $C_1$-$C_3$ alkyl is optionally substituted with one to three $R^a$;

each occurrence of $R^a$ is independently hydrogen, halogen, $C_1$-$C_3$alkyl, —$NR^cR^d$ or —$OR^e$;

Z is $C_1$-$C_3$ alkylene, optionally substituted with one to three $R^b$;

each occurrence of $R^b$ is independently —$C_1$-$C_8$ alkyl, —$C_3$-$C_7$ cycloalkyl, —$C(O)OR^e$, —$C(O)NR^cR^d$, tetrazolyl, oxadiazolonyl, HetA, AryA, —$S(O)_mR^e$, —$S(O)_m NR^cR^d$, or $P(O)(R^e)_p$ wherein said —$C_1$-$C_8$ alkyl and said —$C_3$-$C_7$ cycloalkyl are optionally substituted with one to three $R^a$;

AryA is a 5- to 6-membered monocyclic aromatic ring with 0, 1, 2, or 3 ring atoms independently selected from N, N as a quaternary salt, O and S, optionally substituted with one to four $R^4$;

HetA is a 4- to 6-membered saturated or monounsaturated monocyclic ring with 1, 2, or 3 heteroatom ring atoms independently selected from N, N as a quaternary salt, O and S, optionally substituted with one to four $R^4$;

Y is a bond, O, NR², S, or $CH_2$;

R² is hydrogen, —$C_1$-$C_3$ alkyl, —$C(O)R^e$, —$C(O)NR^cR^d$, —$S(O)_mR^e$, or —$S(O)_m NR^cR^d$, wherein said —$C_1$-$C_3$ alkyl is optionally substituted with one to three $R^a$;

A¹ is AryA;

A² is:

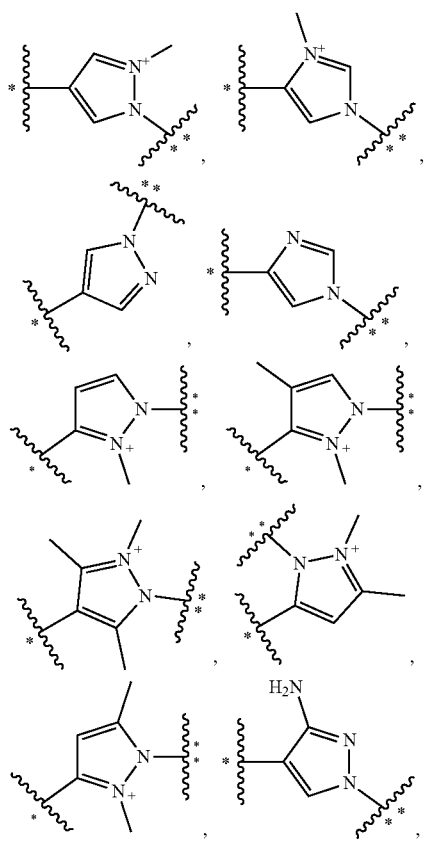

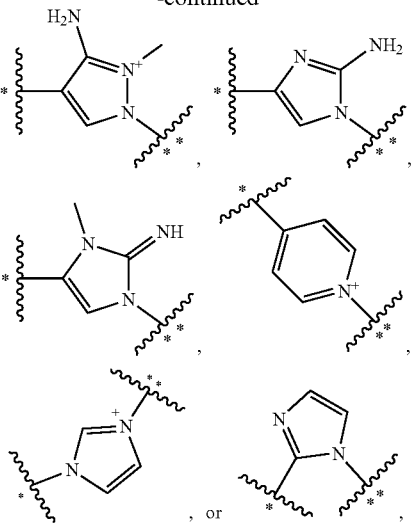

wherein * indicates attachment to Q and ** indicates attachment to M;

each occurrence of $R^4$ is independently: —$C_1$-$C_8$ alkyl, —$C_2$-$C_8$ alkenyl, —$C_2$-$C_8$ alkynyl, halogen, —$OR^e$, —$S(O)_mR^e$, —$S(O)_mNR^cR^d$, —$C(O)R^e$, —$OC(O)R^e$, —$C(O)OR^e$, —CN, —$C(O)NR^cR^d$, —$NR^cR^d$, —$NR^cC(O)R^e$, —$NR^cC(O)OR^e$, —$NR^cC(O)NR^cR^d$, —$NR^cS(O)_mR^e$, =NH, —$CF_3$, —$OCF_3$, —$OCHF_2$, —$C_3$-$C_6$ cycloalkyl, —O—$C_3$-$C_6$cycloalkyl, —$C_1$-$C_{10}$alkylene-$C_3$-$C_6$cycloalkyl, —O—$C_1$-$C_{10}$ alkylene-$C_3$-$C_6$cycloalkyl, HetB, —O-HetB, —$C_1$-$C_{10}$alkylene-HetB, —O—$C_1$-$C_{10}$ alkylene-HetB, AryA, —O-AryA, —$C_1$-$C_{10}$ alkylene-AryA, or —O—$C_1$-$C_{10}$alkylene-AryA;

HetB is a 3- to 6-membered saturated or monounsaturated monocyclic ring with 1, 2, or 3 heteroatom ring atoms independently selected from N, N as a quaternary salt, O and S, optionally substituted with one to three $R^a$;

Q is a bond, $CH_2$, O, S, —$(CH_2)_nNR^3$—, or —$NR^3(CH_2)_n$—;

R³ is hydrogen or —$C_1$-$C_3$ alkyl, wherein said —$C_1$-$C_3$ alkyl is optionally substituted with one to three $R^a$;

M is $R^5$, —$NHR^5$, —$N(R^5)_2$, —$OR^5$, —$(CH_2)_nR^5$, —$C(O)R^5$, —$CH(NH)R^5$, or —$S(O)_mR^5$;

$R^5$ is $C_2$-$C_{10}$ alkyl, $C_3$-$C_7$ cycloalkyl, HetB, or AryB, wherein said $C_2$-$C_{10}$ alkyl and said $C_3$-$C_7$ cycloalkyl are optionally substituted with one to four $R^6$;

AryB is a 5- to 6-membered monocyclic aromatic ring with 0, 1, 2, or 3 ring atoms independently selected from N, O and S, optionally substituted with one to four $R^4$;

each occurrence of $R^6$ is independently selected from the group consisting of: halogen, —$OR^e$, —$S(O)_mR^e$, —$S(O)_mNR^cR^d$, —$C(O)R^e$, —$OC(O)R^e$, —$C(O)OR^e$, —CN, —$C(O)NR^cR^d$, —$C(NH)NR^cR^d$, —$NR^cR^d$, —$N(R^c)(C(O)R^e)$, —$N(R^c)(C(O)OR^e)$, —$N(R^c)(C(O)NR^cR^d)$, and —$N(R^c)(S(O)_mR^e)$;

each occurrence of $R^c$ and $R^d$ is independently: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, or, alternatively, $R^c$ and $R^d$ together with the nitrogen atom to which they are attached, come together to form a 4- to 7-membered cycloheteroalkyl optionally containing one to two additional heteroatoms independently selected from O, S and —NR$^g$, and wherein each R$^c$ and R$^d$ is optionally substituted with one to three R$^f$;

each occurrence of R$^e$ is independently: hydrogen, —C$_1$-C$_{10}$alkyl, —C$_2$-C$_{10}$ alkenyl, —OH, —OC$_1$-C$_4$ alkyl, —C$_3$-C$_6$ cycloalkyl, —C$_1$-C$_{10}$ alkylene-C$_3$-C$_6$ cycloalkyl, HetB, —C$_1$-C$_{10}$ alkylene-HetB, AryB, —C$_1$-C$_{10}$ alkylene-AryB, or —C$_1$-C$_{10}$ alkylene-HetB; wherein each R$^e$ is optionally substituted with one to three R$^h$;

each occurrence of R$^f$ is independently: halogen, —C$_1$-C$_{10}$ alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_{10}$ alkyl is optionally substituted with one to three substituents independently selected from: —OH, halogen, cyano, and —S(O)$_2$CH$_3$;

each occurrence of R$^g$ is independently: hydrogen, —C(O)R$^e$, and or —C$_1$-C$_{10}$ alkyl, wherein said —C$_1$-C$_{10}$alkyl is optionally substituted with one to five fluorines;

each occurrence of R$^h$ is independently: halogen, —C$_1$-C$_{10}$alkyl, —OH, —OC$_1$-C$_4$ alkyl, —S(O)$_m$C$_1$-C$_4$ alkyl, —CN, —CF$_3$, —OCHF$_2$, or —OCF$_3$; wherein said —C$_1$-C$_{10}$ alkyl is optionally substituted with one to three substituents independently selected from: —OH, halogen, cyano, or —S(O)$_2$CH$_3$;

each n is independently 0, 1, 2, 3 or 4;

each m is independently 0, 1 or 2, and each p is 1 or 2.

3. A compound of claim 2, or a pharmaceutically acceptable salt thereof, having the formula II-1, II-2, II-3, III-1, III-2, or III-3:

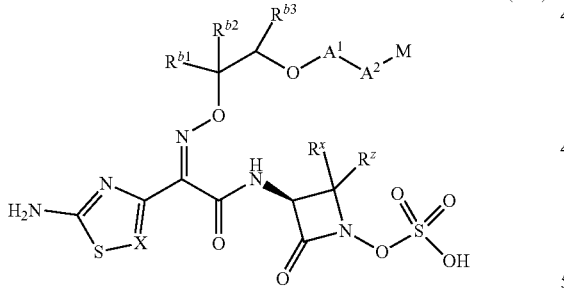
(II-1)

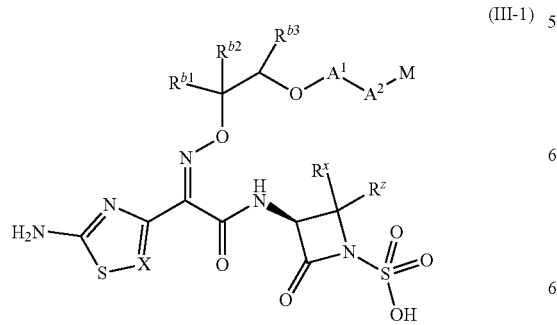
(III-1)

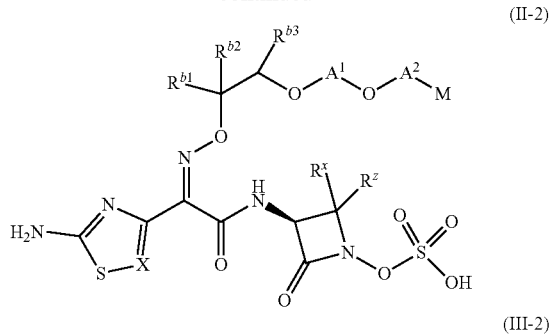
(II-2)

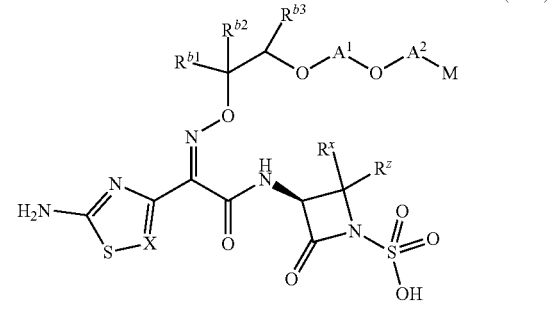
(III-2)

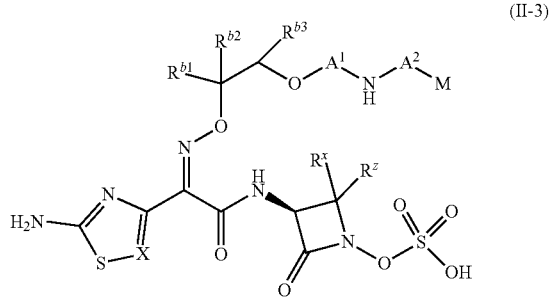
(II-3)

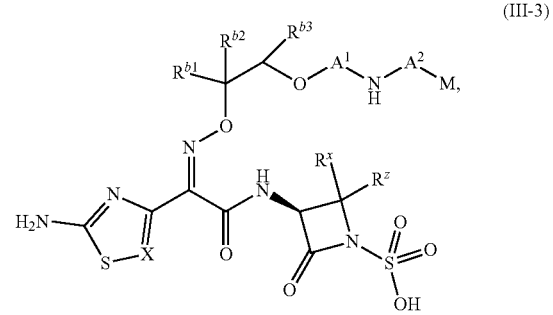
(III-3)

wherein R$^{b1}$, R$^{b2}$, and R$^{b3}$ are independently hydrogen, C$_1$-C$_8$ alkyl, C$_3$-C$_7$ cycloalkyl, —C(O)OR$^e$, —C(O)NR$^c$R$^d$, tetrazolyl, oxadiazolonyl, HetA, AryA, —S(O)$_m$R$^e$, —S(O)$_m$NR$^c$R$^d$, or —P(O)(R$^e$)$_p$, wherein said C$_1$-C$_8$ alkyl and said C$_3$-C$_7$ cycloalkyl are optionally substituted with one to three R$^a$.

4. The compound of claim 3, or a pharmaceutically acceptable salt thereof, wherein R$^{b1}$ and R$^{b2}$ are independently hydrogen, C$_1$-C$_3$ alkyl, tetrazolyl, oxadiazolonyl or —C(O)OR$^e$; and R$^{b3}$ is hydrogen.

5. The compound of claim 2, or a pharmaceutically acceptable salt thereof, wherein X is N.

6. The compound of claim 2, or a pharmaceutically acceptable salt thereof, wherein X is CRl.

7. The compound of claim 2, or a pharmaceutically acceptable salt thereof, wherein A$^1$ is:

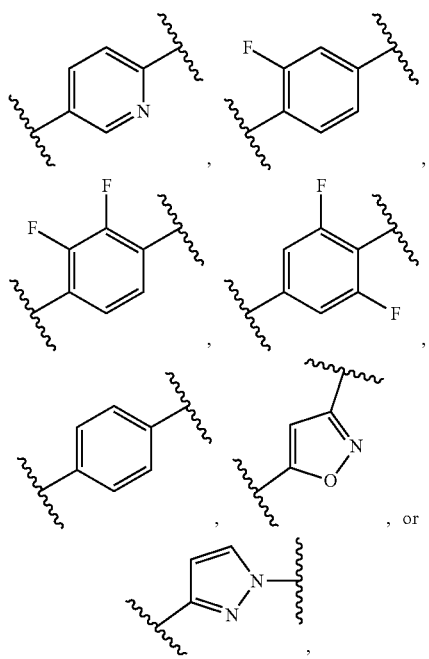

wherein ∼∼∼ indicates the points of attachment to the rest of the compound.

8. The compound of claim 2, or a pharmaceutically acceptable salt thereof, wherein $A^2$ is HetC or a 5- to 6-membered monocyclic aromatic ring with 1, 2, or 3 ring atoms independently selected from N, N as a quaternary salt, O and S, optionally substituted with one to four $R^4$.

9. The compound of claim 2, or a pharmaceutically acceptable salt thereof, wherein M is —$(CH_2)_n R^5$ or $R^5$.

10. The compound of claim 2, or a pharmaceutically acceptable salt thereof, wherein M is $C_2$-$C_{10}$ alkyl substituted with —$NR^c R^d$.

11. The compound of claim 2, or a pharmaceutically acceptable salt thereof, wherein $R^x$ and $R^z$ are methyl, or $R^x$ is methyl and $R^z$ is hydrogen.

12. A compound of claim 2, having the structure:

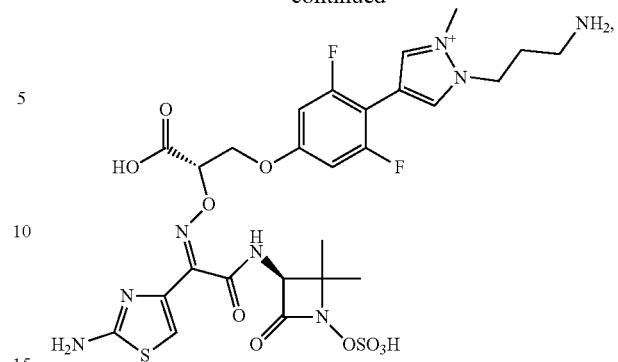

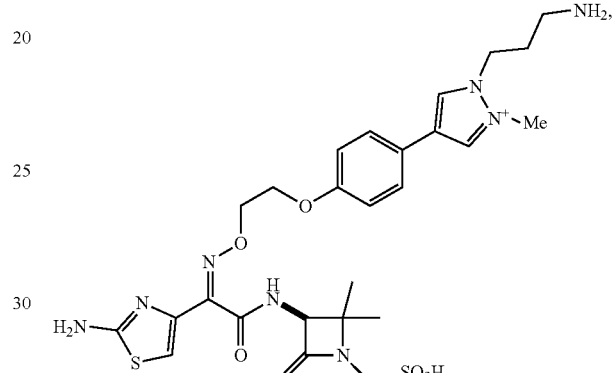

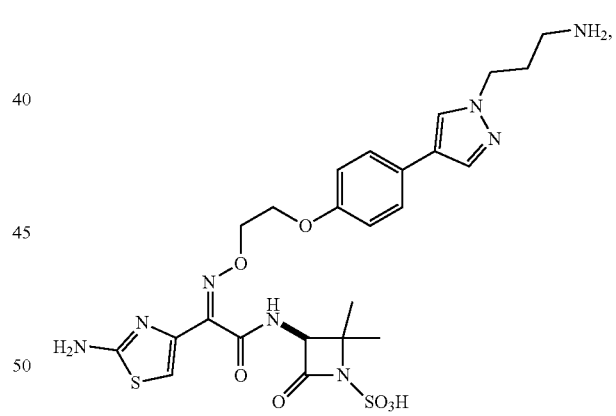

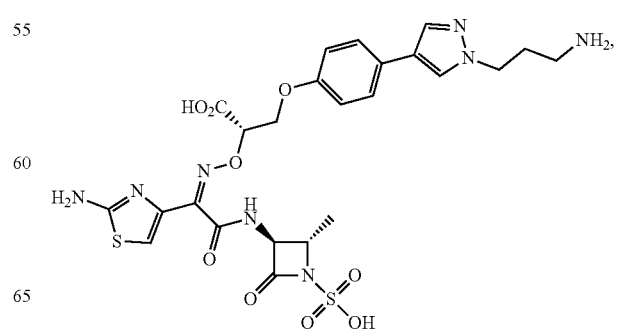

263
-continued
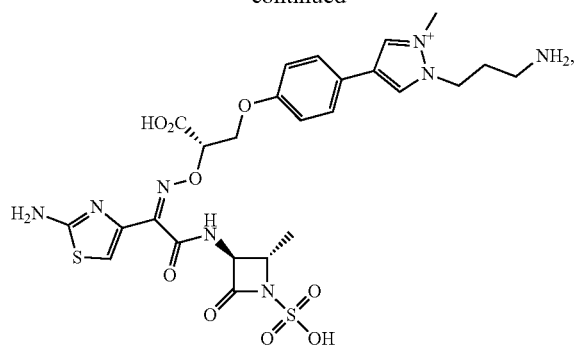
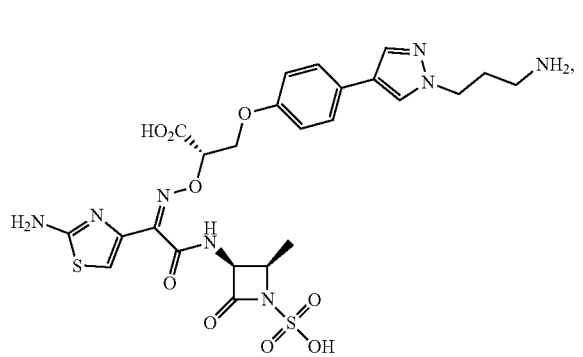
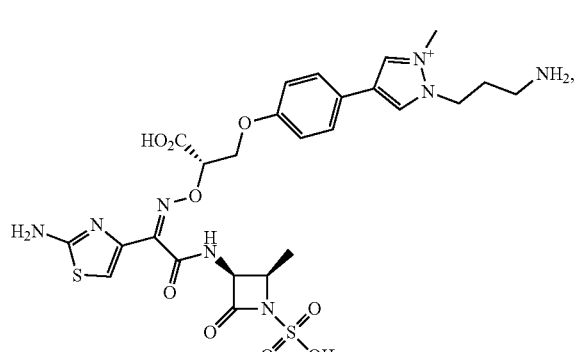
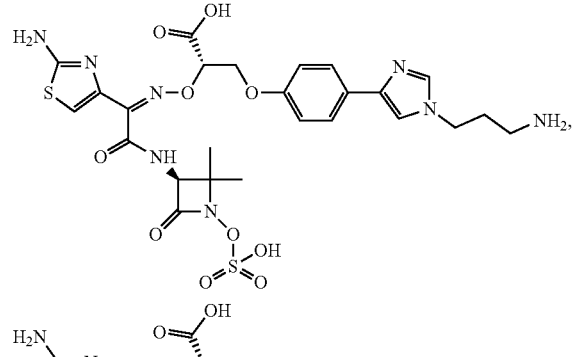
264
-continued
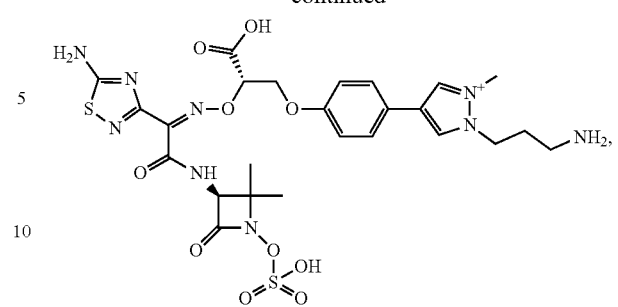
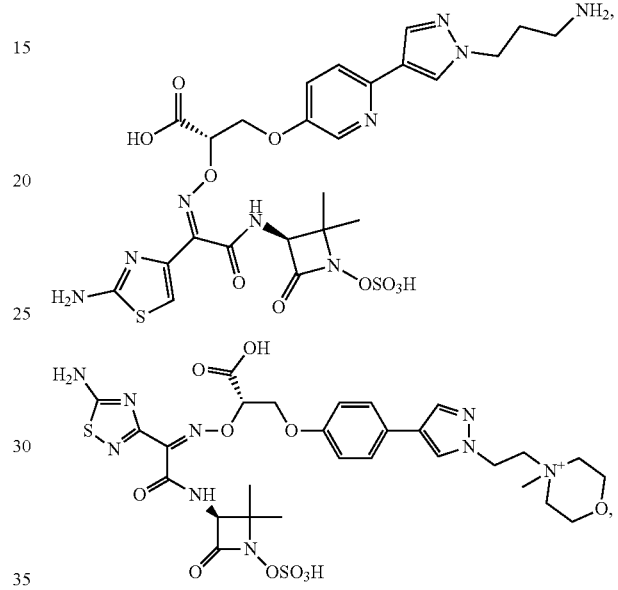
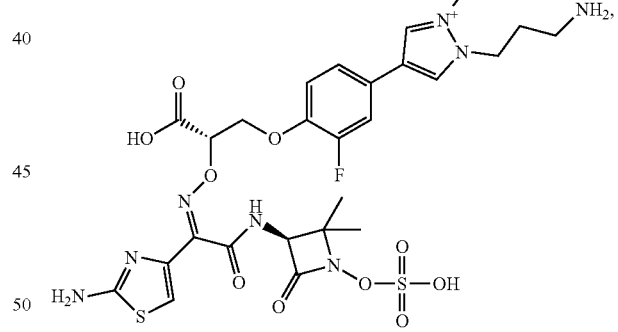
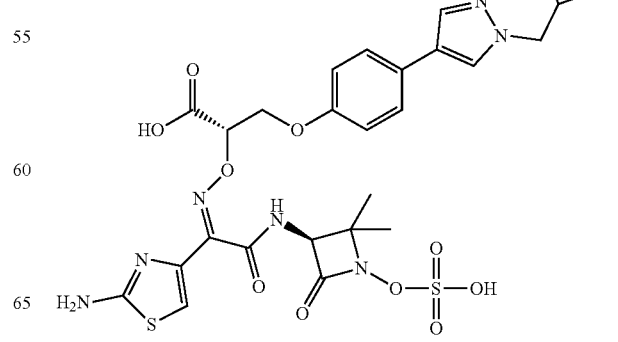

265
-continued
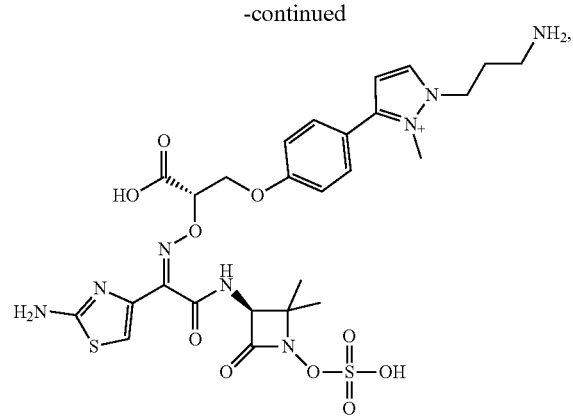
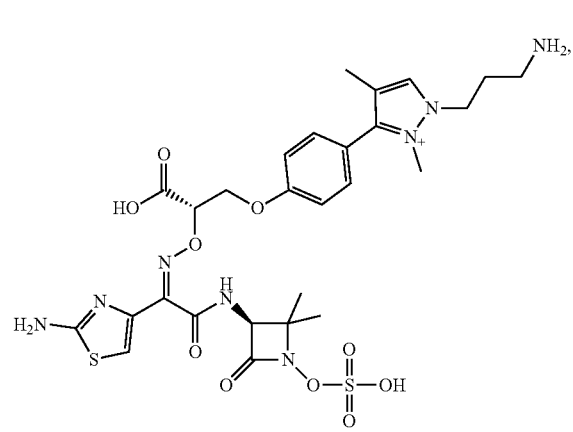
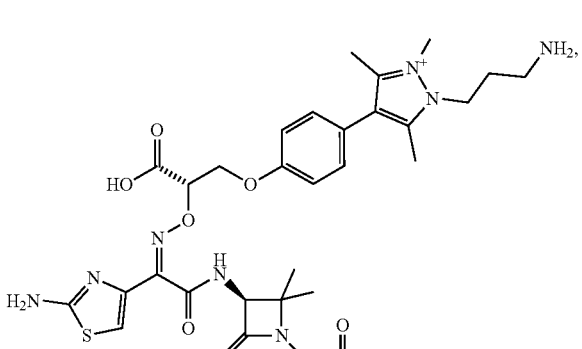
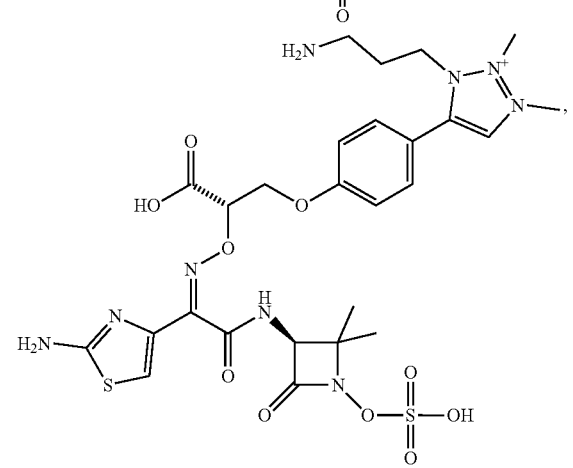
266
-continued
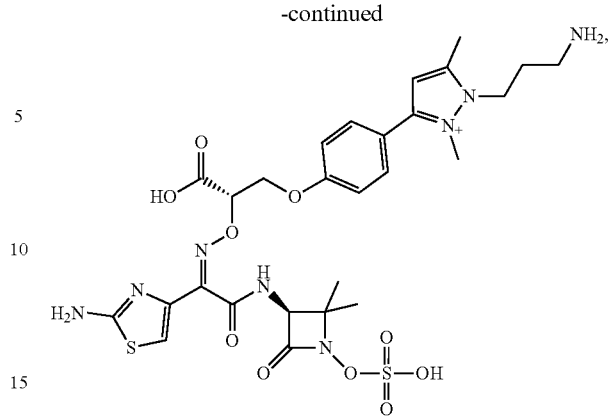
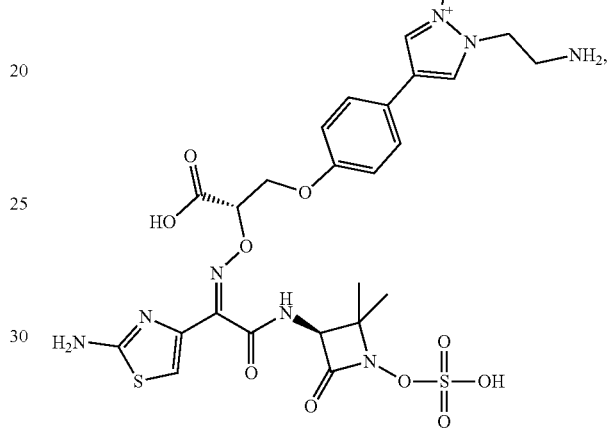
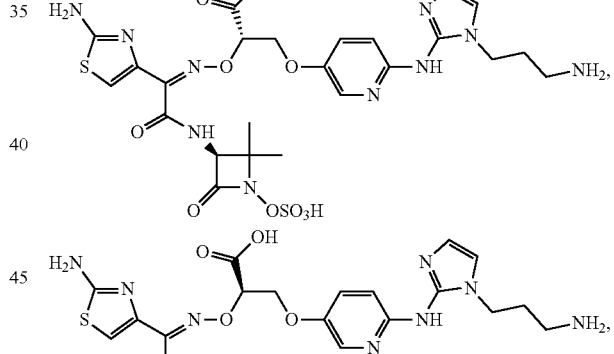
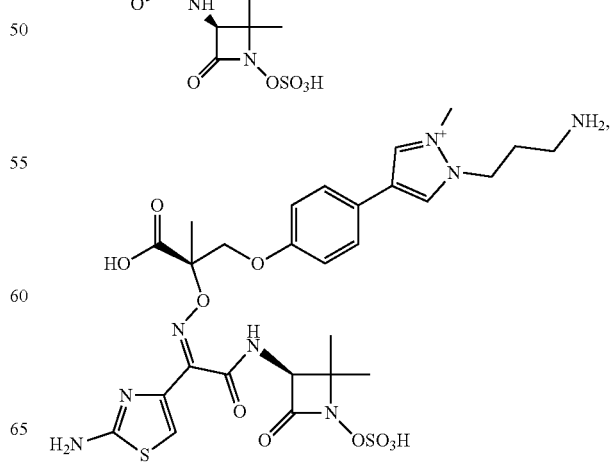

267
-continued
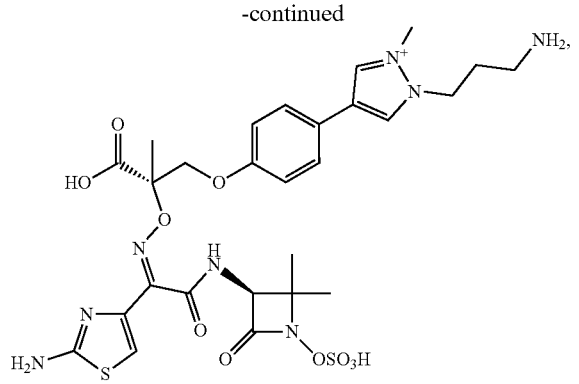
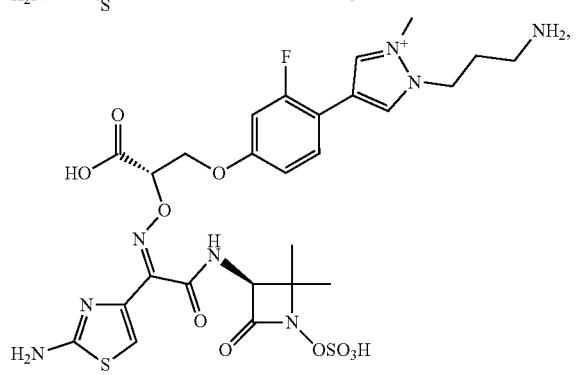
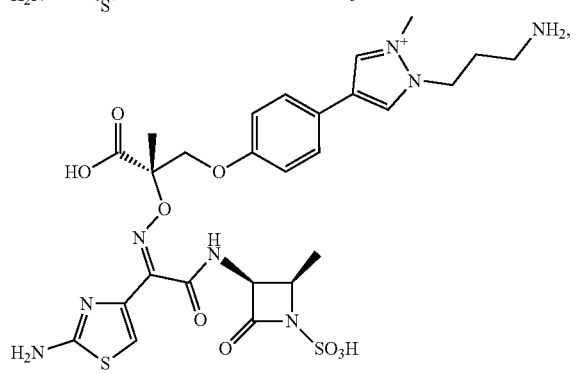
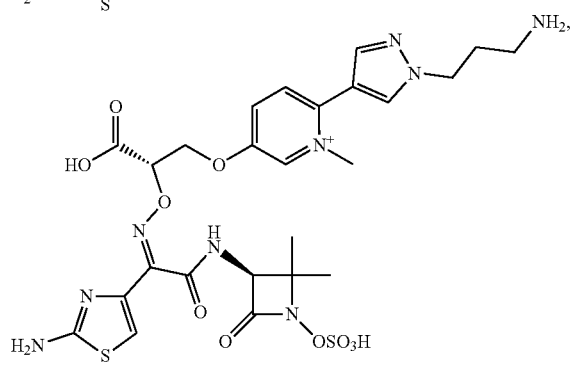
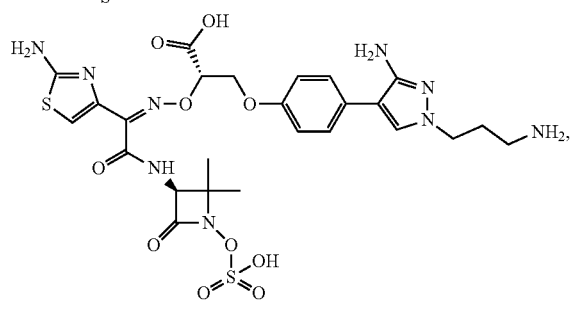
268
-continued
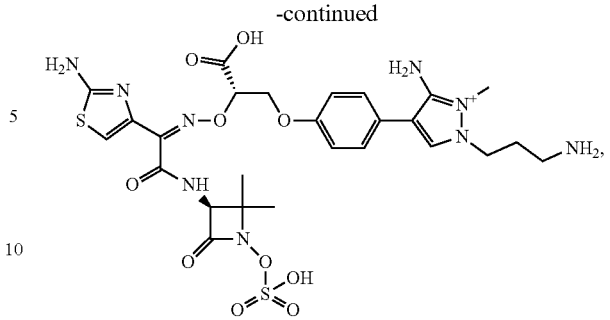
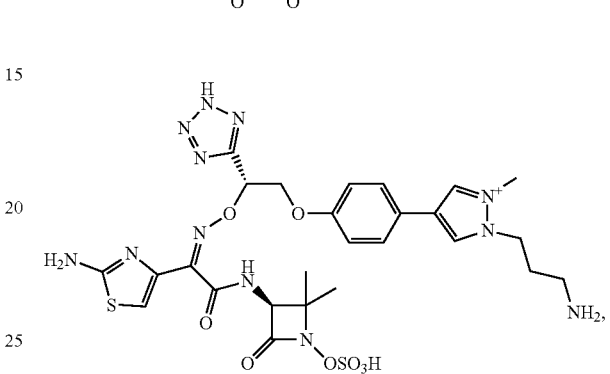
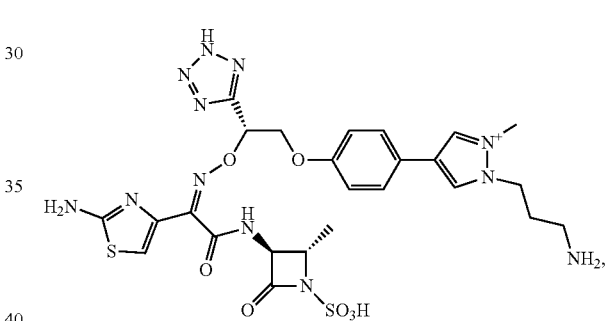
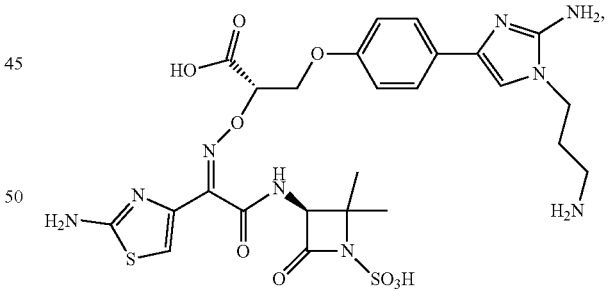
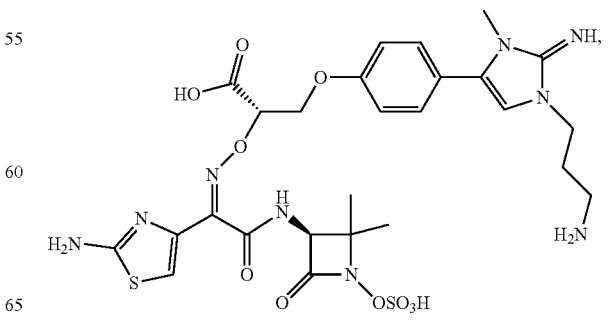

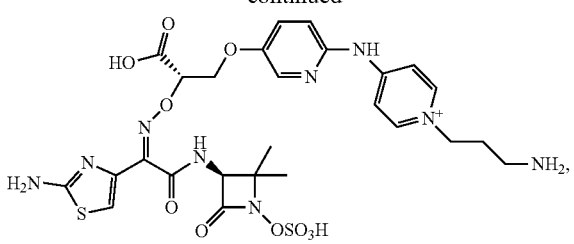

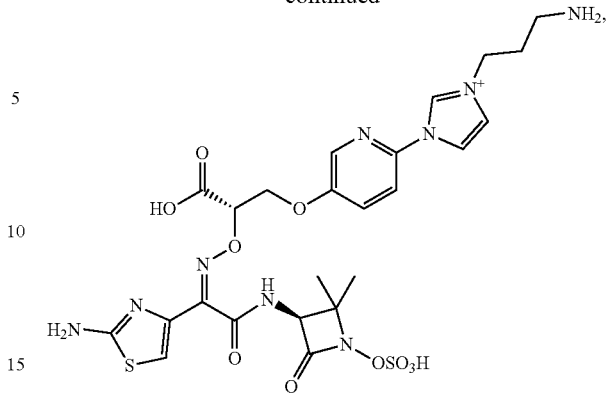

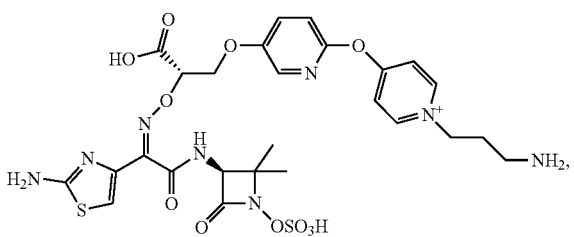

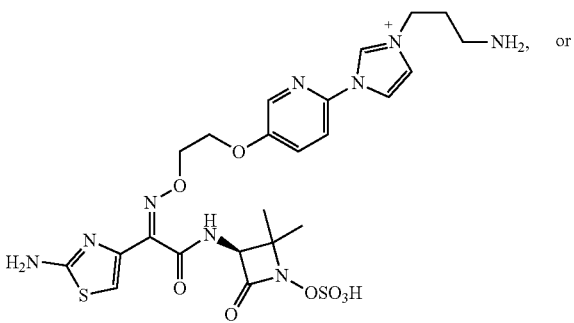

or a pharmaceutically acceptable salt thereof.

13. A trifluoroacetic acid salt of the compound of claim 12.

14. A trifluoroacetic acid salt of the compound of claim 2.

15. A pharmaceutical composition comprising a therapeutically effective amount of a compound according to claim 1, or a pharmaceutically acceptable salt thereof, and a pharmaceutically acceptable carrier.

16. A pharmaceutical composition according to claim 15, which further comprises a therapeutically effective amount of a beta-lactamase inhibitor compound.

17. A pharmaceutical composition according to claim 16, wherein the beta-lactamase inhibitor compound is selected from the group consisting of relebactam, tazobactam, clavulanic acid, sulbactam, and avibactam.

18. A method for treating a bacterial infection which comprises administering to a subject in need of such treatment (i) a therapeutically effective amount of a compound according to claim 1 or a pharmaceutically acceptable salt thereof, optionally in combination with a beta-lactamase inhibitor.

19. The method of claim 18, wherein the beta-lactamase inhibitor compound is selected from the group consisting of relebactam, tazobactam, clavulanic acid, sulbactam, and avibactam.

20. The method of claim 18, wherein the bacterial infection is due to *Pseudomonas* spp., *Klebsiella* spp., *Enterobacter* spp., *Escherichia* spp., *Morganella* spp., *Citrobacter* spp., *Serratia* spp. or *Acinetobacter* spp.

* * * * *